United States Patent
Sigurjonsson et al.

(10) Patent No.: US 12,260,934 B2
(45) Date of Patent: Mar. 25, 2025

(54) SYSTEMS AND METHODS FOR DETECTION OF ANEUPLOIDY

(71) Applicant: Natera, Inc., San Carlos, CA (US)

(72) Inventors: Styrmir Sigurjonsson, San Jose, CA (US); Naresh Vankayalapati, San Francisco, CA (US); Allison Ryan, Belmont, CA (US); Zachary Demko, San Francisco, CA (US); Milena Banjevic, Los Altos Hills, CA (US)

(73) Assignee: Natera, Inc., San Carlos, CA (US)

( * ) Notice: Subject to any disclaimer, the term of this patent is extended or adjusted under 35 U.S.C. 154(b) by 1187 days.

(21) Appl. No.: 16/677,017

(22) Filed: Nov. 7, 2019

(65) Prior Publication Data

US 2020/0126634 A1  Apr. 23, 2020

Related U.S. Application Data

(63) Continuation of application No. 14/732,632, filed on Jun. 5, 2015, now abandoned.

(60) Provisional application No. 62/079,257, filed on Nov. 13, 2014, provisional application No. 62/032,785, filed on Aug. 4, 2014, provisional application No. 62/008,235, filed on Jun. 5, 2014.

(51) Int. Cl.
| | |
|---|---|
| *G01N 33/48* | (2006.01) |
| *G16B 5/00* | (2019.01) |
| *G16B 5/20* | (2019.01) |
| *G16B 20/00* | (2019.01) |
| *G16B 20/10* | (2019.01) |
| *G16B 30/00* | (2019.01) |
| *G16H 10/40* | (2018.01) |

(52) U.S. Cl.
CPC .............. *G16B 20/10* (2019.02); *G16B 5/00* (2019.02); *G16B 5/20* (2019.02); *G16B 20/00* (2019.02); *G16B 30/00* (2019.02); *G16H 10/40* (2018.01)

(58) Field of Classification Search
CPC . G16B 20/10; G16B 5/00; G16B 5/20; G16B 20/00; G16B 30/00; G16H 10/40
See application file for complete search history.

(56) References Cited

U.S. PATENT DOCUMENTS

| | | |
|---|---|---|
| 3,957,654 A | 5/1976 | Ayres |
| 4,040,785 A | 8/1977 | Kim et al. |
| (Continued) | | |

FOREIGN PATENT DOCUMENTS

| | | |
|---|---|---|
| BR | 112017023232 A2 | 8/2018 |
| CA | 2875281 A1 | 12/2013 |
| (Continued) | | |

OTHER PUBLICATIONS

US 8,501,409 B2, 08/2013, Simen et al. (withdrawn)
(Continued)

*Primary Examiner* — Russell S Negin

(57) ABSTRACT

Provided herein are improved methods for detecting aneuploidy in a sample. The methods in certain embodiments are used for the analysis of circulating DNA in serum samples, such as circulating fetal DNA or circulating tumor DNA. In certain embodiments, chromosome or chromosome segments of interest are used to set a bias model and/or a control value for a z-score determination, in illustrative examples without the use of a control chromosome.

24 Claims, 3 Drawing Sheets

(56) References Cited

U.S. PATENT DOCUMENTS

| | | |
|---|---|---|
| 4,683,195 A | 7/1987 | Mullis et al. |
| 4,942,124 A | 7/1990 | Church et al. |
| 5,180,812 A | 1/1993 | Dower et al. |
| 5,314,809 A | 5/1994 | Erlich et al. |
| 5,319,071 A | 6/1994 | Dower et al. |
| 5,464,937 A | 11/1995 | Sims et al. |
| 5,486,477 A | 1/1996 | Carver |
| 5,488,032 A | 1/1996 | Dower et al. |
| 5,492,888 A | 2/1996 | Dower et al. |
| 5,569,582 A | 10/1996 | Tavernarakis et al. |
| 5,595,890 A | 1/1997 | Newton et al. |
| 5,635,366 A | 6/1997 | Cooke et al. |
| 5,645,988 A | 7/1997 | Vande Woude et al. |
| 5,648,220 A | 7/1997 | Bianchi et al. |
| 5,714,320 A | 2/1998 | Kool |
| 5,716,776 A | 2/1998 | Bogart |
| 5,736,033 A | 4/1998 | Coleman et al. |
| 5,753,467 A | 5/1998 | Jensen et al. |
| 5,824,467 A | 10/1998 | Mascarenhas |
| 5,854,033 A | 12/1998 | Lizardi |
| 5,860,917 A | 1/1999 | Comanor et al. |
| 5,891,734 A | 4/1999 | Gill et al. |
| 5,952,170 A | 9/1999 | Stroun et al. |
| 5,962,223 A | 10/1999 | Whiteley et al. |
| 5,972,602 A | 11/1999 | Hyland et al. |
| 5,976,790 A | 11/1999 | Pinkel et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,235,472 B1 | 2/2001 | Landegren et al. |
| 6,214,558 B1 | 4/2001 | Shuber et al. |
| 6,221,603 B1 | 4/2001 | Mahtani |
| 6,258,540 B1 | 7/2001 | Lo et al. |
| 6,300,077 B1 | 10/2001 | Shuber et al. |
| 6,329,179 B1 | 12/2001 | Kopreski |
| 6,335,167 B1 | 1/2002 | Pinkel et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,605,451 B1 | 8/2003 | Marmaro et al. |
| 6,617,137 B2 | 9/2003 | Dean et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,858,412 B2 | 2/2005 | Willis et al. |
| 6,927,028 B2 | 8/2005 | Lo et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,101,663 B2 | 9/2006 | Godfrey et al. |
| 7,153,656 B2 | 12/2006 | Nolan et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,410,764 B2 | 8/2008 | Gocke et al. |
| 7,414,118 B1 | 8/2008 | Mullah et al. |
| 7,442,506 B2 | 12/2008 | Dhallan |
| 7,459,273 B2 | 12/2008 | Jones et al. |
| 7,537,897 B2 | 5/2009 | Brenner et al. |
| 7,645,576 B2 | 1/2010 | Lo et al. |
| 7,655,399 B2 | 2/2010 | Cantor et al. |
| 7,700,325 B2 | 5/2010 | Cantor et al. |
| 7,718,367 B2 | 5/2010 | Lo et al. |
| 7,718,370 B2 | 6/2010 | Dhallan |
| 7,741,463 B2 | 6/2010 | Gormley et al. |
| 7,785,798 B2 | 8/2010 | Cantor et al. |
| 7,727,720 B2 | 9/2010 | Dhallan |
| 7,790,393 B2 | 9/2010 | Lyamichev et al. |
| 7,790,418 B2 | 9/2010 | Mayer |
| 7,805,282 B2 | 11/2010 | Casey |
| 7,838,647 B2 | 11/2010 | Hahn et al. |
| 7,981,609 B2 | 7/2011 | Rubin et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,236,503 B2 | 8/2012 | Faham et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,318,434 B2 | 11/2012 | Cuppens et al. |
| 8,323,897 B2 | 12/2012 | Andersen et al. |
| 8,372,584 B2 | 2/2013 | Shoemaker et al. |
| 8,389,557 B2 | 3/2013 | Singh et al. |
| 8,389,578 B2 | 3/2013 | Went et al. |
| 8,450,063 B2 | 5/2013 | Dube et al. |
| 8,467,976 B2 | 8/2013 | Lo et al. |
| 8,515,679 B2 | 9/2013 | Rabinowitz et al. |
| 8,532,930 B2 | 9/2013 | Rabinowitz et al. |
| 8,609,338 B2 | 12/2013 | Mitchell et al. |
| 8,679,741 B2 | 3/2014 | Hoyal-Wrightson et al. |
| 8,682,592 B2 | 3/2014 | Rabinowitz et al. |
| 8,703,652 B2 | 4/2014 | Quake et al. |
| 8,706,422 B2 | 4/2014 | Lo et al. |
| 8,748,103 B2 | 6/2014 | Faham et al. |
| 8,822,153 B2 | 9/2014 | Hayes et al. |
| 8,825,412 B2 | 9/2014 | Rabinowitz et al. |
| 9,005,894 B2 | 4/2015 | Ladner et al. |
| 9,051,602 B2 | 6/2015 | Oliphant et al. |
| 9,085,798 B2 | 7/2015 | Chee |
| 9,206,475 B2 | 12/2015 | Gerdes et al. |
| 9,228,234 B2 | 1/2016 | Rabinowitz et al. |
| 9,290,815 B2 | 3/2016 | Di Pasquale et al. |
| 9,323,888 B2 | 4/2016 | Rava et al. |
| 9,364,829 B2 | 6/2016 | Heid et al. |
| 9,404,150 B2 | 8/2016 | Lee et al. |
| 9,424,392 B2 | 8/2016 | Rabinowitz et al. |
| 9,453,257 B2 | 9/2016 | Hoyal-Wrightson et al. |
| 9,476,095 B2 | 10/2016 | Vogelstein et al. |
| 9,487,829 B2 | 11/2016 | Vogelstein et al. |
| 9,493,828 B2 | 11/2016 | Rava et al. |
| 9,506,119 B2 | 11/2016 | Faham et al. |
| 9,598,731 B2 | 3/2017 | Talasaz |
| 9,677,118 B2 | 6/2017 | Zimmermann et al. |
| 9,784,742 B2 | 10/2017 | Benz et al. |
| 9,926,593 B2 | 3/2018 | Ehrich et al. |
| 9,957,558 B2 | 5/2018 | Leamon et al. |
| 10,011,870 B2 | 7/2018 | Zimmermann et al. |
| 10,017,810 B2 | 7/2018 | Iafrate et al. |
| 10,041,127 B2 | 8/2018 | Talasaz |
| 10,061,890 B2 | 8/2018 | Rabinowitz et al. |
| 10,081,839 B2 | 9/2018 | Rabinowitz et al. |
| 10,083,273 B2 | 9/2018 | Rabinowitz et al. |
| 10,174,369 B2 | 1/2019 | Rabinowitz et al. |
| 10,179,937 B2 | 1/2019 | Babiarz et al. |
| 10,227,652 B2 | 3/2019 | Rabinowitz et al. |
| 10,229,244 B2 | 3/2019 | Ghosh |
| 10,240,202 B2 | 3/2019 | Rabinowitz et al. |
| 10,260,096 B2 | 4/2019 | Rabinowitz et al. |
| 10,266,893 B2 | 4/2019 | Rabinowitz et al. |
| 10,308,981 B2 | 6/2019 | Sparks et al. |
| 10,316,362 B2 | 6/2019 | Babiarz et al. |
| 10,351,906 B2 | 7/2019 | Zimmermann et al. |
| 10,385,396 B2 | 8/2019 | Mitchell et al. |
| 10,392,664 B2 | 8/2019 | Rabinowitz et al. |
| 10,450,597 B2 | 10/2019 | Iafrate et al. |
| 10,472,680 B2 | 11/2019 | Mitchell et al. |
| 10,522,242 B2 | 12/2019 | Rabinowitz et al. |
| 10,526,658 B2 | 1/2020 | Babiarz et al. |
| 10,538,814 B2 | 1/2020 | Babiarz et al. |

(56) References Cited

U.S. PATENT DOCUMENTS

| | | |
|---|---|---|
| 10,557,172 B2 | 2/2020 | Babiarz et al. |
| 10,597,708 B2 | 3/2020 | Zimmermann et al. |
| 10,597,709 B2 | 3/2020 | Zimmermann et al. |
| 10,597,723 B2 | 3/2020 | Babiarz et al. |
| 10,640,819 B2 | 5/2020 | Rosenfeld et al. |
| 10,655,180 B2 | 5/2020 | Babiarz et al. |
| 10,683,552 B2 | 6/2020 | Giulio et al. |
| 10,711,309 B2 | 7/2020 | Rabinowitz et al. |
| 10,731,220 B2 | 8/2020 | Babiarz et al. |
| 10,774,380 B2 | 9/2020 | Ryan et al. |
| 10,793,912 B2 | 10/2020 | Babiarz et al. |
| 10,894,976 B2 | 1/2021 | Stray et al. |
| 11,111,543 B2 | 9/2021 | Rabinowitz et al. |
| 11,111,544 B2 | 9/2021 | Rabinowitz et al. |
| 11,111,545 B2 | 9/2021 | Babiarz et al. |
| 11,130,995 B2 | 9/2021 | Quake et al. |
| 11,319,596 B2 | 5/2022 | Babiarz et al. |
| 11,371,100 B2 | 6/2022 | Babiarz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2002/0119478 A1 | 8/2002 | Umansky et al. |
| 2002/0182622 A1 | 12/2002 | Nakamura et al. |
| 2002/0197630 A1 | 12/2002 | Knapp et al. |
| 2003/0009295 A1 | 1/2003 | Markowitz et al. |
| 2003/0040620 A1 | 2/2003 | Langmore et al. |
| 2003/0044388 A1 | 3/2003 | Lo et al. |
| 2003/0065535 A1 | 4/2003 | Karlov et al. |
| 2003/0077586 A1 | 4/2003 | Pavlovic et al. |
| 2003/0087276 A1 | 5/2003 | Kopreski et al. |
| 2003/0101000 A1 | 5/2003 | Bader et al. |
| 2003/0108900 A1 | 6/2003 | Oliphant et al. |
| 2003/0119004 A1 | 6/2003 | Wenz et al. |
| 2003/0138780 A1 | 7/2003 | Gill et al. |
| 2003/0148301 A1 | 8/2003 | Aono et al. |
| 2003/0191005 A1 | 10/2003 | Coelho et al. |
| 2003/0211489 A1 | 11/2003 | Shen et al. |
| 2003/0228613 A1 | 12/2003 | Bornarth et al. |
| 2003/0232348 A1 | 12/2003 | Jones et al. |
| 2003/0232353 A1 | 12/2003 | Kennedy et al. |
| 2003/0235848 A1 | 12/2003 | Neville et al. |
| 2004/0009518 A1 | 1/2004 | Lo et al. |
| 2004/0033596 A1 | 2/2004 | Threadgill et al. |
| 2004/0067493 A1 | 4/2004 | Matsuzaki et al. |
| 2004/0096874 A1 | 5/2004 | Neville et al. |
| 2004/0115629 A1 | 6/2004 | Panzer et al. |
| 2004/0126760 A1 | 7/2004 | Broude |
| 2004/0136967 A1 | 7/2004 | Weiss et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0185495 A1 | 9/2004 | Schueler et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0043894 A1 | 2/2005 | Fernandez |
| 2005/0049793 A1 | 3/2005 | Paterlini-brechot |
| 2005/0053950 A1 | 3/2005 | Ubani et al. |
| 2005/0064476 A1 | 3/2005 | Huang et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0164252 A1 | 7/2005 | Yeung |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2005/0282185 A1 | 12/2005 | Lo et al. |
| 2006/0014179 A1 | 1/2006 | Roberts |
| 2006/0019278 A1 | 1/2006 | Lo et al. |
| 2006/0040300 A1 | 2/2006 | Dapprich et al. |
| 2006/0046258 A1 | 3/2006 | Lapidus et al. |
| 2006/0051799 A1 | 3/2006 | Iwaki et al. |
| 2006/0052945 A1 | 3/2006 | Rabinowitz et al. |
| 2006/0057618 A1 | 3/2006 | Piper et al. |
| 2006/0068369 A1 | 3/2006 | Coelho et al. |
| 2006/0068394 A1 | 3/2006 | Langmore et al. |
| 2006/0088574 A1 | 4/2006 | Manning et al. |
| 2006/0088871 A1 | 4/2006 | Finkelstein et al. |
| 2006/0088912 A1 | 4/2006 | Yan et al. |
| 2006/0094010 A1 | 5/2006 | Giles et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216153 A1 | 9/2006 | Wobben et al. |
| 2006/0216738 A1 | 9/2006 | Wada et al. |
| 2006/0228721 A1 | 10/2006 | Leamon et al. |
| 2006/0234264 A1 | 10/2006 | Hardenbol |
| 2006/0248031 A1 | 11/2006 | Kates et al. |
| 2006/0281105 A1 | 12/2006 | Li et al. |
| 2006/0292599 A1 | 12/2006 | Ritz et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0037166 A1 | 2/2007 | Wohlgemuth et al. |
| 2007/0042384 A1 | 2/2007 | Li et al. |
| 2007/0059700 A1 | 3/2007 | Tao et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0134658 A1 | 6/2007 | Bohmer |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0231823 A1 | 10/2007 | McKernan et al. |
| 2007/0243549 A1 | 10/2007 | Bischoff |
| 2007/0259351 A1 | 11/2007 | Chinitz |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0161420 A1 | 7/2008 | Shuber et al. |
| 2008/0164204 A1 | 7/2008 | Hatamian et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0293589 A1 | 11/2008 | Shapero |
| 2008/0299562 A1 | 12/2008 | Oeth et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |

(56) References Cited

U.S. PATENT DOCUMENTS

| | | |
|---|---|---|
| 2009/0176234 A1 | 7/2009 | Drmanac et al. |
| 2009/0176662 A1 | 7/2009 | Rigatti et al. |
| 2009/0221620 A1 | 9/2009 | Luke et al. |
| 2009/0233802 A1 | 9/2009 | Bignell et al. |
| 2009/0253183 A1 | 10/2009 | Han |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0012598 A1 | 1/2010 | Dicesare et al. |
| 2010/0035232 A1 | 2/2010 | Ecker et al. |
| 2010/0041048 A1 | 2/2010 | Diehl et al. |
| 2010/0086914 A1 | 4/2010 | Bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0155343 A1 | 6/2010 | Battles et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216145 A1 | 8/2010 | Duvdevani |
| 2010/0216151 A1 | 8/2010 | Lapdus et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2010/0326218 A1 | 12/2010 | Boeckh et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0110931 A1 | 5/2011 | Matsui |
| 2011/0111410 A1 | 5/2011 | Ryan et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0189677 A1 | 8/2011 | Adli et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1* | 11/2011 | Rabinowitz ............ G16B 20/40 702/19 |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2011/0318734 A1 | 12/2011 | Lo et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0021442 A1 | 1/2012 | Buhimschi et al. |
| 2012/0028814 A1 | 2/2012 | Toloue et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0115140 A1 | 5/2012 | Rivkees et al. |
| 2012/0122701 A1 | 5/2012 | Ryan et al. |
| 2012/0122702 A1 | 5/2012 | Leproust et al. |
| 2012/0135872 A1 | 5/2012 | Chuu et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0251411 A1 | 10/2012 | Jeon |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0059733 A1 | 3/2013 | Lo et al. |
| 2013/0060483 A1 | 3/2013 | Struble et al. |
| 2013/0069869 A1 | 3/2013 | Akao et al. |
| 2013/0071844 A1 | 3/2013 | Makino et al. |
| 2013/0073214 A1 | 3/2013 | Hyland et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0143219 A1 | 6/2013 | Mitchell et al. |
| 2013/0150253 A1* | 6/2013 | Deciu .................... G16B 30/10 506/2 |
| 2013/0157870 A1 | 6/2013 | Pushkarev et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0231252 A1 | 9/2013 | Mitchell et al. |
| 2013/0237431 A1 | 9/2013 | Lo et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0274135 A1 | 10/2013 | Zhang et al. |
| 2013/0288252 A1 | 10/2013 | Sparks et al. |
| 2013/0303461 A1 | 11/2013 | Iafrate et al. |
| 2013/0310260 A1 | 11/2013 | Kim et al. |
| 2013/0323727 A1 | 12/2013 | Huang et al. |
| 2013/0323731 A1 | 12/2013 | Lo et al. |
| 2013/0325360 A1 | 12/2013 | Deciu et al. |
| 2013/0344066 A1 | 12/2013 | Faham et al. |
| 2014/0032128 A1 | 1/2014 | Rabinowitz et al. |
| 2014/0038830 A1 | 2/2014 | Srinivasan et al. |
| 2014/0045181 A1 | 2/2014 | Lo et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |
| 2014/0100121 A1 | 4/2014 | Lo et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0113795 A1 | 4/2014 | Emerson et al. |

(56) References Cited

U.S. PATENT DOCUMENTS

| | | |
|---|---|---|
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0186827 A1 | 7/2014 | Pieprzyk et al. |
| 2014/0193816 A1 | 7/2014 | Rabinowitz et al. |
| 2014/0206552 A1 | 7/2014 | Rabinowitz et al. |
| 2014/0227691 A1 | 8/2014 | May et al. |
| 2014/0227705 A1 | 8/2014 | Vogelstein et al. |
| 2014/0242588 A1 | 8/2014 | Van Den Boom et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1 | 10/2014 | Diehn et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0056617 A1 | 2/2015 | Whitt et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0099673 A1 | 4/2015 | Fodor |
| 2015/0147815 A1 | 5/2015 | Babiarz et al. |
| 2015/0157606 A1* | 6/2015 | Chow Maneval ...... A61P 35/00 424/1.45 |
| 2015/0167069 A1 | 6/2015 | Schutz et al. |
| 2015/0167077 A1 | 6/2015 | Fehr et al. |
| 2015/0197786 A1 | 7/2015 | Osborne et al. |
| 2015/0211050 A1 | 7/2015 | Iafrate et al. |
| 2015/0218631 A1 | 8/2015 | Chuu et al. |
| 2015/0232938 A1 | 8/2015 | Mhatre |
| 2015/0246103 A1 | 9/2015 | Hazout |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0024581 A1 | 1/2016 | Sarwal et al. |
| 2016/0032396 A1 | 2/2016 | Diehn et al. |
| 2016/0046986 A1 | 2/2016 | Eltoukhy et al. |
| 2016/0053320 A1 | 2/2016 | Schuh et al. |
| 2016/0115541 A1 | 4/2016 | Schutz et al. |
| 2016/0138106 A1 | 5/2016 | Schulze |
| 2016/0138112 A1 | 5/2016 | Janne et al. |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0011166 A1 | 1/2017 | Rabinowitz et al. |
| 2017/0107576 A1 | 4/2017 | Babiarz et al. |
| 2017/0114411 A1 | 4/2017 | Mitchell |
| 2017/0121716 A1 | 5/2017 | Rodi et al. |
| 2017/0137882 A1 | 5/2017 | Goossens et al. |
| 2017/0145475 A1 | 5/2017 | Hunsley et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0298427 A1 | 10/2017 | Buis et al. |
| 2017/0314014 A1 | 11/2017 | Green et al. |
| 2017/0342477 A1 | 11/2017 | Jensen et al. |
| 2017/0362649 A1 | 12/2017 | Lieberman-Aiden et al. |
| 2018/0023128 A1 | 1/2018 | Yanai et al. |
| 2018/0025109 A1 | 2/2018 | Rabinowitz et al. |
| 2018/0105807 A1 | 4/2018 | Lo et al. |
| 2018/0127744 A1 | 5/2018 | Hu et al. |
| 2018/0142296 A1 | 5/2018 | Mitchell et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0187241 A1 | 7/2018 | Selvaraj et al. |
| 2018/0201995 A1 | 7/2018 | Rabinowitz et al. |
| 2018/0237841 A1 | 8/2018 | Stray et al. |
| 2018/0251553 A1 | 9/2018 | McGranahan et al. |
| 2018/0265917 A1 | 9/2018 | Barany et al. |
| 2018/0288982 A1 | 10/2018 | Sinha |
| 2018/0298439 A1 | 10/2018 | Ryan et al. |
| 2018/0300448 A1 | 10/2018 | Rabinowitz et al. |
| 2018/0303870 A1 | 10/2018 | Golobish et al. |
| 2018/0320171 A1 | 11/2018 | Withey |
| 2018/0320239 A1 | 11/2018 | Babiarz et al. |
| 2018/0371531 A1 | 12/2018 | Quake et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0112661 A1 | 4/2019 | Khan et al. |
| 2019/0153521 A1 | 5/2019 | Mitchell et al. |
| 2019/0153525 A1 | 5/2019 | Mitchell et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211376 A1 | 7/2019 | Quake et al. |
| 2019/0211385 A1 | 7/2019 | Sarwar et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256924 A1 | 8/2019 | Vogelstein et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360033 A1 | 11/2019 | Stamm et al. |
| 2019/0360036 A1 | 11/2019 | Rabinowitz et al. |
| 2019/0367972 A1 | 12/2019 | Mitchell et al. |
| 2020/0024653 A1 | 1/2020 | Bethke |
| 2020/0032323 A1 | 1/2020 | Talasaz et al. |
| 2020/0032340 A1 | 1/2020 | Mitchell |
| 2020/0109449 A1 | 4/2020 | Stamm et al. |

(56) References Cited

U.S. PATENT DOCUMENTS

| | | |
|---|---|---|
| 2020/0121718 A1 | 4/2020 | Novik et al. |
| 2020/0123612 A1 | 4/2020 | Babiarz et al. |
| 2020/0140950 A1 | 5/2020 | Babiarz et al. |
| 2020/0141925 A1 | 5/2020 | Liaw et al. |
| 2020/0149111 A1 | 5/2020 | Babiarz et al. |
| 2020/0157629 A1 | 5/2020 | Babiarz et al. |
| 2020/0165678 A1 | 5/2020 | Mitchell et al. |
| 2020/0172977 A1 | 6/2020 | Rabinowitz et al. |
| 2020/0181681 A1 | 6/2020 | Mitchell et al. |
| 2020/0181697 A1 | 6/2020 | Rabinowitz et al. |
| 2020/0190570 A1 | 6/2020 | Ryan et al. |
| 2020/0190573 A1 | 6/2020 | Rabinowitz et al. |
| 2020/0190591 A1 | 6/2020 | Rabinowitz et al. |
| 2020/0208196 A1 | 7/2020 | Zimmermann et al. |
| 2020/0208221 A1 | 7/2020 | Babiarz et al. |
| 2020/0224273 A1 | 7/2020 | Rabinowitz et al. |
| 2020/0232036 A1 | 7/2020 | Rabinowitz et al. |
| 2020/0232037 A1 | 7/2020 | Babiarz et al. |
| 2020/0248264 A1 | 8/2020 | Rabinowitz et al. |
| 2020/0248266 A1 | 8/2020 | Swanton et al. |
| 2020/0316498 A1 | 10/2020 | Mitchell |
| 2020/0318191 A1 | 10/2020 | Babiarz et al. |
| 2020/0347454 A1 | 11/2020 | Babiarz et al. |
| 2020/0350034 A1 | 11/2020 | Rabinowitz et al. |
| 2020/0362415 A1 | 11/2020 | Rabinowitz et al. |
| 2020/0370129 A1 | 11/2020 | Quinn et al. |
| 2020/0385809 A1 | 12/2020 | Ramani et al. |
| 2020/0407788 A1 | 12/2020 | Ryan et al. |
| 2020/0407798 A1 | 12/2020 | Babiarz et al. |
| 2021/0009990 A1 | 1/2021 | Stray et al. |
| 2021/0025005 A1 | 1/2021 | Babiarz et al. |
| 2021/0032692 A1 | 2/2021 | Mitchell et al. |
| 2021/0054459 A1 | 2/2021 | Rabinowitz et al. |
| 2021/0071246 A1 | 3/2021 | Zimmermann et al. |
| 2021/0139969 A1 | 5/2021 | Mitchell et al. |
| 2021/0139983 A1 | 5/2021 | Mitchell et al. |
| 2021/0139988 A1 | 5/2021 | Mitchell et al. |
| 2021/0155988 A1 | 5/2021 | Rabinowitz et al. |
| 2021/0189498 A1 | 6/2021 | Babiarz et al. |
| 2021/0198733 A1 | 7/2021 | Moshkevich et al. |
| 2021/0198742 A1 | 7/2021 | Rabinowitz et al. |
| 2021/0198743 A1 | 7/2021 | Rabinowitz et al. |
| 2021/0222230 A1 | 7/2021 | Zimmermann et al. |
| 2021/0222240 A1 | 7/2021 | Moshkevich et al. |
| 2021/0257048 A1 | 8/2021 | Zimmermann et al. |
| 2021/0269879 A1 | 9/2021 | Mitchell et al. |
| 2021/0301320 A1 | 9/2021 | Mitchell et al. |
| 2021/0324463 A1 | 10/2021 | Rabinowitz et al. |
| 2021/0327538 A1 | 10/2021 | Egilsson et al. |
| 2021/0327542 A1 | 10/2021 | Ryan et al. |
| 2021/0348229 A1 | 11/2021 | Maguire et al. |
| 2021/0355536 A1 | 11/2021 | Rabinowitz et al. |
| 2022/0025455 A1 | 1/2022 | Zimmermann et al. |
| 2022/0025456 A1 | 1/2022 | Rabinowitz et al. |
| 2022/0033908 A1 | 2/2022 | Rabinowitz et al. |
| 2022/0033909 A1 | 2/2022 | Babiarz et al. |
| 2022/0042103 A1 | 2/2022 | Rabinowitz et al. |
| 2022/0056509 A1 | 2/2022 | Zimmermann |
| 2022/0056534 A1 | 2/2022 | Rivers |
| 2022/0009866 A1 | 3/2022 | Rabinowitz et al. |
| 2022/0073978 A1 | 3/2022 | Rabinowitz et al. |
| 2022/0073979 A1 | 3/2022 | Rabinowitz et al. |
| 2022/0139495 A1 | 5/2022 | Rabinowitz et al. |
| 2022/0145391 A1 | 5/2022 | Mitchell et al. |
| 2022/0154249 A1 | 5/2022 | Zimmermann et al. |
| 2022/0154290 A1 | 5/2022 | Babiarz et al. |
| 2022/0195526 A1 | 6/2022 | Rabinowitz et al. |
| 2022/0213561 A1 | 7/2022 | Babiarz et al. |
| 2022/0251654 A1 | 8/2022 | Hafez et al. |
| 2022/0267849 A1 | 8/2022 | Mitchell et al. |
| 2022/0282335 A1 | 9/2022 | Babiarz et al. |
| 2022/0307086 A1 | 9/2022 | Babiarz et al. |
| 2022/0340963 A1 | 10/2022 | North et al. |
| 2022/0356522 A1 | 11/2022 | Mitchell et al. |
| 2022/0356526 A1 | 11/2022 | Babiarz et al. |
| 2022/0356530 A1 | 11/2022 | Sharma |
| 2022/0403461 A1 | 12/2022 | Kirkizlar et al. |
| 2022/0411875 A1 | 12/2022 | Rabinowitz et al. |
| 2023/0054494 A1 | 2/2023 | Rabinowitz et al. |
| 2023/0053752 A1 | 3/2023 | Rabinowitz et al. |
| 2023/0060579 A1 | 3/2023 | Bethke et al. |
| 2023/0360723 A1 | 11/2023 | Rabinowitz et al. |
| 2023/0368865 A1 | 11/2023 | Rabinowitz et al. |
| 2023/0383348 A1 | 11/2023 | Rabinowitz et al. |
| 2023/0420071 A1 | 12/2023 | Rabinowitz et al. |
| 2024/0002938 A1 | 1/2024 | Rabinowitz et al. |
| 2024/0038328 A1 | 2/2024 | Rabinowitz et al. |
| 2024/0060124 A1 | 2/2024 | Ryan et al. |
| 2024/0062846 A1 | 2/2024 | Rabinowitz |
| 2024/0068031 A1 | 2/2024 | Rabinowitz |
| 2024/0132957 A1 | 4/2024 | Mitchell et al. |

FOREIGN PATENT DOCUMENTS

| | | |
|---|---|---|
| CN | 1650032 A | 8/2005 |
| CN | 1674028 A | 9/2005 |
| CN | 101675169 A | 3/2010 |
| CN | 102892901 A | 1/2013 |
| CN | 104736722 A | 6/2015 |
| CN | 105229175 A | 1/2016 |
| CN | 107365769 A | 11/2017 |
| CN | 107849604 A | 3/2018 |
| CN | 109661476 A | 4/2019 |
| CN | 116287197 A | 6/2023 |
| EA | 201792389 A1 | 5/2018 |
| EP | 0270017 A2 | 6/1988 |
| EP | 1325963 A1 | 7/2003 |
| EP | 1524321 A1 | 4/2005 |
| EP | 1325963 B1 | 9/2006 |
| EP | 1524321 B1 | 7/2009 |
| EP | 2163622 A1 | 3/2010 |
| EP | 2128169 A1 | 12/2010 |
| EP | 2551356 A1 | 1/2013 |
| EP | 2653562 A1 | 10/2013 |
| EP | 2902500 A1 | 8/2015 |
| EP | 3026124 A1 | 6/2016 |
| EP | 2315849 B1 | 11/2017 |
| EP | 3285193 A1 | 2/2018 |
| EP | 2877594 B1 | 12/2019 |
| EP | 3187597 B1 | 6/2020 |
| EP | 3134541 B1 | 8/2020 |
| EP | 3760730 A1 | 1/2021 |
| EP | 3760731 A1 | 1/2021 |
| EP | 3760732 A1 | 1/2021 |
| EP | 3824470 | 5/2021 |
| EP | 3443119 B1 | 2/2022 |
| GB | 2488358 | 8/2012 |
| JP | 2965699 | 8/1999 |
| JP | 2002-530121 A | 9/2002 |
| JP | 2002-300894 A | 10/2002 |
| JP | 2003/521252 A | 7/2003 |
| JP | 2004502466 A | 1/2004 |
| JP | 2004121087 A | 4/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2008-263974 A | 11/2008 |
| JP | 2008/271980 A | 11/2008 |
| JP | 2010-509922 A | 4/2010 |
| JP | 2011/508662 A | 3/2011 |
| JP | 2011/516069 A | 5/2011 |
| JP | 2012-085556 A | 5/2012 |
| JP | 2013509883 A | 3/2013 |
| JP | 2014118334 A1 | 8/2014 |
| JP | 2015-535681 | 12/2015 |
| JP | 2016502849 A | 2/2016 |
| RU | 2290078 C1 | 12/2006 |
| WO | 95/01796 | 1/1995 |
| WO | WO9623067 A1 | 8/1996 |
| WO | 1996036736 A2 | 11/1996 |
| WO | 98/39474 | 9/1998 |
| WO | 98/44151 | 10/1998 |
| WO | WO9937773 A1 | 7/1999 |

(56) References Cited

FOREIGN PATENT DOCUMENTS

| | | |
|---|---|---|
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 179851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |
| WO | 03/020974 A3 | 3/2003 |
| WO | 2003031646 A1 | 4/2003 |
| WO | 3050532 A1 | 6/2003 |
| WO | 2003062441 A1 | 7/2003 |
| WO | 3102595 A1 | 12/2003 |
| WO | 3106623 A2 | 12/2003 |
| WO | 2004/051218 A2 | 6/2004 |
| WO | 2004069849 A2 | 8/2004 |
| WO | 2004070005 A2 | 8/2004 |
| WO | 2004070007 A2 | 8/2004 |
| WO | 2004081183 | 9/2004 |
| WO | WO2004078999 A1 | 9/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007070280 A2 | 6/2007 |
| WO | 2007070482 A2 | 6/2007 |
| WO | 2007/075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A1 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/032779 A2 | 3/2009 |
| WO | 2009/036525 A2 | 3/2009 |
| WO | 2009030100 A1 | 3/2009 |
| WO | 2009032781 A2 | 3/2009 |
| WO | 2009033178 A1 | 3/2009 |
| WO | 2009049889 A1 | 4/2009 |
| WO | 2009017784 A2 | 5/2009 |
| WO | 2009064897 A2 | 5/2009 |
| WO | 2009091934 A1 | 7/2009 |
| WO | 2009092035 A2 | 7/2009 |
| WO | 2009/105531 A1 | 8/2009 |
| WO | 2009099602 A1 | 8/2009 |
| WO | 2009100029 A1 | 8/2009 |
| WO | 2009117122 A2 | 9/2009 |
| WO | 2009120808 A2 | 10/2009 |
| WO | 2009145828 A2 | 12/2009 |
| WO | 2009146335 A1 | 12/2009 |
| WO | 2010014920 A1 | 2/2010 |
| WO | 2010017214 A1 | 2/2010 |
| WO | 2010/033639 A2 | 3/2010 |
| WO | 2010/033652 A1 | 3/2010 |
| WO | 2010033578 A2 | 3/2010 |
| WO | 2010042831 A2 | 4/2010 |
| WO | 2010045617 A2 | 4/2010 |
| WO | 2010075459 | 7/2010 |
| WO | 2010/088288 A2 | 8/2010 |
| WO | 2010115016 A2 | 10/2010 |
| WO | 2010115154 A1 | 10/2010 |
| WO | 2010118016 A2 | 10/2010 |
| WO | 2010/127186 A1 | 11/2010 |
| WO | WO2011015944 A2 | 2/2011 |
| WO | 2011/023078 A1 | 3/2011 |
| WO | 2011/032078 A1 | 3/2011 |
| WO | 2011041485 A1 | 4/2011 |
| WO | 2011/051283 A1 | 5/2011 |
| WO | 2011057094 | 5/2011 |
| WO | WO2011057061 A1 | 5/2011 |
| WO | 2011/090556 A1 | 7/2011 |
| WO | 2011087760 | 7/2011 |
| WO | 2011102998 A2 | 8/2011 |
| WO | WO2011094646 A1 | 8/2011 |
| WO | 2011/118603 | 9/2011 |
| WO | 2011109440 A1 | 9/2011 |
| WO | WO2011118603 A1 | 9/2011 |
| WO | 2011/142836 A2 | 11/2011 |
| WO | 2011140433 A2 | 11/2011 |
| WO | 2011146632 A1 | 11/2011 |
| WO | 2012/019200 A2 | 2/2012 |
| WO | 2012/028746 A1 | 3/2012 |
| WO | 2012042374 A2 | 4/2012 |
| WO | 2012/058488 A1 | 5/2012 |
| WO | 2012-083189 A2 | 6/2012 |
| WO | 201283250 | 6/2012 |
| WO | 2012088456 A2 | 6/2012 |
| WO | 20120071621 | 6/2012 |
| WO | 2012092426 | 7/2012 |
| WO | 2012108920 A1 | 8/2012 |
| WO | WO2012122374 A2 | 9/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 2013/123220 A1 | 8/2013 |
| WO | 2013/138510 A1 | 9/2013 |
| WO | 2013/138510 A9 | 9/2013 |
| WO | 20130130848 | 9/2013 |
| WO | WO2013159035 A2 | 10/2013 |
| WO | 2013/169339 A1 | 11/2013 |
| WO | 2013/177220 A1 | 11/2013 |
| WO | 2013/181651 A1 | 12/2013 |
| WO | 2014/004726 A1 | 1/2014 |
| WO | 2014/014497 A1 | 1/2014 |
| WO | 20140018080 | 1/2014 |
| WO | 2014026277 A1 | 2/2014 |
| WO | 2014/035986 A1 | 3/2014 |

(56) References Cited

FOREIGN PATENT DOCUMENTS

| WO | 2014039556 A1 | 3/2014 |
|---|---|---|
| WO | WO2014099919 A2 | 6/2014 |
| WO | 2014/122288 A1 | 8/2014 |
| WO | 2014/1424290 A1 | 8/2014 |
| WO | 2014/145078 A1 | 9/2014 |
| WO | 2014/145232 A2 | 9/2014 |
| WO | 2014/149134 A2 | 9/2014 |
| WO | 2014/150300 A2 | 9/2014 |
| WO | 2014/151117 A1 | 9/2014 |
| WO | WO2014143989 A1 | 9/2014 |
| WO | WO2014194113 A2 | 12/2014 |
| WO | 2015/006668 A1 | 1/2015 |
| WO | 2015035177 A1 | 3/2015 |
| WO | 2015134552 A1 | 3/2015 |
| WO | 2015/048535 A1 | 4/2015 |
| WO | 2015/070086 A1 | 5/2015 |
| WO | WO2015069933 A1 | 5/2015 |
| WO | 2015/100427 A1 | 7/2015 |
| WO | 2015138997 A1 | 9/2015 |
| WO | 2015/148494 A1 | 10/2015 |
| WO | 2015/164432 A1 | 10/2015 |
| WO | WO2015169947 A1 | 11/2015 |
| WO | WO2015178978 A2 | 11/2015 |
| WO | 2016/009059 A1 | 1/2016 |
| WO | 2016009224 A1 | 1/2016 |
| WO | WO2016001411 A1 | 1/2016 |
| WO | WO2016028316 A1 | 2/2016 |
| WO | 2016/065295 A1 | 4/2016 |
| WO | WO2016063122 A1 | 4/2016 |
| WO | 2016/077313 A1 | 5/2016 |
| WO | WO2016123698 A1 | 8/2016 |
| WO | 2016/138080 A1 | 9/2016 |
| WO | 2016/183106 A1 | 11/2016 |
| WO | WO2016176662 A1 | 11/2016 |
| WO | 2016/193490 A1 | 12/2016 |
| WO | 2016192956 A1 | 12/2016 |
| WO | WO2017011329 A1 | 1/2017 |
| WO | 2017-045654 A1 | 3/2017 |
| WO | 2017/058784 A1 | 4/2017 |
| WO | WO2017091865 A1 | 6/2017 |
| WO | 2017/176852 A1 | 10/2017 |
| WO | 2017/181146 A1 | 10/2017 |
| WO | 2017/181202 A2 | 10/2017 |
| WO | 2017205540 A1 | 11/2017 |
| WO | WO2017190106 A1 | 11/2017 |
| WO | 2018/009723 A1 | 1/2018 |
| WO | 2018/083467 A1 | 5/2018 |
| WO | WO2018085597 A1 | 5/2018 |
| WO | WO2018085603 A1 | 5/2018 |
| WO | 2018/106798 A1 | 6/2018 |
| WO | WO2018119422 A1 | 6/2018 |
| WO | 2018/136562 A2 | 7/2018 |
| WO | 2018/156418 A1 | 8/2018 |
| WO | WO2018237078 A1 | 12/2018 |
| WO | WO2018237081 A1 | 12/2018 |
| WO | WO2019006561 A1 | 1/2019 |
| WO | WO2019008408 A1 | 1/2019 |
| WO | 2019/046817 A1 | 3/2019 |
| WO | WO2019053243 A1 | 3/2019 |
| WO | WO2019109053 A1 | 6/2019 |
| WO | WO2019118926 A1 | 6/2019 |
| WO | 2019/140298 A1 | 7/2019 |
| WO | 2019/161244 A1 | 8/2019 |
| WO | 2019/200228 A1 | 10/2019 |
| WO | 2019/241349 A1 | 12/2019 |
| WO | 2020/010255 A1 | 1/2020 |
| WO | 2020/018522 A1 | 1/2020 |
| WO | 2020/041449 A1 | 2/2020 |
| WO | 2020/076957 A1 | 4/2020 |
| WO | 2020/106987 A1 | 5/2020 |
| WO | 2020104670 A1 | 5/2020 |
| WO | 2020/131699 A2 | 6/2020 |
| WO | WO2020131955 A1 | 6/2020 |
| WO | 2020/214547 A1 | 10/2020 |
| WO | WO2020206290 A1 | 10/2020 |
| WO | 2020/247263 A1 | 12/2020 |
| WO | 2021/055968 A1 | 3/2021 |
| WO | 2007100911 A2 | 9/2021 |
| WO | 2021/243045 A1 | 12/2021 |
| WO | 2022/015676 A1 | 1/2022 |
| WO | 2022182878 | 9/2022 |
| WO | 2022197864 | 9/2022 |
| WO | 2023014597 A1 | 2/2023 |
| WO | 2023034090 A1 | 3/2023 |
| WO | 2023/244735 A2 | 12/2023 |
| WO | 2024/076485 A1 | 4/2024 |
| WO | 2024076469 A1 | 4/2024 |
| WO | 2024076484 A1 | 4/2024 |

OTHER PUBLICATIONS

Reynolds et al. The mathematical basis of multivariate risk screening: with special reference to screening for Down's syndrome associated pregnancy. Ann Clin Biochem, vol. 27, pp. 452-458. (Year: 1989).*

Nicolaides et al. Multicenter study of first-trimester screening for trisomy 21 in 75821 pregnancies: results and estimation of the poitential impact of individual risk-oriented two-stage first-trimester screening. Ultrasound Obstet Gynecol, vol. 25, pp. 221-226. (Year: 2005).*

Wang, W.-P. et al., "Multiplex single nucleotide polymorphism genotyping by adapter ligation-mediated allele-specific amplification", Analytical Biochemistry, vol. 355, May 5, 2006, 240-248.

"Abstracts for CNAPS III Circulating Nucleic Acids in Plasma and Serum and Serum Proteomics", Clinical Chemistry, vol. 49, No. 11, 2003, 33 pages.

"Abstracts for CNAPS IV Circulating Nucleic Acids in Plasma/Serum", Fourth International Conference on Circulating Nucleic Acids in Plasma/Serum (CNAPS-IV), 2005, 40 pages.

Abaan, O. D. et al., "The Exomes of the NCI-60 Panel: A Genomic Resource for Cancer Biology and Systems Pharmacology", Cancer Res., vol. 73, No. 14, Jul. 15, 2013, 4372-4382.

Abd-Elsalam, Kamel A. , "Bioinformatic Tools And Guideline for PCR Primer Design", African Journal of Biotechnology, vol. 2, 2003, pp. 91-95.

Adalsteinsson, V. A. et al., "Scalable whole-exome sequencing of cell-free DNA reveals high concordance with metastatic tumors", Nature Communications, vol. 18, No. 1324, 2017, 13 pages.

Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.

Agbor-Enoh, S. et al., "Donor-derived cell-free DNA predicts allograft failure and mortality after lung transplantation", EBioMedicine, vol. 40, 2019, 541-553.

Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.

Ambardar, S. et al., "High Throughput Sequencing: An Overview of Sequencing Chemistry", Indian J. Microbiol., vol. 56, No. 4, 2016, 394- 404.

Amicucci, P. et al., "Prenatal Diagnosis of Myotonic Dystrophy Using Fetal DNA Obtained from Maternal Plasma", Clinical Chemistry, vol. 46, No. 2, 2000, 301-302.

Anker, P. et al., "Circulating DNA in Plasma or Serum", Medicina, vol. 60, 2000, 699-702.

Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.

Ansorge, Wilhelm J. , "Next-generation DNA Sequencing Techniques", New Biotechnology, vol. 25, No. 4, Feb. 2, 2009, 195-203.

Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.

(56) References Cited

OTHER PUBLICATIONS

Auld, D. S., "Use of Chelating Agents to Inhibit Enzymes", Methods in Enzymology, vol. 158, 1988, 110-114.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6,, May 28, 2009, 581-591.
Balavoine, Guillaume, "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Bale, J. R. et al., "Reducing Birth Defects: Meeting the Challenge in the Developing World", Institute of Medicine of the National Academies, 2003, 270 pgs.
Banfi, G. et al., "The role of ethylenediamine tetraacetic acid (EDTA) as in vitro anticoagulant for diagnostic purposes", Clin. Chem., vol. 45, No. 5, 2007, 565-576.
Barbazuk, et al., "SNP Discovery via 454 Transcriptome Sequencing", The Plant Journal, vol. 51, Jul. 27, 2007, 910-918.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al., "High-Resolution Profiling of Histone Methylations in the Human Genome", Cell, vol. 129, May 18, 2007, 823-837.
Bartlett, John M. et al., "PCR Protocols", PCR Protocols, vol. 226, 2003, 519 pages.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.
Baxter-Lowe, et al., "Tracking Microchimeric DNA In Plasma To Diagnose And Manage Organ Transplant Rejection", Clinical Chemistry, vol. 52, No. 4, Apr. 1, 2006, 559-561.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Profile of the Circulating DNA in Apparently Healthy Individuals", Clinical Chemistry, vol. 55, No. 4, 2009, 730-738.
Belostotsky, Dmitry A. et al., "Plant Systems Biology", Methods in Molecular Biology, vol. 553, Aug. 25, 2009, 3-408.
Bender, et al., "A Multiplex SNP Typing Approach For The DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Bennett, S. T. et al., "Toward the $1000 human genome", Pharmacogenomics, vol. 6, No. 4, 2005, 373-382.
Bentley, et al., "High-resolution, High-throughput HLA Genotyping by Next-generation Sequencing", Tissue Antigens, vol. 74, No. 5, Nov. 1, 2009, 393-403.

Bergen, A. W. et al., "Effects of DNA mass on multiple displacement whole genome amplification and genotyping performance", BMC Biotechnology, vol. 5, No. 24, Sep. 16, 2005, 11 pgs.
Bianchi, D W. et al., "Insights Into Fetal and Neonatal Development Through Analysis of Cell-Free RNA in Body Fluids", Early Human Development, vol. 86, No. 11, Nov. 2010, 747-752.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Blomquist, T M. et al., "Targeted RNA-Sequencing with Competitive Multiplex-PCR Amplicon Libraries", Plos One, vol. 8, Issue 11, Nov. 2013, 14 pages.
Blow, N., "The personal side of genomics", Nature, vol. 449, Oct. 4, 2007, 627-630.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.
Bordoni, et al., "Evaluation Of Human Gene Variant Detection In Amplicon Pools By The GS-FLX Parallel Pyrosequencer", BMC Genomics, vol. 9, Oct. 8, 2008, 1-8.
Boudsocq, F. et al., "Sulfolobus solfataricus P2 DNA polymerase IV (Dpo4): an archael DinB-like DNA polymerase with lesion-bypass properties akin to eukaryotic poln", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Brinza, D. et al., "2SNP: scalable phasing based on 2-SNP haplotypes", Bioinformatics, vol. 22, No. 3, 2006, 371-373.
Brockman, et al., "Quality Scores And SNP Detection In Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.
Bryant, A. P., "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance In The Diagnosis Of Acute Heart Transplant Rejection: A Review", Journal of Cardiovascular Magnetic Resonance, vol. 11, No. 1, Mar. 12, 2009, 1-11.
Calin, G. A. et al., "A MicroRNA Signature Associated with Prognosis and Progression in Chronic Lymphocytic Leukemia", N Engl J Med, vol. 353, 2005, 1793-1801.
Campbell, P. J. et al., "Subclonal phylogenetic structures in cancer revealed by ultra-deep sequencing", PNAS, vol. 105, No. 35, Sep. 2, 2008, 13081-13086.

(56) References Cited

OTHER PUBLICATIONS

Canick, J. A. et al., "The impact of maternal plasma DNA fetal fraction on next generation sequencing tests for common fetal aneuploidies", Prenatal Diagnosis, vol. 33, 2013, 667-674.

Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.

Castleberry, C. D. et al., "Quantification of Circulating Cell--Free DNA in Pediatric Heart Transplant Recipients", Journal of Heart and Lung Transplantation, vol. 30, No. 4, Apr. 1, 2011, S139.

Chan, Allen K. et al., "Cell-free Nucleic Acids In Plasma, Serum And Urine: A New Tool In Molecular Diagnosis", Annals of Clinical Biochemistry, vol. 40, Issue 2, Mar. 1, 2003, 122-130.

Chavali, Sreenivas et al., "Oligonucleotide Properties Determination And Primer Designing: A Critical Examination of Predictions", Bioinformatics, vol. 21, 2005, pp. 3918-3925.

Chen, Bing-Yuan et al., "PCR Cloning Protocols", PCR Cloning Protocols, vol. 192, 2002, 434 pages.

Chen, C. P. et al., "Fetal DNA in maternal plasma: the prenatal detection of a paternally inherited fetal aneuploidy", Prenatal Diagnosis, vol. 20, 2000, 353-357.

Chim, S. S. et al., "Detection and Characterization of Placental MicroRNAs in Maternal Plasma", Clinical Chemistry, vol. 54, No. 3, 2008, 482-490.

Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.

Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.

Chiu, R.W.K. et al., "Hypermethylation of RASSF1A in Human and Rhesus Placentas", The American Journal of Pathology, vol. 170, No. 3, Mar. 2007, 941-950.

Choi, Y. et al., "Comparison of phasing strategies for whole human genomes", PLOS Genetics, Apr. 5, 2018, 26 pages.

Chung, G. T. et al., "Lack of Dramatic Enrichment of Fetal DNA in Maternal Plasma by Formaldehyde Treatment", Clinical Chemistry, vol. 51, No. 3, 2005, 655-658.

Church, et al., "Multiplex DNA Sequencing", Science, vol. 240, No. 4849, Apr. 8, 1988, 185-188.

Ciriello, G. et al., "Emerging landscape of oncogenic signatures across human cancers", Nature Genetics, vol. 45, No. 10, Oct. 2013, 1127-1135.

Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.

Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.

Couraud, S. et al., "Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002", 2014, 13 pages.

Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.

Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.

Cunningham, K. S. et al., "An approach to endomyocardial biopsy interpretation", Journal of Clinical Pathology, vol. 59, No. 2, Mar. 2006, 121-129.

Dahl, et al., "Multigene Amplification and Massively Parallel Sequencing for Cancer Mutation Discovery", Proceedings of the National Academy of Sciences, vol. 104, No. 22, May 29, 2007, 9387-9392.

Dambrin, et al., "A New Rejection Criteria In The Heterotopically Placed Rat Heart By Non-invasive Measurement Of Dp/Dtmax", The Journal of Heart and Lung Transplantation, vol. 18, No. 6, Jun. 18, 1999, 524-531.

De Jong, M. M. et al., "Genes other than BRCA 1 and BRCA2 involved in breast cancer susceptibility", J. Med. Genet., vol. 39, 2009, 225-242.

Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.

Delaneau, O. et al., "Shape-IT: new rapid and accurate algorithm for haplotype inference", BMC Bioinformatics, vol. 9, No. 540, Dec. 16, 2008, 14 pages.

Delgado, P. O. et al., "Characterization of cell-free circulating DNA in plasma in patients with prostate cancer", Tumor Biol., vol. 34, 983-986, 2013.

Di, X. et al., "Dynamic model based algorithms for screening and genotyping", Bioinformatics, vol. 21, No. 9, 2005, 1958-1963.

Dias-Santagata, D. et al., "BRAF V600E Mutations Are Common in Pleomorphic Xanthoastrocytoma: Diagnostic and Therapeutic Implications", PLOS One, vol. 6, No. 3, Mar. 2011, 9 pages.

Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.

Ding, C. et al., "MS analysis of single-nucleotide differences in circulating nucleic acids: Application to noninvasive prenatal diagnosis", PNAS, vol. 101, No. 29, Jul. 20, 2004, 10762-10767.

Doostzadeh, et al., "High Throughput Automated Allele Frequency Estimation by Pyrosequencing", Plos One, vol. 3, No. 7, Jul. 16, 2008, 1-4.

Dorit, D. L. , "cDNA Amplification Using One-sided (Anchored) Pcr", Current Protocols in Molecular Biology, vol. 17, 1992, pp. 15.6.1-15.6.10.

Dorit, Robert L. et al., "One-sided Anchored Polymerase Chain Reaction for Amplification and Sequencing of Complementary DNA", Methods in Enzymology, vol. 218 1993, pp. 36-47.

Dowd, P. et al., "On the mechanism of the anticlotting action of vitamin R quinone", Proc. Natl. Acad. Sci. USA, vol. 92, 1995, 8171-8175.

Downward, J. , "Targeting Ras Signalling Pathways in Cancer Therapy", Nature Reviews, vol. 3, Jan. 2003, 11-22.

Dressman, D. et al., "Transforming single DNA molecules into fluorescent magnetic particles for detection and enumeration of genetic variations", PNAS, vol. 100, No. 15, Jul. 22, 2003, 8817-8822.

Edwards, M. C. et al., "Multiplex PCR: Advantages, Development, and Applications", Genome Research, vol. 3, 1994, S65-S75.

Efron, B. et al., "Bootstrap Methods for Standard Errors, Confidence Intervals, and Other Measures of Statistical Accuracy", Statistical Science, vol. 1, No. 1, 1986, 54-77.

Elnifro, Elfath M. , "Multiplex PCR: Optimization and Application in Diagnostic Virology", Clinical Microbiology Reviews, vol. 13, 2000, pp. 559-570.

Eltoukhy, H. et al., "Modeling and Base-Calling for DNA Sequencing-By-Synthesis", IEEE, 2006, II-1032-II-1035.

Erijman, Ariel et al., "Transfer-PCR (TPCR): A Highway For DNA Cloning and Protein Engineering", Journal of Structural Biology, vol. 175, 2011, pp. 171-177.

Erlich, R. L. et al., "Next-generation sequencing for HLA typing of class loci", BMC Genomics, vol. 12, No. 42, 2011, 13 pages.

Eronen, L. et al., "HaploRec: efficient and accurate large-scale reconstruction of haplotypes", BMC Bioinformatics, vol. 7, No. 542, Dec. 22, 2006, 18 pages.

European Commission, , "The 7th International Conference on Circulating Nucleic Acids in Plasma and Serum (CNAPS VII) in Madrid-Spain", The International Conference on Circulating Nucleic Acids in Plasma and Serum, Oct. 24, 2011, 2 pgs.

(56) References Cited

OTHER PUBLICATIONS

Fackenthal, J. D. et al., "Aberrant RNA splicing and its functional consequences in cancer cells", Disease Models & Mechanisms, vol. 1, 2008, 37-42.
Faham, M. et al., "Deep-sequencing approach for minimal residual disease detection in acute lymphoblastic leukemia", Blood Journal, vol. 120, No. 26, Dec. 20, 2012, 5173-5180.
Falcon, O., "Screening for trisomy 21 by fetal tricuspid regurgitation, nuchal translucency and maternal serum free b-hCG and PAPP-A at 11 + 0 to 13 + 6 weeks", Ultrasound Obstet Gynecol, vol. 27, 2006, 151-155.
Fan, C H. et al., "Detection of Aneuploidy with Digital Polymerase Chain Reaction", Analytical Chemistry, vol. 79, No. 19, Oct. 1, 2007, 7576-7579.
Fan, H. C. et al., "In Principle Method for Noninvasive Determination of the Fetal Genome", Nat. Prec., 2010, 16 pgs.
Fan, J.-B. et al., "Highly Parallel SNP Genotyping", Cold Spring Harbor Symposia on Quantitative Biology, vol. LXVIII, Feb. 2003, 69-78.
Fitzgerald, , "Intravascular Ultrasound Imaging Of Coronary Arteries: Is Three Layers The Norm?", Circulation, vol. 86, No. 1, Jul. 1, 1992, 154-158.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Fournie, et al., "Plasma DNA As A Marker Of Cancerous Cell Death. Investigations In Patients Suffering From Lung Cancer And In Nude Mice Bearing Human Tumours", Cancer Letters, vol. 91, No. 2, May 8, 1995, 221-227.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Frohman, M A. et al., "On Beyond Classic RACE (Rapid Amplification of cDNA Ends)", Genome Research, vol. 4, 1994, S40-S58.
Fu, Yao-Wen et al., "Presence Of Donor-and-recipientderived Dna Microchimerism In The Cell-free Blood Samples Of Renal Transplantation Recipients Associates With The Acceptance Of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Gao, et al., "Relation Of Donor Age And Preexisting Coronary Artery Disease On Angiography And Intracoronary Ultrasound To Later Development Of Accelerated Allograft Coronary Artery Disease", The American Journal of Cardiology, vol. 29, No. 3, Mar. 1, 1997, 623-629.
Gao, F. et al., "Characterizing Immunoglobulin Repertoire from Whole Blood by a Personal Genome Sequencer", PLOS One, vol. 8, No. 9, Sep. 13, 2013, 8 pgs.
Gao, Ming et al., "Characterization of dull1, a Maize Gene Coding for a Novel Starch Synthase", The Plant Cell, vol. 10, 1998, pp. 399-412.
Garcia Moreira, V. et al., "Cell-Free DNA as a Noninvasive Acute Rejection Marker in Renal Transplantation", Clinical Chemistry, vol. 55, No. 11, 2009, 1958-1966.
Gautier, E. et al., "Fetal RhD genotyping by maternal serum analysis: A two-year experience", American Journal of Obstetrics and Gynecology, vol. 192, 2005, 666-669.
Geifman-Holtzman, et al., "Prenatal Diagnosis: Update On Invasive Versus Noninvasive Fetal Diagnostic Testing From Maternal Blood", Expert Review of Molecular Diagnostics, vol. 8, No. 6, Nov. 1, 2008, 727- 751.
Gielis, E. M. et al., "Cell-Free DNA: An Upcoming Biomarker in Transplantation", American Journal of Transplantation, vol. 15, 2015, 2541-2551.
Gineikiene, Egle et al., "Single Nucleotide Polymorphism-based System Improves The Applicability Of Quantitative PCR For Chimerism Monitoring", Journal of Molecular Diagnostics, vol. 11, No. 1, Jan. 1, 2009, 66-74.
Gingeras, et al., "Fifty Years of Molecular (DNA/RNA) Diagnostics", Clinical Chemistry, vol. 51, No. 3, Jan. 13, 2005, 661-671.
Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.
Gnirke, A. et al., "Solution hybrid selection with ultra-long oligonucleotides for massively parallel targeted sequencing", Nature Biotechnology, vol. 27, No. 2, Feb. 2009, 182-189.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.
Gordon, et al., "Disease-Specific Motifs Can Be Identified In Circulating Nucleic Acids From Live Elk And Cattle Infected With Transmissible Spongiform Encephalopathies", Nucleic Acids Research, vol. 37. No. 2, Feb. 1, 2009, 550-556.
Gorringe, et al., "Large-scale Genomic Analysis of Ovarian Carcinomas", Molecular oncology, vol. 3, No. 2, Apr. 1, 2009, 157-164.
Gouya, et al., "Coronary Artery Stenosis In High-risk Patients: 64-section Ct And Coronary Angiography-Prospective Study And Analysis of Discordance", Radiology, vol. 252, No. 2, Aug. 1, 2009, 377-385.
Gregory, et al., "Comparison of Sixty-Four-Slice Multidetector Computed Tomographic Coronary Sngiography To Coronary Angiography With Intravascular Ultrasound For The Detection Of Transplant Vasculopathy", The American Journal of Cardiology, vol. 98, No. 7, Aug. 4, 2006, 877-884.
Griffiths, A. J. et al., "An Introduction to Genetic Analysis", Sixth Edition, 1996, 5 pages.
Grunenwald, H. , "Optimization of Polymerase Chain Reactions", Methods in Biology, vol. 226, 2003, 89-99.
Gu, H. et al., "Diagnostic role of microRNA expression profile in the serum of pregnant women with fetuses with neural tube defects", Journal of Neurochemistry, vol. 122, 2012, 641-649.
Guo, H et al., "A Specific and Versatile Genome Walking Technique", Gene, vol. 381, 2006, 18-23.
Gwee, Pai-Chung et al., "Simultaneous Genotyping of Seven Single-nucleotide Polymorphisms in the Mdr1 Gene by Single-tube Multiplex Minisequencing", Pai-Chung Gwee. et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.
Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.
Hahn, S. et al., "Current applications of single-cell PCR", CMLS Cellular and Molecular. Life Sciences, vol. 57, 2000, 96-105.
Hahn, S. et al., "Quantification of Circulating DNA: In the Preparation Lies the Rub", Clinical Chemistry, vol. 47, No. 9, 2001, 1577-1578.
Halford, William P. , "The Essential Prerequisites for Quantitative RT-PCR", Nature Biotechnology, vol. 17, 1999, 1 page.
Handley, D. et al., "Noninvasive prenatal chromosomal aneuploidy detection using plasma cell-free nucleic acid", Expert Rev Obstet. Gynecol, vol. 5, No. 5, 2010, 581-590.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.

(56) References Cited

OTHER PUBLICATIONS

Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method For Assessment Of Hematopoietic Chimerism After Allogeneic Stem Cell Transplantation", Blood, vol. 101, No. 1, Jan. 1, 2003, 363-369.
Hodges, et al., "Genome-wide In Situ Exon Capture For Selective Resequencing", Nature Genetics, vol. 39, No. 12, Nov. 4, 2007, 1522-1527.
Hodgkinson, C. L. et al., "Tumorigenicity and genetic profiling of circulating tumor cells in small-cell lung cancer", Nature Medicine, vol. 20, No. 8, Aug. 2014, 897-905.
Hoffmann, Steven et al., "Donor Genomics Influence Graft Events: The Effect Of Donor Polymorphisms On Acute Rejection And Chronic Allograft Nephropathy", Kidney International, vol. 66, No. 4, Oct. 1, 2004, 1686-1693.
Holt, et al., "Detecting SNPS And Estimating Allele Frequencies In Clonal Bacterial Populations By Sequencing Pooled DNA", Bioinformatics, vol. 25, No. 16, Aug. 15, 2009, 2074-2075.
Horai, et al., "Novel Implantable Device To Detect Cardiac Allograft Rejection", Circulation, vol. 120, No. Suppl 1, Sep. 15, 2009, 185-190.
Hosmillo, Myra D. et al., "Development of Universal SYBR Green Real-time RT-PCR for The Rapid Detection and Quantitation of Bovine and Porcine Toroviruses", Journal of Virological Methods, vol. 168, 2010, pp. 212-217.
Hosono, S. et al., "Unbiased Whole-Genome Amplification Directly From Clinical Samples", Genome Research, vol. 13, 2003, 954-964.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Howie, B. N. et al., "A Flexible and Accurate Genotype Imputation Method for the Next Generation of Genome-Wide Association Studies", PLOS Genetics, vol. 5, No. 6, Jun. 2009, 15 pages.
Hu, Hao et al., "Mutation Screening in 86 Known X-linked Mental Retardation Genes by Droplet-based Multiplex Pcr and Massive Parallel Sequencing", Hao Hu et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.
Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.
Huang, D. J. et al., "Reliable detection of Trisomy 21 using MALDI-TOF mass spectrometry", Genetics in Medicine, vol. 8, Nov. 2006, 728-734.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Huang, J. et al., "Whole genome DNA copy number changes identified by high density oligonucleotide arrays", Human Genomics, vol. 1, No. 4, May 2004, 287-299.
Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.
Hung, E.C.W. et al., "Detection of circulating fetal nucleic acids: a review of methods and applications", J. Clin. Pathol., vol. 62, 2009, 308-313.
Hyndman, D L. et al., "PCR Primer Design", Methods in Molecular Biology, vol. 226, Second Edition, 2003, 81-88.
Illumina, "Automated GoldenGate™ Genotyping on the BeadStation 500", Pub. No. 970-2004-002, 2004, 2 pages.
Illumina, "Genomic Sequencing", Data Sheet: Sequencing, 2010, 38939-38944.
Illumina, "GoldenGate" Assay Workflow: Illumina's GoldenGate assay protocol provides high-quality, high-multiplex genotyping results with a streamlined workflow, Pub. No. 370-2004-006, 2004, 2 pages.
Illumina, "HiSeq 2500 Sequencing System", System Specification Sheet: Sequencing, available via URL https://www.illumina.com/documents/products/datasheets/datasheet_hiseq2500.pdf, 2015, 4 pgs.
Illumina, "History of Sequencing by Synthesis", https://www.illumina.com/science/technology/next-generation-sequencing/illumina-sequencing-history.html, 2020, 3 pages.
Illumina, "Illumina Extends BeadArray Technology to Address Wider Range of SNP Genotyping Projects; New Microarray Offerings Enable Genotyping at 384 and 786 Multiplex", Businesswire, May 4, 2004, 2 pages.
Illumina, "Illumina® Beadstation 500: A Scalable System That Grows With Your Research Requirements", Pub. No. 970-2005-003, Jul. 1, 2005, 4 pages.
Illumina, "Illumina Announces Benchtop SNP Genotyping System", Press Release, Nov. 5, 2003, 3 pages.
Illumina, "Illumina Begins Shipment of BeadStation 500G Benchtop Genotyping System", Press Release, Apr. 15, 2004, 3 pages.
Illumina, "MiSeq System Information Sheet", 2018, 3 pgs.
Illumina, "Preparing Samples for Sequencing Genomic DNA", Part # 11251892 Rev. A, 2007, 18 pages.
Illumina, "Preparing Samples for Sequencing Genomic DNA", Part # 1003806 Rev. A, 2007, 20 pages.
Illumina, "Products & Services", Product Literature, Mar. 21, 2007, 3 pages.
Illumina, "Technology: Solexa Sequencing Technology", May 21, 2007, 1 page.
Illumina, "TruSeq™ RNA and DNA Library Preparation Kits v2", Data Sheet: Illumina® Sequencing, 2014, 4.
Ingman, et al., "SNP Frequency Estimation Using Massively Parallel Sequencing of Pooled DNA", European Journal of Human Genetics, vol. 17, No. 3, Oct. 15, 2008, 383-386.
Innan, H. et al., "The Pattern of Polymorphism on Human Chromosome 21", Genome Research, vol. 13, 2003, 1158-1168.
Interewicz, B. et al., "DNA Released from Ischemic and Rejecting Organs as an Indicator of Graft Cellular Damage", Annals of Transplantation, vol. 9, No. 2, May 1, 2004, 42-45.
Iskow, R. C. et al., "Natural Mutagenesis of Human Genomes by Endogenous Retrotransposons", Cell, vol. 141, Jun. 25, 2010, 1253-1261.
Ivanov, M. et al., "Non-random fragmentation patterns in circulating cell-free DNA reflect epigenetic regulation", BMC Genomics, vol. 16 (Suppl 13):S1, Jun. 2015, 12 pgs.
Jen, J. et al., "An Overview on the Isolation and Analysis of Circulating Tumor DNA in Plasma and Serum", Annals New York Academy of Sciences, 2000, 8-12.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jett, K. et al., "Clinical and genetic aspects of neurofibromatosis 1", Genetics In Medicine, vol. 12, No. 1, Jan. 2010, 11 pages.
Jewesburty, E.C.O. , "Reactions after Transfusion of Stored Blood", The British Medical Journal, vol. 1, No. 4191, 1941, 664-665.
Jiang, P. et al., "The Long and Short of Circulating Cell-Free DNA and the Ins and Outs of Molecular Diagnostics", Trends in Genetics, vol. 32, No. 6, Jun. 2016, 360-371.

(56) References Cited

OTHER PUBLICATIONS

Johnson, D. S. et al., "Genome-Wide Mapping of in Vivo Protein-DNA Interactions", Science, vol. 316, Jun. 8, 2007, 1497-1502.
Johnson, J. B. et al., "Differential mechanisms of complementmediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Jung, K. et al., "Cell-free DNA in the blood as a solid tu1nor biomarker—A critical appraisal of the literature", Clinica Chimica Acta, vol. 411, 2010, 1611--1624.
Juppner, H. et al., "Functional Properties of the PTH/PTHrP Receptor", Bone, vol. 17, No. 2 Supplement, Aug. 1995, 39S-42S.
Kalendar, Ruslan et al., "Java Web Tools for PCR, in Silico PCR, and Oligonucleotide Assembly and Analysis", Genomics, vol. 98, 2011, pp. 137-144.
Kamel, A. M. et al., "A simple strategy for breakpoint fragment determination in chronic myeloid leukemia", Cancer Genetics and Cytogenetics, vol. 122, 2000, 110-115.
Kane, M. et al., "Application of Less Primer Method to Commercial Kits", Forensic Science International: Genetics Supplement Series, vol. 1, Issue 1, 2008, 41-43.
Kane, M. , "Application of Less Primer Method To Multiplex PCR", International Congress Series, vol. 1288, 2006, pp. 694-696.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Kapadia, Samir R. et al., "Impact of Intravascular Ultrasound in Understanding Transplant Coronary Artery Disease", Current Opinion In Cardiology, vol. 14, No. 2, Mar. 1, 1999, 1-19.
Karger, et al., "DNA Sequencing By Capillary Electrophoresis", Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis Of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Keith, L. et al., "Clinical Experience With the Prevention of Rh-Isoimmunization: A Historical Comparative Analysis", American Journal of Reproductive Immunology, vol. 5, 1984, 84-89.
Keller, M. C. et al., "Non-Pathological Paternal Isodisomy of Chromosome 2 Detected From a Genome-Wide SNP Scan", American Journal of Medical Genetics, Part A, 2009, 1823-1826.
Kennedy, S. R. et al., "Detecting ultralow-frequency mutations by Duplex Sequencing", Nature Protocols, vol. 9, No. 11, 2014, 2586-2606.
Kibbe, Warren A. , "Oligocalc: An Online Oligonucleotide Properties Calculator", Nucleic Acids Research, vol. 35, 2007, pp. W43-W46.
Kiernan, J. A. , "Formaldehyde, formalin, paraformaldehyde and glutaraldehyde: What they are and what they do.", Microscopy Today, vol. 1, 2000, 8-12.
Kimmel, G. et al., "GERBIL: Genotype resolution and block identification using likelihood", PNAS, vol. 102, No. 1, Jan. 4, 2005, 158-162.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kirkness, E. F. et al., "Sequencing of isolated sperm cells for direct haplotyping of a human genome", Genome Research, vol. 23, 2013, 826-832.
Kivioja, T. et al., "Counting absolute number of molecules using unique molecular identifiers", Nature Proceedings, Apr. 14, 2011, 18 pgs.
Kivioja, T. et al., "Counting absolute numbers of molecules using unique molecular identifiers", Nature Methods, vol. 9, No. 1, Jan. 2012, 72-76.
Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection In Massively Parallel Sequencing Of Individual And Pooled Samples", Bioinformatics, vol. 25, No. 17, Jun. 19, 2009, 2283-2285.
Koelman, et al., "Donor-derived Soluble HLA Plasma Levels Can Not Be Used To Monitor Graft Rejection In Heart Transplant Recipients", Transplant Immunology, vol. 8, No. 1, Mar. 1, 2000, 57-64.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Konfortov, B A. et al., "A High-Resolution HAPPY Map of Dictyostelium discoideum Chromosome 6", Genome Research, vol. 10, No. 11, Nov. 2000, 1737-1742.
Kopreski, MS et al., "Detection of mutant K-ras DNA in plasma or serum of patients with colorectal cancer", British Journal of Cancer, vol. 76, No. 10, 1997, 1293-1299.
Koressaar, Triinu et al., "Enhancements and Modifications of Primer Design Program Primer3", Bioinformatics, vol. 23, 2007, pp. 1289-1291.
Korn, et al., "Integrated Genotype Calling And Association Analysis Of SNPS, Common Copy Number Polymorphisms And Rare CNVS", Nature Genetics, vol. 40, No. 10, Oct. 1, 2008, 1253-1260.
Kuhn, H. et al., "Rolling-circle amplification under topological constraints", Nucleic Acids Research, vol. 30, No. 2, 2002, 574-580.
Kukita, Y. et al., "High-fidelity target sequencing of individual molecules identified using barcode sequences: de nova detection and absolute quantitation of mutations in plasma cell-free DNA from cancer patients", DNA Research, vol. 22, No. 4, Jun. 29, 2015, 269-277.
Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.
Lambert, et al., "Quantification of Maternal Microchimerism by HLA-Specific Real-time Polymerase Chain Reaction", Arthritis and Rheumatism, vol. 50, No. 3, Mar. 1, 2004, 906-914.
Landegren, U. et al., "Padlock and proximity probes for in situ and array-based analyses: tools for the post-genomic era", Comparative and Functional Genomics, vol. 4, 2003, 525-530.
Langmore, J. , "Quality Control and Pre-Qualifications of NGS Libraries Made from Clinical Samples", ABRF 2013 Satellite Workshop, Mar. 2, 2013, 35 pages.
Lapaire, O. et al., "Array-CGH analysis of cell-free fetal DNA in 10 mL of amniotic fluid supernatant", Prenatal Diagnosis, vol. 27, May 17, 2007, 616-621.
Lapierre, J.M. et al., "Analysis of uncultured amniocytes by comparative genomic hybridization: a prospective prenatal study", Prenatal Diagnosis, vol. 20, 2000, 123-131.
Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.
Larsen, J. B. et al., "Single-step Nested Multiplex PCR to Differentiate Between Various Bivalve Larvae", Marine Biology, vol. 146, 2005, pp. 1119-1129.

(56) References Cited

OTHER PUBLICATIONS

Lasken, R. S. et al., "Whole genome amplification: abundant supplies of DNA from precious samples or clinical specimens", Trends in Biotechnology, vol. 21, No. 12, Dec. 2003, 531-535.

Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.

Lavebratt, Catharina et al., "Pyrosequencing-based SNP Allele Frequency Estimation In DNA Pools", Human Mutation, vol. 23, Issue 1, Dec. 19, 2003, 92-97.

Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.

Leamon, John H. et al., "A massively parallel PicoTiterPlate based platform for discrete picoliter-scale polymerase chain reactions", Electrophoresis, vol. 24, No. 21, Nov. 1, 2003, 3769-3777.

Lecomte, T. et al., "Detection of Free-Circulating Tumor-Associated DNA in Plasma of Colorectal Cancer Patients and Its Association With Prognosis", Int. J. Cancer, vol. 100, 2002, 542-548.

Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.

Lee, T. et al., "Down syndrome and cell-free fetal DNA in archived maternal serum", AmJ Obstet Gynecol, vol. 187, No. 5, 1217-1221, Nov. 2002.

Lee, T.H. et al., "Quantitation of genomic DNA in plasma and serum samples: higher concentrations of genomic DNA found in serum than in plasma", Transfusion, vol. 41, Feb. 2001, 276-282.

Levsky, Jeffrey M. et al., "Efficacy of Coronary Ct Angiography: Where We Are, Where We Are Going and Where We Want to Be", Journal Of Cardiovascular Computed Tomography, vol. 3, Supplement 2, Nov. 2, 2009, s99-s108.

Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.

Li, et al., "Mapping Short DNA Sequencing Reads And Calling Variants Using Mapping Quality Scores", Genome Research, vol. 18, No. 11,, Aug. 19, 2008, 1851-1858.

Li, et al., "Multiplex Padlock Targeted Sequencing Reveals Human Hypermutable CpG Variations", Genome Research, vol. 19, No. 9, Jun. 12, 2009, 1606-1615.

Li, et al., "SOAP2: An Improved Ultrafast Tool For Short Read Alignment", Bioinformatics, vol. 25, No. 15, Aug. 1, 2009, 1966-1967.

Li, R. et al., "SNP detection for massively parallel whole-genome resequencing", Genome Research, vol. 19, 2009, 1124-1132.

Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.

Li, Ying et al., "Detection of Donor-specific DNA Polymorphisms in the Urine of Renal Transplant Recipients", Clinical Chemistry, vol. 49, No. 4, Apr. 1, 2003, 655-658.

Li, Ying et al., "Ready detection of donor-specific single-nucleotide polymorphisms in the urine of renal transplant recipients by matrix-assisted laser desorption/ionization time-of-flight mass spectrometry", Ying Li. et al., "Ready detection of donor-specific single-nucleotide polymorphisms in the urine of renal transplant recipients by matrix-assisted laser desorption/ionization time-of-flight mass spectrometry", Clin Chem, Oct. 2005,vol. 51,Issue. 10,pp. 1903-1904, Oct. 1, 2005, 1903-1904.

Lichtenstein, A. V. et al., "Circulating Nucleic Acids and Apoptosis", Annals New York Academy of Sciences, vol. 945, Aug. 1, 2001, 239-249.

Liljedahl, Ulrika et al., "Detecting Imbalanced Expression Of SNP Alleles by Minisequencing On Microarrays", BMC Biotechnology, vol. 4, Article No. 24, Oct. 22, 2004, 1-10.

Lo, et al., "Next-generation Sequencing Of Plasma/Serum DNA: An Emerging Research And Molecular Diagnostic Tool", Clinical Chemistry, vol. 55, No. 4, Apr. 1, 2009, 607-608.

Lo, et al., "Presence Of Donor-specific Dna In Plasma Of Kidney And Liver-transplant Recipients", Lancet, vol. 351, No. 9112, May 2, 1998, 1329-1330.

Lo, Y M. et al., "Circulating Nucleic Acids in Plasma and Serum: An Overview", Annals of the New York Academy of Sciences, vol. 945, Sep. 1, 2001, 1-7.

Lo, Y.M.D. , "Fetal DNA in Maternal Plasma: Biology and Diagnostic Applications", Clinical Chemistry, vol. 46, No. 12, 2000, 1903-1906.

Lo, Y.M.D. et al., "Prenatal diagnosis: progress through plasma nucleic acids", Nature Reviews, vol. 8, 2007, 71-77.

Loh, Elwyn , "Anchored PCR: Amplification with Single-sided Specificity", Methods, vol. 2, 1991, pp. 11-19.

Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.

Lu, S. et al., "Probing Meiotic Recombination and Aneuploidy of Single Sperm Cells by Whole-Genome Sequencing", Science, vol. 338, Dec. 21, 2012, 1627-1630.

Lui, Yanni Y. et al., "Circulating DNA in Plasma and Serum: Biology, Preanalytical Issues And Diagnostic Applications", Clinical Chemistry and Laboratory Medicine, vol. 40, No. 10, Oct. 29, 2002, 962-968.

Lui, Yanni Y. et al., "Origin of Plasma Cell-Free DNA after Solid Organ Transplantation", Clinical Chemistry, vol. 49, No. 3, Mar. 1, 2003, 495-496.

Lun, Fiona M. et al., "Microfluidics Digital PCR Reveals A Higher Than Expected Fraction Of Fetal DNA In Maternal Plasma", Clinical Chemistry, vol. 54, No. 10, Aug. 14, 2008, 1664-1672.

Mackiewicz, D. et al., "Distribution of Recombination Hotspots in the Human Genome—A Comparison of Computer Simulations with Real Data", PLOS One, vol. 8, No. 6, Jun. 2013, 11 pages.

Marguiles, M. et al., "Genome Sequencing in Open Microfabricated High Density Picoliter Reactors", Nature, vol. 437, No. 7057, Sep. 15, 2005, 376-380.

Marianes, Alexis E. et al., "Targets of Somatic Hypermutation within Immunoglobulin Light Chain Genes in Zebrafish", Immunology, vol. 132, 2010, pp. 240-255.

Maron, Jill L. et al., "Cell-free Fetal DNA Plasma Extraction and Real-time Polymerase Chain Reaction Quantification", Methods In Molecular Medicine, vol. 132, Aug. 1, 2007, 51-63.

Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.

Martinez-Lopez, J. et al., "Real-time PCR Quantification of Haematopoietic Chimerism after Transplantation: A Comparison Between TaqMan And Hybridization Probes Technologies", International Journal of Laboratory Hematology, vol. 32, Issue 1, Part 1, May 12, 2009, e17-e25.

Martins, et al., "Quantification Of Donor-derived DNA In Serum: A New Approach Of Acute Rejection Diagnosis In A Rat Kidney Transplantation Model", Transplantation Proceedings, vol. 37, No. 1,, Jan. 1, 2005, 87-88.

Masuzaki, H. et al., "Detection of cell free placental DNA in maternal plasma: direct evidence from three cases of confined placental mosaicism", J Med Genet, vol. 41, 2004, 289-292.

Matsubara, T. et al., "Pantropic Retroviral Vectors Integrate and Express In Cells of the Malaria Mosquito, Anopheles Gambiae", PNAS, vol. 93, 1996, pp. 6181-6185.

Matsuzaki, H. et al., "Genotyping over 100,000 SNPs on a pair of oligonucleotide arrays", Nature Methods, vol. 1, No. 2, Nov. 2004, 109-111.

McDonald, J. P. et al., "Novel thermostable Y-family polymerases: applications for the PCR amplification of damaged or ancient DNAs", Nucleic Acids Research, vol. 34, No. 4, 2006, 1102-1111.

Messmer, Trudy O. et al., "Application of a Nested, Multiplex PCR to Psittacosis Outbreaks", Journal of Clinical Microbiology, vol. 35, No. 8, 1997, pp. 2043-2046.

(56) References Cited

OTHER PUBLICATIONS

Metzker, M. L. et al., "Polymerase Chain Reaction", Encyclopedia of Medical Devices and Instrumentation, vol. 5, Second Edition, 2006, 380-387.

Metzker, M. L. et al., "Quantitation of Mixed-Base Populations of HIV- 1 Variants by Automated DNA Sequencing with BODIPY* Dye-Labeled Primers", BioTechniques, vol. 25, Sep. 1998, 446-462.

Meuzelaar, Linda S. et al., "Megaplex PCR: A Strategy for Multiplex Amplification", Nature Methods, vol. 4, 2007, pp. 835-837.

Meyer, M et al., "Illumina Sequencing Library Preparation for Highly Multiplexed Target Capture and Sequencing", Cold Spring Harbor Protocols, vol. 2010, Issue 6, Jun. 2010, 1-10.

Meyerson, M. et al., "Advances in understanding cancer genomes through second-generation sequencing", Nature Reviews: Genetics, vol. 11, Oct. 2010, 685-696.

Mikkelsen, T. S. et al., "Genome-wide maps of chromatin state in pluripotent and lineage-committed cells", Nature, vol. 448, No. 2, Aug. 2007, 553-562.

Milani, et al., "Genotyping Single Nucleotide Polymorphisms By Multiplex Minisequencing Using Tag-arrays", DNA Microarrays for Biomedical Research, vol. 529, Jan. 16, 2009, 215-229.

Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.

Mitra, S. et al., "Chapter 4 Classification Techniques", Introduction to Machine Learning and Bioinformatics, First Edition, 2008, 101-127.

Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.

Moreira, et al., "Increase In And Clearance Of Cell-free Plasma DNA In Hemodialysis Quantified By Real-time PCR", Clinical Chemistry and Laboratory Medicine, vol. 44, No. 12, Dec. 13, 2006, 1410-1415.

Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.

Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.

Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.

Nakamura, N. et al., "Ex Vivo Liver Perfusion with Arterial Blood from A Pig with Ischemic Liver Failure", Artificial Organs, vol. 23, No. 2, 1999, 153-160.

Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.

Nawroz, H et al., "Microsatellite Alterations in Serum DNA of Head and Neck Cancer Patients", Nature Medicine, vol. 2, No. 9, Sep. 1996, 1035-1037.

Neve, B. et al., "Rapid SNP Allele Frequency Determination in Genomic DNA Pools by Pyrosequencing", BioTechniques, vol. 32, No. 5, May 1, 2002, 1138-1142.

Ng, et al., "Multiplex Sequencing Of Paired-end Ditags (MS-PET): A Strategy For The Ultra-high-throughput Analysis Of Transcriptomes And Genomes", Nucleic Acids Research, vol. 34, No. 12, Jul. 13, 2006, 1-10.

Nilsson, M. et al., "Padlock Probes: Circularizing Oligonucleotides for Localized DNA Detection", Science, vol. 265, Sep. 10, 1994, 2085-2088.

Nishigaki, K. et al., "Random PCR-Based Genome Sequencing: A Non-Divide-and-Conquer Strategy", DNA Research, vol. 7, 2000, 19-26.

Nishiwaki, Morie et al., "Genotyping of Human Papillomaviruses by A Novel One-step Typing Method With Multiplex PCR and Clinical Applications", Journal of Clinical Microbiology, vol. 46, 2008, pp. 1161-1168.

Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.

Nui, A. et al., "The Functional Integrity of a Normothermic Perfusion System Using Artificial Blood in Pig Liver", Journal of Surgical Research, Vo. 131, 2006, 189-198.

O'Connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.

Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.

Ohara, O et al., "One-sided Polymerase Chain Reaction: The Amplification of cDNA", Proceedings of the National Academy of Sciences, vol. 86, 1989, 5673-5677.

Ohira, T. et al., "Tumor volume determines the feasibility of cell-free DNA sequencing for mutation detection in non-small cell lung cancer", Cancer Science, vol. 107, 2016, 1660-1666.

Okou, et al., "Microarray-based Genomic Selection For High-throughput Resequencing", Nature Methods, vol. 4, No. 11, Oct. 14, 2007, 907-909.

Okou, David T. et al., "Combining Microarray-based Genomic Selection (MGS) with The Illumina Genome Analyzer Platform To Sequence Diploid Target Regions", Annals of Human Genetics, vol. 73, No. 5, Aug. 6, 2009, 502-513.

Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.

Oliphant, A. et al., "Bead.Array™ Technology: Enabling an Accurate, Cost-Effective Approach to High-Throughput Genotyping", Bio Techniques, vol. 32, Jun. 2002, S56-S6.

Olivarius, S et al., "High-throughput Verification of Transcriptional starting Sites by Deep-RACE", Bio Techniques, vol. 46, No. 2, Feb. 2009, 130-132.

Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.

Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.

Olivier, et al., "The Invader Assay for SNP Genotyping", Mutation Research, vol. 573, No. 1-2, Jun. 3, 2005, 103-110.

Olney, R. S. et al., "Chorionic Villus Sampling and Amniocentesis: Recommendations for Prenatal Counseling", MMWR: Recommendations and Reports, 44(RR-9), Jul. 21, 1995, 1-12.

Orsouw, et al., "Complexity Reduction Of Polymorphic Sequences (Crops): A Novel Approach For Large-scale Polymorphism Discovery In Complex Genomes", Plos One, vol. 11:e1172, Nov. 14, 2017, 1-10.

Owczarzy, Richard et al., "Melting Temperatures of Nucleic Acids: Discrepancies in Analysis", Biophysical Chemistry, vol. 117, 2005, pp. 207-215.

Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.

Pakstis, et al., "Candidate SNPs For A Universal Individual Identification Panel", Human Genetics, vol. 121, No. 3-4,, Feb. 27, 2007, 305-317.

(56) References Cited

OTHER PUBLICATIONS

Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Panjkovich, Alejandro et al., "Comparison of Different Melting Temperature Calculation Methods for Short DNA Sequences", Bioinformatics, vol. 21, 2005, pp. 711-722.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Parker, A. V. et al., "The Effect of Sodium Citrate on the Stimulation of Polymorphonuclear Leukocytes", Investigative Ophthalmology & Visual Science, vol. 26, 1985, 1257-1261.
Paruzynski, A. et al., "Genome-wide high-throughput integrome analyses by nrLAM-PCR and next-generation sequencing", Nature Protocols, vol. 5, No. 8, Jul. 8, 2010, 1379-1395.
Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.
Patil, N. et al., "Blocks of Limited Haplotype Diversity Revealed by High-Resolution Scanning of Human Chromosome 21", Science, vol. 294, Nov. 23, 2001, 1719-1723.
Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.
Pelizzari, C. A. et al., "Quantitative analysis of DNA array autoradiographs", Nucleic Acids Research, vol. 28, No. 22, 2000, 4577-4581.
Perakis, S. et al., "Advances in Circulating Tumor DNA Analysis", Advances in Clinical Chemistry, vol. 80, 2017, 73-153.
Pfaffl, Michael W., "Quantification Strategies in Real-time PCR", A-Z of quantitative PCR, 2004, pp. 87-112.
Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pirker, C. et al., "Whole Genome Amplification for CGH Analysis: Linker-Adapter PCR as the Method of Choice for Difficult and Limited Samples", Cytometry Part A, vol. 61A, 2004, 26-34.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Profitt, J et al., "Isolation And Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Puszyk, William M. et al., "Noninvasive Prenatal Diagnosis Of Aneuploidy Using Cell-free Nucleic Acids In Maternal Blood: Promises And Unanswered Questions", Prenatal Diagnosis, vol. 28, No. 1, Nov. 16, 2007, 1-6.
Qiagen,, "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.

Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.
Quan, P. C. et al., "Studies on the mechanism of NK cell lysis", The Journal of Immunology, vol. 128, 1982, 1786-1791.
Quinlan, M. P., "Amniocentesis: Indications and Risks", American Medical Association Journal of Ethics: Virtual Mentor, vol. 10, No. 5, May 2008, 304-306.
Rabinowitz, M., "A System and Method for Integrating, Validating and Applying Genetic and Clinical Data to Enhance Medical Decisions", Nov. 29, 2005, 155 pgs.
RainDance Technologies, et al., "RainDance Technologies Introduces the RDT 1000", RainDance Technologies, Nov. 12, 2008.
Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.
Reeves, R. H. et al., "Too much of a good thing: mechanisms of gene action in Down syndrome", Trends in Genetics, vol. 17, No. 2, Feb. 2, 2001, 83-88.
Rhoads, A. et al., "PacBio Sequencing and Its Applications", Genomics Proteomics Bioinformatics, vol. 13, Nov. 2, 2015, 278-289.
Robertson, G. et al., "Genome-wide profiles of STAT1 DNA association using chromatin immunoprecipitation and massively parallel sequencing", Nature Methods, vol. 4, No. 8, Aug. 2007, 651-657.
Roche Diagnostics, et al., "Versatile Nucleic Acid Purification", MagnaPure Manual, Feb. 3, 2012.
Roman, B. L. et al., "Non-Radioisotopic AFLP Method Using PCR Primers Fluorescently Labeled with CyA 5", BioTechniques, vol. 26, Feb. 1999, 236-238.
Rosado, J. A. et al., "Tyrosine kinases activate store-mediated Ca2+ entry in human platelets through the reorganization of the actin cytoskeleton", Biochem. J., vol. 351, 2000, 429-437.
Rosen, D. R. et al., "Mutations in Cu/Zn superoxide dismutase gene are associated with familial amyotrophic lateral sclerosis", Nature, vol. 362, Mar. 4, 1993, 59-62.
Ross, P. et al., "Quantitative Approach to Single-Nucleotide Polymorphism Analysis Using MALDI-TOF Mass Spectrometry", BioTechniques, vol. 29, Sep. 2000, 620-629.
Rothberg, et al., "The Development and Impact of 454 Sequencing", Nature Biotechnology, vol. 26, No. 10, Oct. 9, 2008, 1117-1124.
Ruano, G. et al., "Haplotype of multiple polymorphisms resolved by enzymatic amplification of single DNA molecules", Proc. Nati. Acad. Sci. USA, vol. 87, Aug. 1990, 6296-6300.
Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine And Hygiene, vol. 60, 1999, pp. 183-187.
Ruschendorf, et al., "Alohomora: A Tool For Linkage Analysis Using 10K SNP Array Data", Bioinformatics Applications Notes, vol. 21, No. 9, Jan. 12, 2005, 2123-2125.
Ryan, B. M. et al., "A prospective study of circulating mutant KRAS2 in the serum of patients with colorectal neoplasia: strong prognostic indicator in postoperative follow up", Gut, vol. 52, 2003, 101-108.
Sahukhal, G. S. et al., "msaABCR operon positively regulates biofilm development by repressing proteases and autolysis in *Staphlococcus aureus*", FEMS Microbiology Letters, vol. 362, No. 4, 2015, 1-10.
Saito, H. et al., "Prenatal DNA diagnosis of a single-gene disorder from maternal plasma", The Lancet, vol. 356, Sep. 30, 2000, 1170.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Sanger, et al., "Nucleotide Sequence of Bacteriophage Lambda DNA", Journal of Molecular Biology, vol. 162, No. 4, Dec. 25, 1982, 729-773.

(56) References Cited

OTHER PUBLICATIONS

Santalucia, Jr., J. , "Physical Principles and Visual-OMP Software for Optimal PCR Design", Methods in Molecular Biology, vol. 402, 2007, 3-33.
Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.
Schaaf, C. P. et al., "Copy Number and SNP Arrays In Clinical Diagnostics", Annu. Rev. Genomics Hum. Genet., vol. 12, 2011, 25-51.
Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schubert, , "Picking out prenatal DNA", Nature Medicine, vol. 10, No. 785, Aug. 2004, 1 page.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Schwarzenbach, H. et al., "Evaluation of cell-free tumour DNA and RNA in patients with breast cancer and benign breast disease", Molecular BioSystems, vol. 7, 2011, 2848-2854.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Shapero, M. H. et al., "MARA: A Novel Approach for Highly Multiplexed Locus-specific SNP Genotyping Using High-density DNA Oligonucleotide Arrays", Nucleic Acids Research, vol. 32, No. 22, 2004, 1-9.
Sharples, et al., "Diagnostic Accuracy Of Coronary Angiography And Risk Factors For Post-heart-transplant Cardiac Allograft Vasculopathy", Transplantation, vol. 76, No. 4, Aug. 27, 2003, 679-682.
Shendure, J. et al., "Accurate Multiplex Polony Sequencing of an Evolved Bacterial Genome", Science, Nov. 30, 2007, 18-24.
Shendure, J. et al., "Next-generation DNA sequencing", Nature Biotechnology, vol. 26, No. 10, Oct. 2008, 1135-1145.
Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.
Shokralla, S. et al., "Next-generation DNA barcoding: using next-generation sequencing to enhance and accelerate DNA barcode capture from single specimens", Molecular Ecology Resources, vol. 14, 2014, 892-901.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Shyamala, Venkatakrishna et al., "Genome Walking by Single-Specific-Primer Polymerase Chain Reaction: SSP-PCR", Gene, vol. 84, 1989, pp. 1-8.
Siebert, P. D. et al., "An improved PCR method for walking in uncloned genomic DNA", Nucleic Acids Research, vol. 23, No. 6, 1995, 1087-1088.
Singh, Vinayak K. et al., "PCR Primer Design", Molecular Biology Today, vol. 2, 2001, pp. 27-32.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Solexa, "Application Note: DNA Sequencing", 2006, 1-2.
Solomon, M. J. et al., "Formaldehyde-mediated DNA-protein crosslinking: A probe for in vivo chromatin structures", Proc. Natl. Acad. Sci. USA, vol. 82, 1985, 6470-6474.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
Spencer, K. et al., "Maternal serum levels of dimeric inhibin A in pregnancies affected by trisomy 21 in the first trimester", Prenatal Diagnosis, vol. 21, 2001, 441-444.
Spencer, K. et al., "Maternal serum levels of total activin-A in first-trimester trisomy 21 pregnancies", Prenatal Diagnosis, vol. 21, 2001, 270-273.
Spes, et al., "Diagnostic And Prognostic Value Of Serial Dobutamine Stress Echocardiography For Noninvasive Assessment Of Cardiac Allograft Vasculopathy: A Comparison With Coronary Angiography And Intravascular Ultrasound", Circulation, vol. 100, No. 5, Aug. 3, 1999, 509-515.
Spindler, K.L. G. et al., "Cell-free DNA in healthy individuals, noncancerous disease and strong prognostic value in colorectal cancer", International Journal of Cancer, vol. 135, 2014, 2984-2991.
Spindler, K.-L. G. et al., "Cell-Free DNA in Metastatic Colorectal Cancer: A Systematic Review and Meta-Analysis", The Oncologist, vol. 22, 2017, 1049-1055.
Stephens, M. et al., "Accounting for Decay of Linkage Disequilibrium in Haplotype Inference and Missing-Data Imputation", Am. J. Hum. Genet., vol. 76, 2005, 449-462.
Stewart, C. M. et al., "Circulating cell-free DNA for non-invasive cancer management", Cancer Genetics, vol. 228-229, 2018, 169-179.
Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.
Stiller, et al., "Direct Multiplex Sequencing (DMPS)—A Novel Method For Targeted High-thoroughput Sequencing Of Ancient And Highly Degraded DNA", Genome Research, vol. 19, No. 10, Jul. 27, 2009, 1843-1848.
Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.
Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.
Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.
Swarup, V. et al., "Circulating (cell-free) nucleic acids—A promising, non-invasive tool for early detection of several human diseases", FEBS Letters, vol. 581, 2007, 795-799.
Swinkels, D. W. et al., "Effects of Blood-Processing Protocols on Cell-free DNA Quantification in Plasma", Clinical Chemistry, vol. 49, No. 3, 2003, 525-526.
Syvanen, A.C. , "Toward genome-wide SNP genotyping", Nature Genetics Supplement, vol. 37, Jun. 2005, S5-S10.
Taback, B. et al., "Quantification of Circulating DNA in the Plasma and Serum of Cancer Patients", Ann. N.Y. Acad. Sci, vol. 1022, 2004, 17-24.
Takala, et al., "A High-throughput Method for Quantifying Alleles and Haplotypes of The Malaria Vaccine Candidate Plasmodium Falciparum Merozoite Surface Protein-1 19 kDa", Malaria Journal, vol. 5:31, Apr. 20, 2006, 1-10.
Takashima, Y. et al., "Expansion-contraction of photoresponsive artificial muscle regulated by host-guest interactions", Nature Communications, vol. 3, No. 1270, Dec. 11, 2012, 8 pages.
Tewhey, R. et al., "Microdroplet-based PCR enrichment for large-scale targeted sequencing", Nature Biotechnology, vol. 27, No. 11, Nov. 2009, 1025-1031.

(56) References Cited

OTHER PUBLICATIONS

Thavarajah, R. et al., "Chemical and physical basics of routine formaldehyde fixation", Journal of Oral and Maxillofacial Pathology, vol. 16, No. 3, 2012, 400-405.
Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.
Thornton, Brenda et al., "Real-time Pcr (qPCR) Primer Design Using Free Online Software", Biochemistry and Molecular Biology Education, vol. 39, 2011, pp. 145-154.
Tong, et al., "Diagnostic Developments Involving Cell-free (Circulating) Nucleic Acids", Clinica Chimica Acta, vol. 363, No. (1-2), Aug. 26, 2005, 187-196.
Toshikazu, et al., "Estimation Of Haplotype Frequencies, Linkage-disequilibrium Measures, And Combination of Haplotype Copies in Each Pool By Use Of Pooled DNA Data", American Journal of Human Genetics, vol. 72, Jan. 17, 2003, 384-398.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163- 171.
Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.
Troeger, C. et al., "Approximately Half of The Erythroblasts in Maternal Blood are of Fetal Origin", Molecular Human Reproduction, vol. 5, No. 12, Dec. 1, 1999, 1162-1165.
Troutt, et al., "Ligation-anchored PCR: A Simple Amplification Technique with Single-sided Specificity", Proceedings of the National Academy of Sciences, vol. 89, Oct. 1992, 9823-9825.
Tsang, Jason C. et al., "Circulating Nucleic Acids in Plasma/Serum", Pathology, vol. 39, No. 2, Apr. 1, 2007, 197-207.
Tsangaris, G. T. et al., "Proteomic analysis of amniotic fluid in pregnancies with Down syndrome", Proteomics, vol. 6, 2006, 4410-4419.
Tsui, N. B. et al., "Systematic micro-array based identification of placental mRNA in maternal plasma: towards non-invasive prenatal gene expression profiling", J. Med. Genet, vol. 41, 2004, 461-467.
Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.
Tuzcu, et al., "Intravascular Ultrasound Evidence Of Angiographically Silent Progression In Coronary Atherosclerosis Predicts Long-term Morbidity And Mortality After Cardiac Transplantation", The American Journal of Cardiology, vol. 45, No. 9, May 3, 2005, 1538-1542.
Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.
Urbaniak, S. J. et al., "RhD haemolytic disease of the fetus and the newborn", Blood Reviews, vol. 14, 2000, 44-61.
Urbanova, M. et al., "Circulating Nucleic Acids as a New Diagnostic Tool", Cellular & Molecular Biology Letters, vol. 15, 2010, 242-259.
Vallone, Peter M. et al., "Demonstration of Rapid Multiplex PCR Amplification Involving 16 Genetic Loci", Forensic Science International: Genetics, vol. 3, 2008, pp. 42-45.
Van Uitert, I. et al., "The influence of different membrane components on the electrical stability of bilayer lipid membranes", Biochimica et Biophysica Acta, vol. 1798, 2010, 21-31.
Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.
Verlaan, et al., "Allele-specific Chromatin Remodeling in The ZPBP22/GSDMB/ORMDL3 Locus Associated with the Risk of Asthma And Autoimmune Disease", The American Journal of Human Genetics, vol. 85, No. 3, Sep. 11, 2009, 377-393.
Verlaan, et al., "Targeted Screening of Cis-Regulatory Variation in Human Haplotypes", Genome Research, vol. 19, No. 1, Jan. 1, 2009, 118-127.
Vlaminck, I. D. et al., "Circulating Cell-Free DNA Enables Non-invasive Diagnosis of Heart Transplant Rejection", Sci Transl Med., vol. 6, No. 241, Jun. 18, 2018, 26 pages.
Voelkerding, et al., "Next-generation Sequencing: From Basic Research To Diagnostics", Clinical Chemistry, vol. 55, No. 4, Apr. 1, 2009, 641-658.
Vogelstein, B. et al., "Digital PCR", Proc. Natl. Acad. Sci. USA, vol. 96, Aug. 1999, 9236-9241.
Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.
Von Eggeling, F. et al., "Applications of Random PCR", Cellular and Molecular Biology, vol. 41, No. 5, 1995, 653-670.
Wang, J. et al., "Genome-wide Single-Cell Analysis of Recombination Activity and De Novo Mutation Rates in Human Sperm", Cell, vol. 150, Jul. 20, 2012, 402-412.
Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.
Wartell, Roger M. et al., "Thermal Denaturation of DNA Molecules: A Comparison of Theory with Experiment", Physics Reports, vol. 126, 1985, pp. 67-107.
Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.
Watt, Heather L. , "Sex Diagnosis of Preimplantation Porcine Embryos through PCR Amplification of The Sry Gene", Sex Diagnosis of Preimplantation Porcine Embryos Through PCR Amplification of the SRY Gene (1998) ("Watt (1998)"), 1998, 151 pages.
Wei, C. et al., "Detection and Quantification by Homogeneous PCR of Cell-free Fetal DNA in Maternal Plasma", Clinical Chemistry, vol. 47, No. 2, 2001, 336-338.
Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.
Wellnhofer, et al., "Angiographic Assessment Of Cardiac Allograft Vasculopathy: Results Of A Consensus Conference Of The Task Force For Thoracic Organ Transplantation of the German Cardiac Society", Transplant International, vol. 23, No. 11, Aug. 19, 2010, 1094-1104.
Wiedmann, Ralph T. et al., "SNP Discovery in Swine by Reduced Representation and High Throughput Pyrosequencing", BMC Genetics, vol. 9, Article No. 81, Dec. 4, 2008, 1-7.
Wilkening, Stefan et al., "Determination of Allele Frequency In Pooled DNA: Comparison of Three PCR-based Methods", Bio Techniques, vol. 39, No. 6, May 30, 2005, 853-857.
Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.
Winsor, E. J. et al., "Maternal Cell Contamination in Uncultured Amniotic Fluid", Prenatal Diagnosis, vol. 16, 1996, 49-54.
Witherspoon, David J. et al., "Mobile Element Scanning (Me-scan) by Targeted High-throughput Sequencing", BMC Genomics, vol. 410, 2010, 15 pages.
Wong, K. H. et al., "Multiplex Illumina Sequencing Using DNA Barcoding", Current Protocols in Molecular Biology, vol. 101, Jan. 2013, 7.11.1-7.11.11.
Wright, Caroline et al., "Cell-free Fetal Nucleic Acids for Noninvasive Prenatal Diagnosis", PHG Foundation, Jan. 1, 2009, 1-64.

(56) References Cited

OTHER PUBLICATIONS

Wu, T.L. et al., "Cell-free DNA: measurement in various carcinomas and establishment of normal reference range", Clinica Chimica Acta, vol. 321, 2002, 77-87.
Xia, et al., "Simultaneous Quantitative Assessment Of Circulating Cell-free Mitochondrial And Nuclear DNA By Multiplex Real-time PCR", Genetics and Molecular Biology, vol. 32, No. 1, Mar. 1, 2009, 20-24.
Xian, et al., "Advances On Circulating Fetal DNA In Maternal Plasma", Chinese Medical Journal, vol. 120, No. 14, Jul. 2, 2007, 1256-1259.
Xie, et al., "CNV-SEQ, A New Method to Detect Copy Number Variation Using Highthroughput Sequencing", BMC Bioinformatics, vol. 10:80, Mar. 6, 2009, 1-9.
Xu, W. et al., "A Novel Universal Primer-Multiplex-PCR Method with Sequencing Gel Electrophoresis Analysis", PLOS One, vol. 7, No. 1, Jan. 17, 2012, 10 pgs.
Xue, et al., "Optimizing The Yield And Utility Of Circulating Cell-free DNA From Plasma And Serum", Clinica Chimica Acta, vol. 404, No. 2, Jun. 27, 2009, 100-104.
Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.
Yamada, T. et al., "PrimerStation: a highly specific multiplex genomic PCR primer design server for the human genome", Nucleic Acids Research, vol. 34, 2006, W665-W669.
Yang, Lin et al., "64-MDCT Coronary Angiography of Patients With Atrial Fibrillation: Influence of Heart Rate On Image Quality and Efficacy In Evalution of Coronary Artery Disease", AJR, vol. 193, No. 3, Sep. 1, 2009, 795-801.
Yaron, Y., "The implications of non-invasive prenatal testing failures: a review of an under-discussed phenomenon", Prenatal Diagnosis, vol. 36, 2016, 391-396.
Yijen, et al., "Noninvasive Evaluation Of Cardiac Allograft Rejection By Cellular And Functional Cardiac Magnetic Resonance", JACC: Cardiovacular Imaging, vol. 2, No. 6, Jun. 1, 2009, 731-741.
Yilmaz, A. et al., "Comparative Evaluation of Left and Right Ventricular Endomyocardial Biopsy", Circulation, vol. 122, No. 9, Aug. 31, 2010, 900-909.
Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.
Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.
Zhang, et al., "Use Of PCR And PCR-SSP For Detection Of Urinary Donor-Origin Dna In Renal Transplant Recipients With Acute Rejection", Chinese Medical Journal, vol. 116, No. 2, Feb. 2003, 191-194.
Zhang, Kun et al., "Digital RNA Alleotyping Reveals Tissue-specific and Allele-specific Gene Expression in Human", Nature Methods, vol. 6, No. 8, Jul. 20, 2009, 613-618.
Zhao, et al., "Urinary Thromboxane B2 In Cardiac Transplant Patients As A Screening Method Of Rejection", Prostaglandins, vol. 54, No. 6, Dec. 1, 1997, 881-889.
Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.
Zheng, Z et al., "Anchored Multiplex PCR for Targeted Next-generation Sequencing", Nature Medicine, vol. 20, No. 12, Dec. 2014, 1479-1486.
Zhong, X Y. et al., "Detection of Fetal Rhesus D And Sex Using Fetal DNA from Maternal Plasma by Multiplex Polymerase Chain Reaction", British Journal of Obstetrics and Gynaecology, vol. 107, Jun. 2000, 766-769.

Zhong, Xiao Y. et al., "Cell-free DNA In Urine: A Marker for Kidney Graft Rejection, but Not for Prenatal Diagnosis ?", Annals of the New York Academy of Sciences, vol. 945, Sep. 1, 2001, 250-257.
Zhou, et al., "Pyrosequencing, A High-throughput Method For Detecting Single Nucleotide Polymorphisms In The Dihydrofolate Reductase And Dihydropteroate Synthetase Genes Of Plasmodiym Falciparum", Journal of Clinical Microbiology, vol. 44, No. 11, Nov. 1, 2006, 3900-3910.
Zhou, W et al., "Counting alleles to predict recurrence of early-stage colorectal cancers", The Lancet, vol. 359, Jan. 19, 2002, 219-225.
Zimmer, et al., "Transplant Coronary Artery Disease", JACC: Cardiovascular Interventions, vol. 3, No. 4, Apr. 1, 2010, 367-377.
Zimmermann, B. et al., "Digital PCR: a powerful new tool for noninvasive prenatal diagnosis?", Prenatal Diagnosis, vol. 28, Nov. 10, 2008, 1087-1093.
Zimmermann, B. et al., "Novel Real-Time Quantitative PCR Test for Trisomy 21", Clinical Chemistry, vol. 48, No. 2, 2002, 362-363.
Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Zlotogora, J., "Penetrance and expressivity in the molecular age", Genetics in Medicine, vol. 5, No. 5, 2003, 347-352.
Gholami, M. et al., "A tailed PCR procedure for cost-effective, two-order multiplex sequencing of candidate genes in polyploid plants", Plant Biotechnology Journal, vol. 10, 2012, 635-645.
Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.
He, Qz et al., "A method for improving the accuracy of non-invasive prenatal screening by cell-free foetal DNA size selection", British Journal of Biomedical science, vol. 75, No. 3, Jul. 2018, 133-138.
Sanchez, C. et al., "New insights into structural features and optimal detection of circulating tumor DNA determined by single-strand DNA analysis", Nature Partner Journals, vol. 3, No. 31, Nov. 23, 2018, 12 pgs.
Vallone, P. M. et al., "A multiplex allele-specific primer extension assay for forensically informative SNPs distributed throughout the mitochondrial genome", Int J Legal Medicine, vol. 118, Feb. 4, 2004, 147-157.
Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.
Wittwer, C. T. et al., "Real-Time Multiplex PCR Assays", Methods, vol. 25, 2001, 430-448.
Zhang, J. et al., "Presence of Donor-and Recipient-derived DNA in Cell-free Urine Samples of Renal Transplantation Recipients: Urinary DNA Chimerism", Clinical Chemistry, vol. 45, No. 10, 1999, 1741-1746.
"European Application No. 014198110, European Search Report dated Apr. 28, 2015, 3 pages."
"Finishing the Euchromatic Sequence of the Human Genome", Nature vol. 431,(Oct. 21, 2004),931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.
"Multiplexing with RainDrop Digital PCR", RainDance Technologies, Application Note, 2013, 1-2.
"NucleicAcids, Linkers and Primers: Random Primers", New England BioLabs 1998/99Catalog, 1998, 121 and 284.

(56) References Cited

OTHER PUBLICATIONS

"PRIMER3, information sheet, Sourceforge.net. [retrieved on Nov. 12, 2012]. Retrieved from the Internet: <URL: http://primer3.sourceforge.net/>", 2009, 1 pg.

"Db SNP rs2056688 (http://www.ncbi.nlm.nih.gov/projects/SNP/snp_ref.cgi?rs=2056688, downloaded May 4, 2015", 3 pages.

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.

What To Expect (Weird Harmony results, May 1, 2015), 7 pages.

The Bump (Panorama Test, attached, Jul. 1, 2013), 8 pages.

"Blast of AAAAAAAAATTTAAAAAAAAATTT(http://blast.ncbi.nlm.nih.gov/Blast.cgi, downloaded May 4, 2015)", 9 pages.

"Guideline related to genetic examination", Societies Related to Genetic Medicine, Japanese Society for Genetic Counseling, Japanese Society for Gene Diagnosis and Therapy, Japan Society of Obstetrics and Gynecology, 2003, 2-15.

"How Many Carbs in a Potato?, [Online]", Retrieved from the Internet: <http://www.newhealthguide.org/How-Many-Carbs-In-A-Potato.html>, Nov. 1, 2014, 3 pages.

"Random variable", In The Penguin Dictionary of Mathematics. Retrieved from http://www.credoreference.com/entry/penguinmath/random _ variable, 2008, 1 page.

Abbosh, C. et al., "Phylogenetic ctDNA analysis depicts early-stage lung cancer evolution", Nature, vol. 545, May 25, 2017, 446-451.

Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.

Agarwal, Ashwin et al., "Commercial Landscape of Noninvasive Prenatal Testing in the United States", Prenatal Diagnosis,33, 2013, 521-531.

Alaeddini, R. et al., "Forensic implications of genetic analyses from degraded DNA—A review", Forensic Science International: Genetics, vol. 4, 2010, 148-157.

Alberts, B. et al., "Chapter 20: Germ Cells and Fertilization", Molecular Biology of the Cell, Fourth Edition, 2002, 1127-1156.

Alberts, B. et al., "Chapter 4: DNA and Chromosomes", Molecular Biology of the Cell, Fourth Edition, 2002, 191-234.

Alkan, Can et al., "Personalized Copy Number and Segmental Duplication Maps Using Next-Generation Sequencing", Nature Genetics, 41, 10, 2009, 1061-1068.

Allaire, F R. , "Mate selection by selection index theory", Theoretical Applied Genetics, 57(6), 1980, 267-272.

Allan, J. et al., "Micrococcal Nuclease Does Not Substantially Bias Nucleosome Mapping", Journal of Molecular Biology, vol. 417, Jan. 30, 2012, 152-164.

Allawi, Hatim T. et al., "Thermodynamics of internal C•T Mismatches in DNA", Nucleic Acids Research, 26 (11), 1998, 2694-2701.

Andras, S. C. et al., "Strategies for Signal Amplification in Nucleic Acid Detection", Molecular Biotechnology, vol. 19, 2001, 29-44.

Anker, P. et al., "Detection of circulating tumour DNA in the blood (plasma/serum) of cancer patients", Cancer and Metastasis Reviews, vol. 18, 1999, 65-73.

Antonarakis, S. E. et al., "Chromosome 21 and Down Syndrome: From Genomics To Pathophysiology", Nature Reviews Genetics, vol. 5, Oct. 2004, 725-738.

Aoki, Yasuhiro , "Statistical and Probabilistic Bases of Forensic DNA Testing", The Journal of the Iwate Medical Association, 2002, vol. 54, p. 81-94.

Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.

Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.

Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.

Bada, Michael A. et al., "Computational Modeling of Structural Experimental Data", Methods in Enzymology,317, 2000, 470-491.

Ballif, B. C. et al., "Detection of Low-Level Mosaicism by Array CGH in Routine Diagnostic Specimens", American Journal of Medical Genetics Part A, vol. 140A, 2006, 2757-2767.

Beaumont, Mark A et al., "The Bayesian Revolution in Genetics", Nature Reviews Genetics, 5, 2004, 251-261.

Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.

Beer, Alan E. et al., "The Biological Basis of Passage of Fetal Cellular Material into the Maternal Circulation", Annals New York Academy of Sciences, 731, 1994, 21-35.

Beerenwinkel, et al., "Methods for Optimizing Antiviral Combination Therapies", Bioinformatics, 19(1), 2003, i16-i25.

Beerenwinkel, N. et al., "Geno2pheno: estimating phenotypic drug resistance from HIV-1 genotypes", Nucleic Acids Research, 31(13), 2003, 3850-3855.

Benn, P. et al., "Non-Invasive Prenatal Testing for Aneuploidy: Current Status and Future Prospects", Ultrasound Obstet Gynecol, 42, 2013, 15-33.

Benn, P et al., "Non-Invasive prenatal Diagnosis for Down Syndrome: the Paradigm Will Shift, but Slowly", Ultrasound Obstet. Gynecol., 39, 2012, 127-130.

Bentley, David R et al., "Accurate Whole Human Genome Sequencing Using Reversible Terminator Chemistry", Nature, 456, 6, 2008, 53-59.

Bermudez, M. et al., "Single-cell sequencing and mini-sequencing for preimplantation genetic diagnosis", Prenatal Diagnosis, 23, 2003, 669-677.

Beroud, C. et al., "Prenatal diagnosis of spinal muscular atrophy by genetic analysis of circulating fetal cells", The Lancet, vol. 361, Mar. 22, 2003, 1013-1014.

Bevinetto, Gina , Bevinetto (5 Foods All Pregnant Women Need, American Baby, available at http://www.parents.com/pregnancy/mybody/nutrition/5greatpregnancyfoods/, Apr. 15, 2008), 8 pgs.

Bianchi, D W. et al., "Fetal gender and aneuploidy detection using fetal cells maternal blood: analysis of NIFTY I data", Prenat Diagn 2002; 22, 2002, 609-615.

Bianchi, D. W. , "Circulating Fetal DNA: Its Origin and Diagnostic Potential—A Review", Placenta, vol. 25, Supplemental A, May 2004, S93-S101.

Bianchi, D. W. et al., "Genome-Wide Fetal Aneuploidy Detection by Maternal Plasma DNA Sequencing", Obstetrics & Gynecology, vol. 119, No. 5, May 2012, 890-901.

Bianchi, D. W. , "Review: Fetal Cells in the Maternal Circulation: Feasibility for Prenatal Diagnosis", British Journal of Haematology, vol. 105, 1999, 574-583.

Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.

Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.

Bisignano, et al., "PGD and Aneuploidy Screening for 24 Chromosomes: Advantages and Disadvantages of Competing Platforms", Reproductive BioMedicine Online, 23, 2011, 677-685.

Bodenreider, O. , "The Unified Medical Language System (UMLS): Integrating Biomedical Terminology", Nucleic Acids Research, 32, (Database issue), 2004, D267-D270.

Breithaupt, Holger , "The Future of Medicine", EMBO Reports, 21(61), 2001, 465-467.

Brownie, Jannine et al., "The Elimination of Primer-Dimer Accumulation in PCR", Nucleic Acids Research, 25(16), 1997, 3235-3241.

(56) References Cited

OTHER PUBLICATIONS

Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.

Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.

Butler, J. et al., "The Development of Reduced Size STR Amplicons as Tools for Analysis of Degraded DNA*", Journal of Forensic Sciences, vol. 48, No. 5, 2003, 1054-1064.

Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.

Cairns, Paul et al., "Homozygous Deletions of 9p21 in Primary Human Bladder Tumors Detected by Comparative Multiplex Polymerase Chain Reaction", Cancer Research, 54, 1994, 1422-1424.

Caliendo, Angela , "Multiplex PCR and Emerging Technologies for the Detection of Respiratory Pathogens", Clinical Infectious Diseases, 52(4), 2011, S326-S330.

Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.

Carnevale, Alessandra et al., "Attitudes of Mexican Geneticists Towards Prenatal Diagnosis and Selective Abortion", American Journal of Medical Genetics, 75, 1998, 426-431.

Carvalho, B. et al., "Exploration, normalization, and genotype calls of high-density oligonucleotide SNP array data", Biostatistics, vol. 8, No. 2, 2007, 485-499.

Casbon, J. A. et al., "A method for counting PCR template molecules with application to next-generation sequencing", Nucleic Acids Research, vol. 39, No. 12, Apr. 13, 2011, 1-8.

Chakraborty, R. et al., "Paternity Exclusion by DNA Markers: Effects of Paternal Mutations", Journal of Forensic Sciences, vol. 41, No. 4, Jul. 1996, 671-677.

Chan, K.C. et al., "Size Distributions of Maternal and Fetal DNA in Maternal Plasma", Clinical Chemistry, vol. 50, No. 1, 2004, 88-92.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Chen, E. et al., "Noninvasive Prenatal Diagnosis of Fetal Trisomy 18 and Trisomy 13 by Maternal Plasma DNA Sequencing", PLoS One, 6 (7), e21791, 2011, 7 pgs.

Chen, X. Q. et al., "Microsatallite alterations in plasma DNA of small cell lung cancer patients", Nature Medicine, vol. 2, No. 9, Sep. 1996, 1033-1035.

Chetty, Shilpa et al., "Uptake of Noninvasive Prenatal Testing (NIPT) in Women Following Positive Aneuploidy Screening", Prenatal Diagnosis,33, 2013, 542-546.

Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.

Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.

Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.

Chiu, Rossa W. et al., "Effects of Blood-Processing Protocols on Fetal and Total DNA Quantification in Maternal Plasma", Clinical Chemistry, 47(9), 2001, 1607-1613.

Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.

Chiu, Rossa W.K. et al., "Non-Invasive Prenatal Diagnosis by Single Molecule Counting Technologies", Trends in Genetics, 25 (7), 2009, 324-331.

Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.

Choi, M. et al., "Genetic diagnosis by whole exome capture and massively parallel DNA sequencing", PNAS, vol. 106, No. 45, Nov. 10, 2009, 19096-19101.

Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.

Chu, Tianjiao et al., "A Novel Approach Toward the Challenge of Accurately Quantifying Fetal DNA in Maternal Plasma", Prenatal Diagnosis,30, 2010, 1226-1229.

Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.

Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.

Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.

Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.

Cossu, Gianfranco et al., "Rh D/d Genotyping by Quantitative Polymerase Chain Reaction and Capillary Zone Electrophoresis", Electrophoresis, 17, 1996, 1911-1915.

Coyle, J. F. et al., "Standards for detailed clinical models as the basis for medical data exchange and decision support", International Journal of Medical Informatics, 69(2-3), 2003, 157-174.

Craig, D. W. et al., "Identification of genetic variants using barcoded multiplexed sequencing", Nature Methods, vol. 5, Oct. 2008, 887-893.

Cross, Jillian et al., "Resolution of trisomic mosaicism in prenatal diagnosis: estimated performance of a 50K SNP microarray", Prenat Diagn 2007; 27, 2007, 1197-1204.

D'Aquila, Richard et al., "Maximizing sensitivity and specificity of PCR by pre-amplification heating", Nucleic Acids Research, 19(13), 1991, p. 3749.

Daruwala, Raoul-Sam et al., "A Versatile Statistical Analysis Algorithm to Detect Genome Copy Number Variation", PNAS, 101(46), 2004, 16292-16297.

Dawson, S.J. et al., "Analysis of Circulating Tumor DNA to Monitor Metastatic Breast Cancer", The New England Journal of Medicine, vol. 368, No. 13, Mar. 2, 280136, 1199-1209.

De Bruin, E. et al., "Spatial and temporal diversity in genomic instability processes defines lung cancer evolution", Science, vol. 346, No. 6206, Oct. 10, 2014, 251-256.

De Vries, et al., "Diagnostic genome profiling in mental retardation", Am J Hum Genet, 77, published online Aug. 30, 2005, 2005, 606-616.

Deangelis, M. et al., "Solid-phase Reversible Immobilization for the Isolation of PCR Products", Nucleic Acids Research, 23 (22), 1995, 4742-4743.

Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.

(56) References Cited

OTHER PUBLICATIONS

Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Dieffenbach, C W. et al., "General concepts for PCR primer design", Genome Research. PCR methods and Applications vol. 3, 1993, S30-S37.
Diehl, F. et al., "Circulating mutant DNA to assess tumor dynamics", Nature Medicine, vol. 14, No. 9, Jul. 31, 2008, 985-990.
Dietmaier, W. et al., "Multiple Mutation Analyses in Single Tumor Cells with Improved Whole Genome Amplification", American Journal of Pathology, vol. 154, No. 1, Jan. 1999, 83-95.
Ding, C et al., "Direct molecular haplotyping of long-range genomic DNA with M1-PCR", PNAS 100(13), 2003, 7449-7453.
Dodge, Y. , "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na-K+ -Cl-Cotransporter (NKCC1) in Asthmatic Subjects", Genome Res., 11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series, 1261, 2004, 12-14.
EP06838311.6, , "European Communication and Extended European Search Report", dated Dec. 30, 2008, 8 pgs.
EP08742125.1, , "European Communication pursuant to Article 94(3) EPC and Examination Report", dated Feb. 12, 2010, 5 pgs.
Everitt, B. S. , "Medical Statistics From A to Z", 2003, 3 pages.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS One, vol. 5, Issue 5 (e10439), May 3, 2010, 1-6.
Fan, Jian-Bing et al., "Highly Parallel Genomic Assay", Nature Reviews, 7, 2006, 632-644.
Fat Secret, , "5 Foods to Never Eat", "www.fatsecret.com" (printed from internet Nov. 1, 2014)., 2 pages.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S et al., "Differential Effects of Chronic Pulsatile Versus Chronic Constant Maternal Hyperglycemia on Fetal Pancreatic B- Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Garcia-Murillas, I. et al., "Mutation tracking in circulating tumor DNA predicts relapse in early breast cancer", Science Translational Medicine, vol. 7, No. 302, Aug. 26, 2015, 1-2.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Geiss, G. K. et al., "Direct multiplexed measurement of gene expression with color-coded probe pairs", Nature Biotechnology, vol. 26, No. 3, Feb. 17, 2008, 317-325.

(56) References Cited

OTHER PUBLICATIONS

Ghanta, Sujana et al., "Non-Invasive Prenatal Detection of Trisomy 21 Using Tandem Single Nucleotide Polymorphisms", PLoS One, 5 (10), 2010, 10 pgs.

Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.

Gjertson, David W. et al., "Assessing Probability of Paternity and the Product Rule in DNA Systems", Genetica, 96, 1995, 89-98.

Greenwalt, T. et al., "The Quantification of Fetomaternal Hemorrhage by an Enzyme-Linked Antibody Test with Glutaraldehyde Fixation", Vox Sang, 63, 1992, 268-271.

Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.

Guerra, J., "Terminal Contributions for Duplex Oligonucleotide Thermodynamic Properties in the Context of Nearest Neighbor Models", Biopolymers, 95(3), (2010), 2011, 194-201.

Guetta, Esther et al., "Analysis of Fetal Blood Cells in the Maternal Circulation: Challenges, Ongoing Efforts, and Potential Solutions", Stem Cells and Development, 13, 2004, 93-99.

Guichoux, et al., "Current Trends in Microsatellite Genotyping", Molecular Ecology Resources, 11, 2011, 591-911.

Gunderson, K. L. et al., "A genome-wide scalable SNP genotyping assay using microarray technology", Nature Genetics, vol. 37, No. 5, May 2005, 549-554.

Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].

Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.

Handyside, et al., "Isothermal whole genome amplification from single and small Nos. of cells: a new era for preimplantation genetic diagnosis of inherited disease", Molecular Human Reproduction vol. IO, No. 10 pp. 767-772, 2004.

Hara, Eiji et al., "Subtractive cDNA cloning using oligo(dT)30-latex and PCR: isolation of cDNA clones specific to undifferentiated human embryonal carcinoma cells", Nucleic Acids Research, 19(25), 1991, 7097-7104.

Hardenbol, P., "Multiplexed Genotyping With Sequence-Tagged Molecular Inversion Probes", Nature Biotechnology, 21 (6), 2003, 673-678.

Hardenbol, Paul et al., "Highly multiplexed molecular inversion probe genotyping: Over 10,000 targeted SNPs genotyped in a singled tube assay", Genome Research, 15, 2005, 269-275.

Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.

Harper, J. C. et al., "Recent Advances and Future Developments in PGD", Prenatal Diagnosis, 19, 1999, 1193-1199.

Harton, G.L. et al., "Preimplantation Genetic Testing for Marfan Syndrome", Molecular Human Reproduction, 2 (9), 1996, 713-715.

Hartwell, L. H. et al., "Chapter 11: The Direct Detection of Genotype Distinguishes Individual Genomes", Genetics: From Genes To Genomes, Second Edition, 2004, 371-414.

Hartwell, L. H. et al., "Chapter 13: Chromosomal Rearrangements and Changes in Chromosome Number Reshape Eukaryotic Genomes", Genetics: From Genes To Genomes, Second Edition, 2004, 441-486.

Hattori, M. et al., "The DNA sequence of human chromosome 21", Nature, vol. 405, May 18, 2000, 311-319.

Hawkins, T. et al., "Whole genome amplification—applications and advances", Current Opinion in Biotechnology, 13, 2002, 65-67.

Hayden, et al., "Multiplex-Ready Pcr: A new method for multiplexed SSR and SNP genotyping", BMC Genomics 2008, 9(80), 1-12.

Hellani, A. et al., "Clinical Application of Multiple Displacement Amplification in Preimplantation Genetic Diagnosis", Reproductive BioMedicine Online, 10 (3), 2005, 376-380.

Hellani, Ali et al., "Multiple displacement amplification on single cell and possible PGD applications", Molecular Human Reproduction, 10(11), 2004, 847-852.

Hojsgaard, S. et al., "BIFROST—Block recursive models induced from relevant knowledge, observations, and statistical techniques", Computational Statistics & Data Analysis, 19(2), 1995, 155-175.

Hollas, B. et al., "A stochastic approach to count RN A molecules using DNA sequencing methods", Lecture Notes in Computer Science, vol. 2812, 2003, 55-62.

Holleley, et al., "Multiplex Manager 1.0: a Cross-Platform Computer Program that Plans and Optimizes Multiplex PCR", BioTechniques46:511-517 (Jun. 2009), 511-517.

Hollox, E. et al., "Extensive Normal Copy Number Variation of a β-Defensin Antimicrobial-Gene Cluster", Am. J. Hum. Genet., 73, 2003, 591-600.

Homer, et al., "Resolving Individuals Contributing Trace Amounts of DNA to Highly Complex Mixtures Using High-Density SNP Genotyping Microarrays", PLOS Genetics, 4(8), 2008, 9 pgs.

Hoogendoorn, Bastiaan et al., "Genotyping Single Nucleotide Polymorphisms by Primer Extension and High Performance Liquid Chromatography", Hum Genet, 104, 1999, 89-93.

Hornak, M. et al., "Aneuploidy Detection in Pigs Using Comparative Genomic Hybridization: From the Oocytes to Blastocysts", PLoS One, vol. 7, No. 1, Jan. 2012, 6 pages.

Hospital, F. et al., "A General Algorithm to Compute Multilocus Genotype Frequencies Under Various Mating Systems" vol. 12, No. 6, Jan. 1, 1996 (Jan. 1, 1996), pp. 455-462.

Howie, et al., "Fast and accurate genotype imputation in genome-wide association studies through pre-phasing", Nature Genetics, vol. 44, No. 8, Jul. 22, 2012, 955-959.

Hu, Dong Gui et al., "Aneuploidy Detection in Single Cells Using DNA Array-Based Comparative Genomic Hybridization", Molecular Human Reproduction, 10(4), 2004, 283-289.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina, , "Patent Owner Illumina's Preliminary Response To Petition", Oct. 17, 2018, 75 pgs.

Illumina, , "Petition for Inter Partes Review of U.S. Pat. No. 8,682,592", Jun. 13, 2019, 91 pages.

Illumina, , "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.

Illumina, , "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.

Illumina Catalog, , "Paired-End Sample Preparation Guide, Illumina Catalog# PE-930-1 001, Part# 1005063 Rev. E", 2011, 1-40.

Illumina, Inc., , "Declaration of David Peters, Ph.D. in Support of Petition for Inter Partes Review of U.S. Pat. No. 8,682,592", Jun. 13, 2019, 136 pages.

*Illumina, Inc. V. Natera, Inc.*, , "Order Re: Claim Construction", Jan. 30, 2019, 16 pgs.

Imielinski, M. et al., "Mapping the Hallmarks of Lung Adenocarcinoma with Massively Parallel Sequencing", Cell, vol. 150, Sep. 14, 2012, 1107-1120.

Ishii, et al., "Optimization of Annealing Temperature To Reduce Bias Caused by a Primer Mismatch in Multitemplate PCR", Applied and Environmental Microbiology, Aug. 2001, p. 3753-3755.

(56) References Cited

OTHER PUBLICATIONS

Jabara, C. B. et al., "Accurate sampling and deep sequencing of the HIV-1 protease gene using a Primer ID", PNAS, vol. 108, No. 50, Dec. 13, 2011, 20166-20171.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T. , "Next generation sequencing technologies", Drug Discovery Today: Technologies, vol. 2, No. 3, 2005, 255-260.

Jenkins, S. et al., "High-throughput SNP genotyping", Comparative and Functional Genomics, vol. 3, Dec. 5, 2001, 57-66.

Johnson, D.S. et al., "Comprehensive Analysis of Karyotypic Mosaicism Between Trophectoderm and Inner Cell Mass", Molecular Human Reproduction, 16(12), 2010, 944-949.

Johnson D.S, et al., "Preclinical Validation of a Microarray Method for Full Molecular Karyotyping of Blastomeres in a 24-h Protocol", Human Reproduction, 25 (4), 2010, 1066-1075.

Kamat, A. A. et al., "Quantification of total plasma cell-free DNA in ovarian cancer using real-time PCR", Ann N Y Acad Sci., vol. 1075, Sep. 2006, 230-234.

Kaplinski, Lauris et al., "MultiPLX: Automatic Grouping and Evaluation of PCR Primers", Bioinformatics, 21(8), 2005, 1701-1702.

Kazakov, V.I. et al., "Extracellular DNA in the Blood of Pregnant Women", Tsitologia, vol. 37, No. 3, 1995, 1-8.

Kijak, G. et al., "Discrepant Results in the Interpretation of HIV-1 Drug-Resistance Genotypic Data Among Widely Used Algorithms", HIV Medicine, 4, 2003, 72-78.

Kim, H. et al., "Whole-genome and multisector exome sequencing of primary and post-treatment glioblastoma reveals patterns of tumor evolution", Genome Research, vol. 25, No. 3, Feb. 3, 2015, 316-327.

Kinde, I. et al., "Detection and quantification of rare mutations with massively parallel sequencing", PNAS, vol. 108, No. 23, Jun. 7, 2011, 9530-9535.

Kinnings, S. L. et al., "Factors affecting levels of circulating cell-free fetal DNA in maternal plasma and their implications for noninvasive prenatal testing", Prenatal Diagnosis, vol. 35, 2015, 816-822.

Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.

Kivioja, T. et al., "Counting absolute numbers of molecules using unique molecular identifiers", Nature Methods, Advance Online Publication, Nov. 20, 2011, 1-5.

Konfortov, Bernard A. et al., "An Efficient Method for Multi-Locus Molecular Haplotyping", Nucleic Acids Research, 35(1), e6, 2007, 8 pgs.

Krjutskov, K. et al., "Development of a single tube 640-plex genotyping method for detection of nucleic acid variations on microarrays", Nucleic Acids Research, vol. 36, No. 12, May 23, 2008, 7 pages.

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.

Kunishima, S. et al., "First description of somatic mosaicism in MYH9 disorders", British Journal of Haematology, vol. 128, 2005, 360-365.

Kwok, P. Y. , "High-throughput genotyping assay approaches", Pharmacogenomics, vol. 1, No. 1, 2000, 1-5.

Lambert-Messerlian, G. et al., "Adjustment of Serum Markers in First Trimester Screening", Journal of Medical Screening, 16 (2), 2009, 102-103.

Lander, E. S. et al., "Initial sequencing and analysis of the human genome", Nature, vol. 409, Feb. 15, 2001, 860-921.

Lathi, Ruth B. et al., "Informatics Enhanced SNP Microarray Analysis of 30 Miscarriage Samples Compared to Routine Cytogenetics", PLoS One, 7(3), 2012, 5 pgs.

Leary, R. J. et al., "Development of Personalized Tumor Biomarkers Using Massively Parallel Sequencing", Science Translational Medicine, vol. 2, No. 20, Feb. 24, 2010, 1-8.

Leary, Rebecca J et al., "Detection of Chromosomal Alterations in the Circulation of Cancer Patients with Whole-Genome Sequencing", Science Translational Medicine, 4, 162, 2012, 12.

Levsky, J. M. et al., "Fluorescence in situ hybridization: past, present and future", Journal of Cell Science, vol. 116, No. 14, 2003, 2833-2838.

Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.

Li, Ying et al., "Size Separation of Circulatory DNA in Maternal Plasma Permits Ready Detection of Fetal DNA Polymorphisms", Clinical Chemistry, 50, 6, 2004, 1002-1011.

Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).

Liew, Michael et al., "Genotyping of Single-Nucleotide Polymorphisms", Clinical Chemistry, 50(7), 2004, 1156-1164.

Life Technologies, , "Ion AmpliSeq™ Designer provides full flexibility to sequence genes of your choice", Retrieved from the Internet<URL: http://tools.lifetechnologies.com/content/sfs/brochures/IonAmpliSeq_Cust omPanels_AppNote_CO1, 2012, 4 pages.

Lindberg, J. et al., "Exome Sequencing of Prostate Cancer Supports the Hypothesis of Independent Tumour Origins", European Urology, vol. 63, 2013, 347-353.

Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.

Lo, et al., "Digital PCR for the Molecular Detection of Fetal Chromosomal Aneuploidy", PNAS, vol. 104, No. 32, Aug. 7, 2007, 13116-13121.

Lo, et al., "Fetal Nucleic Acids in Maternal Blood: the Promises", Clin. Chem. Lab. Med., 50(6), 2012, 995-998.

Lo, et al., "Free Fetal DNA in Maternal Circulation", JAMA, 292(23), (Letters to the Editor), 2004, 2835-2836.

Lo, , "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet,2, 8676, 1989, 1363-1365.

Lo, et al., "Rapid Clearance of Fetal DNA from Maternal Plasma", Am. J. Hum. Genet., 64, 1999, 218-224.

Lo, et al., "Strategies for the Detection of Autosomal Fetal DNA Sequence from Maternal Peripheral Blood", Annals New York Academy of Sciences,731, 1994, 204-213.

(56) References Cited

OTHER PUBLICATIONS

Lo, et al., "Two-way cell traffic between mother and fetus: biologic and clinical implications", Blood, 88(11), Dec. 1, 1996, 4390-4395.
Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.
Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine,, 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y-M D. , "Non-invasive prenatal diagnosis using fetal cells in maternal blood", J. Clin. Pathol., vol. 47, 1994, 1060-1065.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D et al., "Detection of Fetal RhD Sequence from Peripheral Blood of Sensitized RhD-Negative Pregnant Women", British Journal of Haematology, 87, 1994, 658-660.
Lo, Y-M.D et al., "Prenatal Determination of Fetal RhD Status by Analysis of Peripheral Blood of Rhesus Negative Mothers", The Lancet, 341, 1993, 1147-1148.
Lu, I. et al., "Establishment of a system based on universal multiplex-PCR for screening genetically modified crops", Anal. Bioanal. Chem, vol. 396, Oct. 24, 2009, 2055-2064.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Ma, Xiaotu et al., "Rise and fall of subclones from diagnosis to relapse in pediatric B-acute lymphoblastic leukaemia", Nature Communications, vol. 6, Mar. 19, 2015, 1-12.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 TRIAL", Cancer Research, vol. 79, No. 4 Supplement, Feb. 15, 2019.
Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Mardis, E. R. , "The impact of next-generation sequencing technology on genetics", Trends in Genetics, vol. 24, No. 3, Feb. 11, 2008, 133-141.
Margulies, M. et al., "Genome sequencing in microfabricated high-density picolitre reactors", Nature, vol. 437, Sep. 15, 2005, 376-380.
Margulies, M. et al., "Genome sequencing in microfabricated high-density picolitre reactors plus Supplemental Methods", Nature, vol. 437, Sep. 15, 2005, 40 pgs.
Markoulatos, P. et al., "Multiplex Polymerase Chain Reaction: A Practical Approach", Journal of Clinical Laboratory Analysis, vol. 16, 2002, 47-51.
May, Robert M. , "How Many Species Are There on Earth?", Science, 241, Sep. 16, 1988, 1441-1449.
McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.
McCloskey, M. L. et al., "Encoding PCR Products with Batch-stamps and Barcodes", Biochem Genet., vol. 45, Oct. 23, 2007, 761-767.
McCray, Alexa T. et al., "Aggregating UMLS Semantic Types for Reducing Conceptual Complexity", Medinfo 2001: Proceedings of the 10th World Congress on Medical Informatics (Studies in Health Technology and Informatics, 84, V. Patel et al. (eds.), IOS Press Amsterdam, 2001, 216-220.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
Mennuti, M. et al., "Is It Time to Sound an Alarm About False-Positive Cell-Free DNA Testing for Fetal Aneuploidy?", American Journal of Obstetrics, 2013, 5 pgs.
Merriam-Webster, , "Medical Definition of Stimulant", http://www.merriam-webster.com/medical/stimulant, Mar. 14, 2016, 7 pages.
Merriam-Webster, , "Universal Definition", "Merriam-Webster.com (http://www.merriam-webster.com/dictionary/universal, downloaded Jul. 23, 2014)", 3 pages.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Mertes, F. et al., "Targeted enrichment of genomic DNA regions for next-generation sequencing", Briefings in Functional Genomics, vol. 10, No. 6, Nov. 26, 2011, 374-386.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Miner, B. E. et al., "Molecular barcodes detect redundancy and contamination in hairpin-bisulfite PCR", Nucleic Acids Research, vol. 32, No. 17, Sep. 30, 2004, 1-4.
Minkoff, E. et al., "Stem Cells, Cell Division, and Cancer", Biology Today Third Edition, Chapter 12, 2004, 10 pages.
Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
Munne, S. et al., "Chromosome Abnormalities in Human Embryos", Textbook of Assisted Reproductive Techniques, 2004, pp. 355-377.
Munne, S. et al., "Chromosome abnormalities in human embryos", European Society of Human Reproduction and Embryology: Human Reproduction Update, vol. 4, No. 6, 1998, 842-855.
Munne, S. et al., "Improved implantation after preimplantation genetic diagnosis of aneuploidy", Reproductive BioMedicine Online, vol. 7., No. 1., May 15, 2003, 91-97.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V. , "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.

(56) References Cited

OTHER PUBLICATIONS

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Natera, Inc., , "Declaration of Sandra L. Haberny", May 16, 2019, 3 pages.
Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., , "Exhibit 8 EHRICH Invalidity Chart", Aug. 20, 2018, 16 pages.
Natera, Inc., , "Exhibits A-H to Haberny Declaration", May 16, 2019, 192 pages.
Natera, Inc., , "Motion to Dismiss", May 16, 2019, 2 pages.
Natera, Inc., , "Natera Inc.'s First Amended Answer, Affirmative Defenses and Counterclaims", Aug. 16, 2018, 28 pages.
Natera, Inc., , "Natera, Inc.'s Supplemental Objections and Response To Plaintiff Illumina, Inc.'s Interrogatory No. 8", Mar. 20, 2019, 29 pages.
Natera, Inc., , "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
NCBI, , "dbSNP record for rs1294331", Retrieved from the Internet: <URL: www.ncbi.nlm.nih.gov/snp/?term=rs 1294331 >, 2019, 2 pgs.
NCBI, , "dbSNP record for rs1872575", Retrieved from the Internet: <URL: www.ncbi.nlm.nih.gov/snp/?term=rs1872575, 2019, 2 pgs.
NCBI, , "dbSNP record for rs2362450", Retrieved from the Internet: <URL: www.ncbi.nlm.nih.gov/snp/?term=rs2362450>, 2019, 1 pg.
NCBI, , "dbSNP record for rs2384571", Retrieved from the Internet: <URL: www.ncbi.nlm.nih.gov/snp/?term=rs2384571>, 2019, 2 pgs.
NCBI, , "dbSNP record for rs2498982", Retrieved from the Internet: <URL: www.ncbi.nlm.nih.gov/snp/?term=rs2498982>, 2019, 3 pgs.
NCBI, , "dbSNP record for rs3731877", Retrieved from the Internet: <URL: www.ncbi.nlm.nih.gov/snp/?term=rs3731877>, 2019, 2 pgs.
Newman, A. M. et al., "Integrated digital error suppression for improved detection of circulating tumor DNA", Nature Biotechnology, vol. 34, No. 5, May 2016, 547-555.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T. , "A high-plex PCR approach for massively parallel sequencing", BioTechniques, vol. 55, No. 2, Aug. 2013, 69-74.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.

Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
O'Malley, R. et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of $\phi 29$ polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, G. E. et al., "DNA sequencing of maternal plasma to detect Down syndrome: An international clinical validation study", Genetics In Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Papadopoulou, E. et al., "Cell-Free DNA and RNA in Plasma as a New Molecular Marker for Prostate Cancer", Oncology Research, vol. 14, 2004, 439-445.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Pastinen, T. et al., "Minisequencing: A Specific Tool for DNA Analysis and Diagnostics on Oligonucleotide Arrays", Genome Research, vol. 7, 1997, 606-614.
Pathak, A. et al., "Circulating Cell-Free DNA in Plasma/Serum of Lung Cancer Patients as a Potential Screening and Prognostic Tool", Clinical Chemistry, 52, 2006, 1833-1842.
PCT/US2006/045281, , "International Preliminary Report on Patentability", dated May 27, 2008, 1 pg.
PCT/US2006/045281, , "International Search Report and Written Opinion", dated Sep. 28, 2007, 7 pgs.
PCT/US2008/003547, , "International Search Report", dated Apr. 15, 2009, 5 pgs.
PCT/US2009/034506, , "International Search Report", dated Jul. 8, 2009, 2 pgs.
PCT/US2009/045335, , "International Search Report", dated Jul. 27, 2009, 1 pg.
PCT/US2009/052730, , "International Search Report", dated Sep. 28, 2009, 1 pg.
PCT/US2010/050824, , "International Search Report", dated Nov. 15, 2010, 2 pgs.
PCT/US2011/037018, , "International Search Report", dated Sep. 27, 2011, 2 pgs.
PCT/US2011/061506, , "International Search Report", dated Mar. 16, 2012, 1 pgs.
PCT/US2011/066938, , "International Search Report", dated Jun. 20, 2012, 1 pg.
PCT/US2012066339, , "International Search Report", dated Mar. 5, 2013, 1 pg.
PCT/US2013/028378, , "International Search Report and Written Opinion", dated May 28, 2013, 11 pgs.
PCT/US2013/57924, , "International Search Report and Written Opinion", dated Feb. 18, 2014, 8 pgs.
PCT/US2014/051926, , "International Search Report and Written Opinion", dated Dec. 9, 2014, 3 pgs.
Pearson, K. , "On the criterion that a given system of deviations from the probable in the case of a correlated system of variables is

(56) References Cited

OTHER PUBLICATIONS such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends In Genetics, 10, 6, 1994, 204-209.
Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M., "Overcoming the Challenges of Multiplex PCR", Biocompare Editorial Article, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, D., "List of Materials Considered By David Peters, Ph.D.", Jun. 13, 2019, 2 pages.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST®) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics, 1(5), 2008, 1-15.
Poirier, K. et al., "Maternal mosaicism for mutations in the ARX gene in a family with X linked mental retardation", Human Genetics, vol. 118, Aug. 3, 2005, 45-48.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterility, vol. 97, No. 2, Feb. 2012, 395-401.
Rabinowitz, Matthew et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.

Ragoussis, J., "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Reinert, T. et al., "Analysis of circulating tumour DNA to monitor disease burden following colorectal cancer surgery", Gut, vol. 65, 2016, 625-634.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet:<http://www.youandyourfamily.com/article.php?story=Eating+by+Trimester>, 2014, 3.
Riley, D. E., "DNA Testing: An Introduction For Non-Scientists An Illustrated Explanation", Scientific Testimony: An Online Journal, http://www.scientific.org/tutorials/articles/riley/riley.html, Apr. 6, 2005, 22 pages.
Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.
Rogaeva, E. et al., "The Solved and Unsolved Mysteries of the Genetics of Early-Onset Alzheimer's Disease", NeuroMolecular Medicine, vol. 2, 2002, 1-10.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L. M., "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Sahota, A., "Evaluation of Seven PCR-Based Assays for the Analysis of Microchimerism", Clinical Biochemistry, vol. 31, No. 8., 1998, 641-645.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, vol. 46, No. 1, 2001, 43-46.
Schmitt, M. W. et al., "Detection of ultra-rare mutations by next-generation sequencing", PNAS, vol. 109, No. 36, Sep. 4, 2012, 14508-14513.
Schoumans, J et al., "Detection of chromosomal imbalances in children with idiopathic mental retardation by array based comparative genomic hybridisation (array-CGH)", JMed Genet, 42, 2005, 699-705.

(56) References Cited

OTHER PUBLICATIONS

Schwarzenbach, H. et al., "Cell~free nucleic acids as biomarkers in cancer patients", Nature Reviews: Cancer, vol. 11, Jun. 2011, 426-437.

Sebat, Jonathan et al., "Strong Association of De Novo Copy Number Mutations with Autism", Science, 316, 2007, 445-449.

Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.

Sermon, Karen et al., "Preimplantation genetic diagnosis", The Lancet, Lancet Limited. 363(9421), 2000, 1633-1641.

Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.

Sham, P. et al., "DNA Pooling: A Tool for Large-Scale Association Studies", Nature Reviews Genetics, vol. 3, Nov. 2002, 862-871.

Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.

Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.

Shen, R. et al., "High-throughput SNP genotyping on universal bead arrays", Mutation Research, vol. 573, Feb. 11, 2005, 70-82.

Shen, Zhiyong, "MPprimer: a program for reliable multiplex PCR primer design", BMC Bioinformatics 2010, 11:143, 1-7.

Sherlock, J et al., "Assessment of Diagnostic Quantitative Fluorescent Multiplex Polymerase Chain Reaction Assays Performed on Single Cells", Annals of Human Genetics,62, 1, 1998, 9-23.

Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.

Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.

Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.

Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.

Simpson, J. et al., "Fetal Cells in Maternal Blood: Overview and Historical Perspective", Annals New York Academy of Sciences, 731, 1994, 1-8.

Sint, Daniela et al., "Advances in Multiplex PCR: Balancing Primer Efficiencies and Improving Detection Success", Methods in Ecology and Evolution, 3, 2012, 898-905.

Slater, Howard et al., "High-Resolution Identification of Chromosomal Abnormalities Using Oligonucleotide Arrays Containing 116,204 SNPs", Am. J. Hum. Genet., 77, 5, 2005, 709-726.

Snijders, Antoine et al., "Assembly of Microarrays for Genome-Wide Measurement of DNA Copy Number", Nature Genetic, 29, 2001, 263-264.

Snyder, T. M. et al., "Universal noninvasive detection of solid organ transplant rejection", PNAS, vol. 108, No. 15, Apr. 12, 2011, 6229-6234.

Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1--319.e9.

Sparks, Andrew B. et al., "Selective Analysis of Cell-Free DNA in Maternal Blood for Evaluation of Fetal Trisomy", Prenatal Diagnosis, 32, 2012, 1-7.

Spiro, Alexander et al., "A Bead-Based Method for Multiplexed Identification and Quantitation of DNA Sequences Using Flow Cytometry", Applied and Environmental Microbiology, 66, 10, 2000, 4258-4265.

Spits, C et al., "Optimization and Evaluation of Single-Cell Whole Genome Multiple Displacement Amplification", Human Mutation, 27(5), 496-503, 2006.

Srinivasan, et al., "Noninvasive Detection of Fetal Subchromosome Abnormalities via Deep Sequencing of Maternal Plasma", The American Journal of Human Genetics 92, 167-176, Feb. 7, 2013.

Stephens, Mathews et al., "A Comparison of Bayesian Methods for Haplotype Reconstruction from Population Genotype Data", Am. J. Hum. Genet.,73, 2003, 1162-1169.

Stevens, Robert et al., "Ontology-Based Knowledge Representation for Bioinformatics", Briefings in Bioinformatics, 1, 4, 2000, 398-414.

Steyerberg, E.W et al., "Application of Shrinkage Techniques in Logistic Regression Analysis: A Case Study", Statistica Neerlandica, 55(1), 2001, 76-88.

Strom, C. et al., "Three births after preimplantation genetic diagnosis for cystic fibrosis with sequential first and second polar body analysis", American Journal of Obstetrics and Gynecology, 178 (6), 1998, 1298-1306.

Strom, Charles M. et al., "Neonatal Outcome of Preimplantation Genetic Diagnosis by Polar Body Removal: The First 109 Infants", Pediatrics, 106( 4), 2000, 650-653.

Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.

Su, S.Y. et al., ""Inferring combined CNV/SNP haplotypes from genotype data"", Bioinformatics, vol. 26, No. 11,1, Jun. 1, 2010, 1437-1445.

Sun, Guihua et al., "SNPs in human miRNA genes affect biogenesis and function", RNA, 15(9), 2009, 1640-1651.

Sweet-Kind Singer, J. A. et al., "Log-penalized linear regression", IEEE International Symposium on Information Theory, 2003. Proceedings, 2003, 286.

Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.

Takara Biomedicals, , "Competitive PCR Guide", Lit. # L0126, Aug. 1999, 9 pages.

Taliun, D. et al., "Efficient haplotype block recognition of very long and dense genetic sequences", BMC Bioinformatics, vol. 15 (10), 2014, 1-18.

Tamura, et al., "Sibling Incest and formulation of paternity probability: case report", Legal Medicine, 2000, vol. 2, p. 189-196.

Tang, et al., , Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.

Tang, N. et al., "Detection of Fetal-Derived Paternally Inherited X-Chromosome Polymorphisms in Maternal Plasma", Clinical Chemistry, 45 (11), 1999, 2033-2035.

Tebbutt, S. J. et al., "Microarray genotyping resource to determine population stratification in genetic association studies of complex disease", BioTechniques, vol. 37, Dec. 2004, 977-985.

Ten Bosch, J. , "Keeping Up With the Next Generation Massively Parallel Sequencing in Clinical Diagnostics", Journal of Molecular Diagnostics, vol. 10, No. 6, 2008, 484-492.

Tewhey, R. et al., "The importance of phase information for human genomics", Nature Reviews Genetics, vol. 12, No. 3, Mar. 1, 2011, 215-223.

The International Hapmap Consort, , "The International HapMap Project", NATURE, vol. 426, Dec. 18, 2003, 789-796.

Thermofisher Scientific, , "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.

(56) References Cited

OTHER PUBLICATIONS

Thomas, M.R et al., "The Time of Appearance and Disappearance of Fetal DNA from the Maternal Circulation", Prenatal Diagnosis, 15, 1995, 641-646.
Tiersch, T. R. et al., "Reference Standards for Flow Cytometry and Application in Comparative Studies of Nuclear DNA Content", Cytometry, vol. 10, Mar. 21, 1989, 706-710.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Tounta, G. et al., "A Multiplex PCR for Non-invasive Fetal RHD Genotyping Using Cell-free Fetal DNA", in vivo, vol. 25, 2011, 411-418.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Turner, E. et al., "Massively Parallel Exon Capture and Library-Free Resequencing Across 16 Genomes", Nature Methods, 6 (5), 2009, 315-316.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Tzimagiorgis, G. et al., "Recovering circulating extracellular or cell-free RNA from bodily fluids", Cancer Epidemiology, vol. 35, 2011, 580-589.
Vallone, Peter , "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, D. G. et al., "Large-Scale Identification, Mapping, and Genotyping of Single-Nucleotide Polymorphisms in the Human Genome", Science, vol. 280, May 15, 1998, 1077-1082.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, T.L. et al., "Digital karyotyping", PNAS, vol. 99, No. 25, Dec. 10, 2002, 16156-16161.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Weiss, C. A. , "Chapter 8: Confidence Intervals for One Population Mean", Introductory Statistics, Sixth Edition, 2002, 340-381.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8(32), NULL, 2012, 1-9.
Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.
Wikipedia, , "Buffy coat", Retrieved from "https://en.wikipedia.orgJw/index.php?title=Buffy_coat&oldid=900992886", Jun. 9, 2019, 2 pgs.
Wikipedia, , "Maximum a posteriori estimation", https://en.wikipedia.org/w/index.php?title=Maximum_a_posteriori_estimat ion&oldid=26878808, [retrieved on Aug. 1, 2017], Oct. 30, 2005, 2 pages.
Wikipedia, , "Stimulant", (available at https://en.wikipedia.org/wiki/Stimulant, accessed Mar. 14, 2016), 17 pages.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Yuan, X. et al., "Probability Theory-based SNP Association Study Method for Identifying Susceptibility Loci and Genetic Disease

(56) References Cited

OTHER PUBLICATIONS

Models in Human Case-Control Data", IEEE Trans Nanobioscience, vol. 9, No. 4, Dec. 2010, 232-241.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.
Zachariah, R. et al., "Circulating cell-free DNA as a potential biomarker for minimal and mild endometriosis", Reproductive BioMedicine Online, vol. 18, No. 3, Jan. 27, 2009, 4007-411.
Zhang, L. et al., "Whole genome amplification from a single cell: Implications for genetic analysis", Proc. Nat'l. Acad. Sci. USA, vol. 89, Jul. 1992, 5847-5851.
Zhang, Rui et al., "Quantifying RNA allelic ratios by microfluidic multiplex PCR and sequencing", Nature Methods, 11(1), 2014, 51-56.
Zhao, Xiaojun et al., "An Integrated View of Copy Number and Allelic Alterations in the Cancer Genome Using Single Nucleotide Polymorphism Arrays", Cancer Research,64, 2004, 3060-3071.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Zimmermann, B., "Declaration Under 37 CFR 1.32", filed in U.S. Appl. No. 14/171,587, filed Feb. 3, 2014, 4 pgs.
Zimmermann, B., "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Bau, Stephan, et al., "Targeted next-generation sequencing by specific capture of multiple genomic loci using low-volume microfluidic DNA arrays", Anal Bioanal Chem, 2009, 171-175.
Lanman, et al., "Analytical and Clinical Validation of a Digital Sequencing Panel for Quantitative, Highly Accurate Evaluation of Cell-Free Circulating Tumor DNA", Plos One, 2015, 1-27.
Lee, et al., "ERBB2 kinase domain mutation in the lung squamous cell carcinoma", Cancer Letters, 2006, 89-94.
Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.
Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Diehl, F. et al., "Detection and quantification of mutations in the plasma of patients with colorectal tumors", PNAS, vol. 102, No. 45, Nov. 8, 2005, 16368-16373.
Fouquet, C. et al., "Rapid and Sensitive p53 Alteration Analysis in Biopsies from Lung Cancer Patients Using a Functional Assay and A Universal Oligonudeotide Array: A Prospective Study", Clinical Cancer Research, vol. 10, May 15, 2004, 3479-3489.
Spertini, D. et al., "Screening of Transgenic Plants by Amplification of Unknown Genomic DNA Flanking T-DNA", BioTechniques, vol. 27, Aug. 1999, 308-314.
"HumanOmni 1—Quad BeadChip", Illumina DNA Analysis, HumanOmni 1 array product information datasheet, 2009, 1 page.
"HumanOmni2.5-8 BeadChips", Illumina; Data Sheet: DNA Analysis, HumanOmni2.5-8 array product information datasheet, 2011, 1 page.

"Quantitative Detection of Circulating Donor-Specific DNA in Organ Transplant Recipients (DTRT-Multi-Center Study) (DTRT)", ClinicalTrials.gov Identifier: NCT02109575., Apr. 10, 2014, Last updated Mar. 26, 2021, 9 pages.
"The Journal of Heart and Lung Transplantation", Apr. 2012., vol. 31, Issue 4, Supplement, pp. A1-A4, S1-S310. https://www.google.de/searchq=The+Journal+of+Heart+and+Lung+Transplantation+Volume+31,+Issue+4,+Supplement&sourceid=ie7&rls=com.microsoft:en-US:IE-Address&ie=&oe=#spf=1604593918239, Last Accessed: Oct. 13, 2015., A1-A4.
18820195.8, "Extended European Search Report", dated Jan. 27, 2021, 9 pages.
18821381.3, "Extended European Search Report", dated Feb. 15, 2021, 9 pages.
Adamek, Martina et al., "A fast and simple method for detecting and quantifying donor-derived cell-free DNA in sera of solid organ transplant recipients as a biomarker for graft function", Clinical Chemistry and Laboratory Medicine : Journal of the Forum of the European Societies of Clinical Chemistry, vol. 54, No. 7, doi:10.1515/CCLM-2015-0622, ISSN 1437-4331, (Jul. 1, 2016), pp. 1147-1155.
Agbor-Enoh, et al., "Applying rigor and reproducibility standards to assay donor-derived cell-free DNA as a non-invasive method for detection of acute rejection and graft injury after heart transplantation", J Heart Lung Transplant, 36(9):1004-1012. doi: 10.1016/j.healun.2017.05.026. Epub May 20, 2017., 17 pages.
Agbor-Enoh, et al., "Cell-Free DNA to Detect Heart Allograft Acute Rejection", Circulation, Mar. 23, 2021;143(12): doi: 10.1161/CIRCULATIONAHA.120.049098. Epub Jan. 13, 2021, 1184-1197.
Ahmadian, A. et al., "Analysis of the p53 Tumor Suppressor Gene by Pyrosequencing", BioTechniques, vol. 28, Jan. 2000, 140-147.
Ahmed, et al., "Cell Free DNA and Procalcitonin as Early Markers of Complications in ICU Patients with Multiple Trauma and Major Surgery", Clin Lab, Dec. 1, 2016;62(12) ; doi: 10.7754/Clin.Lab.2016.160615., 2395-2404.
Alachkar, "Serum and urinary biomarkers in acute kidney transplant rejection", Nephrol Ther., Feb. 2012;8(1): doi: 10.1016/j.nephro.2011.07.409. Epub Oct. 21, 2011, 13-19.
Almeida, et al., "Evaluation of 16 SNPs allele-specific to quantify post hSCT chimerism by SYBR green-based qRT-PCR", J Clin Pathol., Mar. 2013;66(3):. doi: 10.1136/jclinpath-2012-201224. Epub Jan. 2, 2013., 238-242.
Andargie, et al., "Cell-free DNA maps COVID-19 tissue injury and risk of death and can cause tissue injury", JCI Insight, Apr. 8, 2021;6(7):e147610. doi: 10.1172/jci.insight.147610, 20 pages.
Arshad, et al., "Elevated Cell-Free Mitochondrial DNA in Filtered Plasma Is Associated With HIV Infection and Inflammation", J Acquir Immune Defic Syndr., May 1, 2018;78(1): doi: 10.1097/QAI.0000000000001650., 111-118.
Avriel, et al., "Admission Cell Free DNA Levels Predict 28-Day Mortality in Patients with Severe Sepsis in Intensive Care", PLoS One., Jun. 2, 20143;9(6):e100514. doi: 10.1371/journal.pone.0100514. eCollection 2014., 7 pages.
Ayyadevara, et al., "Discrimination of primer 3'-nucleotide mismatch by taq DNA polymerase during polymerase chain reaction", Anal Biochem. Aug. 15, 2000, 284(1), 11-18.
Bai, et al., "Detection and quantification of heteroplasmic mutant mitochondrial DNA by real-time amplification refractory mutation system quantitative PCR analysis: a single-step approach", Clin Chem., Jun. 2004; 50(6); Epub Apr. 8, 2004., 996-1001.
Benesova, et al., "Mutation-based detection and monitoring of cell-free tumor DNA in peripheral blood of cancer patients", Analytical Biochemistry, vol. 433, 2013, 227-234.
Benn, Peter et al., "Current Controversies in Prenatal Diagnosis 2: NIPT results suggesting maternal cancer should always be disclosed", Prenetal Diagnosis, vol. 39, No. 5, 2018, 339-343.
Bergallo, et al., "A novel TaqMAMA assay for allelic discrimination of TLR9 rs352140 polymorphism", J Virol Methods, May 2017;243. doi: 10.1016/j.jviromet.2017.01.015. Epub Jan. 28, 2017., 25-30.
Bergallo, et al., "Evaluation of IFN-y polymorphism+874 T/A in patients with recurrent tonsillitis by PCR real time mismatch amplification mutation assay (MAMA real time PCR)", Cytokine., Feb. 2015; 71(2): Epub Dec. 2014., 278-282.

(56) References Cited

OTHER PUBLICATIONS

Bezieau, et al., "High incidence of N and K-Ras activating mutations in multiple myeloma and primary plasma cell leukemia at diagnosis", Hum Mutat., Sep. 2001;18(3):. doi: 10.1002/humu. 1177, 212-224.

Bianchi, Diana W. et al., "Noninvasive Prenatal Testing and Incidental Detection of Occult Maternal Malignancies", JAMA The Journal of the American Medical Association, vol. 314, No. 2, 2015, 162.

Bienkowski, et al., "Liquid biopsy for minimally invasive heart transplant monitoring: a pilot study", J Clin Pathol., Aug. 2020;73(8): doi: 10.1136/jclinpath-2019-205926. Epub Dec. 5, 2019., 507-510.

Birkenkamp-Demtroder, et al., "Longitudinal assessment of multiplex patient-specific ctDNA biomarkers in bladder cancer for diagnosis, surveillance and recurrence", Annals of Oncology, Oxford University Press NLD, vol. 29, No. Supplement 8, 2018, viii26.

Board, et al., "Detection of PIK3CA mutations in circulating free DNA in patients with breast cancer", Breast Cancer Res Treat, Apr. 2010;120(2): doi: 10.1007/s10549-010-0747-9. Epub Jan. 28, 2010, 461-467.

Board, et al., "Multiplexed assays for detection of mutations in PIK3CA", Clin Chem., Apr. 2008; 54(4), 757-760.

Bolotin, D. A. et al., "MiXCR: software for comprehensive adaptive immunity profiling", Nature, vol. 12, No. 5, May 2015, 380-381.

Braun, et al., "Limitation of Circulating cfDNA Under the Use of a Cytokine Elimination Adsorber (CytoSorb) in Cardiac Surgery", The Thoracic and Cardiovascular Surgeon, Jan. 2018; 66(S01): S1-S110, 1 page.

Brochet, X. et al., "IMGT/V-QUEST: the highly customized and integrated system for IG and TR standardized V-J and V-D-J sequence analysis", Nucleic Acids Research, vol. 36, May 23, 2008, W503-W508.

Bronkhorst, et al., "The emerging role of cell-free DNA as a molecular marker for cancer management", Biomol Detect Quantif, Mar. 18, 2019;17:100087. doi: 10.1016/j.bdq.2019.100087., 23 pages.

Bunnapradist, S. et al., "Using both the fraction and Quantity of Donor-Derived Cell-free DNA to Detect Kidney Allograft Rejection", JASN, vol. 32, 2021, 2439-2441.

Burgstaller, et al., "Mitochondrial DNA heteroplasmy in ovine fetuses and sheep cloned by somatic cell nuclear transfer", BMC Dev Biol., Dec. 21, 2007;7:141, 10 pages.

Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.

Cabel, et al., "Circulating tumor DNA changes for early monitoring of anti-PD1 immunotherapy: a proof-of-concept study", Ann Oncol., Aug. 1, 2017;28(8); doi: 10.1093/annonc/mdx212., 1996-2001.

Cagliani, et al., "Deoxyribonuclease Reduces Tissue Injury and Improves Survival After Hemorrhagic Shock", J Surg Res., May 2020;249: doi: 10.1016/j.jss.2019.11.036. Epub Jan. 8, 2020., 104-113.

Castells, et al., "K-ras mutations in DNA extracted from the plasma of patients with pancreatic carcinoma: diagnostic utility and prognostic significance", J Clin Oncol., Feb. 1999;17(2): doi: 10.1200/JCO.1999.17.2.578., 578-584.

Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, S139.

Cawkwell, L. et al., "Rapid detection of allele loss in colorectal tumours using microsatellites and fluorescent DNA technology", Br. J. Cancer, vol. 67, 1993, 1262-1267.

Chan, et al., "Bioinformatics analysis of circulating cell-free DNA sequencing data", Clin Biochem., Oct. 2015;48(15); doi: 10.1016/j.clinbiochem.2015.04.022. Epub May 9, 2015., 962-975.

Chen, et al., "Non-invasive prenatal diagnosis using fetal DNA in maternal plasma: a preliminary study for identification of paternally-inherited alleles using single nucleotide polymorphisms", BMJ Open, Jul. 22, 2015;5(7):e007648. doi: 10.1136/bmjopen-2015-007648., 8 pages.

Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.

Chen, KE et al., "Multiplex PCR with the Blunt Hairpin Primers for Next Generation Sequencing", Biotechnology and Bioprocess Engineering, vol. 22, 2017, 347-351.

Cheng, et al., "Cell-Free DNA in Blood Reveals Significant Cell, Tissue and Organ Specific injury and Predicts COVID-19 Severity", medRxiv., Jul. 29, 2020;2020.07.27.20163188. doi: 10.1101/2020.07.27.20163188., 16 pages.

Chiu, et al., "Effects of blood-processing protocols on fetal and total DNA quantification in maternal plasma", Clin Chem., Sep. 2001;47(9): PubMed PMID: 11514393., 1607-1613.

Chiu, et al., "Noninvasive prenatal exclusion of congenital adrenal hyperplasia by maternal plasma analysis: a feasibility study", Clin Chem., May 2002;48(5), 778-780.

Chothia, C. et al., "Canonical structures for the hypervariable regions of immunoglobulins", Journal of Molecular Biology, vol. 196, No. 4, Aug. 20, 1987, 901-917.

Chu, et al., "A novel approach toward the challenge of accurately quantifying fetal DNA in maternal plasma", Prenat Diagn., Dec. 2010;30(12-13): doi: 10.1002/pd.2656, 1226-1229.

Chun, et al., "Dual priming oligonucleotide system for the multiplex detection of respiratory viruses and SNP genotyping of CYP2C19 gene", Nucleic Acids Research, vol. 35, No. 6, 2007, 1-6.

Chung, et al., "Cell-free DNA fetal fraction and pregnancy outcome", American Journal of Obstetrics & Gynecology, vol. 222, No. 1, 2019, S157.

Clementi, et al., "The Role of Cell-Free Plasma DNA in Critically Ill Patients with Sepsis", Blood Purif., 2016;41(1-3): doi: 10.1159/000440975. Epub Oct. 20, 2015, 34-40.

Costa, J.-M. et al., "Fetal RHD genotyping in maternal serum during the first trimester of pregnancy", British Journal of Haematology, vol. 119, 2002, 255-260.

Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.

Daly, "Circulating donor-derived cell-free DNA: a true biomarker for cardiac allograft rejection?", Ann Transl Med., Mar. 2015;3(4):47. doi:10.3978/j.issn.2305-5839.2015.01.35, 6 pages.

Dandel, et al., "Non-invasive cardiac allograft rejection surveillance: reliability and clinical value for prevention of heart failure", Heart Fail Rev., Mar. 2021;26(2): doi: 10.1007/s10741-020-10023-3. Epub Sep. 5, 2020., 319-336.

Daniels, G. et al., "Fetal blood group genotyping from DNA from maternal plasma: an important advance in the management and prevention of haemolytic disease of the fetus and newborn", Vox Sanguinis, vol. 87, 2004, 223-232.

Dastsooz, et al., "Multiplex ARMS PCR to Detect 8 Common Mutations of ATP7B Gene in Patients With Wilson Disease", Hepat Mon., May 16, 2013;13(5):e8375. doi: 10.5812/hepatmon.8375. eCollection 2013., 7 pages.

De Vlaminck, et al., "Circulating cell-free DNA enables noninvasive diagnosis of heart transplant rejection", Sci Transl Med., Jun. 18, 2014;6(241):241ra77. doi: 10.1126/scitranslmed.3007803, 20 pages.

De Vlaminck, et al., "Circulating cell-free DNA enables noninvasive diagnosis of heart transplant rejection", Sci Transl Med., Jun. 18, 2014;6(241):241ra77. Supplemental Materials., 6 pages.

De Vlaminck, et al., "Noninvasive monitoring of infection and rejection after lung transplantation", Proc Natl Acad Sci U S A, Oct. 27, 2015;112(43): doi: 10.1073/pnas.1517494112. Epub Oct. 12, 2015., 13336-13341.

Delgado, et al., "Characterization of cell-free circulating DNA in plasma in patients with prostate cancer", Tumour Biol., Apr. 2013;34(2): doi: 10.1007/s13277-012-0634-6. Epub Dec. 27, 2012, 983-986.

(56) References Cited

OTHER PUBLICATIONS

Deshpande, et al., "Relationship Between Donor Fraction Cell-Free DNA and Treatment for Rejection in Heart Transplantation", Pediatric Transplantation, Jun. 2022; 26(4):e14264. https://doi.org/10.1111/petr.14264, 11 pages.
Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.
Dey, et al., "A plasma telomeric cell-free DNA level in unaffected women with BRCA1 or/and BRCA2 mutations: a pilot study. Oncotarget", Oncotarget, Dec. 29, 2017;9(3): doi: 10.18632/oncotarget.23767. eCollection Jan. 9, 2018., 4214-4222.
Dharajiya, Nilesh et al., "Incidental Detection of Maternal Neoplasia in Noninvasive Prenatal Testing", Clinical Chemistry, vol. 64, No. 2, 2018, 329-335.
Diaz, et al., "Liquid Biopsies: Genotyping Circulating Tumor DNA", Journal of Clinical Oncology, vol. 32, No. 6, 2014, 579-586.
Diehl, et al., "Detection and quantification of mutations in the plasma of patients with colorectal tumors", Proceedings of the National Academy of Sciences, vol. 102, 2005, 16368-16373.
Ding, et al., "New Progress in Plasma Cell-free DNA in Clinical Applications", Progress in Modern Biomedicine, 2016; 18: 3476, 3593-3596.
Dwivedi, et al., "Prognostic utility and characterization of cell-free DNA in patients with severe sepsis", Crit Care, Aug. 13, 2012;16(4):R151. doi: 10.1186/cc11466., 11 pages.
Ehlayel, A. et al., "Emerging monitoring technologies in kidney transplantation", Pediatric Nephrology, vol. 36, 2021, 3077-3087.
Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.
Fleischhacker, et al., "Circulating nucleic acids (CNAs) and cancer—a survey", Biochim Biophys Acta, Jan. 2007;1775(1): doi: 10.1016/j.bbcan.2006.10.001. Epub Oct. 7, 2006., 181-232.
García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 1958-1966.
Garnacho-Montero, et al., "Prognostic and diagnostic value of eosinopenia, C-reactive protein, procalcitonin, and circulating cell-free DNA in critically ill patients admitted with suspicion of sepsis", Crit Care, Jun. 5, 2014;18(3):R116. doi: 10.1186/cc13908, 9 pages.
Ghanta, et al., "Non-invasive prenatal detection of trisomy 21using tandem single nucleotide polymorphisms", PLoS One, Oct. 8, 2010;5(10):e13184. doi: 10.1371/journal.pone.0013184, 10 pages.
Gielis, et al., "Cell-Free DNA: An Upcoming Biomarker in Transplantation", Am J Transplant, Oct. 2015; 15(10): doi: 10.1111/ajt.13387. Epub Jul. 16, 2015, 2541-2551.
Gielis, et al., "Plasma donor-derived cell-free DNA kinetics after kidney transplantation using a single tube multiplex PCR assay", PLoS One, 2018; 13(12): e0208207, 16 pages.
Glaab, et al., "A novel assay for allelic discrimination that combines the fluorogenic 5' nuclease polymerase chain reaction (TaqMan) and mismatch amplification mutation assay", Mutat Res., Nov. 29, 1999;430(1), 1-12.
Glaab, W. E. et al., "A novel assay for allelic discrimination that combines the fluorogenic 5' nuclease polymerase chain reaction (TaqMan) and mismatch amplification mutation assay", Mutation Research, vol. 430, 1999, 12 pgs.
Gordon, et al., "An Algorithm Measuring Donor Cell-Free DNA in Plasma of Cellular and Solid Organ Transplant Recipients That Does Not Require Donor or Recipient Genotyping", Front Cardiovasc Med., Sep. 22, 2016;3:33. eCollection 2016., 10 pages.
Gordon, Paul et al., "An Algorithm Measuring Donor Cell-Free DNA in Plasma of Cellular and Solid Organ Transplant Recipients That Does Not Require Donor or Recipient Genotyping", Frontiers in Cardiovascular Medicine, 2016, vol. 3.
Gormally, et al., "Amount of DNA in plasma and cancer risk: a prospective study", Int J Cancer, Sep. 20, 2004;111(5): doi: 10.1002/ijc.20327, 746-749.
Gotoh, et al., "Prediction of MYCN amplification in neuroblastoma using serum DNA and real-time quantitative polymerase chain reaction", J Clin Oncol., Aug. 1, 2005;23(22): PubMed PMID: 16051962., 5205-5210.
Grenda, R., "Torque teno (TTV) viral load as a biomarker of immunosuppressive strength after kidney transplantation in children", Pediatric Nephrology, vol. 36, May 27, 2020, 3 pages.
Gripp, et al., "*Homo sapiens* KRAS proto-oncogene, GTPase (KRAS), RefSeqGene (LRG_344) on chromosome 12", GenBank Submission; Accession No. NG_007524, version NG_007524.2, Aug. 16, 2020., 16 Pages.
Grskovic, et al., "Validation of a Clinical-Grade Assay to Measure Donor-Derived Cell-Free DNA in Solid Organ Transplant Recipients", J Mol Diagn., Nov. 2016;18(6): doi: 10.1016/j.jmoldx.2016.07.003. Epub 2016, 890-902.
Guedj, et al., "A refined molecular taxonomy of breast cancer", Oncogene, Mar. 1, 2012;31(9):1196-206. doi: 10.1038/onc.2011.301. Epub Jul. 25, 2011., 34 pages.
Gusella, J. et al., "Precise localization of human B-globin gene complex on chromosome 11*", Proc. Natl. Acad. Sci USA, vol. 76, No. 10, Oct. 1979, 5239-5243.
Hainer & Fazzio, "High-Resolution Chromatin Profiling Using CUT&RUN", Current Protocols in Molecular Biology, 2019, 1-22.
Hasi, et al., "Acetaldehyde dehydrogenase 2 SNP rs671 and susceptibility to essential hypertension in Mongolians: a case control study", Genet Mol Res., Mar. 29, 2011;10(1). doi: 10.4238/vol10-1gmr1056., 537-543.
Hidestrand, et al., "Highly sensitive noninvasive cardiac transplant rejection monitoring using targeted quantification of donor-specific cell-free deoxyribonucleic acid", J Am Coll Cardiol., Apr. 1, 2014;63(12). doi:10.1016/j.jacc.2013.09.029. Epub Oct. 16, 2013., 1224-1226.
Hidestrand, et al., "Highly Sensitive Transplant Rejection Surveillance Using Targeted Detection of Donor Specific Cell Free DNA", J Heart Lung Transplant, Apr. 2012; 31(4), S91-S92.
Hidestrand, et al., "Influence of temperature during transportation on cellfree DNA analysis", Fetal Diagn Ther., 2012; 31, 122-128.
Hidestrand, et al., "Quantification of Circulating Donor Specific Cell Free DNA Is an Exquisitely Sensitive Non-Invasive Indicator of Injury to the Donor Heart", J Heart Lung Transplant, 2013; 32, S101-S102.
Hiendleder, et al., "Functional genomics: tools for improving farm animal health and welfare", Rev. Sci. Tech. Off. Int. Epiz., 24 (1), 2005, 354-377.
Hoerning, et al., "Quantitative real-time ARMS-qPCR for mitochondrial DNA enables accurate detection of microchimerism in renal transplant recipients", Pediatr Transplant, Dec. 2011; 15(8). doi: 10.1111/j.1399-3046.2011.01581.x. Epub Oct. 4, 2011, 809-818.
Hou, et al., "Application of tetra primer ARMS-PCR approach for detection of Fusarium graminearum genotypes with resistance to carbendazim", Australian Plant Pathology, Jan. 1, 2013; 42(1), 73-78.
Huang, et al., "Circulating cell-free DNA levels correlate with postresuscitation survival rates in out-of-hospital cardiac arrest patients", Resuscitation, Feb. 2012;83(2): doi: 10.1016/j.resuscitation.2011.07.039. Epub Aug. 22, 2011., 213-218.
Huang, et al., "*Homo sapiens* TSC complex subunit 1 (TSC1), RefSeqGene (LRG_486) on chromosome 9", GenBank Submission; Accession No. NG_012386, version NG_012386.1, Sep. 21, 2020, 20 Pages.
Hudecova, "Digital PCR analysis of circulating nucleic acids", Clin Biochem., Oct. 2015;48(15): doi: 10.1016/j.clinbiochem.2015.03.015. Epub Mar. 28, 2015, 948-956.
Hugon, et al., "Influence of intention to adhere, beliefs and satisfaction about medicines on adherence in solid organ transplant recipients", Transplantation., Jul. 27, 2014;98(2): doi: 10.1097/TP.0000000000000221, 222-228.
Illumina, "HumanOmni1-Quad BeadChip", Illumina DNA Analysis, Pub. No. 370-21009-007, 2009, 1 page.

(56) References Cited

OTHER PUBLICATIONS

Illumina, "HumanOmni2.5-8 BeadChips: Next-Generation GWAS Content for Genotyping and CNV Analysis", Data Sheet: DNA Analysis, Pub. No. 370-2011-008, 2011, 1 page.
Illumina, "Illumina Adapter Sequences", Published by Illumina, 2018, 1-45.
Ji, Xing et al., "Copy number variation profile in noninvasive prenatal testing (NIPT) can identify co-existing maternal malignancies: Case reports and a literature review", Taiwanese Journal of Obstetrics and Gynecology, vol. 57, No. 6, 2018, 871-877.
Jing, et al., "Cell-free DNA: characteristics, detection and its applications in myocardial infarction", Curr Pharm Des., 2013;19(28): doi: 10.2174/1381612811319280012., 5135-5145.
Jordan, et al., "Donor-derived Cell-free DNA Identifies Antibody-mediated Rejection in Donor Specific Antibody Positive Kidney Transplant Recipients", Transplant Direct, 2018;4(9):e379, 5 pages.
Jordens, et al., "Amplification with molecular beacon primers and reverse line blotting for the detection and typing of human papillomaviruses", Journal of Virological Methods, vol. 89, 2000, 29-37.
Jung, et al., "Cell-free DNA in the blood as a solid tumor biomarker—a critical appraisal of the literature", Clin Chim Acta., Nov. 11, 2010;411(21-22): doi: 10.1016/j.cca.2010.07.032. Epub Aug. 2, 2010., 1611-1624.
Kaboev, et al., "PCR hot start using primers with the structure of molecular beacons (hairpin-like structure)", Nucleic Acids Research, vol. 28, 2000, 1-2.
Karapetis, et al., "K-ras mutations and benefit from cetuximab in advanced colorectal cancer", N Engl J Med., Oct. 23, 2008;359(17). doi: 10.1056/NEJMoa0804385., 1757-1765.
Keshavjee, S. H. et al., "The role of dextran 40 and potassium in extended hypothermic lung preservation for transplantation", The Journal of Thoracic and Cardiovascular Surgery, vol. 103, No. 2, 1992.
Khater & Khauli, "Pseudorejection and true rejection after kidney transplantation: classification and clinical significance", Urol Int., 90(4), 2012, 373-80.
Khush, et al., "Circulating cell-free DNA as a non-invasive marker of pediatric heart transplant rejection and immunosuppressive treatment", J Heart Lung Transplantation, Apr. 2016. 35(4):Abstract 181, S75.
Khush, et al., "Noninvasive detection of graft injury after heart transplant using donor derived cell free DNA: A prospective multicenter study", Am J Transplant, Oct. 2019;19(10): doi: 10.1111/ajt.15339. Epub Apr. 8, 2019., 2889-2899.
Kim, et al., "Personalized therapy on the horizon for squamous cell carcinoma of the lung", Lung Cancer, vol. 80, 2013, 249-255.
Kindel, et al., "Early Changes in Donor Fraction Cell-free DNA in Newly Transplanted Heart Transplant Patients", ISHLT DF cfDNA declanation poster, 2018, 1 Page.
Kirkizlar, et al., "Detection of Clonal and Subclonal Copy-Number Variants in Cell-Free DNA from Patients with Breast Cancer Using a Massively Multiplexed PCR Methodology", Transl Oncol., Oct. 2015;8(5): doi: 10.1016/j.tranon.2015.08.004., 407-416.
Kittler, R. et al., "A Whole Genome Amplification Method to Generate Long Fragments from Low Quantities of Genomic DNA", Analytical Biochemistry, vol. 300, 2002, 237-244.
Ku, et al., "Exome versus transcriptome sequencing in identifying coding region variants", Expert Review of Molecular Diagnostics, vol. 12, 2012, 241-251.
Kulifaj, D. et al., "Development of a standardized real time PCR for Torque teno viruses (TTV) viral load detection and quantification: A new tool for immune monitoring", Journal of Clinical Virology, vol. 105, 2018, 118-127.
Kuo, et al., "Preimplantation and prenatal genetic diagnosis of aromatic L-amino acid decarboxylase deficiency with an amplification refractory mutation system-quantitative polymerase chain reaction", Taiwan J Obstet Gynecol, Dec. 2011;50(4): doi: 10.1016/j.tjog.2011.10.012., 468-473.

Kustanovich, et al., "Life and death of circulating cell-free DNA", Cancer Biol Ther., 2019;20(8): doi: 10.1080/15384047.2019. 1598759. Epub Apr. 16, 2019, 1057-1067.
Lajin, et al., "A quadruplex tetra-primer ARMS-PCR method for the simultaneous detection of TP53 Arg72Pro, IVS3 16bp Del/Ins and IVS6+62A>G, and NQO1 C609T polymorphisms", Gene., Aug. 10, 2012; 504(2): Epub May 23, 2012., 268-273.
Lajoie, B. R. et al., "The Hitchhiker's Guide to Hi-C Analysis: Practical guidelines", Methods: Author manuscript, vol. 72, Jan. 2015, 65-75.
Landegren, U. et al., "Reading Bits of Genetic Information: Methods for Single-Nucleotide Polymorphism Analysis", Genome Research, vol. 8, No. 8, 769-776, 1997.
Lang, et al., "Optimized allele-specific real-time PCR assays for the detection of common mutations in KRAS and BRAF", J Mol Diagn., Jan. 2011;13(1): doi: 10.1016/j.jmoldx.2010.11.007. Epub Dec. 23, 2010., 23-28.
Laurent-Puig, et al., "Clinical relevance of KRAS-mutated subclones detected with picodroplet digital PCR in advanced colorectal cancer treated with anti-EGFR therapy", Clin Cancer Res., Mar. 1, 2015;21(5): doi: 10.1158/1078-0432.CCR-14-0983. Epub Sep. 23, 2014., 1087-1097.
Lecomte, et al., "Detection of free-circulating tumor-associated DNA in plasma of colorectal cancer patients and its association with prognosis", Int J Cancer, Aug. 10, 2002;100(5): doi: 10.1002/ijc. 10526., 542-548.
Lee, et al., "Allele-Specific Quantitative PCR for Accurate, Rapid, and Cost-Effective Genotyping", Hum Gene Ther., Jun. 2016;27(6): doi: 10.1089/hum.2016.011. Epub Mar. 17, 2016., 425-435.
Lefebure, et al., "Prognostic value of circulating mutant DNA in unresectable metastatic colorectal cancer", Ann Surg., Feb. 2010;251(2): doi: 10.1097/SLA.0b013e3181c35c87, 275-280.
Lenaerts, Liesbeth et al., "Noninvasive Prenatal Testing and Detection of Occult Maternal Malignancies", Clinical Chemistry, vol. 65, No. 12, 2019, 1484-1486.
Levy, et al., "Analysis of Cell-Free DNA to Assess Risk of Tumoremia Following Endoscopic Ultrasound Fine-Needle Aspiration of Pancreatic Adenocarcinomas", Clin Gastroenterol Hepatol., Oct. 2018; 16(10): e1. doi: 10.1016/j.cgh.2018.02.048. Epub Mar. 8, 2018., 1632-1640.
Li, et al., "Multiplex co-amplification of 24 retinoblastoma gene exons after pre-amplification by long-distance PCR", Nucleic Acids Res., Feb. 1, 1996;24(3), 538-539.
Liang, et al., "Cationic nanoparticle as an inhibitor of cell-free DNA-induced inflammation", Nat Commun., Oct. 16, 2018;9(1):4291. doi: 10.1038/s41467-018-06603-5, 14 pages.
Lievre, et al., "KRAS mutations as an independent prognostic factor in patients with advanced colorectal cancer treated with cetuximab", J Clin Oncol., Jan. 20, 2008;26(3): doi: 10.1200/JCO.2007.12. 5906., 374-379.
Lin, et al., "A new diagnostic system for ultra-sensitive and specific detection and quantification of Candidatus Liberibacter asiaticus, the bacterium associated with citrus Huanglongbing", J Microbial Methods, 2010, 17-25.
Liu, et al., "ABO chimerism determined by real-time polymerase chain reaction analysis after ABO-incompatible haematopoietic stem cell transplantation", Blood Tranfus, Jan. 2013;11(1): doi: 10.2450/2012.0013-12. Epub Jul. 4, 2012., 43-52.
Liu, et al., "Comparison of next-generation sequencing systems", J Biomed Biotechnol., 2012;2012: doi: 10.1155/2012/251364. Epub Jul. 5, 2012., 1-11.
Livergood, "Adverse perinatal outcomes and cell free DNA no calls: Beyond low fetal fraction", American Journal of Obstetrics & Gynecology, vol. 218, No. 1, 2018, S169.
Llop, et al., "Development of a highly sensitive nested-PCR procedure using a single closed tube for detection of Erwinia amylovora in asymptomatic plant material", Appl Environ Microbial., 2000, 2071-8.
Lo, et al., "Plasma placental RNA allelic ratio permits noninvasive prenatal chromosomal aneuploidy detection", Nat Med., Feb. 2007; 13(2): doi: 10.1038/nm1530. Epub Jan. 7, 2007., 218-223.

(56) References Cited

OTHER PUBLICATIONS

Lo, et al., "Transplantation monitoring by plasma DNA sequencing", Clin Chem., Jul. 2011;57(7): doi: 10.1373/clinchem.2011.166686. PubMed PMID: 21566070., 941-942.
Lo, Y.M. D. et al., "Prenatal Diagnosis of Fetal RhD Status by Molecular Analysis of Maternal Plasma", The New England Journal of Medicine, vol. 339, No. 24, 1998, 1734-1738.
Luo, et al., "Detection of usual and atypical aldehyde dehydrogenase alleles by mismatch amplification mutation assay", Clin Chem Lab Med., Dec. 2001;39(12): doi: 10.1515/CCLM.2001.189., 1195-1197.
Mak, et al., "Rapid diagnosis of Wilson disease by a 28-mutation panel: real-time amplification refractory mutation system in diagnosing acute Wilsonian liver failure", Clin Chim Acta., Dec. 2008; 398(1-2): doi: 10.1016/j.cca.2008.08.002. Epub Aug. 8, 2008., 39-42.
Manage, et al., "Genotyping single nucleotide polymorphisms in human genomic DNA with an automated and self-contained PCR cassette", J Mol Diagn., Sep. 2014;16(5): doi:10.1016/j.jmoldx.2014.04.004. Epub Jul. 2, 2014., 550-557.
Margulies, et al., "Genome Sequencing in Open Microfabricated High Density Picoliter Reactors", Nature, 437(7057), 2005, 376-380.
Martinez-Herrero, et al., "Cancer protection elicited by a single nucleotide polymorphism close to the adrenomedullin gene", J Clin Endocrinol Metab., Apr. 2013;98(4): doi: 10.1210/jc.2012-4193. Epub Feb. 28, 2013., E807-E810.
Marusyk, et al., "Causes and consequences", Biochimica et Biophysica Acta, vol. 1805, 2010, 105-117.
Mehra, et al., "Gene expression profiles and B-type natriuretic peptide elevation in heart transplantation: more than a hemodynamic marker", Circulation, Jul. 4, 2006;114(1 Suppl), I21-I26.
Mehra, et al., "International Society for Heart and Lung Transplantation working formulation of a standardized nomenclature for cardiac allograft vasculopathy-2010", J Heart Lung Transplant, Jul. 2010;29(7) .doi: 10.1016/j.healun.2010.05.017., 717-727.
Mengel, et al., "The molecular phenotype of heart transplant biopsies: relationship to histopathological and clinical variables", Am J Transplant, Sep. 2010;10(9): doi: 10.1111/j.1600-6143.2010.03182.x., 2105-2115.
Misale, et al., "Emergence of KRAS mutations and acquired resistance to anti-EGFR therapy in colorectal cancer", Nature, Jun. 28, 2012;486(7404): doi: 10.1038/nature11156., 532-536.
Mouliere, et al., "Circulating Cell-Free DNA from Colorectal Cancer Patients May Reveal High KRAS or BRAF Mutation Load", Transl Oncol., Jun. 1, 2013;6(3): doi: 10.1593/tlo.12445. Print Jun. 2013., 319-328.
Myers, et al., "ACB-PCR quantification of somatic oncomutation", Methods Mol Biol., 2014;1105: doi:10.1007/978-1-62703-739-6_27, 345-363.
Namlos, H.M. et al., "Use of liquid biopsies to monitor disease progression in a sarcoma patient: a case report", BMC Cancer, vol. 17, No. 1, 2017, 2-3.
Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.
Newton, et al., "Analysis of any point mutation in DNA. The amplification refractory mutation system (ARMS)", Nucleic Acids Res., Apr. 11, 1989;17(7): doi: 10.1093/nar/17.7.2503, 2503-2516.
Nilsson, et al., "Analyzing genes using closing and replicating circles", Trends in Biotechnology, 24, 2006, 83-88.
North, et al., "Cell-free DNA donor fraction analysis in pediatric and adult heart transplant patients by multiplexed allele-specific quantitative PCR: Validation of a rapid and highly sensitive clinical test for stratification of rejection probability", PLoS One, Jan. 13, 2020;15(1):e0227385. doi: 10.1371/journal.pone.0227385. eCollection 2020., 48 pages.

Norton, et al., "Perinatal and genetic outcomes associated with no call cfDNA results in 18,496 pregnancies", American Journal of Obstetrics & Gynecology, vol. 224, No. 2, 2021, S3.
Oeth, et al., "Qualitative and quantitative genotyping using single base primer extension coupled with matrix-assisted laser desorption/ionization time-of-flight mass spectrometry (MassARRAY®).", Methods Mol. Biol., 2009; 578, 307-343.
Ohya, K. et al., "Detection of the CTG Repeat Expansion in Congenital Myotonic Dystrophy", Jpn J. Human Genet, vol. 42, 1997, 169-180.
Orou, et al., "Allele-specific competitive blocker PCR: a one-step method with applicability to pool screening", Hum Mutat., 1995;6(2): doi: 10.1002/humu.1380060209., 163-169.
Parsons, et al., "Allele-specific competitive blocker-PCR detection of rare base substitution", Methods Mol Biol., 2005;291, 235-245.
PCT/US2017/059808, "International Preliminary Report on Patentability", dated May 16, 2019, 8 pages.
PCT/US2017/059808, "International Search Report and Written Opinion for Application", dated Jan. 25, 2018, 12 pages.
PCT/US2018/038598, "International Preliminary Report on Patentability", dated Jan. 2, 2020, 6 pages.
PCT/US2018/038598, "International Search Report and Written Opinion", dated Sep. 7, 2018, 8 pages.
PCT/US2018/038609, "International Preliminary Report on Patentability", dated Jan. 2, 2020, 7 pages.
PCT/US2018/038609, "International Search Report and Written Opinion", dated Sep. 10, 2018, 9 pages.
Peng, et al., "Comparison of K-ras mutations in lung, colorectal and gastric cancer", Oncol Lett., Aug. 2014;8(2): doi: 10.3892/ol.2014.2205. Epub May 30, 2014., 561-565.
Peyster, et al., "Advanced Morphologic Analysis for Diagnosing Allograft Rejection: The Case of Cardiac Transplant Rejection", Transplantation, Aug. 2018;102(8): doi: 10.1097/TP.0000000000002189., 1230-1239.
Price, et al., "Cost-effective interrogation of single nucleotide polymorphisms using the mismatch amplification mutation assay and capillary electrophoresis", Electrophoresis, Dec. 2010;31(23-24): doi: 10.1002/elps.201000379., 3881-3888.
Purhonen, et al., "Human plasma cell-free DNA as a predictor of infectious complications of neutropenic fever in hematological patients", Infect Dis (Lond)., Apr. 2015;47(4): doi: 10.3109/00365548.2014.985711. Epub Feb. 9, 2015., 255-259.
Qin, et al., "Quantitative assessment of hematopoietic chimerism by quantitative real-time polymerase chain reaction of sequence polymorphism systems after hematopoietic stem cell transplantation", Chin Med J (Engl), Aug. 2011;124(15), 2301-2308.
Quail, et al., "A tale of three next generation sequencing platforms: comparison of Ion torrent, pacific biosciences and illumina MiSeq sequencers", BMC Genomics, Jul. 24, 2012;13:341. doi: 10.1186/1471- 2164-13-341, 13 pages.
Raemdonck, Dirk Van et al., "Ex-vivo lung perfusion", Transplant International, vol. 28, Issue 6, Special Issue: Focus Issue: Machine Perfusion, 2014, 643-656.
Ragalie, et al., "Description of Longitudinal Measurement of Donor Fraction of Cell-Free DNA and Correlation to Clinical Outcomes", ISHLT poster, 2018, 1 page.
Ragalie, et al., "Noninvasive Assay for Donor Fraction of Cell-Free DNA in Pediatric Heart Transplant Recipients", J Am Coll Cardiol., Jun. 26, 2018;71(25): doi: 10.1016/j.jacc.2018.04.026, 2982-2983.
Rechitsky, S. et al., "Allele Dropout in Polar Bodies and Blastomeres", Journal of Assisted Reproduction and Genetics, vol. 15, No. 5, 1998, 253-257.
Richmond, et al., "Donor fraction cell-free DNA and rejection in adult and pediatric heart transplantation", J Heart Lung Transplant, May 2020;39(5): doi: 10.1016/j.healun.2019.11.015. Epub Nov. 29, 2019., 454-463.
Roedder, et al., "Biomarkers in solid organ transplantation: establishing personalized transplantation medicine", Genome Med., Jun. 8, 2011;3(6):37, 12 pages.
Sanmamed, et al., "Quantitative cell-free circulating BRAFV600E mutation analysis by use of droplet digital PCR in the follow-up of

(56) References Cited

OTHER PUBLICATIONS patients with melanoma being treated with BRAF inhibitors", Clin Chem., Jan. 2015;61(1): doi: 10.1373/clinchem.2014.230235. Epub Nov. 19, 2014., 297-304.

Sapio, et al., "Detection of BRAF mutation in thyroid papillary carcinomas by mutant allele-specific PCR amplification (MASA)", Eur J Endocrinol., Feb. 2006;154(2): doi: 10.1530/eje.1.02072, 341-348.

Saukkonen, et al., "Cell-free plasma DNA as a predictor of outcome in severe sepsis and septic shock.", Clin Chem., Jun. 2008;54(6): doi: 10.1373/clinchem.2007.101030. Epub Apr. 17, 2008. PubMed PMID: 18420731., 1000-1007.

Scheffer, et al., "Association between low fetal fraction in cell-free DNA testing and adverse pregnancy outcome: A systematic review", Prenatal Diagnosis, vol. 41, No. 10, 2021, 1287-1295.

Schnittger, et al., "Development and validation of a real-time quantification assay to detect and monitor BRAFV600E mutations in hairy cell leukemia", Blood., Mar. 29, 2012;119(13): doi: 10.1182/blood-2011-10-383323. Epub Feb. 13, 2012., 3151-3154.

Schutz, et al., "Graft-derived cell-free DNA, a noninvasive early rejection and graft damage marker in liver transplantation: A prospective, observational, multicenter cohort study", PLoS Med., Apr. 25, 2017;14(4):e1002286. doi: 10.1371/journal.pmed.1002286. eCollection Apr. 2017., 19 pages.

Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.

Schwarzenbach, et al., "Cell-free nucleic acids as biomarkers in cancer patients", Nat Rev Cancer, Jun. 2011; 11(6): doi: 10.1038/nrc3066. Epub May 12, 2011, 426-437.

Scott, et al., "Elevated nuclear and mitochondrial cell-free deoxyribonucleic acid measurements are associated with death after infant cardiac surgery", J Thorac Cardiovasc Surg., Aug. 2022;164(2): doi: 10.1016/j.jtcvs.2021.10.066. Epub Dec. 24, 2021., 367-375.

Scott, et al., "Total Cell-Free DNA Predicts Death and Infection Following Pediatric and Adult Heart Transplantation", Ann Thorac Surg., Oct. 2021;112(4): doi: 10.1016/j.athoracsur.2020.08.006. Epub Oct. 8, 2020., 1282-1289.

Sefrioui, et al., "Clinical value of chip-based digital-PCR platform for the detection of circulating DNA in metastatic colorectal cancer", Dig Liver Dis., Oct. 2015;47(10): doi: 10.1016/j.dld.2015.05.023. Epub Jun. 5, 2015, 884-890.

Selzner, Markus et al., "Normothermic Ex Vivo Liver Perfusion Using Steen Solution as Perfusate for Human Liver Transplantation: First North American Results", Liver Transplantation, vol. 22, Issue 11, 2016.

Sethi, Himanshu et al., "Analytical validation of the Signatera (TM) RUO assay, a highly sensitive patient-specific multiplex PCR NGS-based noninvasive cancer recurrence detection and therapy monitoring assay", Cancer Research, vol. 78, No. 13, 2018, 4542.

Sheffield, et al., "Attachment of a 40-base-pair G + C-rich sequence (GC-clamp) to genomic DNA fragments by the polymerase chain reaction results in improved detection of single-base changes", Proc Natl Acad Sci U S A, Jan. 1989;86(1), 232-236.

Shi, et al., "Development of a single multiplex amplification refractory mutation system PCR for the detection of rifampin-resistant *Mycobacterium tuberculosis*", Gene., Nov. 1, 2013; 530(1): Epub Aug. 19, 2013, 95-99.

Shimabukuro-Vornhagen, et al., "Cytokine release syndrome", J Immunother Cancer, Jun. 15, 2018;6(1):56. doi: 10.1186/s40425-018-0343-9, 14 pages.

Sigdel, et al., "A rapid noninvasive assay for the detection of renal transplant injury", Transplantation, Jul. 15, 2013;96(1): doi: 10.1097/TP.0b013e318295ee5a., 97-101.

Sigdel, Tara et al., "Optimizing Detection of Kidney Transplant Injury by Assessment of Donor-Derived Cell-Free DNA via Massively Multiplex PCR", Journal of Clinical Medicine, vol. 8, No. 1, 2018, 19.

Sigdel, Tara et al., "Plasma Donor-Derived Cell-Free DNA Quantification by massively multiplex PCR Distinguishes Kidney Transplant Acute Rejection", Transplantation, vol. 102, No. 7s, 2018, s178-s179.

Singh, et al., "Aspergillus infections in transplant recipients", Clin Microbiol Rev., Jan. 2005;18(1), 44-69.

Snyder, et al., "Universal noninvasive detection of solid organ transplant rejection", Proc Natl Acad Sci U S A, Apr. 12, 2011;108(15); doi: 10.1073/pnas.1013924108. Epub Mar. 28, 2011. PubMed PMID: 21444804; PubMed Central Pmcid: PMC3076856., 6229-6234.

Sparks, et al., "Noninvasive prenatal detection and selective analysis of cell-free DNA obtained from maternal blood: evaluation for trisomy 21 and trisomy 18", Am J Obstet Gynecol., Apr. 2012;206(4): doi: 10.1016/j.ajog.2012.01.030. Epub Jan. 26, 2012, 319.e1-319.e9.

Sparks, et al., "Selective analysis of cell-free DNA in maternal blood for evaluation of fetal trisomy", Prenat Diagn., Jan. 2012;32(1). Epub Jan. 6, 2012., 3-9.

Spindler, et al., "Cell-free DNA in healthy individuals, noncancerous disease and strong prognostic value in colorectal cancer", Int J Cancer, Dec. 15, 2014;135(12): doi: 10.1002/ijc.28946. Epub Jun. 17, 2014, 2984-2991.

Spindler, et al., "KRAS-mutated plasma DNA as predictor of outcome from irinotecan monotherapy in metastatic colorectal cancer", Br J Cancer, Dec. 10, 2013;109(12). doi: 10.1038/bjc.2013.633. Epub Nov. 21, 2013., 3067-3072.

Spindler, et al., "Quantitative cell-free DNA, KRAS, and BRAF mutations in plasma from patients with metastatic colorectal cancer during treatment with cetuximab and irinotecan", Clin Cancer Res., Feb. 15, 2012;18(4). doi: 10.1158/1078-0432.CCR-11-0564. Epub Jan. 6, 2012., 1177-1185.

Stein, "Next-Generation Sequencing Update", Genetic Engineering & Biotechnology News, Sep. 1, 2008; 28(15). https://www.genengnews.com/magazine/97/next-generation-sequencing-update/, 10 pages.

Steinborn, et al., "Coexistence of Bos taurus and B. indicus mitochondrial DNAs in nuclear transfer-derived somatic cattle clones", Genetics, Oct. 2002;162(2), 823-829.

Stemmer, et al., "Use of magnetic beads for plasma cell-free DNA extraction: toward automation of plasma DNA analysis for molecular diagnostics", Clin Chem., Nov. 2003;49(11): PubMed PMID: 14578335., 1953-1955.

Strausberg, et al., "*Homo sapiens* placenta-specific 4, mRNA (cDNA clone MGC:120720 Image:7939530), complete cds", GenBank Submission; Accession No. BC093685, version BC093685.1., Jan. 18, 2007, 2 Pages.

Strohmeier, et al., "Multiplex genotyping of KRAS point mutations in tumor cell DNA by allele-specific real-time PCR on a centrifugal microfluidic disk segment", Microchimica Acta., 2014;181 (13-14), 1681-1688.

Suzuki, et al., "Characterization of circulating DNA in healthy human plasma", Clin Chim Acta., Jan. 2008;387(1-2): doi: 10.1016/j.cca.2007.09.001. Epub Sep. 8, 2007., 55-58.

Swinkels, et al., "Effects of blood-processing protocols on cell-free DNA quantification in plasma", Clin Chem., Mar. 2003;49(3): PubMed PMID: 12600978, 525-526.

Tabernero, et al., "Analysis of circulating DNA and protein biomarkers to predict the clinical activity of regorafenib and assess prognosis in patients with metastatic colorectal cancer: a retrospective, exploratory analysis of the Correct trial", Lancet Oncol., Aug. 2015;16(8): doi: 10.1016/S1470-2045(15)00138-2. Epub Jul. 13, 2015., 937-948.

Taira, et al., "Novel high-speed droplet-allele specific-polymerase chain reaction: application in the rapid genotyping of single nucleotide polymorphisms", Clin Chim Acta., Sep. 23, 2013;424: doi: 10.1016/j.cca.2013.04.024. Epub May 17, 2013., 39-46.

Taira, et al., "Quantitative monitoring of single nucleotide mutations by allele-specific quantitative PCR can be used for the assessment of minimal residual disease in patients with hematological malignancies throughout their clinical course", Clin Chim Acta., Jan. 14, 2011;412(1-2): doi: 10.1016/j.cca.2010.09.011. Epub Sep. 16, 2010., 53-58.

(56) References Cited

OTHER PUBLICATIONS

Takai, et al., "Clinical utility of circulating tumor DNA for molecular assessment in pancreatic cancer", Sci Rep., Dec. 16, 2015;5:18425. doi: 10.1038/srep18425., 10 pages.
Taly, et al., "Multiplex picodroplet digital PCR to detect KRAS mutations in circulating DNA from the plasma of colorectal cancer patients", Clin Chem., Dec. 2013;59(12): doi: 10.1373/clinchem.2013.206359. Epub Aug. 12, 2013., 1722-1731.
Tamkovich, et al., "Circulating nucleic acids in blood of healthy male and female donors", Clin Chem., Jul. 2005; 51(7): PubMed PMID: 15976134., 1317-1319.
Tanem, et al., "Abstract 16873: Association of Preoperative Cell-Free DNA Levels and Outcome Following Pediatric Cardiopulmonary Bypass", Circulation, Nov. 17, 2020; 142(S3): https://doi.org/10.1161/circ.142.suppl_3.16873., 1-6.
Thermofisher Scientific, "How Ion AmpliSeq Targeted Sequencing Technology Works", https://www.thermofisher.com/us/en/home/life-science/ sequencing/next-generation-sequencing/ion-torrent-next-generation-sequencing-workflow/ion-torrent-next-generation-sequencing-select-targets/ampliseq-target-selection/how-ampliseq-technology-work.
Thierry, et al., "A Targeted Q-PCR-Based Method for Point Mutation Testing by Analyzing Circulating DNA for Cancer Management Care", Methods Mol Biol., 2016;1392: doi: 10.1007/978-1-4939-3360-0_1, 1-16.
Thierry, et al., "Clinical validation of the detection of KRAS and BRAF mutations from circulating tumor DNA", Nat Med., Apr. 2014;20(4): doi: 10.1038/nm.3511. Epub Mar. 23, 2014., 430-435.
Tie, et al., "Circulating tumor DNA as an early marker of therapeutic response in patients with metastatic colorectal cancer", Annals of Oncology, vol. 26, No. 8, 2015, 1715-1722.
Tomita-Mitchell, et al., "Human gene copy number spectra analysis in congenital heart malformations", Physiol Genomics, May 1, 2012;44(9): doi: 10.1152/physiolgenomics.00013.2012. Epub Feb. 7, 2012., 518-541.
Tong, et al., "Diagnostic developments involving cell-free (circulating) nucleic acids", Clin Chim Acta., Jan. 2006;363(1-2): Epub Aug. 26, 2005. Review. PubMed PMID: 16126188, 187-196.
Toth, T. et al., "Prenatal Detection of Trisomy 13 From Amniotic Fluid by Quantitative Fluorescent Polymerase Chain Reaction", Prenatal Diagnosis, vol. 18, 1998, 669-674.
Tungwiwat, et al., "Non-invasive fetal sex determination using a conventional nested PCR analysis of fetal DNA in maternal plasma", Clinica Chimica Acta, vol. 334, No. 1-2, 2003, 173-177.
Van Orsouw, et al., "Rapid design of denaturing gradient-based two-dimensional electrophoretic gene mutational scanning tests", Nucleic Acids Res., May 15, 1998;26(10), 2398-2406.
Vannucchi, et al., "A quantitative assay for JAK2(V617F) mutation in myeloproliferative disorders by ARMS-PCR and capillary electrophoresis", Leukemia, Jun. 2006;20(6), 1055-1060.
Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.
Veseloskva, "The use of cell-free nucleic acids in maternal plasma for non-invasive prenatal diagnosis of monogenic diseases, placental insufficiency-related complications and Down syndrome", Thesis from Charles University in Prague, 2011, 104 pages.
Volckmar, et al., "A field guide for cancer diagnostics using cell-free DNA: From principles to practice and clinical applications", Genes Chromosomes Cancer, 2018, 123-139.
Wagner, F. F. et al., "RHD gene deletion occurred in the Rhesus box", Blood, vol. 95, No. 12, 2000, 3662-3668.
Wang, et al., "DNA Degradation Test Predicts Success in Whole-Genome Amplification from Diverse Clinical Samples", Journal of Molecular Diagnostics, vol. 9, 2007, 441-451.
Wang, et al., "Molecular inversion probes: a novel microarray technology and its application in cancer research", Cancer Genetics, 205, 2012, 341-355.
Wangkumhang, et al., "WASP: a Web-based Allele-Specific PCR assay designing tool for detecting SNPs and mutations", BMC Genomics, Aug. 14, 2007;8:275, 9 Pages.
Wangkumhang, P. et al., "WASP: a Web-based Allele-Specific PCR assay designing tool for detecting SNPs and mutations", BMC Genomics, vol. 8, No. 275, Aug. 14, 2007, 9 pgs.
Wapner, et al., "Expanding the scope of noninvasive prenatal testing: detection of fetal microdeletion syndromes", Am J Obstet Gynecol., Mar. 2015;212(3): doi: 10.1016/j.ajog.2014.11.041. Epub Dec. 2, 2014., 332.e1-332.e9.
Whitlam, J. B. et al., "Diagnostic application of kidney allograft-derived absolute cell-free DNA levels during transplant dysfunction", Am J Transplant, vol. 19, 2019, 1037-1049.
Wilkins, et al., "IMP PCR primers detect single nucleotide polymorphisms for *Anopheles gambiae* species identification, Mopti and Savanna rDNA types, and resistance to dieldrin in Anopheles arabiensis", Malar J., Dec. 19, 2006;5:125., 7 pages.
Wood, et al., "Molecular histology of lung cancer: From targets to treatments", Cancer Treatment Reviews, vol. 41, 2015, 361-375.
Woude, et al., "Methods of identifying drugs with selective effects against cancer cells", Oct. 7, 1997, Nucleic acid sequence search reports AC: 151794, Accession 151796., 2 Pages.
Xie, et al., "Designing highly multiplex PCR primer sets with Simulated Annealing Design using Dimer Likelihood Estimation (SADDLE)", Nat Commun., 2022, 1881.
Yamada, et al., "Detection of K-ras gene mutations in plasma DNA of patients with pancreatic adenocarcinoma: correlation with clinicopathological features", Clin Cancer Res., Jun. 1998;4(6), 1527-1532.
Ye, et al., "Primer-BLAST: a tool to design target-specific primers for polymerase chain reaction", BMC Bioinformatics, 13:134, 2012, 11 pages.
Yi, et al., "PCR/LDR/capillary electrophoresis for detection of single-nucleotide differences between fetal and maternal DNA in maternal plasma", Prenat Diagn., Mar. 2009;29(3): doi: 10.1002/pd.2072., 217-222.
Zangwill, et al., "Effect of endomyocardial biopsy on levels of donor-specific cell-free DNA", J Heart Lung Transplant, Oct. 2019;38(10): doi: 10.1016/j.healun.2019.06.005. Epub Jun. 28, 2019., 1118-1120.
Zhang, et al., "A novel multiplex tetra-primer ARMS-PCR for the simultaneous genotyping of six single nucleotide polymorphisms associated with female cancers", PLoS One, Apr. 17, 2013;8(4):e62126. doi: 10.1371/journal.pone.0062126. Print 2013., 8 pages.
Zheng, et al., "Whole-exome sequencing to identify novel somatic mutations in squamous cell lung cancers", International Journal of Oncology, vol. 43, 2015, 755-764.
Bewersdorf, Jan Philipp et al., "From clonal hematopoiesis to myeloid leukemia and what happens in between: Will improved understanding lead to new therapeutic and preventive opportunities?", Blood Reviews, vol. 37, 2019, 6.
Coombs, Catherine et al., "Therapy-Related Clonal Hematopoiesis in Patients with Non-hematologic Cancers Is Common and Associated with Adverse Clinical Outcomes", Cell Stem Cell, vol. 21, No. 3, 2017, 374.
Giulio, Genovese et al., "Hematopoiesis and Blood-Cancer Risk Inferred from Blood Dna Sequence", The New England Journal of Medicine, vol. 371, No. 26, 2014, 2477-2487.
Jaiswal, Siddhartha et al., "Clonal hematopoiesis in human aging and disease", Science, vol. 366, No. 6465, 2019, 4.
Kiyomi, Morita et al., "Clearance of Somatic Mutations at Remission and the Risk of Relapse in Acute Myeloid Leukemia", J Clin Oncol, vol. 36, No. 18, 2018, 1788-1797.
Maheswaran, S. et al., "Detection of Mutations in EGFR in Circulating Lung-Cancer Cells", N Engl J Med, vol. 359, No. 4, Jul. 24, 2008, 366-377.
Steensma, D. P. et al., "Clonal hematopoiesis of indeterminate potential and its distinction from myelodysplastic syndromes", Blood, vol. 126, No. 1, 2015, 9-16.
Vandekerkhove, G et al., "Circulating Tumor Dna Reveals Clinically Actionable Somatic Genome of Metastatic Bladder Cancer", Clinical Cancer Research, 2017, 6487-6497.

(56) References Cited

OTHER PUBLICATIONS

Yamauchi Medical Clinic, "Chromosome abnormality", http://www.yamauchi-iin.com/kaisetu/1241.htm, (Dec. 10, 2015 updated), Dec. 10, 2015, 3 pages.
Abbosh, et al., "Phylogenetic ctDNA analysis depicts early-stage lung cancer evolution", Nature, 2017, 446-453.
Blomquist, et al., "Targeted RNA-Sequencing with Competitive Multiplex-PCR Amplicon Libraries", Plos One, 2013, vol. 8, Issue 11.
Chang, et al., "Identification of individual DNA molecule of *Mycobacterium tuberculosis* by nested PCR-RLFP and capillary electrophoresis", National Library of Medicine, 2008, 182-8.
Fire, et al., "Rolling replication of short DNA circles", PNAS, 1995, 4641-4645.
Kane, et al., "Application of less primer method to PCR", DNA Polymorphism, 2004, vol. 13, pp. 34-37.
Koeppe, et al., "HIV-1-Specific CD4+ T-Cell Responses Are Not Associated With Significant Viral Epitope Variation in Persons With Persistent Plasma Viremia", J Acquir Immune Defic Syndr, 2006, 41:140-148.
Krishnakumar, S. et al., "A comprehensive assay for targeted multiplex amplification of human DNA sequences", PNAS, vol. 105, No. 27, Jul. 8, 2008, 9296-9301.
Lizardi, et al., "Mutation detection and single-molecule counting using isothermal rolling-circle amplification", Nature Genetics, 1998, 225-232.
Mamanova, L. et al., "Target-enrichment strategies for next-generation sequencing", Nat Methods, vol. 7, 2010, 111-118.
Mamun, et al., "The *Escherichia coli* UVM response is accompanied by an SOS-independent error-prone DNA replication activity demonstrable in vitro", Molecular Microbiology, 2000, 368-380.
Metzker, Michael, Declaration of Michael L. Metzker, Ph.D. from IPR2018-01317, 2004.
Mueller, P. R. et al., "In Vivo Footprinting of a Muscle Specific Enhancer by Ligation Mediated PCR", Science, vol. 249, Nov. 10, 1989, 780-786.
No Author Listed, "Jury Rules in Favor of Natera, Finding All Asserted Patents Valid and Infrindged by ArcherDX/Invitae; Awards $19.35 Million in Past Damages for Royalties and Lost Profits", Natera Press Release, 2023, 4 pgs.
No Author Listed, "*Natera Inc.* vs. *ArcherDx Verdict Form*, Case 1:20-cv-00125-GBW", 2023, 1-12.
Peng, Q et al., "Reducing amplification artifacts in high multiplex amplicon sequencing by using molecular barcodes", BMC Genomics, vol. 16. No. 586, 2015, 12 pages.
Reinert, et al., "Analysis of Plasma Cell-Free DNA by Ultradeep Sequencing in Patients With Stages I to UI Colorectal Cancer", JAMA Oncology, 2019, 1-74.
Stone, J. P. et al., "Altered Immunogenicity of Donor Lungs via Removal of Passenger Leukocytes Using Ex Vivo Lung Perfusion", American Journal of Transplantation, vol. 16, 2016, 33-43.
Valenza, F. et al., "The Consumption of Glucose During Ex Vivo Lung Perfusion Correlates with Lung Edema", Transplantation Proceedings, vol. 43, 2011, 993-996.
Vargas, D. Y. et al., "Multiplex Real-Time PCR Assays that Measure the Abundance of Extremely Rare Mutations Associated with Cancer", PLOS One, vol. 11, No. 5, May 31, 2016, 26 pgs.
Avanzini, Stefano et al., "A mathematical model of ctDNA shedding predicts tumor detection size", Science Advances, vol. 6, Issue eabc4308, Dec. 11, 2020, 9 pages.

Chan, Allen et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry, 2013, 211-224.
Chan, Allen, "Scanning for Cancer Genomic Changes in Plasma: Toward an Era of Personalized Blood-Based Tumor Markers", Clinical Chemistry, 2013, 1553-1555.
Chen, Kevin et al., "Commercial ctDNA Assays for Minimal Residual Disease Detection of Solid Tumors", Molecular Diagnosis & Therapy, vol. 25, Issue 6, Nov. 1, 2021, 757-774.
Goessl, C. et al., "DNA Alterations in Body Fluids as Molecular Tumor Markers for Urological Malignancies", European Urology, vol. 41, 2002, 668-676.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1 pg.
Wong, I. H. et al., "Quantitative Analysis of Tumor-derived Methylated p16INK4a Sequences in Plasma, Serum, and Blood Cells of Hepatocellular Carcinoma Patients", Clinical Cancer Research, vol. 9, Mar. 2003, 1047-1052.
Agbor-Enoh, Sean et al., "Circulating cell free DNA as a biomarker of tissue injury: Assessment in a cardiac xenotransplantation model", Journal of Heart and Long Transplantation, vol. 37, No. 8, 2018, 967-975.
Ali, N. M. et al., "Fetal and Donor-Derived Cell-Free Dna May Assist in Differentiating Pregnancy Related Changes from Allograft Rejection in Kidney Transplant Recipients", American Journal of Transplantation, vol. 23, No. 6, Poster Abstract., 2023.
Antoniou, A. et al., "Data augmentation generative adversarial networks.", arXiv preprint arXiv:1711.04340, (Year: 2017), Nov. 12, 2017, 14 pages.
Liao, W et al., "Noninvasive detection of tumor-associated mutations from circulating cell-free DNA in hepatocellular carcinoma patients by targeted deep sequencing.", Oncotarget, 7(26), (Year: 2016), Jun. 28, 2016, 40481-40490.
Malapelle, U. et al., "Next generation sequencing techniques in liquid biopsy: focus on non-small cell lung cancer patients.", Transl Lung Cancer Res., 5(5), (Year: 2016), Oct. 2016, 505-510.
Min, S. et al., "Deep learning in bioinformatics.", Brief Bioinform., 18(5), (Year: 2017), Sep. 1, 2017, 851-869.
Moscow, J. A. et al., "Engraftment of MDR1 and NeoR Gene-Transduced Hematopoietic Cells After Breast Cancer Chemotherapy", Blood, vol. 94, No. 1, 1999, 52-61.
Neocleous, A. C. et al., "First Trimester Noninvasive Prenatal Diagnosis: A Computational Intelligence Approach", in IEEE Journal of Biomedical and Health Informatics, vol. 20, No. 5, (Year: 2016), Sep. 2016, pp. 1427-1438.
Oustimov, A. , "Artificial neural networks in the cancer genomics frontier.", Translational cancer research., 3(3), (Year: 2014), Jun. 2014, 11 pages.
Stephens, Z. D. et al., "Simulating Next-Generation Sequencing Datasets from Empirical Mutation and Sequencing Models.", PLoS One., 11(11):e0167047. (Year: 2016), Nov. 28, 2016, 18 pages.
Tang, Jessica et al., "Donor-derived cell free DNA (dd-cfDNA) in pregnant kidney transplant recipients", American Journal of Obstetrics & Gynecology, vol. 228, No. 1, 2023.

* cited by examiner

SYSTEMS AND METHODS FOR DETECTION OF ANEUPLOIDY

CROSS-REFERENCE TO RELATED APPLICATIONS

This application is a continuation of U.S. Utility application Ser. No. 14/732,632, filed on Jun. 5, 2015. U.S. Utility application Ser. No. 14/732,632 claims the benefit of and priority to U.S. Provisional Application Ser. No. 62/008,235, filed Jun. 5, 2014; U.S. Provisional Application Ser. No. 62/032,785, filed Aug. 4, 2014; and U.S. Provisional Application Ser. No. 62/079,257, filed Nov. 13, 2014. The entireties of all these applications are each hereby incorporated by reference for the teachings therein.

FIELD OF THE INVENTION

The present invention generally relates to molecular biology methods and systems, and more specifically to methods and systems for detecting ploidy of a chromosome segment.

BACKGROUND

Measurement of the number of copies of a chromosome or chromosome segment in a cell of interest is an important technique in molecular biology. The technique has wide applicability in fields such as prenatal diagnosis and the analysis of cancer cells. Older techniques such as karyotyping are being supplanted by techniques employing high levels of DNA sequencing. For example, such techniques can be used to detect copy number variation (CNV).

Copy number variation (CNV) has been identified as a major cause of structural variation in the genome, involving both duplications and deletions of sequences that typically range in length from 1,000 base pairs (1 kb) to 20 megabases (mb). Deletions and duplications of chromosome segments or entire chromosomes are associated with a variety of conditions, such as susceptibility or resistance to disease.

CNVs are often assigned to one of two main categories, based on the length of the affected sequence. The first category includes copy number polymorphisms (CNPs), which are common in the general population, occurring with an overall frequency of greater than 1%. CNPs are typically small (most are less than 10 kilobases in length), and they are often enriched for genes that encode proteins important in drug detoxification and immunity. A subset of these CNPs is highly variable with respect to copy number. As a result, different human chromosomes can have a wide range of copy numbers (e.g., 2, 3, 4, 5, etc.) for a particular set of genes. CNPs associated with immune response genes have recently been associated with susceptibility to complex genetic diseases, including psoriasis, Crohn's disease, and glomerulonephritis.

The second class of CNVs includes relatively rare variants that are much longer than CNPs, ranging in size from hundreds of thousands of base pairs to over 1 million base pairs in length. In some cases, these CNVs may have arisen during production of the sperm or egg that gave rise to a particular individual, or they may have been passed down for only a few generations within a family. These large and rare structural variants have been observed disproportionately in subjects with mental retardation, developmental delay, schizophrenia, and autism. Their appearance in such subjects has led to speculation that large and rare CNVs may be more important in neurocognitive diseases than other forms of inherited mutations, including single nucleotide substitutions.

Gene copy number can be altered in cancer cells. For instance, duplication of Chr1p is common in breast cancer, and the EGFR copy number can be higher than normal in non-small cell lung cancer. Cancer is one of the leading causes of death; thus, early diagnosis and treatment of cancer is important, since it can improve the patient's outcome (such as by increasing the probability of remission and the duration of remission). Early diagnosis can also allow the patient to undergo fewer or less drastic treatment alternatives. Many of the current treatments that destroy cancerous cells also affect normal cells, resulting in a variety of possible side-effects, such as nausea, vomiting, low blood cell counts, increased risk of infection, hair loss, and ulcers in mucous membranes. Thus, early detection of cancer is desirable since it can reduce the amount and/or number of treatments (such as chemotherapeutic agents or radiation) needed to eliminate the cancer.

Copy number variation has also been associated with severe mental and physical handicaps, and idiopathic learning disability. Non-invasive prenatal testing (NIPT) using cell-free DNA (cfDNA) can be used to detect abnormalities, such as fetal trisomies 13, 18, and 21, triploidy, and sex chromosome aneuploidies. Subchromosomal microdeletions, which can also result in severe mental and physical handicaps, are more challenging to detect due to their smaller size. Eight of the microdeletion syndromes have an aggregate incidence of more than 1 in 1000, making them nearly as common as fetal autosomal trisomies.

In addition, a higher copy number of CCL3L1 has been associated with lower susceptibility to HIV infection, and a low copy number of FCGR3B (the CD16 cell surface immunoglobulin receptor) can increase susceptibility to systemic lupus erythematosus and similar inflammatory autoimmune disorders.

Thus, improved methods are needed to detect deletions and duplications of chromosome segments or entire chromosomes. Preferably, these methods can be used to more accurately diagnose disease or an increased risk of disease, such as cancer or CNVs in a gestating fetus.

In many clinical trials concerning a diagnostic that employs molecular biology, for example for detecting CNVs, a protocol with a number of parameters is set, and then the same protocol is executed with the same parameters for each of the patients in the trial. In the case of determining the ploidy status of a fetus gestating in a mother using sequencing as a method to measure genetic material one pertinent parameter is the number of reads. The number of reads may refer to the number of actual reads, the number of intended reads, fractional lanes, full lanes, or full flow cells on a sequencer. In these studies, the number of reads is typically set at a level that will ensure that all or nearly all of the samples achieve the desired level of accuracy. Sequencing is currently an expensive technology, a cost of roughly $200 per 5 mappable million reads, and while the price is dropping, any method which allows a sequencing based diagnostic to operate at a similar level of accuracy but with fewer reads will necessarily save a considerable amount of money.

Accordingly, there is a need for new improved techniques for the determination of aneuploidy in a chromosome or chromosome segment of interest, especially by employing DNA sequencing in a more accurate and cost-effective manner by reducing the required number of reads. This will bring down the cost of such molecular diagnostics, resulting in better diagnostics that are available to more people. The improved techniques would for example, be particularly valuable in the analysis of cell free DNA derived from fetal cells or tumor cells to provide improved prenatal and cancer diagnostics.

SUMMARY

Provided herein in one embodiment are methods and systems for determining the copy number, or detecting aneuploidy of a chromosome or chromosome segment of interest in a cell of interest that are performed using the chromosome or chromosome segment of interest to set a bias model, that is to set test parameters, using samples analyzed in the same parallel analysis, that are identified as diploid samples with high confidence, for the analysis of aneuploidy for the same chromosome or chromosome segment of interest of other sample(s) in the set of on-test samples. Accordingly, in one example of this embodiment, provided herein is a method for determining a presence or absence of aneuploidy of a chromosome or chromosome segment of interest in a test sample, that includes the following steps:
  a) obtaining genetic data for the chromosome or chromosome segment of interest from each sample of a set of samples that includes the test sample and at least one diploid sample, wherein the genetic data is obtained from a parallel analysis of the set of samples;
  b) setting a bias model using the genetic data for the chromosome or chromosome segment of interest in the diploid sample determined to be disomic for the chromosome or chromosome segment of interest;
  c) adjusting the genetic data for the chromosome or chromosome segment of interest for the test sample using the bias model; and
  d) establishing the presence or absence of aneuploidy for the chromosome or chromosome segment of interest in the test sample using the normalized data.

In certain illustrative examples of this embodiments, the at least one diploid sample is determined to be disomic for the chromosome or chromosome segment of interest by analyzing the genetic data from the parallel analysis. In certain illustrative examples, the diploid sample is determined to be disomic (i.e. selected as being disomic) for the chromosome or chromosome segment of interest without using a control chromosome or control chromosome segment.

In certain examples of this embodiment of the invention, one or two maximum likelihood analysis are used to carry out the method. As disclosed above, the first maximum likelihood method can be used to identify diploid samples in the set of samples and to determine a first probability that the other samples in the set of samples are aneuploidy. Accordingly, in certain embodiments, one or more or all of the chromosome(s) or chromosome segment(s) of interest are determined to be disomic using a first maximum likelihood method. The method includes the following steps:
creating, for each sample in the set of samples, a plurality of first hypotheses wherein each first hypothesis is associated with a specific copy number for the chromosome or chromosome segment of interest,
determining a first probability value for each first hypothesis, wherein the first probability value indicates the likelihood that the sample has the number of copies of the chromosome or chromosome segment that is associated with the first hypothesis, wherein the first probability values are derived from the genetic data associated with the sample, and
selecting at least one diploid sample by selecting those one or more samples that most closely match a disomic copy number hypothesis for the chromosome or chromosome segment of interest, with at least a minimum level of confidence. That is, by selecting those samples that yield the highest probability of being disomic for the chromosome or chromosome segment of interest.

In certain embodiments, the method includes at least two maximum likelihood analysis, the presence or absence of aneuploidy, or the number of copies of the chromosome or chromosome segment of interest, is determine by creating a plurality or set of $2^{nd}$ hypotheses, also called ploidy hypotheses herein, wherein each $2^{nd}$ hypothesis is associated with a specific copy number of the chromosome or chromosome segment of interest in the target cell. The models are then used to test how well the genetic data from each patient fits each $2^{nd}$ hypothesis. The goodness of fit for each $2^{nd}$ hypothesis is determined. A second probability value is calculated for each second hypothesis wherein the second probability value indicates the likelihood that the genome of the target cell has the number of chromosomes or chromosome segments that is specified by the second hypothesis. Thus by selecting the $2^{nd}$ hypothesis with the maximum likelihood, one may determine the copy number for the chromosome or chromosome segment in the genome of the target cell. Such first and second hypothesis can be considered in combination to increase the confidence of the aneuploidy determination In another embodiment, provide herein is a method for determining a presence or absence of aneuploidy for a first chromosome or chromosome segment of interest in a test sample from a test subject, includes the following steps:
obtaining genetic sequencing data from a parallel analysis of the first chromosome or chromosome segment of interest from cell free DNA from each sample in a set of liquid samples comprising the test sample, wherein the set of liquid samples comprises at least 3 samples and wherein the genetic sequencing data determines an amount of DNA corresponding to each locus in a first set of loci present on the first chromosome or chromosome segment of interest respectively;
selecting a diploid subset of samples from the set of liquid samples, wherein the diploid subset of samples are samples that are initially determined to be disomic for the first chromosome or chromosome segment of interest using an initial bias model, wherein the subset of samples comprises at least 2 samples;
setting a confirmatory bias model from the genetic data from the first chromosome or chromosome segment of interest from the diploid subset of patients;
adjusting the genetic data for the test subject using the confirmatory bias model, to give normalized genetic data for the test subject; and
determining, using the normalized data, whether genetic data from the test subject is indicative of an aneuploidy in the first chromosome or chromosome segment of interest.

In another embodiment, a method of the invention includes both a non-allelic z-score based quantitative method and a maximum likelihood method based on allelic or non-allelic data. Accordingly, provided herein is a method for detecting a presence or absence of aneuploidy of a chromosome or chromosome segment of interest in a test sample, that includes the following steps: obtaining genetic data for the chromosome or chromosome segment of interest from each sample in a set of samples comprising the test sample, wherein the genetic data is obtained from a parallel analysis of the samples;

determining whether aneuploidy is present in the test sample by a first method comprising:
  a. determining a depth of reads or a proportion of reads that map to the chromosome or chromosome segment of interest;
  b. calculating a z-score for the depth of reads or the proportion of reads that map to the chromosome or chromosome segment of interest; and
  c. determining whether the test sample is aneuploidy at the chromosome or chromosome segment of interest based on the z-score, thereby providing a first result; and determining whether aneuploidy is present in the test sample by a second method comprising:
  d. creating a plurality of ploidy hypotheses wherein each ploidy hypothesis is associated with a specific copy number for the chromosome or chromosome segment of interest,
  e. determining a ploidy probability value for each ploidy hypothesis, wherein the ploidy probability value indicates the likelihood that the test sample has the specific copy number for the chromosome or chromosome segment of interest that is associated with the ploidy hypothesis, and
  f. determining which ploidy hypothesis is most likely to be correct by selecting the ploidy hypothesis with the maximum likelihood, thereby providing a second result, detecting the aneuploidy by considering the first result and the second result.

In certain illustrative examples of the above embodiments, the sample is a liquid sample, such as a sera sample. The genetic data, in these examples, can be derived from circulating DNA, such as circulating fetal DNA or circulating tumor DNA.

In certain examples of any of the above embodiments, the method further includes estimating a fetal fraction for each sample in the set of samples, wherein the fetal fraction is used in the selecting the diploid subset of samples and/or the determining whether the genetic data from the test subject is indicative of an aneuploidy.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
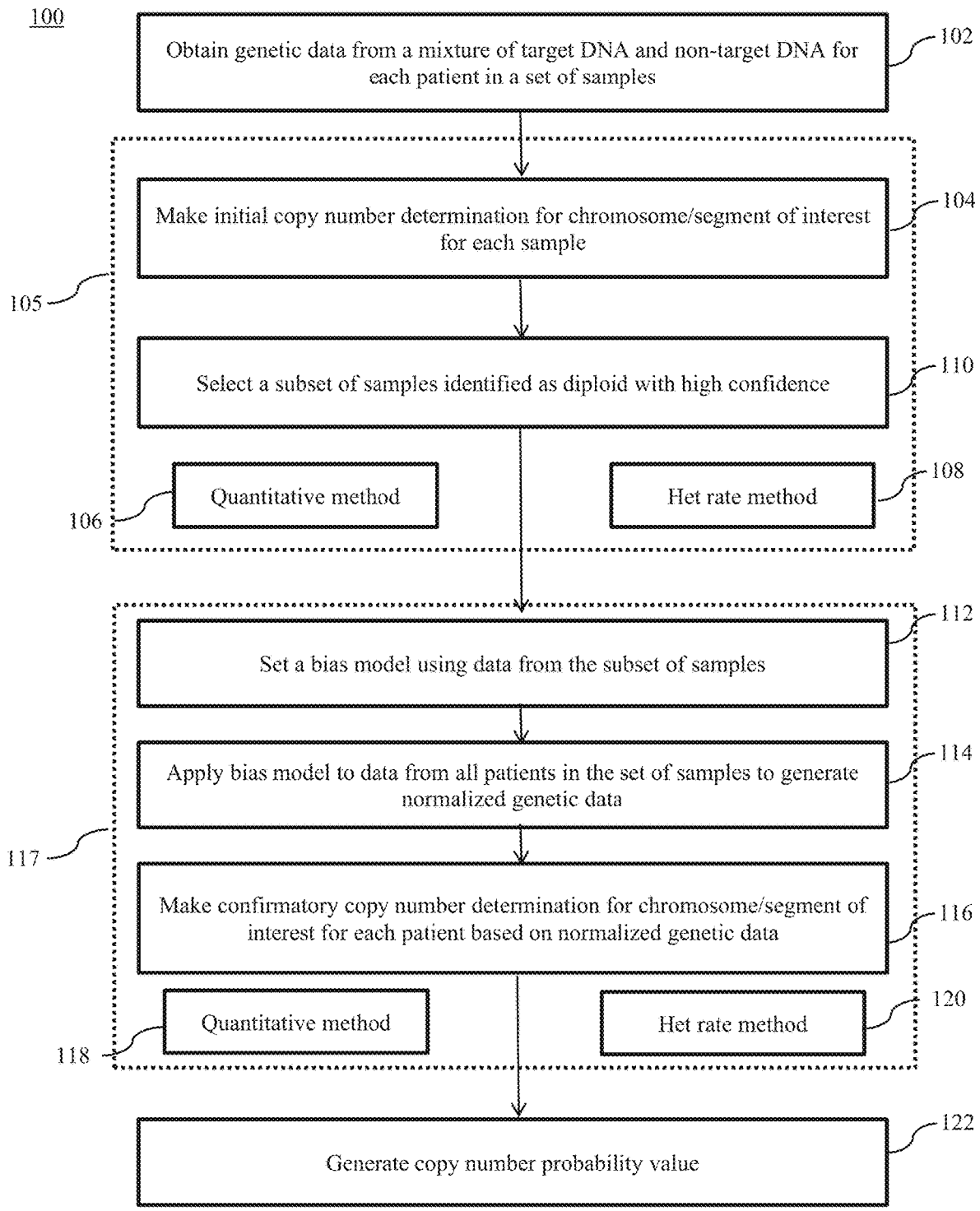
FIG. 1 is a flow chart of a method according to one embodiment of the invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Some embodiments of the present invention utilize the fact that a typical analysis for aneuploidy of a set of blood samples for example a set of blood samples from pregnant mothers in an NIPT assay, or from cancer patients in an analysis of circulating free tumor DNA (cfDNA), are run in parallel in the same set of assays, wherein many and probably most DNA in the samples originates from diploid cells. Thus, not only can on-test samples be identified that are diploid with high confidence and used as controls for analysis of other samples in the set of samples without the need for running additional control samples, in many embodiments of the present invention, the chromosome or chromosome segment of interest in test samples that are initially identified as diploid with high confidence, are used as controls for subsequent methods that analyze the rest of the set of samples for aneuploidy at that same chromosome(s) or chromosome segment(s) of interest. This substantially reduces the cost of such analysis and substantially improves the confidence in the analysis since the on-test and control data comes from the same parallel analysis of the same chromosome or same chromosome segment of interest.

Accordingly, provided herein are numerous methods and systems for determining the copy number, or detecting aneuploidy of a chromosome or chromosome segment of interest in a cell of interest that are performed using the chromosome or chromosome segment of interest to set a bias model, that is to set test parameters, or to set a threshold cutoff value, using samples analyzed in the same parallel analysis, that are identified as diploid samples with high confidence, for the analysis of aneuploidy for the same chromosome or chromosome segment of interest of other sample(s) in the set of on-test samples. The subject methods and systems can employ high throughput DNA sequencers (capable of sequencing large number of DNA templates in parallel) so as to produce quantitative information about the amount of various DNA sequences of interest in a set of samples obtained from a test subject. This quantitative sequence information can be used to determine the copy number of a chromosome or chromosome segment of interest in a cell of interest, e.g., a cell of a developing fetus or a tumor cell.

The term "depth of read" as used herein refers to the number of sequencing reads that map to a given locus. The depth of read may be normalized over the total number of reads. When "depth of read" refers to a sample, it may mean the average depth of read over the targeted loci. When "depth of read" refers to a locus, it may refer to the number of reads measured by the sequencer mapping to that locus. In general, the greater the depth of read of a locus, the closer the ratio of alleles at the locus will tend to be to the ratio of alleles in the original sample of DNA.

The term "relative fraction" can also be used to express a similar concept as depth of read. Depth of read can be expressed in variety of different ways, including but not limited to the percentage or proportion. Thus for example in a highly parallel DNA sequencer such as an Illumina HISEQ, which for example would produce sequence of 1 million clones, the sequencing of one locus 3,000 times, would result in a depth of read of 3,000 reads at that locus. The proportion of reads at that locus would be 3,000 divided by 1 million total reads, or 0.3% of the total reads.

The term "allelic data" as used herein means a quantitative measurement indicative of the number of copies of a specific allele of a polymorphic locus. Typically, quantitative measurements will be obtained for all possible alleles of the polymorphic locus of interest. In some embodiments, the polymorphic loci is a SNP, and the SNP is dimorphic, and the allelic data will comprise the quantity of each of the two alleles observed at that locus. In some embodiments, the polymorphic loci is a SNP, and the SNP is trimorphic or tetramorphic, and the allelic data will comprise the quantity of each of the three or four alleles observed at that locus. The allelic data may be obtained using a variety of well-known molecular biology techniques such as DNA sequencing or real-time PCR. High throughput DNA sequencing in which the number of individual reads of a given locus obtained can be used to obtain allelic data. When the allelic data is measured using high-throughput sequencing, the allelic data will typically comprise the number of reads of each allele mapping to the locus of interest.

The term "non-allelic data" as use herein means a quantitative measurement indicative of the number of copies of a specific locus. The locus may be polymorphic or non-polymorphic. If the locus is non-polymorphic, the non-allelic data will not contain information about the relative or absolute quantity of the individual alleles that may be present at that locus. Typically, quantitative measurements will be obtained for all possible alleles of the polymorphic locus of interest. The allelic data may be obtained using a variety of well-known molecular biology techniques such as DNA sequencing or real-time PCR. High throughput DNA sequencing in which the number of individual reads of a given locus obtained can be used to obtain allelic data. Non-allelic data for a polymorphic locus may be obtained by summing the quantitative allelic for each allele at that locus. When the allelic data is measured using high-throughput sequencing, the non-allelic data will typically comprise the number of reads of mapping to the locus of interest. The sequencing measurements could indicate the relative and/or absolute number of each of the alleles present at the locus, and the non-allelic data would comprise the sum of the reads, regardless of the allelic identity, mapping to the locus. Note that it is possible to measure the DNA at a plurality of loci, for example using high throughput sequencing, to yield allelic data; it is then possible, by summing the number of reads that correspond to each allele, at each locus, to produce non-allelic data. In some embodiments the same set of measurements can be used to yield both allelic data and non-allelic data. In some embodiments, the produced allelic data can be used as part of a method to determine copy number at a chromosome of interest, and the produced non-allelic data can be used as part of a method to determine copy number at a chromosome of interest, where the two methods are statistically orthogonal.

The term "chromosomal abnormality" as used herein refers to any deviation and the copy number of a specific chromosome or chromosome segment from the most common number of copies of that segment or chromosome, for example in a human somatic cell, any deviation from 2 copies could be regarded as a chromosomal abnormality.

The term "obtaining genetic data" as used herein refers to both, unless specifically where implicitly indicated otherwise by context, (1) acquiring DNA sequence information by laboratory techniques, e.g. use of an automated high throughput DNA sequencer, and (2) acquiring information that had been previously obtained by laboratory techniques, wherein the information is electronically transmitted, e.g. by computer over the Internet, by electronic transfer from the sequencing device, etc.

The term "target cell" as used herein refers to the cell (or cell type) that contains the chromosomes or chromosome segments that are to be quantitatively measured as a result of the subject methods. Examples of target cells include fetal cells and tumor cells. As the cells of most individuals contain a nearly identical set of nuclear DNA, the term "target cell" may be used interchangeably with the term "individual."

The term "non-target cell" as used herein refers to cell (or cell type) that supply DNA that is analyzed in the process of performing the subject methods, but is not the cell contains the chromosomes or chromosome segments that is required to be quantitatively measured as a result of the subject methods. In some embodiments, the "non-target cell" may be closely related to the "target cell", for example if a prostate tumor cell is the target cell a noncancerous prostate cell from the same individual may (although not necessarily) be used as a "non-target cell". Alternately, in the case where the measurements are made on a mixture of cfDNA taken from a pregnant woman, the target cell could be from the placenta of a fetus gestating in the mother, and the non-target cells could be from the mother of the fetus. Typically, non-target cells are euploid, though this is not required.

Methods for measuring chromosome copy number in fetal cells based counting the number of DNA sequence-based reads that map to a given chromosome or chromosome segment are conveniently referred to as "counting methods", or "quantitative methods" for analyzing chromosome copy number or chromosome segment copy number. Examples of such methods can be found, among other places, in published patent application US 2013/0172211 A1 U.S. Pat. Nos. 8,008,018; 8,467,976 B2; US published patent application US 2012/0003637 A1. Such methods typically involve creation of a reference value (cut-off value) for the number of DNA sequence reads mapping to a specific chromosome, where in a number of reads in excess of the value is indicative of a specific genetic abnormality.

Confidence refers to the statistical likelihood that the called SNP, allele, set of alleles, ploidy call, or determined number of chromosome segment copies correctly represents the real genetic state of the individual.

Ploidy Calling, also "Chromosome Copy Number Calling," or "Copy Number Calling" (CNC), refers to the act of determining the quantity and chromosomal identity of one or more chromosomes present in a cell.

Aneuploidy refers to the state where the wrong number of chromosomes are present in a cell. In the case of a somatic human cell it refers to the case where a cell does not contain 22 pairs of autosomal chromosomes and one pair of sex chromosomes. In the case of a human gamete, it refers to the case where a cell does not contain one of each of the 23 chromosomes. In the case of a single chromosome, it refers to the case where more or less than two homologous but non-identical chromosomes are present, and where each of the two chromosomes originate from a different parent.

Ploidy State refers to the quantity and chromosomal identity of one or more chromosomes in a cell.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic Distribution refers to the distribution of the set of alleles observed at a set of loci. An allelic distribution for one locus is an allele ratio.

Allelic Distribution Pattern refers to a set of different allele distributions for different parental contexts. Certain allelic distribution patterns may be indicative of certain ploidy states.

Allelic Bias refers to the degree to which the measured ratio of alleles at a heterozygous locus is different to the ratio that was present in the original sample of DNA. The degree of allelic bias at a particular locus is equal to the observed allelelic ratio at that locus, as measured, divided by the ratio of alleles in the original DNA sample at that locus. Allelic bias may be defined to be greater than one, such that if the calculation of the degree of allelic bias returns a value, x, that is less than 1, then the degree of allelic bias may be restated as 1/x.

Haplotype refers to a combination of alleles at multiple loci that are transmitted together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where the haplotype has been determined.

Target Individual refers to the individual whose genetic data is being determined. In one context, only a limited amount of DNA is available from the target individual. In one context, the target individual is a fetus. In some embodiments, there may be more than one target individual. In some embodiments, each fetus that originated from a pair of parents may be considered to be target individuals.

Child is used interchangeably with the terms embryo, blastomere, and fetus. Note that in the presently disclosed embodiments, the concepts described apply equally well to individuals who are a born child, a fetus, an embryo or a set of cells therefrom. The use of the term child may simply be meant to connote that the individual referred to as the child is the genetic offspring of the parents.

Parental Context refers to the genetic state of a given SNP, on each of the two relevant chromosomes for each of the two parents of the target.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also the sequences have been mapped to the genome.

Joint Distribution Model refers to a model that defines the probability of events defined in terms of multiple random variables, given a plurality of random variables defined on the same probability space, where the probabilities of the variable are linked.

Methods for Determining Aneuploidy by Using Data for a Chromosome of Interest from a Diploid Sample(s) to Set a Bias Model for Other Samples in a Parallel Analysis Provided herein in one embodiment are methods and systems for determining the copy number, or detecting aneuploidy of a chromosome or chromosome segment of interest in a cell of interest that are performed using the chromosome or chromosome segment of interest to set a bias model, that is to set test parameters, using samples analyzed in the same parallel analysis, that are identified as diploid samples with high confidence, for the analysis of aneuploidy for the same chromosome or chromosome segment of interest in other sample(s) in the set of on-test samples. Accordingly, in one example of this embodiment, provided herein is a method for determining a presence or absence of aneuploidy of a chromosome or chromosome segment of interest in a test sample, that includes the following steps:

a) obtaining genetic data for the chromosome or chromosome segment of interest from each sample of a set of samples that includes the test sample and at least one diploid sample, wherein the genetic data is obtained from a parallel analysis of the set of samples;

b) setting a bias model using the genetic data for the chromosome or chromosome segment of interest in the diploid sample determined to be disomic for the chromosome or chromosome segment of interest;

c) adjusting the genetic data for the chromosome or chromosome segment of interest for the test sample using the bias model; and d) establishing the presence or absence of aneuploidy for the chromosome or chromosome segment of interest in the test sample using the normalized data.

In the present embodiment of the invention for determining the presence or absence of aneuploidy, the set of samples comprises the test sample and a subset of high probability diploid samples that includes at least one diploid sample. The subset of samples can include, for example, 1-1,056 samples. In illustrative methods the set or subset can be made up of 2, 3, 4, 5, 10, 20, 25, 30, 40, 50, 95, 96, 100, 150, 200, 250, 500, 750, 959, 960, 1046, 1050, 1055, 1056, or 1500 samples on the low end of the range, 3, 4, 5, 10, 20, 25, 30, 40, 50, 95, 96, 100, 150, 200, 250, 500, 750, 959, 960, 1046, 1050, 1051, 1055, 1056, or 1150, 1500, 2000, or 2500 samples on the high end of the range. The set is at least 1 sample more than the subset, and can be 2, 3, 4, 5, 10, 15, 20, 25, 30, 40, 47, 50, 95, 100, 150, 200, 250, 500, 750, or 1000 samples more in certain embodiments.

In certain examples of the invention, at least one sample known to be diploid is used as a control, and run alongside one or more target samples. For example, 2, 3, 4, 5, 10, 15, 20, 25, 30, 35, 40 or 50 control samples identified in advance of the run to be diploid, can be run alongside on-test samples. Any of the analytical methods disclosed herein can then be used to determine the presence or absence of aneuploidy in one or more test samples.

In certain illustrative examples of this embodiment, the at least one diploid sample is determined to be disomic for the chromosome or chromosome segment of interest by analyzing the genetic data from the parallel analysis. In certain examples, an initial or first analytical technique, identifies samples that are disomic for one or more chromosome regions with high confidence. The identity of these diploid samples that are disomic at all of the chromosome or chromosome segments of interest, are then used to set a bias model for a different analytical technique, or a second run of the same analytical technique. Thus, for examples where a sample is a sera sample, the present invention provides an advantage in that less sequencing reads, and accordingly less cost, is associated with performing the method. This is the result of the fact that for sera samples in methods analyzing circulating free DNA, especially circulating fetal DNA or circulating tumor DNA, many if not most of the samples in a parallel run, contain DNA originating from only diploid cells. In illustrative methods of the present invention, at least some of these samples are identified in an initial analysis, and their identities are used in the analysis of the other samples in the set of samples being analyzed.

Some embodiments of the invention employ the step of selecting, determining or identifying a subset of patients from a larger set of patients. The original set of patients is used as the source of target samples containing DNA from target cells and non-target samples containing DNA from non-target cells for analysis. A skilled artisan will understand that numerous methods are known in the art for obtaining genetic data for a chromosome or chromosome segment of interest from a set of samples in a parallel analysis.

In some embodiments of the invention, the DNA samples obtained, are modified using standard molecular biology techniques in order to be sequenced on a DNA sequencer. In some embodiments the technique will involve forming a genetic library containing priming sites for the DNA sequencing procedure. In some embodiments, a plurality of loci may be targeted for site specific amplification. In some embodiments the targeted loci are polymorphic loci, e.g., a single nucleotide polymorphisms. In embodiments employing the formation of genetic libraries, libraries may be encoded using a DNA sequence that is specific for the patient, e.g. barcoding, thereby permitting multiple patients to be analyzed in a single flow cell (or flow cell equivalent) of a high throughput DNA sequencer. Although the samples are mixed together in the DNA sequencer flow cell, the determination of the sequence of the barcode permits identification of the patient source that contributed the DNA that had been sequenced Methods are known in the art for obtaining genetic data from a sample. Typically this involves amplification of DNA in the sample, a process which transforms a small amount of genetic material to a larger amount of genetic material that contains a similar set of genetic data. This can be done by a wide variety of methods, including, but not limited to, Polymerase Chain Reaction (PCR), ligand mediated PCR, degenerative oligonucleotide primer PCR, Multiple Displacement Amplification, allele-specific amplification techniques, Molecular Inversion Probes (MIP), padlock probes, other circularizing probes, and combination thereof. Many variants of the standard protocol can be used, for example increasing or decreasing the times of certain steps in the protocol, increasing or decreasing the temperature of certain steps, increasing or decreasing the amounts of various reagents, etc. The DNA amplification transforms the initial sample of DNA into a sample of DNA that is similar in the set of sequences, but of much greater quantity. In some cases, amplification may not be required. Provided herein in the sample preparation section, are detailed teachings about isolation and amplification of DNA from a sample.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods and systems include Sanger DNA sequencing, pyrosequencing, the ILLUMINA SOLEXA platform, ILLUMINA's GENOME ANALYZER, ILLUMINA's HISEQ or MISEQ, APPLIED BIOSYSTEM's SOLiD platform, ION TORRENT'S PGM or PROTON platforms, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device en route to being processed.

Any relevant individual's genetic data can be obtained from the following: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood or the blood of a cancer patient, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof. In illustrative embodiments, methods provided herein are used to analyze free DNA originating from the genome of a target sample from a target cell, such as fetal cell or tumor cell.

It will be appreciated by those of ordinary skill in the art that in those embodiments of the invention in which the target DNA is not enriched for specific loci, the entire genome may be sequenced, although assembly of the sequence in to a complete genome is not required for use of the subject methods. Allelic data about specific loci may be readily determined from all genome sequencing. Cell free DNA may be conveniently analyzed in commercially available high throughput DNA sequencers. Such high throughput DNA sequencers may also be used in embodiments of the invention employing the targeted amplification of loci of interest, including polymorphic loci.

The term "cell free DNA" as used herein refers to DNA that is available for analysis without requiring the step of lysing cells. Cell free DNA can be found in blood or other bodily fluids. Cell free DNA may be obtained from a variety of tissues. Such tissues may be tissues that are in liquid form such as blood, lymph, ascites fluid, cerebral spinal fluid, and the like. Cell free DNA may be from a variety of cellular sources. In some cases the cell free DNA will be comprised of DNA derived from fetal cells. The cell free DNA may be a mixture of DNA derived from target cells and non-target cells. In the case of the analysis of DNA for fetal aneuploidies, in some embodiments the cell free DNA may be obtained from the blood of the pregnant woman, wherein the cell free DNA comprises a mixture of maternally derived cell free DNA and fetally derived cell free DNA. In other embodiments, the cell free DNA may be derived from a cancerous tumor cell. The cell free DNA may comprise a mixture of cell free DNA derived from the tumor cell and cell free DNA derived from non-tumor cells elsewhere in the body.

Genetic data, e.g., DNA sequence data, can be obtained from a mixture of DNA comprising DNA derived from one or more target cells and DNA derived from one or more non-target cells. The target cells and non-target cells differ with respect to one another at the genomic level, as by virtue of other criteria. The term "derived" is used to indicate that the cells are the ultimate source of the DNA. Thus, for example, cell-free DNA obtained from maternal blood of pregnant woman is derived from cells from the placenta of the fetus, which are typically genetically identical to the fetus itself, and the mother's cells. The method employs a set of patients.

The genetic data is obtained from each member of the patient set typically in a parallel biochemical analysis (i.e. a single assay run). Each patient in the set of patients is analyzed using essentially the same method of nucleic sequence analysis, e.g., the same amplification and sequencing reagents analyzed at the same time on the same run of the same instruments. In some embodiments, all of the samples in the set of samples are mixed together and analyzed so that the analysis conditions will be essentially identical; the analysis of the mixed samples may be termed an experiment, or a sample run or a parallel analysis. In some embodiments, the samples may be mixed prior to amplification. In some embodiments the samples may be mixed after some amplification steps but before other amplification steps. In some embodiments, the samples may be mixed after the amplification steps, but before the sequencing step. Methods for barcoding, known in the art and further discussed herein, help to facilitate simultaneous analysis of multiple samples because the identity of a sample can be determined by a barcode sequence associated with nucleic acids derived from that sample.

In some embodiments, especially those involving methods that provide likelihoods of a ploidy state using hypothesis testing, genetic information is obtained at a plurality of loci. In some embodiments, at least some, and possibly all of the loci are polymorphic. In some embodiments, all of the loci are non-polymorphic. The same loci are analyzed in both the target and non-target cells. A number of sequence reads is obtained for each locus. In some embodiments the number of each allele at a given locus is quantitated. The quantitative data obtained can be from a combination of the loci from the target cell and the non-target cell genomes. Accordingly, in some embodiments, the genetic data provides an amount of DNA corresponding to each locus in a set of loci wherein the loci are present on the chromosome or chromosome segment of interest. In illustrative examples, each chromosome or chromosome segment of interest, can include 10, 15, 20, 25, 30, 40 50, 100, 250, 500, or 1000, 1500, 2000, 2500, 5000, or 10,000 loci on the low end of the range, and 15, 20, 25, 30, 40 50, 100, 250, 500, or 1000, 1500, 2000, 2500, 5000, 10,000 or 25,000 loci on the high end of the range.

The amount of each locus detected by sequencing preparations of a DNA obtained from target and non-target cells can vary from locus to locus for reasons other than the starting quantity of the locus in the initial sample material prior to preparation for sequencing, e.g. prior to an amplification step such as PCR. Variables such as PCR primer binding efficiency, amplicon length, GC content, and the like can cause variations in the representation of individual loci in a preparation for sequencing or during sequencing. Factors such as these can result in a locus specific bias causing the overrepresentation or underrepresentation of one locus to another. In addition, bias can result from sample-specific inconsistencies. For example, due to a pipetting error or other measurement error during physical processing of the samples, one sample can have more DNA than another sample in the set of samples. In illustrative embodiments, these sample-specific biases are taken into account by sample-specific parameters. Certain sample-specific parameters, such as $alpha_s$ in the QMM section herein, can be identified based on observing certain properties of data. Anther sample specific parameter illustrated in the QMM section herein is the factors $c_s$, and $\tau s$ which are constant per sample, and represents for example the initial quantity of DNA and the total number of sequence reads. It can be thought of as the sample-specific amplification factor.

Independent of the specific method used to produce the genetic information, the amount of genetic sequence information from each locus is dependent upon the relative quantity of the copy numbers of the loci in the original sample. Loci that are believed to be on the same chromosomal segment, or in some embodiments the same chromosome, are presumed to have the same starting amount. Thus, for example, the multiple loci present on chromosome 21 in the genome of the target cell (or the genome of the non-target cell) are presumed to be present in approximately equal amounts in the genomic DNA. Thus differences in the amount of observed genetic information between loci on the same chromosome are the result of locus specific bias. For example if SNP1 and SNP2 are located on the same chromosome and assumed to have the same copy number on the same chromosome, and SNP1 is found to have depth of read of 0.1% and SNP2 is found to have a depth of read of 0.4%, this may be explained by a quantifiable locus specific bias favoring the production of DNA sequence from SNP2 over SNP1. This bias may be additionally normalized by virtue of considering the distribution of possible sampling outcomes for the two different SNPs. Thus, methods of the present invention, analyze bias and provide a bias model, as discussed more fully herein. In illustrative embodiments of the invention, bias models are created from chromosome and chromosome segments of interest, in certain embodiments without the use of control chromosome or chromosome segment.

Accordingly, the selected high confidence diploid subset of patients, in certain examples are used to set a bias model. Small variations in reaction conditions mean that samples run at different times experience slightly different conditions, resulting in different relative rates of enrichment and measurement for different molecules of DNA. Various parameters, including reaction-specific, sample-specific parameters and target locus-specific parameters can be set as part of the bias model, allowing normalization of the differing relative rates of enrichment and measurement.

Examples of such biases include amplification bias, sequencing bias, processing bias, enrichment bias, measurement bias, and combinations thereof. The nature of such biases may vary in accordance with the specific amplification technology, sequencing technology, processing, enrichment technology, and particular conditions present for a specific reaction, etc. selected for implementation of the specific embodiment. For example, the diploid sample subset can be used to calculate a per-sample constant of normalization that reflects the overall number of reads in the sample, e.g. the percentage of reads in a sample. In another embodiment, the diploid sample subset can be used to calculate a per-locus constant of normalization that reflects the overall number of reads in the sample, e.g. the percentage of reads in a sample In some embodiments, the relative amount of DNA from each sample that is present in the experiment can be calculated, and used to normalize other sample data parameters. In some embodiments, the proportion of DNA mapping to a chromosome of interest can be calculated, and the proportion of DNA mapping to the chromosome of interest from the selected subset of patients can be used to calculate a per-experiment constant of normalization that reflects the proportion or overall amount of DNA from the chromosome of interest that is expected for a normal sample, e.g. the percentage of reads in a sample that map to the chromosome of interest. In some embodiments, the relative amount of DNA mapping to each of a plurality of targeted loci can be calculated in the selected subset of patients, and this can be used to calculate a per-experiment, per-locus constant of normalization that reflects the amplification and/or measurement bias for each locus. In some embodiments, the bias model could be used to create a noise parameter that aggregates amplification bias and various possible errors such as transcription error rates, contamination rates, and/or sequencing error rates. In certain examples, a bias model, or a portion thereof, such as an allele-specific amplification bias, can be used by a method that initially analyzed the genetic data to identify diploid samples, that was calculated from data from a prior run.

In some examples of this embodiment of the invention, quantitative allelic and non-allelic data are both analyzed so as to produce an identification of the number of chromosomes or chromosome segments of interest with a higher level of confidence than using the allelic data or non-allelic data alone. The data can be from the same set of loci and in fact the same data, analyzed separately for different alleles or as a combined sum for all alleles of a locus or a haplotype.

In certain illustrative examples of this embodiment, quantitative allelic information is used to determine the copy number of the chromosome of interest or the chromosome segment of interest without relying on a cut-off value. Polymorphic loci, e.g., from SNPs that are heterozygous between the target cell and the non-target cell, e.g. a fetus and its mother, can be used to determine the copy number of chromosomal or chromosomal segment based on quantitative allelic data from the polymorphic loci. Provided herein is an exemplary allele-based maximum likelihood method called the "heterozygote method" or "het rate method" of determining chromosome or chromosome segment copy number. Polymorphic loci that are heterozygous between the target cell and the non-target cell, e.g., a fetus and its mother, can be used to determine the relative amounts of target cell DNA and non-target cell DNA in the sample for analysis. The quantity of genetic information from the polymorphic loci is dependent upon the amount of genetic starting material and the relative amounts of DNA from the target cells and the non-target cells. The ratio of alleles at a plurality of polymorphic loci can be determined and tested against models corresponding to predicted allele ratios for various chromosome copy number (or chromosome segment copy number) hypotheses. The effects on predicted data for differing ratios of target cell DNA and non-target cell DNA are included in such models. For example, in the case of testing cell free DNA in the blood of a pregnant woman, the potential different fetal fractions (ratio of fetal DNA to total DNA; also referred to herein as child fraction) can be modeled.

In certain embodiments, diploid samples are determined and/or aneuploidy of the chromosome or chromosome segment of interest are established using one or two algorithms that provide maximum likelihoods. In these methods the collected data is typically tested against a plurality of copy number hypotheses. The copy number hypotheses can be created for the number of copies of a chromosome or number of copies of a chromosome segment of the target cell. Each hypothesis is tested against the genetic data obtained from the loci. The testing of a hypothesis against the genetic data results in the calculation of a probability value that the copy number hypothesis is correct (or conversely incorrect). In some embodiments wherein the genetic data is obtained from cell free DNA obtained from the blood of a pregnant woman, the hypothesis can include a condition that the mother is carrying multiple fetuses, e.g., twins.

The probability value is used to select a subset of patients consisting of those patients that are the source of genetic data that is found to match a specific copy number hypothesis with a specified level of confidence. In essence, a subset of patients is selected, wherein the selected subset of patients matches the selected hypothesis with a high level of confidence, the high level of confidence being specified for the specific embodiment. In illustrative examples of this embodiment of the invention, for example, the hypothesis could be that chromosome 21 has 2 copies, chromosome 13 has 2 copies, and chromosome 18 has 2 copies. Samples meeting this hypothesis with high confidence in an NIPT analysis are considered diploid samples in this embodiment. These diploid samples are then used to set a bias model. In some embodiments, the bias model is used by the same analysis technique to reassess the samples that were not included in the diploid sample subset. In other embodiments, a second analytical technique is used to analyze one or more samples in the set of samples that were not identified in the initial analysis as members of the diploid subset.

In some embodiments, a set of at least one ploidy state hypothesis can be created for each of the chromosomes of interest of the target individual. Each of the ploidy state hypotheses may refer to one possible ploidy state of the chromosome or chromosome segment of the target individual. The set of hypotheses may include some or all of the possible ploidy states that the chromosome of the target individual may be expected to have. Some of the possible ploidy states may include nullsomy, monosomy, disomy, uniparental disomy, euploidy, trisomy, matching trisomy, unmatching trisomy, maternal trisomy, paternal trisomy, tetrasomy, balanced (2:2) tetrasomy, unbalanced (3:1) tetrasomy, other aneuploidy, and they may additionally involve unbalanced translocations, balanced translocations, Robertsonian translocations, recombinations, deletions, insertions, crossovers, and combinations thereof.

In some embodiments, the knowledge of the determined ploidy state may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy. In some embodiments the clinical decision may involve an intervention designed to decrease the severity of the phenotypic presentation of a genetic disorder, or a decision to take relevant steps to prepare for a special needs child.

Some of the math in the presently disclosed embodiments makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, hexasomy etc., without changing the fundamental concepts of the present disclosure. At the same time, it is possible to focus on a smaller number of ploidy states, for example, only trisomy and disomy. Note that ploidy determinations that indicate a non-whole number of chromosomes may indicate mosaicism in a sample of genetic material.

In some embodiments, the genetic abnormality is a type of aneuploidy, such as Down syndrome (or trisomy 21), Edwards syndrome (trisomy 18), Patau syndrome (trisomy 13), Turner Syndrome (45×0) Klinefelter's syndrome (a male with 2× chromosomes), Prader-Willi syndrome, and DiGeorge syndrome. Congenital disorders, such as those listed in the prior sentence, are commonly undesirable, and the knowledge that a fetus is afflicted with one or more phenotypic abnormalities may provide the basis for a decision to terminate the pregnancy, to take necessary precautions to prepare for the birth of a special needs child, or to take some therapeutic approach meant to lessen the severity of a chromosomal abnormality.

In certain embodiments of the invention, one or two maximum likelihood methods are used. As disclosed above, the first maximum likelihood method can be used to identify diploid samples in the set of samples and to determine a first probability that the other samples in the set of samples are aneuploidy. Accordingly, in certain embodiments, one or more or all of the chromosome(s) or chromosome segment(s) of interest are determined to be disomic using a first maximum likelihood method. The method includes the following steps:

creating, for each sample in the set of samples, a plurality of first hypotheses wherein each first hypothesis is associated with a specific copy number for the chromosome or chromosome segment of interest, determining a first probability value for each first hypothesis, wherein the first probability value indicates the likelihood that the sample has the number of copies of the chromosome or chromosome segment that is associated with the first hypothesis, wherein the first probability values are derived from the genetic data associated with the sample, and selecting at least one diploid sample by selecting those one or more samples that most closely match a disomic copy number hypothesis for the chromosome or chromosome segment of interest, with at least a minimum level of confidence. That is, by selecting those samples that yield the highest probability of being disomic for the chromosome or chromosome segment of interest.

In certain examples using a maximum likelihood allelic method, the method is performed by analyzing a second chromosome or chromosome segment of interest and a third chromosome or chromosome of interest in the parallel analysis, wherein the diploid samples are identified by a method comprising comparing genetic data from the first, second, and third chromosome or chromosome segments of interest for each sample of the set of samples.

In these embodiments wherein the method includes at least two maximum likelihood analysis, the presence or absence of aneuploidy, or the number of copies of the chromosome or chromosome segment of interest, is determine by creating a plurality or set of $2^{nd}$ ploidy hypotheses, wherein each $2^{nd}$ ploidy hypothesis is associated with a specific copy number of the chromosome or chromosome segment of interest in the target cell. The models are then used to test how well the genetic data from each patient fits each $2^{nd}$ hypothesis. The goodness of fit for each $2^{nd}$ hypothesis is determined. A second probability value is calculated for each second hypothesis wherein the second probability value indicates the likelihood that the genome of the target cell has the number of chromosomes or chromosome segments that is specified by the second hypothesis. Thus by selecting the $2^{nd}$ hypothesis with the maximum likelihood, one may determine the copy number for the chromosome or chromosome segment in the genome of the target cell. Such first and second hypothesis can be considered in combination to increase the confidence of the aneuploidy determination, as discussed more fully herein.

In this embodiment of the invention, the subset of samples that is selected because they are identified as diploid samples with high confidence, is used to create a bias model. The bias model is created using the genetic data for the chromosome or chromosome segment of interest. In certain illustrative embodiments, high confidence diploid samples are identified, and/or the bias model is created without using a control chromosome or control chromosome segment.

In some embodiments the $1^{st}$ hypotheses are the same as the $2^{nd}$ hypotheses.

In certain embodiments, determining a first probability value for each first hypothesis includes the following:
a. determining an initial probability of each first hypothesis for each grid point using a uniform hypothesis prior on a $2^{nd}$ grid of fetal fraction and the second bias model;
b. determining a parameter distribution for each chromosome or chromosome segment of interest based on the initial probability;
c. determining a composite parameter distribution from the parameter distribution for each chromosome or chromosome segment of interest;
d. determining a posterior probability of each first hypothesis based on the composite parameter distribution; and
e. repeating steps (a)-(e) using the posterior probability as a new initial probability for each iteration until convergence is reached.

In certain embodiments, determining a ploidy probability value for each ploidy hypothesis comprises:
a. determining an initial probability of each ploidy hypothesis for each grid point using a uniform hypothesis prior on a $2^{nd}$ grid of fetal fraction and the first bias model;
b. determining a parameter distribution for each chromosome or chromosome segment of interest based on the initial probability;
c. determining a composite parameter distribution from the parameter distribution for each chromosome or chromosome segment of interest;
d. determining a posterior probability of each ploidy hypothesis based on the composite parameter distribution; and
e. repeating steps (a)-(e) using the posterior probability as a new initial probability for each iteration until convergence is reached.

In these embodiments, the second bias model, can be the noise parameter discussed herein. The above embodiments that analyze grid points can be used in certain examples, with a quantitative allelic method. Further disclosure related to the above grid point hypothesis testing is found in the het rate section herein.

In some embodiments the genetic data obtained from the target and non-target cells identifies the alleles of polymorphic loci and the number of reads of each allele is quantitatively measured. Each $1^{st}$ hypothesis is tested against a model specifying a specific distribution of quantitative allelic data at the plurality of polymorphic loci. Probability values are determined by calculating for each hypothesis the fit between the expected genetic data and the obtained, i.e. measured, genetic data. The probabilities can be weighted for the biological probability that a given genetic event is likely to occur.

In some embodiments the genetic data obtained from the target and non-target cells identifies the alleles of polymorphic loci and the number of reads of each is quantitatively measured without regard for the identity of the specific alleles. Each first hypothesis, or in illustrative embodiments second hypothesis is tested against a model specifying a specific distribution of quantitative allelic data at the plurality of loci analyzed. Probability values are determined by calculating for each hypothesis the fit between the expected genetic data and the obtained, i.e. measured, genetic data.

In some embodiments, the genetic data comprises quantitative genetic data from a plurality of non-polymorphic loci in which the $2^{nd}$ hypothesis specifies an expected distribution of quantitative data at the plurality of non-polymorphic loci and where in the $2^{nd}$ probability values are determined by calculating, for each $2^{nd}$ hypothesis the goodness of fit between the expected genetic data and the normalized genetic data. In these embodiments, a test statistic, as disclosed herein for the QMM method, or a z-score could be determined.

In one embodiment of the present disclosure, where the method used to determine the ploidy state of a fetus, the method further includes taking into account the fraction of fetal DNA in the sample. In one embodiment of the present disclosure, the method involves calculating the percent of DNA in a sample that is fetal or placental in origin. In one embodiment of the present disclosure, the threshold for calling aneuploidy is adaptively normalized based on the calculated percent fetal DNA. In some embodiments, the method for estimating the percentage of DNA that is of fetal origin in a mixture of DNA, comprises obtaining a mixed sample that contains genetic material from the mother, and genetic material from the fetus, obtaining a genetic sample from the father of the fetus, measuring the DNA in the mixed sample, measuring the DNA in the father sample, and calculating the percentage of DNA that is of fetal origin in the mixed sample using the DNA measurements of the mixed sample, and of the father sample.

In one embodiment of the present disclosure, the fraction of fetal DNA, or the percentage of fetal DNA in the mixture can be measured. In some embodiments the fraction can be calculated using only the genotyping measurements made on the maternal plasma sample itself, which is a mixture of fetal and maternal DNA. In some embodiments the fraction may be calculated also using the measured or otherwise known genotype of the mother and/or the measured or otherwise known genotype of the father. In some embodiments the percent fetal DNA may be calculated using the measurements made on the mixture of maternal and fetal DNA along with the knowledge of the parental contexts. In one embodiment the fraction of fetal DNA may be calculated using population frequencies to adjust the model on the probability on particular allele measurements.

The accuracy of a ploidy determination is typically dependent on a number of factors, including the number of reads and the fraction of fetal DNA in the mixture. The accuracy is typically higher when the fraction of fetal DNA in the mixture is higher. At the same time, the accuracy is typically higher if the number of reads is greater. It is possible to have a situation with two cases where the ploidy state is determined with comparable accuracies wherein the first case has a lower fraction of fetal DNA in the mixture than the second, and more reads were sequenced in the first case than the second. It is possible to use the estimated fraction of fetal DNA in the mixture as a guide in determining the number of reads necessary to achieve a given level of accuracy.

In an embodiment of the present disclosure, a set of samples can be run where different samples in the set are sequenced to different reads depths, wherein the number of reads run on each of the samples is chosen to achieve a given level of accuracy given the calculated fraction of fetal DNA in each mixture. In one embodiment of the present disclosure, this may entail making a measurement of the mixed sample to determine the fraction of fetal DNA in the mixture; this estimation of the fetal fraction may be done with sequencing, it may be done with TaqMan, it may be done with another qPCR method, it may be done with SNP arrays, it may be done with any method that can distinguish different alleles at a given loci. The need for a fetal fraction estimate may be eliminated by including hypotheses that cover all or a selected set of fetal fractions in the set of hypotheses that are considered when comparing to the actual measured data. After the fraction fetal DNA in the mixture has been determined, the number of sequences to be read for each sample may be determined.

Accordingly, certain examples of the method for determining aneuploidy further include estimating a fetal fraction for each sample in the set of samples, wherein the fetal fraction is used to select the diploid subset of samples and/or to determine whether the genetic data from the test subject is indicative of an aneuploidy. That is, fetal fraction can be used in one or both methods used in a method for determining aneuploidy wherein a first method is used to identify diploid samples and a second method uses those diploid centers to determine wither another sample in a set of samples is an aneuploidy sample.

FIG. 1 is a non-limiting example of a method 100 of the invention that includes the use of a first method for identifying a subset of diploid samples and a second method to increase the accuracy and/or confidence of detection of aneuploidy in NIPT. The method starts at block 102, where genetic data is obtained from a mixture of target DNA and non-target DNA for each sample from a set of samples, one for each patient in a set of patients, by running a plurality of samples from pregnant mothers in parallel. That is, the samples are analyzed together at the same time typically using the same common reagents and instruments. In this example, the set of samples are barcoded, mixed, and amplified in the same reaction. Then, the set of samples are amplified in parallel using the same or nearly the same conditions. Next, the set of samples are sequenced on the same sequencing flow cell using the same conditions.

In block 104, a method (block 105) is used to make an initial determination of the copy number of the chromosome of interest in each of the samples from the set of samples. In one example, the initial determination is a made by a method that relies on allelic data, for example, the het rate method 108 provided herein. In other examples, the initial determination is made by a quantitative method 106 that relies on non-allelic data.

In block 110, a subset of samples from the plurality of samples is selected where the likelihood is very high that each of the chromosomes in the subset of samples are normally represented (i.e. diploid). In one example, one could choose only those samples for inclusion into the subset where a non-allelic quantitative method 106, such as a method that determines a depth of read is used and the absolute value of the z-score is less than 0.5, 1, 1.5, or 2, for example, or where the z-score is indicative of disomy with at least a minimum level of confidence (e.g. 90%, 95%, 99%, 99.5%, 99.6%, 99.7%, 99.8% or 99.9%, for example). Alternately, one could choose only those samples for inclusion into the subset where a het rate method 108 is used that calculates a confidence, and where the calculated confidence that the chromosome is disomic is greater than 0.9, 0.95, 0.990, 0.9995, 0.9996, 0.997, 0998, or 0.9999, for example. Alternately, one could simply choose a fixed size subset by choosing those samples with the highest confidence or the z-score closest to zero. For example, one could analyze 96 samples and choose the 24 samples with the highest confidence of disomy for inclusion into the subset.

Once the subset of samples has been chosen, it is possible to use the genetic data measured on the chromosome of interest in the subset of samples as a reference set of samples for a secondary analysis of the samples in the plurality of samples that are not in the subset of samples. For example, the conditions in any given amplification reaction and sequencing run are slightly different, resulting in slightly different profiles of amplification rates and biases for each locus and for each sample. If a plurality of samples are run using the same conditions, and especially if those samples are run in one homogenous mixture, then it is reasonable to believe that the relative amplification and other processing biases will be minimized. A second analytical method (block 117) can then use the reference samples to create a model of the biases (block 112), either on a per-SNP basis (i.e. what is the relative amplification and processing bias for each SNP), a per-region basis (i.e. what is the relative amplification and processing bias for each region of DNA), or on a per-chromosome basis (i.e. what is the relative amplification and other processing bias for each chromosome). In certain examples not illustrated in FIG. 1, the first analytical method (block 105) can use a bias model as well, which can be built using data from the run or which can be built from previous data.

In block 114, the genetic data for all patients in the set of patients from the parallel analysis is then normalized according to the bias model from block 112, to correct bias errors where appropriate.

In block 116, once the data is normalized, samples with unknown ploidy states can then be analyzed a second time to determine the copy number, by comparing a set of copy number hypotheses to the normalized genetic data. This may be done using the same or a different method as the initial determination in block 104. For example, this second analytical method 117 may be performed using a quantitative method 118, such as the QMM method 118 as discussed below, a het rate method 120, as also discussed below, or samples with unknown ploidy could be analyzed by both an allelic method such as a het rate method 120 and a quantitative non-allelic method 188 such as QMM. For methods that generate a maximum likelihood, such as QMM and het rate, a copy number probability value is then determined in block 122 for each copy number hypothesis.

In another example, blood is drawn from 96 pregnant women who want to know if their fetuses have Down syndrome, or trisomy 21. These 96 samples are then all be processed and biochemically analyzed together, or in parallel. In other examples, the number of samples run in parallel could be, for example, at least 3, 8, 24, 36, 48, 72, 108, 144, 288, or 396. In certain examples, no more than 396 samples are analyzed in parallel. The DNA from each of the samples then has a barcode attached, and then all of the sample are pooled and amplified. The amplified DNA is then sequenced using a high throughput sequencer (e.g. block 102). Then a het rate method (e.g. block 108) is used to analyze each of the samples. The 24 samples with the highest confidence for disomy at chromosome 21 is selected to select (i.e. identify) a subset of samples that could act as a reference subset (e.g. block 110). Alternately, a quantitative method could be used to analyze each of the samples to give a preliminary estimate of the proportion of DNA mapping to chromosome 21 (e.g. block 106). The 24 samples with the z-score closest to zero could be selected as a subset of samples that could act as the reference subset (e.g. block 110).

Once the reference or control subset is chosen (e.g. block 112), a second analytical method (117) can make the assumption that these cases are disomic, and then estimate the per-SNP bias, that is, the experiment-specific amplification and other processing bias for each locus using these diploid samples. Then, the second method (117) can use this experiment-specific bias estimate to correct the bias in the measurements of genetic data (e.g. sequencing reads) of the chromosome 21 loci, and for other chromosome loci (e.g. chromosomes 13, 18, X, and Y) as appropriate, for the 72 samples that are not part of the subset where disomy was assumed for chromosome 21 (e.g. block 114).

Once the reference (i.e. control) diploid samples have been selected (i.e. identified) (110), the data from the 72 samples with unknown ploidy state can then be analyzed a second time using the same or a different method (117) to determine whether the fetuses are afflicted with trisomy 21. The reference diploid subset of samples are used to set a bias model (112) that is used by a second method (117) to normalize the genetic data from the samples that were not selected as members of the high confidence diploid subset. For example, a quantitative method could be used on the remaining 72 samples, and a z-score could be calculated using the corrected measured genetic data on chromosome 21 (e.g. block 118).

In certain embodiments, the bias correction or normalization of the genetic data is done as part of the second analysis. As part of the preliminary estimate of the ploidy state of chromosome 21, a fetal fraction, in certain examples, is calculated. The proportion of corrected reads that would be expected in the case of a disomy (the disomy hypothesis), and the proportion of corrected reads that would be expected in the case of a trisomy (the trisomy hypothesis) are calculated for a case with that fetal fraction. Alternately, if the fetal fraction was not measured previously, a set of disomy and trisomy hypotheses are generated for different fetal fractions. For each case, an expected distribution of the proportion of corrected reads are calculated given expected statistical variation in the selection and measurement of the various DNA loci. The observed corrected proportion of reads are compared to the distribution of the expected proportion of corrected reads, and a likelihood ratio is calculated for the disomy and trisomy hypotheses, for each of the 72 samples. The ploidy state associated with the hypothesis with the highest calculated likelihood, for each of the 72 samples, in this example, is selected as the correct ploidy state. In another embodiment, the corrected genetic data for the remaining 72 samples is analyzed using a plurality of orthogonal methods, and the resulting likelihoods are then combined to give a combined likelihood which is used to determine the actual ploidy state of each of the fetuses. In one embodiment, an allelic maximum likelihood method, such as the het rate method and a quantitative method, such as the QMM method, are each used to determine the likelihood of disomy and trisomy in the fetus, and these likelihoods are combined or considered together in a set of rules that provide a output of whether a sample exhibits aneuoploidy in any of the chromosome or chromosome segments of interest. It will be apparent to an ordinary person skilled in the art how any of the approaches disclosed herein could be used for other types of whole chromosome abnormalities. Furthermore, it will be apparent to an ordinary person skilled in the art how any of the approaches disclosed herein could be used for other types of partial chromosomal abnormalities, for example, a microdeletion, a micro duplication, or an unbalanced translocation.

In some embodiments the target cells are fetal cells and non-target cells are from the mother of the fetus. In some embodiments the invention is directed to non-invasive prenatal diagnosis, and the target cells may be fetal cells and the non-target cells may be maternal cells. In some embodiments of the invention an example of a hypothesis that may be used to select the subset of samples is the hypothesis that a specific chromosome or chromosome segment is diploid i.e. present in 2 copies. Examples of chromosomes for analysis include chromosomes 13, 18, 21, X and Y, including segments thereof. For example, the subset of samples may be chosen on the basis of having the highest likelihood that all or nearly all of the DNA in the sample originated from cells with precisely two copies of the chromosome of interest. In certain embodiments, the chromosomes that are analyzed are chromosomes 13, 18, and 21.

In some embodiments, the chromosome segment (s) that is analyzed for copy number is at least 1, 2, 3, 4, 5, 6, 7, 8, 9, 10 or all segments selected from the group consisting of chromosome 22q11.2, chromosome 1p36, chromosome 15q11-q13, chromosome 4p16.3, chromosome 5p15.2, chromosome 17p13.3, chromosome 22q13.3, chromosome 2q37, chromosome 3q29, chromosome 9q34, chromosome 17q21.31, and the terminus of a chromosome.

Note that it has been demonstrated that DNA that originated from cancer that is living in a host can be found in the blood of the host. In the same way that genetic diagnoses can be made from the measurement of mixed DNA found in maternal blood, genetic diagnoses can equally well be made from the measurement of mixed DNA found in host blood. The genetic diagnoses may include aneuploidy states, or gene mutations. Any claim in that patent that reads on determining the ploidy state or genetic state of a fetus from the measurements made on maternal blood can equally well read on determining the ploidy state or genetic state of a cancer from the measurements on host blood.

In some embodiments, the method may allow one to determine the ploidy status of a cancer, the method comprising obtaining a mixed sample that contains genetic material from the host, and genetic material from the cancer, measuring the DNA in the mixed sample, calculating the fraction of DNA that is of cancer origin in the mixed sample, and determining the ploidy status of the cancer using the measurements made on the mixed sample and the calculated fraction. In some embodiments, the method may further comprise administering a cancer therapeutic based on the determination of the ploidy state of the cancer. In some embodiments, the method may further comprise administering a cancer therapeutic based on the determination of the ploidy state of the cancer, wherein the cancer therapeutic is taken from the group comprising a pharmaceutical, a biologic therapeutic, and antibody based therapy and combination thereof.

Accordingly, in some embodiments the target cell is a tumor cell and the non-target cell is a non-tumor cell. In some embodiments the cell free DNA comprises DNA that that has been released by apoptosis. In some embodiments the target cell is a malignant tumor cell.

In certain embodiments, the chromosome or chromosome segment of interest is known to exhibit CNV in cancer (see for example, Liu et al. Oncotarget. 2013 November; 4(11): 1868-188, incorporated by reference in its entirety and Beroukhim et al, Nature. 2010 Feb. 18; 463(7283): 899-905, incorporated by reference in its entirety). For example, the chromosome or chromosome segment of interest in certain embodiments, is a chromosome or chromosome segment comprising at least 1, 2, 3, 4, 5, 10, 15, 20 or more of the following genes: ERBB2, EGFR, MYC, PIK3CA, IGF1R, FGFR1/2, KRAS, CDK4, CCND1, MDM2, MET, CDK6 (in certain embodiments, chromosome or chromosome segments that include these genes are assayed for amplification), and RB1, PTEN, CDKN2A/B, ARID1A, MAP2K4, NF1, SMAD4, BRCA1/2, MSH2/6, DCC, CDH1 (in certain embodiments chromosome or chromosome segments that include these genes are assayed for deletion). In some embodiments wherein at least some of the genetic data is derived from circulating tumor cells, the chromosome segment, or chromosome from which the segment originates, is 1p, 2p, 2q, 3p, 3q, 4p, 5p, 5q, 6p, 6q, 7p, 7q, 8p, 8q, 9p, 9q, 10p, 10q, 11p, 11q, 12p, 12q, 13q, 14q, 15q, 16p, 16q, 17p, 17q, 18p, 18q, 19p, 19q, 20p, 20q, 21q, 22q (See Beroukhim et al. Nature. 2010 Feb. 18; 463 Supp FIG. 6).

The following provides a non-limiting example of a method for the detection of aneuploidy (i.e. copy number variation "CNV") in circulating tumor DNA in a blood sample from an individual at high risk of having cancer, using a method of the invention that includes the use of a first method for identifying a subset of samples having a normal copy number for one or more target chromosome regions, and a second method to increase the accuracy of detection of CNV at the one or more target chromosome regions. Accordingly, a blood sample is collected from each of 48 patients at high-risk for breast cancer, of which for example, eleven actually have breast cancer. Blood samples are centrifuged, plasma separated, and the DNA isolated from the plasma. The isolated DNA is then amplified using a non-specific amplification for six to ten cycles in one example, or it is amplified for four to sixteen cycles in another example. The DNA is then be amplified using a targeted PCR protocol that targets a plurality of loci located across one or more chromosomal regions where amplification or deletion of the chromosomal regions are indicative of cancer; the regions may be focal regions or they may be entire arms of chromosomes, or entire chromosomes. The regions may be commonly observed to be deleted or amplified in specific cancers, they may be directly believed to affect oncogenesis, and/or they may be driver mutations. The targeted amplification or deletion may simultaneously amplify or delete single nucleotide variants implicated in oncogenesis, or correlated with the presence of a tumor. Each region may contain at least 20 loci, at least 50 loci, at least 100 loci, at least 200 loci, at least 500 loci, or at least 1,000 loci. The loci may be comprised of polymorphic loci, for example SNPs. The loci may also be comprised of non-polymorphic loci. The amplified DNA may be measured using high throughput sequencing.

The data from each of the samples is analyzed to determine which of the samples have a high likelihood of not having any CNVs. This analysis can involve analysis of allelic data, it can involve analysis of quantitative data, or it may involve analysis of both allelic and quantitative data. The determination that certain samples are most likely to not have any CNVs (i.e. a normal sample) is based in this example, on selecting the samples with the lowest fraction of tumor DNA, selecting the samples with the z-score closest to zero, selecting the samples where the data fits the hypothesis corresponding to no CNVs with the highest confidence or likelihood, selecting the samples known to be normal, selecting the samples from individuals with the lowest likelihood of having cancer (e.g. having a low age, being a male when screening for breast cancer, having no family history, etc.), selecting the samples with the highest input amount of DNA, selecting the samples with the highest signal to noise ratio, selecting samples based on other criteria believed to be correlated to the likelihood of having cancer, or selecting samples using some combination of criteria.

A subset of the 48 samples with a sufficiently low likelihood of having cancer in this example are selected to act as a control set of samples. The subset can be a fixed number or percent of samples, or it can be a variable number that is based on choosing only those samples that fall below a threshold. For example, the 25, 20, 15, 10, or 5% of samples with the lowest likelihood of aneuploidy or lowest absolute value z score can be selected as the control subset. Alternatively, the 25, 20, 15, 10 or 5 samples with the lowest likelihood of aneuploidy or lowest absolute value z-score can be selected as the control subset. The quantitative data from the subset of samples can be combined, averaged, or combined using a weighted average where the weighting is based on the likelihood of the sample being normal. The quantitative data may be used to determine the per-locus bias for the amplification the sequencing of samples as well as for sample biases and other biases disclosed herein as part of a bias model, in the instant batch of 48 samples. The per-locus bias can also include data from other batches of samples. The per-locus bias can indicate the relative over- or under-amplification that was observed for that locus compared to other loci, making the assumption that the subset of samples do not contain any CNVs, and that any observed over or under-amplification is due to amplification and/or sequencing or other bias. The per-locus bias can take into account the GC content of the amplicon. The loci can be grouped into groups of loci for the purpose of calculating a per-locus bias. Once the per-locus bias has been calculated for each locus in the plurality of loci, the sequencing data for one or more of the samples that are not in the subset of the samples, and optionally one or more of the samples that are in the subset of samples, can be corrected by adjusting the quantitative measurements for each locus to remove the effect of the bias at that locus. For example, if SNP 1 was observed, in the subset of patients, to have a depth of read that is twice as great as the average, the adjustment can involve replacing the number of reads corresponding from SNP 1 with a number that is half as great. If the locus in question is a SNP, the adjustment can involve cutting the number of reads corresponding to each of the alleles at that locus in half.

Once the sequencing data for each of the loci in one or more samples has been normalized, it is analyzed using at least one method, and in illustrative embodiments at least two methods for the purpose of detecting the presence of a CNV at one or more chromosomal regions. The method can be a quantitative maximum likelihood method that uses only quantitative non-allelic data, it can be an allelic maximum likelihood method that only uses allelic data, including allele ratios or allele distributions, it may be a method that uses both quantitative non-allelic and allelic data, or it may be a method that uses other types of data. The likelihood of a CNV is calculated using such a method. The likelihoods produced for a plurality of hypotheses by more than one method is combined; if the methods are not orthogonal, that is, if the likelihoods generated have some correlation, a correction may be applied when combining the likelihoods.

For example, sample A, a mixture of amplified DNA originating from a mixture of normal and cancerous cells, is analyzed using a quantitative method: a region of the q arm on chromosome 22 is found to only have 90% as much DNA mapping to that region as expected; a focal region corresponding to the HER2 gene is found to have 150% as much DNA mapping to that region as expected; and the p-arm of chromosome 5 is found to have 105% as much DNA mapping to it as expected. A clinician can infer that the sample has a deletion of a region on the q arm on chromosome 22, and a duplication of the HER2 gene. The clinician can infer that since the 22q deletions are common in breast cancer, and that since cells with a deletion of the 22q region on both chromosomes usually do not survive, that approximately 20% of the DNA in the sample came from cells with a 22q deletion on one of the two chromosomes. The clinician may also infer that if the DNA from the mixed sample that originated from tumor cells originated from a set of genetically tumor cells whose HER2 region and 22q regions were homogenous, then the cells contained a five-fold duplication of the HER2 region. Of course tumors tend to be heterogeneous, so this may not be an appropriate assumption.

In this example, sample A is also analyzed using an allelic method: the two haplotypes on same region on the q arm on chromosome 22 are observed to be present in a ratio of 4:5; the two haplotypes in a focal region corresponding to the HER2 gene are found to be present in ratios of 1:2; and the two haplotypes in the p-arm of chromosome 5 are observed in ratios of 20:21. All other assayed regions of the genome are found to have no statistically significant excess of either haplotype. A clinician can infer that the sample contains DNA from a tumor with a CNV in the 22q region, the HER2 region, and the 5p arm. Based on the knowledge that 22q deletions are very common in breast cancer, and/or the quantitative analysis showing an under-representation of the amount of DNA mapping to the 22q region of the genome, the clinician can infer the existence of a tumor with a 22q deletion. Based on the knowledge that HER2 amplifications are very common in breast cancer, and/or the quantitative analysis showing an over-representation of the amount of DNA mapping to the HER2 region of the genome, the clinician can infer the existence of a tumor with a HER2 amplification. Based on the inferences, the clinician may decide to pursue additional diagnostic testing such as a tumor biopsy. Based on these inferences, the clinician can perform a mammogram or an ultrasound. Based on these inferences, the clinician can perform a lumpectomy, a mastectomy, or otherwise excise the tumor. Based on these inferences, the clinician can choose a course of radiation therapy, chemotherapy, immunotherapy or other cancer therapy. It is also possible to run other genetic assays in parallel or in the same assay, for example, testing for the presence of one or more SNVs. The clinician can choose the form of therapy, or combination of therapies, based on the genetic footprint, that is, the particular combination of CNVs and other mutations such as SNVs that are observed in the sample, combined with any other data such as clinical data or phenotypic data. It should be apparent to an ordinary person skilled in the art how any of the approaches discussed herein could be used for other types of cancer.

Allelic Joint Distribution Methods

In certain embodiments, methods of the invention include determining whether the distribution of observed allele measurements is indicative of a euploid or an aneuploid sample, such as a fetus or circulating tumor cell, using a joint distribution model. The use of a joint distribution model provides certain advantages over methods that determine heterozygosity rates by treating polymorphic loci independently in that the resultant determinations are of significantly higher accuracy. Without being bound by any particular theory, it is believed that one reason they are of higher accuracy is that the joint distribution model takes into account the linkage between SNPs, and likelihood of crossovers occurring. Another reason it is believed that they are of higher accuracy is that they can take into account alleles where the total number of reads is low, and the allele ratio method would produce disproportionately weighted stochastic noise. The het rate method provided herein, is an example of an allelic joint distribution method that can be used to carry out many of the embodiments provided herein.

In certain embodiments provided herein, methods of the invention include determining whether the distribution of observed allele measurements is indicative of a euploid or an aneuploidy sample using a maximum likelihood technique. The use of a maximum likelihood technique has certain advantages over methods that use single hypothesis rejection technique in that the resultant determinations will be made with significantly higher accuracy. One reason is that single hypothesis rejection techniques set cut off thresholds based on only one measurement distribution rather than two, meaning that the thresholds are usually not optimal. Another reason is that the maximum likelihood technique allows the optimization of the cut off threshold for each individual sample instead of determining a cut off threshold to be used for all samples regardless of the particular characteristics of each individual sample. Another reason is that the use of a maximum likelihood technique allows the calculation of a confidence for each ploidy call.

In certain embodiments provide herein, the method includes determining whether the distribution of observed allele measurements is indicative of a euploid or an aneuploid sample without comparing the distribution of observed allele measurements on a suspect chromosome to a distribution of observed allele measurements on a reference chromosome that is expected to be disomic. This is a significant improvement over methods that require the use of a reference chromosome to determine whether a suspect chromosome is euploid or aneuploid. One example of where a ploidy calling technique that requires a reference chromosome would make an incorrect call is in the case of a 69XXX(trisomic fetus), which would be called euploid since there is no reference diploid chromosome, while the method described herein would be able to determine that the fetus was trisomic.

In certain embodiments provided herein, the method involves using algorithms that analyze the distribution of alleles that have different parental contexts, and comparing the observed allele distributions to the expected allele distributions for different ploidy states for the different parental contexts (different parental genotypic patterns). Such algorithms are different than methods that do not utilize allele distribution patterns for alleles from a plurality of different parental contexts because they allow the use of significantly more genetic measurement data from a set of sequence data in the ploidy determination, resulting in a more accurate determination. In certain embodiments provided herein, the method includes determining whether the distribution of observed allele measurements is indicative of a euploid or an aneuploid fetus using observed allelic distributions measured at loci where the mother is heterozygous. This allows the use of about twice as much genetic measurement data from a set of sequence data in the ploidy determination than methods that do not use observed allelic distributions, resulting in some instances, in a more accurate determination.

In certain embodiments provided herein, genetic data is obtained from DNA that is isolated using a selective enrichment techniques that preserve the allele distributions that are present in the original sample of DNA. In some embodiments the amplification and/or selective enrichment technique may involve targeted amplification, hybrid capture, or circularizing probes. In some embodiments, methods for amplification or selective enrichment may involve using probes where the hybridizing region on the probe is separated from the variable region of the polymorphic allele by a small number of nucleotides. This separation results in lower amounts of allelic bias. This is an improvement over methods that involve using probes where the hybridizing region on the probe is designed to hybridize at the base pair directly adjacent to the variable region of the polymorphic allele. This is an improvement over other methods that involve amplification and/or selective enrichment methods that do not preserve the allele distributions that are present in the original sample of DNA well. Low allelic bias is critical for ensuring that the measured genetic data is representative of the original sample in methods that involve either calculating allele ratios or allele measurement distributions. Since prior methods did not focus on polymorphic regions of the genome, or on the allele distributions, it was not obvious that techniques that preserved the allele distributions would result in more accurate ploidy state determinations. Since prior methods did not focus on using allelic distributions to determine ploidy state, it was not obvious that a composition where a plurality of loci were preferentially enriched with low allelic bias would be particularly valuable for determining a ploidy state of a fetus.

The methods described herein are particularly advantageous when used on samples where a small amount of DNA is available, or where the percent of circulating DNA is low. This is due to the correspondingly higher allele dropout rate that occurs when only a small amount of DNA is available, or the correspondingly higher allele dropout rate when the percent of fetal or tumor DNA is low. A high allele dropout rate, meaning that a large percentage of the alleles were not measured for the target individual, results in poorly accurate fetal fractions calculations, and poorly accurate ploidy determinations. Since the method disclosed herein uses a joint distribution model that takes into account the linkage in inheritance patterns between SNPs, significantly more accurate ploidy determinations may be made.

In embodiments related to NPD, the parental context may refer to the genetic state of a given SNP, on each of the two relevant chromosomes for each of the two parents of the target. Note that in one embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1m_2|f_1f_2$," where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1f_2|m_1m_2$." Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given allele, the mother's genotype was T on one chromosome, and G on the homologous chromosome, and the father's genotype at that allele is G on both of the homologous chromosomes, one may say that the target individual's allele has the parental context of AB|BB; it could also be said that the allele has the parental context of AB|AA. Note that, in theory, any of the four possible nucleotides could occur at a given allele, and thus it is possible, for example, for the mother to have a genotype of AT, and the father to have a genotype of GC at a given allele. However, empirical data indicate that in most cases only two of the four possible base pairs are observed at a given allele. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

When considering which alleles to target, one may consider the likelihood that some parental contexts are likely to be more informative than others. For example, AA|BB and the symmetric context BB|AA are the most informative contexts, because the fetus is known to carry an allele that is different from the mother. For reasons of symmetry, both AA|BB and BB|AA contexts may be referred to as AA|BB. Another set of informative parental contexts are AA|AB and BB|AB, because in these cases the fetus has a 50% chance of carrying an allele that the mother does not have. For reasons of symmetry, both AA|AB and BB|AB contexts may be referred to as AA|AB. A third set of informative parental contexts are AB|AA and AB|BB, because in these cases the fetus is carrying a known paternal allele, and that allele is also present in the maternal genome. For reasons of symmetry, both AB|AA and AB|BB contexts may be referred to as AB|AA. A fourth parental context is AB|AB where the fetus has an unknown allelic state, and whatever the allelic state, it is one in which the mother has the same alleles. The fifth parental context is AA|AA, where the mother and father are heterozygous.

In some examples of an embodiment of the invention for detecting a presence or absence of aneuploidy or for measuring the number of copies of a chromosome or chromosome segment of interest, quantitative non-allelic genetic information can be used to determine the copy number of the chromosome or chromosomal segment of interest in the target cells. For example, a quantitative non-allelic z-score method can be used to identify at least one diploid sample in the set of samples that is disomic for the chromosome or chromosome segment of interest. In such embodiments, each sample in the set of samples can be analyzed in the following manner:

determine a proportion of reads that map to the chromosome or chromosome segment of interest; calculate a z-score for the proportion of reads that map to the chromosome or chromosome segment of interest; and select one or more samples where the absolute value of the z-score is below a threshold value as a diploid sample, or where the z-score indicates disomy with at least a minimum level of confidence (e.g. 90, 95, 96, 97, 98, 99, 99.5, or 99.9%), or select the 20, 15, 10, or 5% of samples or the 50, 25, 20, 15, 10, or 5, 4, 3, 2, or 1 sample(s) with the lowest absolute value z-score for the set of samples.

As another non-limiting example, a quantitative non-allelic threshold method can be used to identify the presence or absence of aneuploidy in the test sample. Such a method can be performed in the following manner for each sample in the set of samples:

determine a proportion of reads that map to the chromosome or chromosome segment of interest; calculate a z-score for the proportion of reads that map to the chromosome or chromosome segment of interest; and output whether the data for the sample yields an absolute value of the z-score above a threshold value, wherein a z score with an absolute value above the threshold is indicative aneuploidy in the sample, or whether the data for the sample yields a z-score indicative of aneuoploidy with at least a minimum level of confidence.

In related examples, non-allelic data can be used to calculate or determine a sequencing depth of read for one or more loci, or in some embodiments a depth of read for an entire chromosome of segment of a chromosome. The depth of read refers to the number of DNA fragments corresponding to the locus, chromosome segment or chromosome of interest. The number of DNA fragments may be measured using a sequencing methodology, and may refer to amplified or unamplified DNA fragments. This non-allelic depth of read information can then be compared to a threshold value (i.e., a cut off value) relating to the depth of sequencing reads from a specific chromosome or specific chromosome segment to a predicted chromosome copy number or chromosome segment copy number. In another embodiment, this non-allelic depth of read information can be used to calculate a z-score with a likelihood that a particular chromosome or chromosome segment has a particular copy number. For example, a z-score can be associated with a 70, 75, 80, 90, 95, 96, 97, 98, 99, or 99.9% confidence of a disomic or an aneuploid state for a chromosome of interest in the test sample.

In further examples non-allelic quantitative threshold methods are used to determine the copy number count of a chromosome or chromosome segment in an individual, for example as part of NPD, where the target individual is the fetus (i.e. the target cells come from the placenta), and where the related individual is the mother (i.e. the non-target cells come from the mother). In this situation, cfDNA from the maternal plasma may be amplified in a targeted or untargeted (random) fashion, and sequenced. The copy number of the chromosome of interest in the target individual may be inferred by comparing the absolute or relative number of sequence reads, or sequence tags, mapping to the chromosome of interest to the number of sequence reads, or sequence tags, mapping to one or a plurality of reference chromosomes. In certain illustrative examples, the reference chromosome is the same as the chromosome of interest for aneuploidy. In other examples, a reference chromosome or set of reference chromosomes that is different from the chromosome of interest may be used. In certain illustrative examples, a subset of samples are determined to be diploid from an initial analysis of data during a parallel analysis. For example, all samples that have a z score below an absolute value threshold such as 3, 2.5, 2, 1.5, 1, or 0.5. If the number of sequence reads mapping to the chromosome of interest for the remaining samples (those that were not determined to be diploid in the initial analysis) is disproportionately higher than would be expected given the number of sequence reads mapping to one or a plurality of reference chromosomes, then a fetal trisomy may be inferred. If the number of sequence reads mapping to the chromosome of interest is disproportionately lower than would be expected given the number of sequence reads mapping to one or plurality of reference chromosomes, then a fetal monosomy may be inferred. If the number of sequence reads mapping to the chromosome of interest is proportionate to what would be expected given the number of sequence reads mapping to the reference chromosome, then disomy may be inferred. There are many way to determine what number of sequence reads mapping to the chromosome of interest is proportionate, or disproportionate, to what would be expected, given the number of sequence reads mapping to the reference chromosome including normalization based on representation in the genome, and also including GC-bias correction, which is where the expected number of reads may be normalized based on the fact that GC-rich regions of the genome may not amplify at an equivalent rate to non-GC-rich regions of the genome.

In a related embodiment, a method of the invention includes both a non-allelic z-score based quantitative method and a maximum likelihood method based on allelic or non-allelic data. Accordingly, provided herein is a method for detecting a presence or absence of aneuploidy of a chromosome or chromosome segment of interest in a test sample, that includes the following steps: obtaining genetic data for the chromosome or chromosome segment of interest from each sample in a set of samples comprising the test sample, wherein the genetic data is obtained from a parallel analysis of the samples;
determining whether aneuploidy is present in the test sample by a first method comprising:
  a. determining a depth of reads or a proportion of reads that map to the chromosome or chromosome segment of interest;
  b. calculating a z-score for the depth of reads or the proportion of reads that map to the chromosome or chromosome segment of interest; and
  c. determining whether the test sample is aneuploidy at the chromosome or chromosome segment of interest based on the z-score, thereby providing a first result; and determining whether aneuploidy is present in the test sample by a second method comprising:
  d. creating a plurality of ploidy hypotheses wherein each ploidy hypothesis is associated with a specific copy number for the chromosome or chromosome segment of interest,
  e. determining a ploidy probability value for each ploidy hypothesis, wherein the ploidy probability value indicates the likelihood that the test sample has the specific copy number for the chromosome or chromosome segment of interest that is associated with the ploidy hypothesis, and
  f. determining which ploidy hypothesis is most likely to be correct by selecting the ploidy hypothesis with the maximum likelihood, thereby providing a second result, detecting the aneuploidy by considering the first result and the second result.

The z-score based on a non-allelic quantitative threshold or cutoff value can be determined in variety of ways, for example an average depth of read (normalized for the length of the specific chromosome) can be obtained from a chromosome or chromosome segment, i.e., a reference chromosome or chromosome segment, that is assumed or proven to have a specific copy with a high degree of certainty (e.g., chromosome 2 in a developing fetus can safely be assume to be diploid). In examples of this embodiment of the invention, the cutoff value is based on a reference chromosome or chromosome segment that is the same as a chromosome or chromosome segment having the copy number that is being measured, and in certain illustrative examples, without the use of a sample known in advance of an assay, as being diploid. In embodiments of the invention where the cutoff value is based on a reference chromosome or chromosome segment that is the same as the chromosome or chromosome segment having the copy number that is being measured, sets of patients (test subjects) can be co-analyzed in a run of a high throughput DNA sequencer, so as to produce a reference value (cutoff value). This reference value can be indicative of the number of copies of a given chromosome or chromosome segment in a patient. For example, if the amount of total DNA sequence information obtained from a specific chromosome exceeds cutoff value, it may be possible to determine that the target cell contains a trisomy on a specific chromosome with a high degree confidence of a correct determination. This probability of a specific chromosome copy number or chromosome copy number segment can be modified using a second probability value, wherein the second probability value is determined from allelic data.

When sequencing is used for ploidy calling of a fetus in the context of non-invasive prenatal diagnosis, there are a number of ways to analyze the sequence data to determine the ploidy of the fetus. In one method that is used in some embodiments provided herein, a non-allelic threshold method is used. In one example of such a method, the sequence data is used by counting the number of reads that map to a given chromosome. For example, consider an example where the goal is to determine the ploidy state of chromosome 21 on the fetus where the DNA in the sample is comprised of 10% DNA of fetal origin, and 90% DNA of maternal origin. In this case, one could identify disomic samples as samples that initially yield a z-score of below a threshold, and compare reads obtained for chromosome 21 for a test sample to average reads of chromosome 21 for the diploid samples. If the on-test fetus were euploid, one would expect the amount of DNA per unit of genome to be about equal in chromosome 21 from a disomic sample to chromosome 21 in a sample from the euploid on-test fetus. If the fetus were trisomic at chromosome 21, one the other hand, then one would expect there to be more slightly more DNA per genetic unit from chromosome 21 from the on-test sample than for the disomic sample(s) Another method that could be used to detect aneuploidy is similar to that above, except that parental contexts could be taken into account.

Methods for Determining the Number of Copies of the Chromosome or Chromosome Segment Employing a Reference Value Derived from a Subset of Patients One embodiment of the invention is a method for determining the number of copies of a chromosome or chromosome segment of interest in the genome of a target cell, such as fetal cell or tumor cell. Genetic data, e.g., DNA sequence data, can be obtained from a mixture of DNA comprising DNA derived from one or more target cells and DNA derived from one or more non-target cells. The target cells and non-target cells differ with respect to one another at the genomic level, as by virtue of other criteria. The term "derived" is used to indicate that the cells are the ultimate source of the DNA. Thus, for example, cell-free DNA obtained from maternal blood of pregnant woman is derived from cells and the mother's cells. The method employs a set of patients. The genetic data is obtained from each member of the patient set. Each patient in the set of patients is analyzed using essentially the same method of nucleic sequence analysis, e.g., the same amplification and sequencing reagents. Genetic information is obtained at a plurality of loci. In some embodiments, at least some, and possibly all of the loci are polymorphic. In some embodiments, all of the loci could be non-polymorphic. In some embodiments, the same loci are analyzed in both the target and non-target cells. In other embodiments the loci comprise non-polymorphic loci and also polymorphic loci; in this case, methods that utilize allelic data can be used with the allelic data measured on the polymorphic data as input, and other methods that utilize non-polymorphic data can be used with the non-polymorphic data measured on non-polymorphic loci as input, optionally including additional non-polymorphic data that can be produced by summing the allelic quantities from each of the alleles at one or more of the polymorphic loci. A number of sequence reads is obtained for each locus. In some embodiments the number of each allele at a given locus is quantitated. The quantitative data obtained can be from a combination of the loci from the target cell and the non-target cell genomes. A depth of sequencing reference value is derived from the genetic data obtained from this set of patients or in some embodiments, the depth of sequencing reference value is derived from a subset of the original set of patients. The genetic data derived from the specific chromosome or chromosome segment of interest from a selected patient in the set of patients is compared to the reference value, wherein the comparison indicates the copy number of the specific chromosome or chromosome segment of interest from the selected patient.

In some embodiments, the genetic data is obtained by sequencing. The sequencing may be performed on a high throughput parallel DNA sequencer.

In some embodiments, genetic data is obtained by simultaneously sequencing a mixture comprising DNA derived from one or more target cells and drive from one or more non-target cells to give genetic data at the set of loci from each member of the set of patients.

In some embodiments the target cells are fetal cells and non-target cells are from the mother of the fetus.

In some embodiments directed to non-invasive prenatal diagnosis, the target cells may be fetal cells and the non-target cells may be maternal cells.

In some embodiments of the invention in example of a hypothesis that may be used to select a subset of samples is the hypothesis that a specific chromosome or chromosome segment is diploid i.e. present in 2 copies. Examples of chromosomes for analysis include chromosomes 13, 18, 21, X and Y, including segments thereof. For example, the subset of samples may be chosen on the basis of having the highest likelihood that all or nearly all of the DNA in the sample originated from cells with precisely two copies of the chromosome of interest.

In some embodiments, the chromosome segment that is analyzed for copy number is selected from the group consisting of chromosome 22q11.2, chromosome 1p36, chromosome 15q11-q13, chromosome 4p16.3, chromosome 5p15 0.2, chromosome 17p13.3, chromosome 22q13.3, chromosome 2q37, chromosome 3q29, chromosome 9q34, chromosome 17q21.31, and the terminus of a chromosome.

In some embodiments, the set of loci are present on a selected region of a chromosome. In some embodiments, the method is performed independently for different chromosomes or chromosome segments. The only upper limit imposed on the number of patients in the set of patients is imposed by the DNA sequence generating capacity of the specific DNA sequencing technology selected (including the patient multiplexing technology, e.g. barcoding, compatible with that sequencing technology) in general there will be at least 10 patients in a patient set. In some embodiments there will be at least 24 patients in the patient set, in other embodiments there will be at least 48 patients, and in other embodiments will be at least 96 patients.

In some embodiments the target cell is a tumor and the non-target cell is a non-tumor cell.

Methods for analyzing genetic data for aneuploidy using a threshold or cutoff method are known in the art. U.S. Pat. No. 7,888,017, incorporated herein by reference, provides a method for determining fetal aneuploidy by counting the number of reads that map to a suspect chromosome and comparing it to the number of reads that map to a reference chromosome, and using the assumption that an overabundance of reads on the suspect chromosome corresponds to a triploidy in the fetus at that chromosome. Teachings provided therein can be useful in carrying out embodiments of the present invention that involve a depth of sequencing reads and a reference value. It will be understood that in this embodiment of the present invention a significant improvement over such methods is provided, because in this embodiment of the present invention the depth of sequencing reference value is derived from a subset of the original set of samples processed in parallel, using the chromosome or chromosome segment of interest in samples initially determined to be diploid in the parallel analysis, for the analysis of other samples in the parallel analysis of the set of samples. A skilled artisan with this disclosure will understand how to modify methods provided in these cited threshold method patents to perform methods provided herein.

Methods for Determining the Number of Copies of a Chromosome or Chromosome Segment in which a Set of Patients that have a Relative Fraction of DNA from the Chromosome of Interest Close to the Median of the Relative Fraction of DNA from the Chromosome of Interest from a Larger Set of Patients One embodiment of the invention is a method for determining the number of copies of a chromosome or chromosome segment of interest in the genome of a target cell, such as fetal cell or tumor cell. Genetic data, e.g., DNA sequence data, can be obtained from a mixture of DNA comprising DNA derived from one or more target cells and DNA derived from one or more non-target cells. The target cells and non-target cells differ with respect to one another at the genomic level, as by virtue of other criteria. The term "derived" is used to indicate that the cells are the ultimate source of the DNA. Thus, for example, cell-free DNA obtained from maternal blood of pregnant woman is derived from cells and the mother's cells. The method employs a set of patients. The genetic data is obtained from each member of the patient set. Each patient in the set of patients is analyzed in parallel using essentially the same method of nucleic sequence analysis, e.g., the same amplification and sequencing reagents. Genetic information is obtained. The quantitative data obtained can be from a combination of the loci from the target cell and the non-target cell genomes. The genetic data obtained from the combination of the target cell DNA and the non-target cell DNA is used to obtain genetic data of the relative fraction of DNA (depth of sequencing read) that corresponds to the chromosome or chromosome segments of interest.

A subset of patients is selected as a control subset, by choosing those patients where the relative fraction of DNA that corresponds to the chromosome or chromosome segments of interest in the obtained genetic data for that patient is closest to the median of the relative fractions for the set of patients. This median can be obtained on a per locus basis, or in other embodiments by grouping loci into subsets of loci, which are generally in close physical proximity to one another (e.g., a genetic linkage with one another) on the chromosome or chromosome segment of interest or by looking at a chromosome or chromosome segment as a whole. A reference value is determined for the relative fraction of DNA in the obtained genetic data that corresponds to the chromosome or chromosome segments of interest from the subset of patients. The reference value for the relative fraction of DNA that corresponds to the chromosome or chromosome segment of interest is compared to the obtained genetic data from a selected patient in the set of patients, wherein the comparison produces an experimental value indicative of the presence or absence of a genetic abnormality in chromosome copy number or chromosome segment copy number in the target cell.

In some embodiments, the subset is selected as the 25, 20, 15, 10, 5, or 2% of patients or the 50, 40, 30, 25, 20, 15, 10, 5, or 2 patients whose genetic data is closest to the mean, or preferably the median for all samples.

In some embodiments, the experimental value may exceed a specific diagnostic threshold value. In some embodiments the genetic data is obtained by DNA sequencing. In some embodiments the genetic data from the set of patients is obtained by simultaneously sequencing a mixture comprising DNA derived from one or more target cells and DNA derived from one or more non-target cells to give genetic data at the set of loci from each member of the set of patients.

In some embodiments, the genetic data is obtained by sequencing. The sequencing may be performed on a high throughput parallel DNA sequencer.

In some embodiments, genetic data is obtained by simultaneously sequencing a mixture comprising DNA derived from one or more target cells and drive from one or more non-target cells to give genetic data at the set of loci from each member of the set of patients.

In some embodiments the target cells are fetal cells and non-target cells are from the mother of the fetus.

In some embodiments direct to non-invasive prenatal diagnosis, the target cells may be fetal cells and the non-target cells may be maternal cells.

In some embodiments of the invention in example of a hypothesis that may be used to determine the subset of samples is the hypothesis that a specific chromosome or chromosome segment is diploid i.e. present in 2 copies. Examples of chromosomes for analysis include chromosomes 13, 18, 21, X and Y, including segments thereof.

In some embodiments, the chromosome segment that is analyzed for copy number is selected from the group consisting of chromosome 22q11.2, chromosome 1p36, chromosome 15q11-q13, chromosome 4p16.3, chromosome 5p15.2, chromosome 17p13.3, chromosome 22q13.3, chromosome 2q37, chromosome 3q29, chromosome 9q34, chromosome 17q21.31, and the terminus of a chromosome.

In some embodiments, the set of loci are present on a selected region of a chromosome. In some embodiments, the method is performed independently for different chromosomes or chromosome segments. The only upper limited imposed on the number of patients in set of patients is imposed by the DNA sequence generating capacity of the specific DNA sequencing technology selected (including the patient multiplexing technology, e.g. barcoding, compatible with that sequencing technology) in general there will be at least 10 patients in a patient set. In some embodiments there will be at least 24 patients, and the patient set in other embodiments there will be at least 48 patients the patient set in other embodiments will be at least 96 patients in the patient set.

In some embodiments the target cell is a tumor and the non-target cell is a non-tumor cell. In some embodiments the first probability value is derived from the genetic data obtained from polymorphic loci that comprise alleles present in the target cells that are not present in the non-target cells. In some the cell free DNA comprises DNA that that has been released by apoptosis. In some embodiments the target cell is tumor cell, such tumor cells may be a malignant tumor cell.

In some embodiments, provided herein is a method for determining a presence or absence of a fetal aneuploidy in a fetus for each of a plurality of maternal blood samples obtained from a plurality of different pregnant women, said maternal blood samples comprising fetal and maternal cell-free genomic DNA, that includes the following steps:

determining a number of enumerated sequence reads corresponding to an chromosome or chromosome segment of interest for each of the plurality of samples;

determining a reference value of enumerated sequence reads from a diploid subset of between 1 and 50 samples of the plurality of samples or between 1-50% of samples of the plurality of samples having a number of enumerated sequence reads closest to the median number of enumerated sequence reads for the plurality of maternal blood samples; and comparing the number of enumerated sequence read from at least of, or each of the other samples of the plurality of samples that are not diploid samples, to the reference value, wherein a value above a cutoff is indicate of aneuploidy in the sample, thereby determining the presence or absence of a fetal aneuploidy in the chromosome or chromosome segment of interest.

In certain embodiments the method further comprises before the determining the number of enumerated sequence reads:

a. obtaining a fetal and maternal cell-free genomic DNA sample from each of the plurality of maternal blood samples;

b. generating a library derived from each fetal and maternal cell-free genomic DNA sample, c. performing massively parallel sequencing of polynucleotide sequences of the library from the chromosome or chromosome segment of interest; and d. enumerating sequence reads corresponding to fetal and maternal polynucleotide sequences selected from the chromosome or chromosome segment of interest.

In certain embodiments, the reference value of enumerated sequence reads is determined from a diploid subset of between 10 and 40 samples closest to the median.

In certain embodiments, the reference value of enumerated sequence reads is determined from a diploid subset of between 15 and 40 samples closest to the median.

In other embodiments, the diploid subset can be determined by selecting a diploid subset of between 1 and 50, 2 and 40, or 10 and 40 of the samples or between 1-50%, 2-40%, 5-25%, or 5-10% of the samples having a number of enumerated sequence reads closest to the median number of enumerated sequence reads for the plurality of maternal blood samples, In these embodiments, each library of polynucleotide sequences can include an indexing nucleotide sequence which identifies a maternal blood sample of the plurality of maternal blood samples. Such examples typically include pooling the libraries generated to produce a pool of enriched and indexed fetal and maternal non-random polynucleotide sequences;

In certain embodiments, the plurality of non-random polynucleotide sequences comprises at least 100 different non-random polynucleotide sequences selected from a first chromosome tested for being aneuploid (i.e. chromosome of interest) wherein each of said plurality of non-random polynucleotide sequences is from 10 to 1000 nucleotide bases in length, In certain embodiments, the method further includes selectively enriching a plurality of non-random polynucleotide sequences of each fetal and maternal cell-free genomic DNA samples.

In methods of the immediately above embodiment, further background teaching can be found in U.S. Pat. No. 8,318,430, hereby incorporated by reference in its entirety.
Embodiments that Determine Aneuploidy with Improved Confidence by Utilizing a Non-Allelic Threshold Method and a Method that Determines Likelihoods In some embodiments of the invention, improved confidence for an aneuploidy determination can be obtained by determining aneuploidy of a sample using a quantitative non-allelic threshold or cutoff method and for the same sample, determining aneuploidy using a method that determines likelihoods. If the sample is identified having aneuploidy in a chromosome or chromosome segment of interest by a threshold method and the sample is identified as having aneuploidy with high confidence using a likelihood determination for a set of hypothesis, then the sample is identified as a sample having aneuploidy at the chromosome or chromosome segment of interest for one or more target cells in a subject that is the source of the sample.

Accordingly, provided herein is a method for determining a presence or absence of aneuploidy of a chromosome or chromosome segment of interest in a test sample, comprising a. obtaining genetic data for the chromosome or chromosome segment of interest from a set of samples comprising the test sample, wherein the genetic data is obtained from a parallel analysis of the samples;

b. determining whether aneuploidy is present in the test sample by a first method comprising
  i. determining a depth of read or a proportion of reads that map to the chromosome or chromosome segment of interest;
  ii. calculating a z-score for the depth of reads or the proportion of reads that map to the chromosome or chromosome segment of interest; and
  iii. determining whether the z-score for the test sample is above a threshold value or whether the z-score is indicative of aneuploidy with a minimum level of confidence;

c. determining whether aneuploidy is present in the test sample by a second method comprising
  i. creating a plurality of ploidy hypotheses wherein each ploidy hypotheses is associated with a specific copy number for the chromosome or chromosome segment of interest,
  ii. determining a ploidy probability value for each ploidy hypotheses, wherein the ploidy probability value indicates the likelihood that the target sample has the number of copies of the chromosome or chromosome segment of interest that is associated with the ploidy hypothesis, and
  iii. determining which ploidy hypotheses is most likely to be correct by selecting the ploidy hypotheses with the maximum likelihood, wherein aneuploidy is determined for the chromosome or chromosome segment of interest in the test sample when both a maximum likelihood ploidy hypothesis is an aneuploidy and a z-score is above the threshold from step Bii.

In the above method, step B is carried out by a non-allelic threshold method and step C is carried out using a likelihood determining method. Methods are known in the art for carrying out a non-allelic threshold analysis, especially for NIPT. For example, U.S. Pat. Nos. 7,888,017 and 8,318,430, incorporated in their entirety herein by reference, provide methods for determining fetal aneuploidy by counting the number of reads that map to a suspect chromosome and comparing it to the number of reads that map to a reference chromosome, and using the assumption that an overabundance of reads on the suspect chromosome corresponds to a triploidy in the fetus at that chromosome. Teachings provided therein can be useful in carrying out embodiments of the present invention that involve a depth of sequencing reads and a reference value.

In certain examples of methods of this embodiment, using a non-allelic threshold value, the non-allelic information can be used to calculate a sequencing depth of read for one or more loci, or in some embodiments a depth of read for an entire chromosome of segment of a chromosome. This non-allelic depth of read information can then be compared to a threshold value (i.e., a cut off value) relating to the depth of sequencing reads from a specific chrome or specific chromosome segment to a predicted chromosome copy number or chromosome segment copy number. This cutoff value can be determined in variety of ways, for example an average depth of read (normalized for the length of the specific chromosome) can be obtained from a chromosome or chromosome segment, i.e., a reference chromosome or chromosome segment, that is assumed or proven to have a specific copy with a high degree of certainty (e.g., chromosome 2 in a developing fetus can safely be assumed to be diploid). In some embodiments of the invention, the cutoff value is based on a reference chromosome or chromosome segment that is different than the chromosome or chromosome segment having the copy number that is being measured, wherein the different chromosome is assumed to have a specific copy number. In some embodiments of the invention, the cutoff value is based on a reference chromosome or chromosome segment that is the same as a chromosome or chromosome segment having the copy number that is being measured, and in certain illustrative examples, without the use of a sample known in advance of an assay, as being diploid.

In embodiments of the invention where the cutoff value is based on a reference chromosome or chromosome segment that is the same as chromosome or chromosome segment having the copy number that is being measured, sets of patients (test subjects) can be co-analyzed in a run of a high throughput DNA sequencer, so as to produce a reference value (cutoff value). This reference value can be indicative of the number of copies of a given chromosome or chromosome segment in a patient. For example, if the amount of total DNA sequence information obtained from a specific chromosome exceeds cutoff value, it may be possible to determine that the target cell contains a trisomy on a specific chromosome with a high degree confidence of a correct determination. In these examples, the same data, or a subset thereof, that is used for the non-allelic threshold method, can be used for a non-allelic or allelic likelihood method. Thus, efficiencies are gained by using the same data or a subset thereof in a parallel experiment with the same set of samples using both the non-allelic threshold analysis and the likelihood determining method.

For the likelihood method in certain examples of methods of this embodiment, the genetic data includes quantitative allelic data from a plurality of polymorphic loci in the set of loci, wherein each of the ploidy hypotheses specifies an expected distribution of quantitative allelic data at a plurality of polymorphic loci, and wherein the ploidy probability values are determined by calculating, for each of the ploidy hypotheses, the fit between the expected genetic data and the obtained genetic data. In certain examples of methods of this embodiment, the genetic data includes quantitative non-allelic data from a plurality of polymorphic loci in the set of loci, and wherein each of the ploidy hypotheses specifies an expected mean value of quantitative non-allelic data at the plurality of polymorphic loci, and wherein the ploidy probability values are determined by calculating, for each of the ploidy hypotheses, the fit between the expected genetic data and the obtained genetic data. Provided throughout this application, are methods that provide likelihoods. This includes both allelic and non-allelic methods. For example, a het-rate method provided herein or a QMM method can be used.

Non-Invasive Prenatal Diagnosis (NPD)

Non-invasive prenatal diagnosis is an important technique that can be used to determine the genetic state of a fetus from genetic material that is obtained in a non-invasive manner, for example from a blood draw on the pregnant mother. The blood could be separated and the plasma isolated, and size selection can optionally be used to isolate the DNA of the appropriate length. This isolated DNA can then be measured by a number of means, such as by hybridizing to a genotyping array and measuring the fluorescence, or by sequencing on a high throughput sequencer.

In illustrative examples the methods and systems provided herein are used for NIPD, also referred to herein as non-invasive prenatal testing (NIPT). The process of non-invasive prenatal diagnosis in certain embodiments involves a number of steps. Some of the steps can include: (1) obtaining the genetic material from the fetus; (2) optionally enriching the genetic material of the fetus, ex vivo; (3) amplifying the genetic material, ex vivo; (4) optionally preferentially enriching specific loci in the genetic material, ex vivo; (5) genotyping the genetic material, ex vivo; and (6) analyzing the genotypic data, on a computer, and ex vivo. Methods to reduce to practice these and other relevant steps are disclosed herein. At least some of the method steps are not directly applied on the body. In an embodiment, the present disclosure relates to methods of treatment and diagnosis applied to tissue and other biological materials isolated and separated from the body. At least some of the method steps are executed on a computer.

Some embodiments of the present disclosure allow a clinician to determine the genetic state of a fetus that is gestating in a mother in a non-invasive manner such that the health of the baby is not put at risk by the collection of the genetic material of the fetus, and that the mother is not required to undergo an invasive procedure. Moreover, in certain aspects, the present disclosure allows the fetal genetic state to be determined with high accuracy, significantly greater accuracy than, for example, the non-invasive maternal serum analyte based screens, such as the triple test, that are in wide use in prenatal care.

The accuracy of the methods disclosed herein is a result of an informatics approach to analysis of the genotype data, as described herein. Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the fetal genetic state. The details of a number of embodiments are given below. Different embodiments may involve different combinations of the aforementioned steps. Various combinations of the different embodiments of the different steps may be used interchangeably.

In one embodiment, a blood sample is taken from a pregnant mother, and the free floating DNA in the plasma of the mother's blood, which contains a mixture of both DNA of maternal origin, and DNA of fetal origin, is used to determine the ploidy status of the fetus. In one embodiment of the present disclosure, a key step of the method involves preferential enrichment of those DNA sequences in a mixture of DNA that correspond to polymorphic alleles in a way that the allele ratios and/or allele distributions remain mostly consistent upon enrichment. In one embodiment of the present disclosure, the method involves sequencing a mixture of DNA that contains both DNA of maternal origin, and DNA of fetal origin. In one embodiment of the present disclosure, a key step of the method involves using measured allele distributions to determine the ploidy state of a fetus that is gestating in a mother.

Screening Maternal Blood Containing Free Floating Fetal DNA

The methods described herein may be used to help determine the genotype of a child, fetus, or other target individual where the genetic material of the target is found in the presence of a quantity of other genetic material. In this disclosure, the discussion focuses on determining the genetic state of a fetus where the fetal DNA is found in maternal blood, but this example is not meant to limit to possible contexts that this method may be applied to. In addition, the method may be applicable in cases where the amount of target DNA is in any proportion with the non-target DNA; for example, the target DNA could make up anywhere between 0.000001 and 99.999999% of the DNA present. In addition, the non-target DNA does not necessarily need to be from one individual, or even from a related individual, as long as genetic data from non-target individual(s) is known. In one embodiment of the present disclosure, the method can be used to determine genotypic data of a fetus from maternal blood that contains fetal DNA. It may also be used in a case where there are multiple fetuses in the uterus of a pregnant woman, or where other contaminating DNA may be present in the sample, for example from other already born siblings.

This technique may make use of the phenomenon of fetal blood cells gaining access to maternal circulation through the placental villi. Ordinarily, only a very small number of fetal cells enter the maternal circulation in this fashion (not enough to produce a positive Kleihauer-Betke test for fetal-maternal hemorrhage). The fetal cells can be sorted out and analyzed by a variety of techniques to look for particular DNA sequences, but without the risks that these latter two invasive procedures inherently have. This technique may also make use of the phenomenon of free floating fetal DNA gaining access to maternal circulation by DNA release following apoptosis of placental tissue where the placental tissue in question contains DNA of the same genotype as the fetus. The free floating DNA found in maternal plasma has been shown to contain fetal DNA in proportions as high as 30-40% fetal DNA.

In one embodiment of the present disclosure, blood may be drawn from a pregnant woman. Research has shown that maternal blood may contain a small amount of free floating DNA from the fetus, in addition to free floating DNA of maternal origin. In addition, there also may be enucleated fetal blood cells containing DNA of fetal origin, in addition to many blood cells of maternal origin, which typically do not contain nuclear DNA. There are many methods known in the art to isolate fetal DNA, or create fractions enriched in fetal DNA. For example, chromatography has been show to create certain fractions that are enriched in fetal DNA.

Once the sample of maternal blood, plasma, or other fluid, drawn in a relatively non-invasive manner, and that contains an amount of fetal DNA, either cellular or free floating, either enriched in its proportion to the maternal DNA, or in its original ratio, is in hand, one may genotype the DNA found in said sample. The method described herein can be used to determine genotypic data of the fetus. For example, it can be used to determine the ploidy state at one or more chromosomes, it can be used to determine the identity of one or a set of SNPs, including insertions, deletions, and translocations. It can be used to determine one or more haplotypes, including the parent of origin of one or more genotypic features.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, HiSEQ or MiSEQ, LIFE TECHNOLGIES' SOLiD SYSTEM, or Ion Torrent Person Genome Machine or Proton. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. In one embodiment, storage of the samples may be done in a way that will minimize degradation (e.g. at −20 C or lower).

Methods for Determining the Number of Copies of a Chromosome or Chromosome Segment of Interest by Combining Allelic and Non-Allelic Genetic Data Other embodiments of the invention include methods for determining the number of copies of a chromosome or chromosome segment of interest in the genome of a target cell, such as fetal cell or tumor cell. Genetic data, e.g., DNA sequence data, can be obtained from a mixture of DNA comprising DNA derived from one or more target cells and DNA derived from one or more non-target cells. The method can employ a single patient or a set of patients. The genetic data is obtained from a patient. Genetic information is obtained at a plurality of loci. At least some, and possible all of the loci are polymorphic. The same loci are analyzed in both the target and non-target cells. A number of sequence reads is obtained for each locus. The number of sequence reads at each allele at a given locus is quantitated. The quantitative data obtained can be from a combination of the loci from the target cell and the non-target cell genomes. The collected data is then tested against a plurality of copy number hypotheses, i.e., the copy number of the chromosome or chromosome segment of interest. A first probability value is calculated for each hypothesis i.e., the probability that the hypothesis is either true or false given the measured genetic data. Thus the likelihood that the genome of the target cell has the number of copies of the chromosome or chromosome segment of interest specified by the hypothesis is determined. This first probability value is obtained using the allelic data. A second probability value is calculated for each hypothesis i.e., the probability that the hypothesis is either true or false given the measured genetic data. Thus the likelihood that the genome of the target cell has the number of copies of the chromosome or chromosome segment of interest specified by the hypothesis is determined. This second probability value is obtained using the non-allelic data. For each hypothesis, the first probability value and the second probability value can be combined, e.g., through multiplication, to give a combined probability indicating the likelihood that the genome of the target cell has the number of copies of the chromosome or chromosome segment that is associated with the hypothesis. The number of copies of the chromosome or chromosome segment of interest in the genome of the target cell can be determined by selecting the number of copies of the chromosome or chromosome segment that is associated with the hypothesis with the greatest combined probability is used to make the determination of the chromosome or chromosome segment copy number in the sample of interest. In some embodiments wherein the genetic data is obtained from cell free DNA obtained from the blood of a pregnant woman, the hypothesis can include a condition that the mother is carrying multiple fetuses, e.g., twins.

Accordingly, in some embodiments, genetic data is obtained by simultaneously sequencing a mixture comprising DNA derived from one or more target cells and derived from one or more non-target cells to give genetic data at the set of loci from each member of the set of patients. In some embodiments the target cells are fetal cells and non-target cells are from the mother of the fetus. That is, in some embodiments directed to non-invasive prenatal diagnosis, the target cells may be fetal cells and the non-target cells may be maternal cells. In some embodiments of the invention in example of a hypothesis that may be used to select the subset of patients may be the hypothesis that a specific chromosome or chromosome segment is diploid i.e. present in 2 copies. Examples of chromosomes for analysis include chromosomes 13, 18, 21, X and Y, including segments thereof. In some embodiments, the chromosome segment that is analyzed for copy number is selected from the group consisting of chromosome 22q11.2, chromosome 1p36, chromosome 15q11-q13, chromosome 4p16.3, chromosome 5p15.2, chromosome 17p13.3, chromosome 22q13.3, chromosome 2q37, chromosome 3q29, chromosome 9q34, chromosome 17q21.31, and the terminus of a chromosome.

In some embodiments, the set of loci are present on a selected region of a chromosome. In some embodiments, the method is performed independently for different chromosomes or chromosome segments. The only upper limited imposed on the number of patients in set of patients is imposed by the DNA sequence generating capacity of the specific DNA sequencing technology selected (including the patient multiplexing technology, e.g. barcoding, compatible with that sequencing technology) in illustrative embodiments there will be at least 10 patients in a patient set. In some embodiments there will be at least 24 patients, and the patient set in other embodiments there will be at least 48 patients the patient set in other embodiments will be at least 96 patients in the patient set.

Methods of Determining the Number of Copies of a Chromosome or Chromosome Segment Employing Hypotheses that are Tested Using a Combination of the Allelic and Non-Allelic Data Embodiments include methods for determining the number of copies of a chromosome or chromosome segment of interest in the genome of a target cell in which genetic data is obtained from DNA derived from target cells and DNA derived from non-target cells, wherein the genetic data comprises (i) quantitative allelic data from a plurality of polymorphic loci and (ii) quantitative non-allelic data from a plurality of polymorphic and/or non-polymorphic loci. The method includes the step of creating a plurality of hypotheses wherein each hypothesis is associated with a specific copy number for the chromosome or chromosome segment in the genome of the target cell. A probability value is calculated for each hypothesis, wherein the probability value indicates the likelihood that the genome of the target cell has the number of copies of the chromosome or chromosome segment that is associated with the hypothesis, and wherein the first probability value is derived from the allelic data and the non-allelic data obtained from at least one first locus. For example, the hypothesis may be tested using a model that incorporates both allelic data and non-allelic data, thereby obtaining a probability value. Each calculated probability value can be combined to give a combined probability indicating the likelihood that the genome of the target cell has the number of copies of the chromosome or chromosome segment that is associated with the hypothesis. The number of copies of the chromosome or chromosome segment of interest in the genome of the target cell is determined by selecting the number of copies of the chromosome or chromosome segment that is associated with the hypothesis with the greatest probability. In some embodiments wherein the genetic data is obtained from cell free DNA obtained from the blood of a pregnant woman, the hypothesis can include a condition that the mother is carrying multiple fetuses, e.g., twins.

In some embodiments the probability value for each hypothesis is obtained from allelic and non-allelic data obtained from a single locus. In some embodiments the allelic data is tested on a model based on a distribution of possible allelic ratios associated with each hypothesis. In some embodiments the probability values for each hypothesis are separately determined for genetic data from at least 1000 polymorphic loci. In some embodiments the step of calculating a probability value for each hypothesis comprises the steps of (1) modeling, for each hypothesis, the expected genetic data from the DNA derived from the target cell based on the obtained genetic data comprising DNA derived from non-target cells, (2) comparing, for each hypothesis, the modeled genetic data from the DNA derived from the target cell and the obtained genetic data from DNA derived from the target cell, and (3) calculating a probability value, for each hypothesis, based on the difference between the modeled genetic data from the DNA derived from the target cell and the obtained genetic data from DNA derived from the target cell. In some embodiments the non-target cells originate from a parent of an individual from which the target cell originated, and the modeling of the expected genetic data further comprises determining the expected genetic data of the target cell using the rules of Mendelian inheritance an adjusting the expected genetic data of the target cell to correct for biases in the system as disclosed herein. Examples of such a system biases include amplification bias, sequencing bias, processing bias, enrichment bias, and combinations thereof. The nature of such biases may vary in accordance with the specific amplification technology, sequencing technology, processing, enrichment technology, etc. selected for implementation of the specific embodiment. In some embodiments the target cell is from a fetus, and wherein the expected genetic data comprises genetic data from the parent of the fetus and genetic data from the fetus. In some embodiments the modeling of the genetic data comprises the steps of predicting, for each locus, an expected distribution of allelic measurements at that locus, and predicting, for each locus, an expected relative quantity of DNA (depth of read) at that locus. In some embodiment the prediction of an expected distribution of allelic measurements can takes into account the linkage and cross-overs between different loci on the genome. In some embodiments, the expected distribution is a binomial distribution.

Different Implementations of the Presently Disclosed Embodiments

Figure 2:
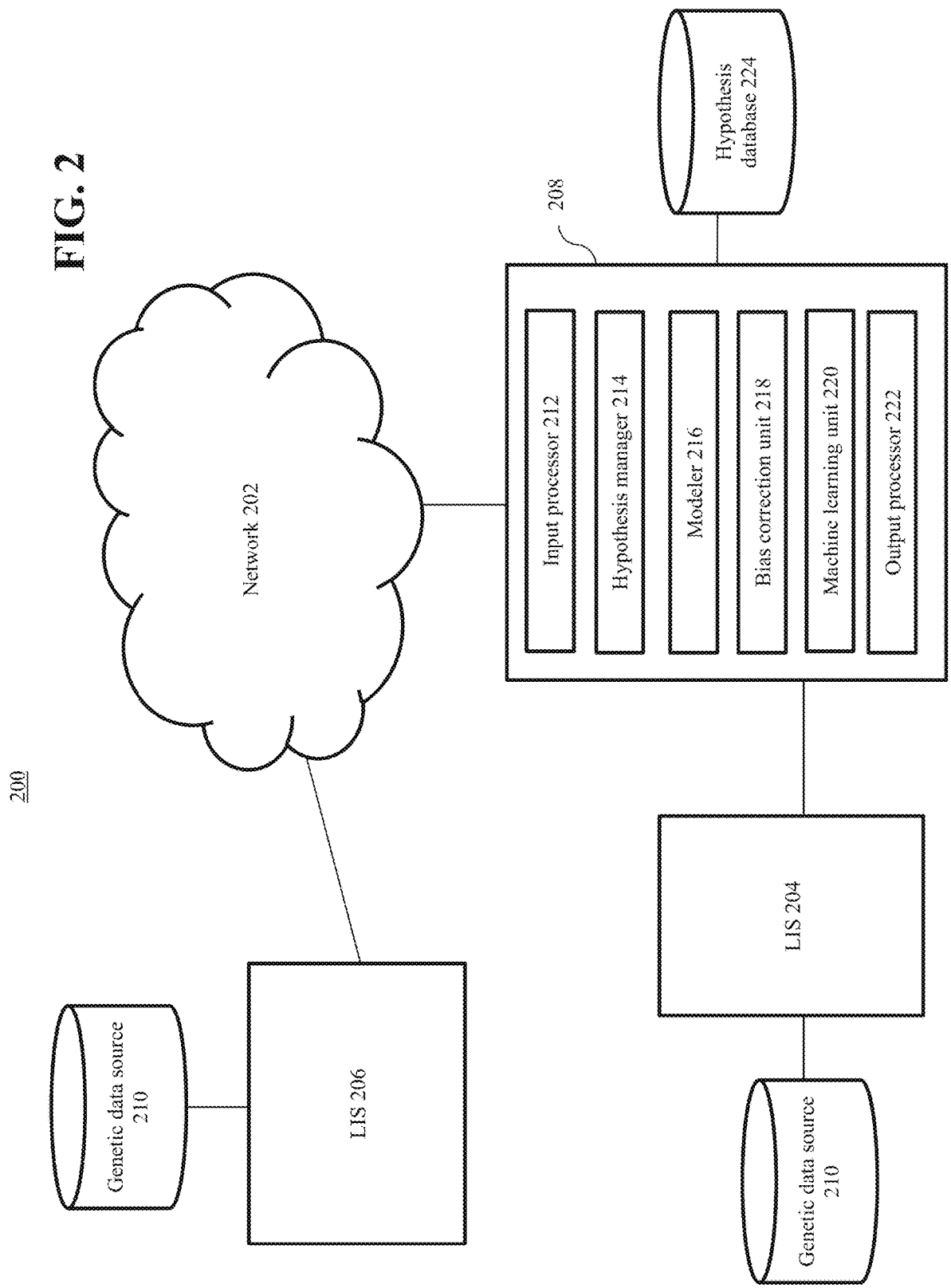
FIG. 2 shows an example system architecture 200 useful for performing embodiments of the present invention.

FIG. 2 shows an example system architecture 200 useful for performing embodiments of the present invention. System architecture 200 includes an analysis platform 208 connected to one or more laboratory information systems ("LISs") 204. Analysis platform 208 may alternatively or additionally be connected directly to LIS 206. As shown in FIG. 2, analysis platform 208 may be connected to LIS 206 over a network 202. Network 202 may include one or more networks of one or more network types, including any combination of LAN, WAN, the Internet, etc. Network 202 may encompass connections between any or all components in system architecture 200. In an embodiment, analysis platform 208 analyzes genetic data provided by LIS 206 in a software-as-a-service model, where LIS 206 is a third-party LIS, while analysis platform 208 analyzes genetic data provided by LIS 204 in a full-service or in-house model, where LIS 204 and analysis platform 208 are controlled by the same party. In an embodiment where analysis platform 208 is providing information over network 202, analysis platform 208 may be a server.

In an example embodiment, laboratory information system 206 includes one or more public or private institutions that collect, manage, and/or store genetic data. A person having skill in the relevant art(s) would understand that methods and standards for securing genetic data are known and can be implemented using various information security techniques and policies, e.g., username/password, Transport Layer Security (TLS), Secure Sockets Layer (SSL), and/or other cryptographic protocols providing communication security.

In an example embodiment, system architecture 200 operates as a service-oriented architecture and uses a client-server model that would be understood by one of skill in the relevant art(s) to enable various forms of interaction and communication between LIS 206 and analysis platform 208. System architecture 200 may be distributed over various types of networks 202 and/or may operate as cloud computing architecture. Cloud computing architecture may include any type of distributed network architecture. By way of example and not of limitation, cloud computing architecture is useful for providing software as a service (SaaS), infrastructure as a service (IaaS), platform as a service (PaaS), network as a service (NaaS), data as a service (DaaS), database as a service (DBaaS), backend as a service (BaaS), test environment as a service (TEaaS), API as a service (APIaaS), integration platform as a service (IPaaS) etc.

In an example embodiment, LISs 204 and 206 each include a computer, device, interface, etc. or any sub-system thereof. In an embodiment, LISs 204 and 206 are high-throughput DNA sequencers that conduct genetic analysis and provide such genetic data to analysis platform 208. In an embodiment, the high-throughput DNA sequencers contain PCR amplifiers. LISs 204 and 206 may include an operating system (OS), applications installed to perform various functions such as, for example, access to and/or navigation of data made accessible locally, in memory, and/or over network 202. In an embodiment, LIS 204 accesses analysis platform 208 through an application programming interface ("API"). LIS 204 may also include one or more native applications that may operate independently of an API.

In an example embodiment, analysis platform 208 includes one or more of an input processor 212, a hypothesis manager 214, a modeler 216, a bias correction unit 218, a machine learning unit 220, and an output processor 218. Input processor 212 receives and processes inputs from LISs 204 and/or 206. Processing may include but is not limited to operations such as parsing, transcoding, translating, adapting, or otherwise handling any input received from LISs 204 and/or 206. Inputs may be received via one or more streams, feeds, databases, or other sources of data, such as may be made accessible by LISs 204 and 206.

In an example embodiment, hypothesis manager 214 is configured to receive the inputs passed from input processor 212 in a form ready to be processed in accordance with hypotheses for genetic analysis that are represented as models and/or algorithms. Such models and/or algorithms may be stored in hypothesis database 224. In an embodiment, hypothesis database 224 stores such information in table format. Data from hypothesis database 224 may be used by modeler 216 to generate probabilities, for example, using the methods disclosed herein such as, for example, the non-allelic quantitative method or the allelic het rate method, and the like. Data used to derive and populate such strategy models and/or algorithms are available to hypothesis manager 214 via, for example, genetic data source 210 via LIS 204 or 206. Genetic data source 210 may include, for example, assays of samples to be analyzed by LIS 204 or 206. Hypothesis manager 214 may be configured to formulate hypotheses based on, for example, the variables required to populate its models and/or algorithms. Alternatively, hypotheses may be provided from a user and stored in hypothesis database 224. Models and/or algorithms, once populated, may be used by modeler 216 to compare one or more hypotheses to observed genetic data as described above. Modeler 216 may also develop bias models as described in various embodiments above. Bias errors, such as amplification errors and the like, may be corrected by bias correction unit 218 through performance of the bias correction mechanisms described herein.

Hypothesis manager 214 may select a particular value, range of values, or estimate based on a most-likely hypothesis as an output as described above. Modeler 216 may operate in accordance with models and/or algorithms trained by machine learning unit 220. For example, machine learning unit 220 may develop such models and/or algorithms by applying a classification algorithm, such as a Bayes classification algorithm, as described above to genetic data to identify diploid samples to be used as a reference set.

Modeler 216 can then use the identified reference set to estimate, for example, copy numbers for original or bias-corrected (adjusted or normalized) genetic data. Modeler 216 can compare expected data (based on each hypothesis) with observed data to generate a probability value for each hypothesis as compared to the observed data for a target sample.

Once hypothesis manager 214 receives probability values for each hypothesis for a given target, hypothesis manager 214 can select a most-likely hypothesis as an output result. Such output may be returned to the particular LIS 204 or 206 requesting the information by output processor 222. Such information can then be transmitted for individual patient samples to their respective representatives.

Figure 3:
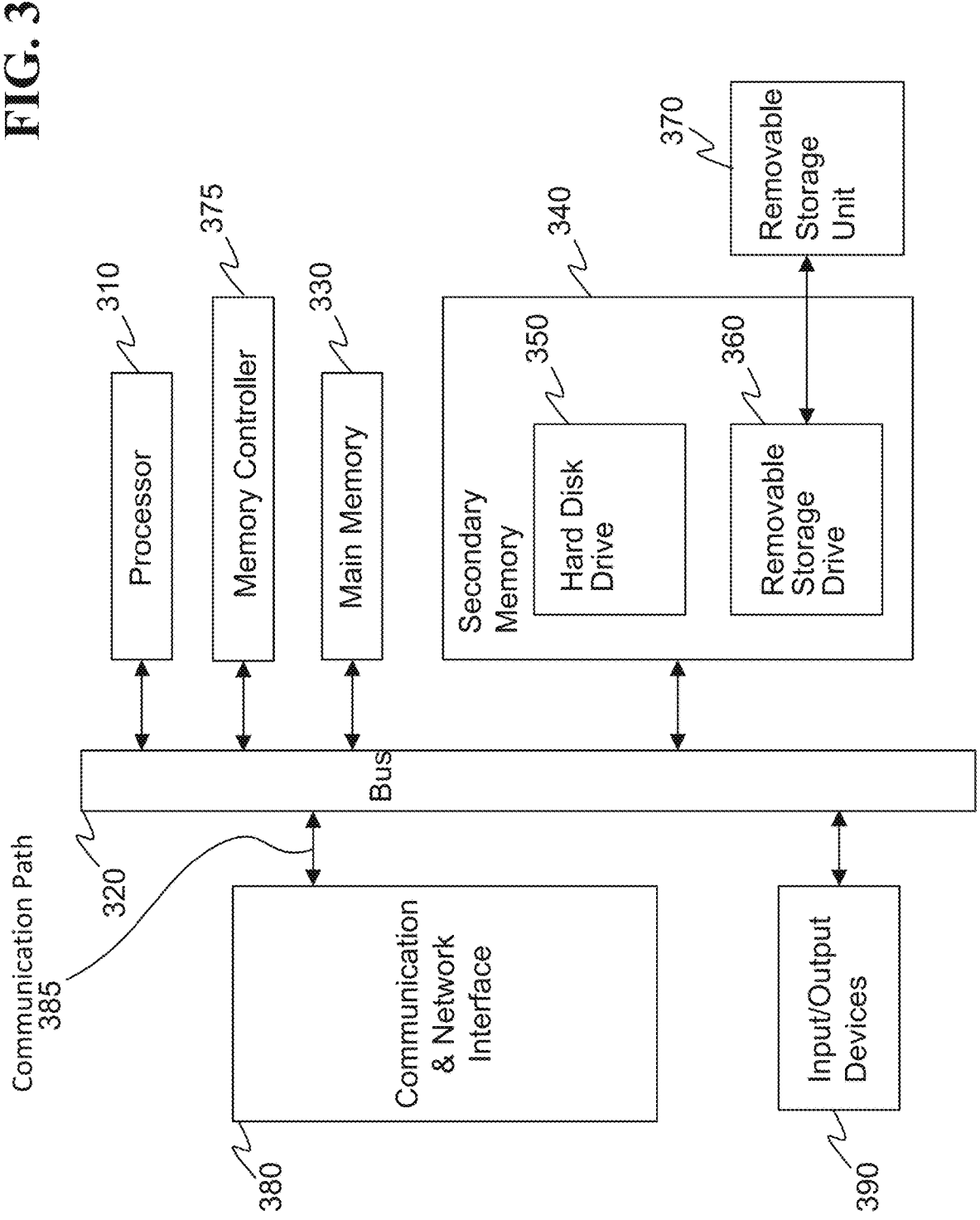
FIG. 3 illustrates an example computer system for performing embodiments of the present invention.

Various aspects of the disclosure can be implemented on a computing device by software, firmware, hardware, or a combination thereof. FIG. 3 illustrates an example computer system 300 in which the contemplated embodiments, or portions thereof, can be implemented as computer-readable code. Various embodiments are described in terms of this example computer system 300. For example, analysis platform 208 and databases 210 and 224 described above may be implemented in system 300. In addition or alternatively, the various methods described herein, such as method 100 and the additional algorithms used therein, may be executed by a computer processing system such as system 300.

Processing tasks in the embodiment of FIG. 3 are carried out by one or more processors 302. However, it should be noted that various types of processing technology may be used here, including programmable logic arrays (PLAs), application-specific integrated circuits (ASICs), multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 302 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data. Alternatively or in addition, one or more of processors 302 may be a special parallel processing without the graphics optimization, such parallel processors performing the mathematically intensive functions described herein. One or more of processors 302 may include a processing accelerator (e.g., DSP or other special-purpose processor).

Computer system 300 also includes a main memory 330, and may also include a secondary memory 340. Main memory 330 may be a volatile memory or non-volatile memory, and divided into channels. Secondary memory 340 may include, for example, non-volatile memory such as a hard disk drive 350, a removable storage drive 360, and/or a memory stick. Removable storage drive 360 may comprise a floppy disk drive, a magnetic tape drive, an optical disk drive, a flash memory, or the like. The removable storage drive 360 reads from and/or writes to a removable storage unit 370 in a well-known manner. Removable storage unit 370 may comprise a floppy disk, magnetic tape, optical disk, etc. which is read by and written to by removable storage drive 360. As will be appreciated by persons skilled in the relevant art(s), removable storage unit 370 includes a computer usable storage medium having stored therein computer software and/or data.

In alternative implementations, secondary memory 340 may include other similar means for allowing computer programs or other instructions to be loaded into computer system 300. Such means may include, for example, a removable storage unit 370 and an interface (not shown). Examples of such means may include a program cartridge and cartridge interface (such as that found in video game devices), a removable memory chip (such as an EPROM, or PROM) and associated socket, and other removable storage units 370 and interfaces which allow software and data to be transferred from the removable storage unit 370 to computer system 300.

Computer system 300 may also include a memory controller 375. Memory controller 375 controls data access to main memory 330 and secondary memory 340. In some embodiments, memory controller 375 may be external to processor 310, as shown in FIG. 3. In other embodiments, memory controller 375 may also be directly part of processor 310. For example, many AMD™ and Intel™ processors use integrated memory controllers that are part of the same chip as processor 310 (not shown in FIG. 3).

Computer system 300 may also include a communications and network interface 380. Communication and network interface 380 allows software and data to be transferred between computer system 300 and external devices. Communications and network interface 380 may include a modem, a communications port, a PCMCIA slot and card, or the like. Software and data transferred via communications and network interface 380 are in the form of signals which may be electronic, electromagnetic, optical, or other signals capable of being received by communication and network interface 380. These signals are provided to communication and network interface 380 via a communication path 385. Communication path 385 carries signals and may be implemented using wire or cable, fiber optics, a phone line, a cellular phone link, an RF link or other communications channels.

The communication and network interface 380 allows the computer system 300 to communicate over communication networks or mediums such as LANs, WANs the Internet, etc. The communication and network interface 380 may interface with remote sites or networks via wired or wireless connections.

In this document, the terms "computer program medium," "computer-usable medium" and "non-transitory medium" are used to generally refer to tangible (i.e. non-signal) media such as removable storage unit 370, removable storage drive 360, and a hard disk installed in hard disk drive 350. Signals carried over communication path 385 can also embody the logic described herein. Computer program medium and computer usable medium can also refer to memories, such as main memory 330 and secondary memory 340, which can be memory semiconductors (e.g. DRAMs, etc.). These computer program products are means for providing software to computer system 300.

Computer programs (also called computer control logic) are stored in main memory 330 and/or secondary memory 340. Computer programs may also be received via communication and network interface 380. Such computer programs, when executed, enable computer system 300 to implement embodiments as discussed herein. In particular, the computer programs, when executed, enable processor 310 to implement the disclosed processes. Accordingly, such computer programs represent controllers of the computer system 300. Where the embodiments are implemented using software, the software may be stored in a computer program product and loaded into computer system 300 using removable storage drive 360, interfaces, hard drive 350 or communication and network interface 380, for example.

The computer system 300 may also include input/output/display devices 390, such as keyboards, monitors, pointing devices, touchscreens, etc.

It should be noted that the simulation, synthesis and/or manufacture of various embodiments may be accomplished, in part, through the use of computer readable code, including general programming languages (such as C or C++), hardware description languages (HDL) such as, for example, Verilog HDL, VHDL, Altera HDL (AHDL), or other available programming tools. This computer readable code can be disposed in any known computer-usable medium including a semiconductor, magnetic disk, optical disk (such as CD-ROM, DVD-ROM). As such, the code can be transmitted over communication networks including the Internet.

The presently disclosed embodiments can be implemented advantageously in one or more computer programs that are executable and/or interpretable on system 300. Each computer program can be implemented in a high-level procedural or object-oriented programming language, or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, (that is, system 300 may be distributed locally) or distributed across multiple sites and interconnected by a communication network (that is, system 300 may be distributed across a network). The embodiments are also directed to computer program products comprising software stored on any computer-usable medium. Such software, when executed in one or more data processing devices, causes a data processing device(s) to operate as described herein. Embodiments employ any computer-usable or -readable medium, and any computer-usable or -readable storage medium known now or in the future. Examples of computer-usable or computer-readable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nano-technological storage devices, etc.), and communication mediums (e.g., wired and wireless communications networks, local area networks, wide area networks, intranets, etc.). Computer-usable or computer-readable mediums can include any form of transitory (which include signals) or non-transitory media (which exclude signals). Non-transitory media comprise, by way of non-limiting example, the aforementioned physical storage devices (e.g., primary and secondary storage devices).

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described in the document for determining genetic data pertaining to a target individual may be combined with the decision to select one or more embryos for transfer in the context of IVF, optionally combined with the process of transferring the embryo to the womb of the prospective mother. Some of the embodiments described in the document for determining genetic data pertaining to a target individual may be combined with the notification of a potential chromosomal abnormality, or lack thereof, with a medical professional, optionally combined with the decision to abort, or to not abort, a fetus in the context of prenatal diagnosis. Some of the embodiments described herein may be combined with the output of the actionable data, and the execution of a clinical decision that results in a clinical treatment, or the execution of a clinical decision to make no action.

Hypotheses

A hypothesis can refer to a possible genetic state. It can refer to a possible ploidy state. It can refer to a possible allelic state. A set of hypotheses refers to a set of possible genetic states. In some embodiments, a set of hypotheses are designed such that one hypothesis from the set will correspond to the actual genetic state of any given individual. In some embodiments, a set of hypotheses are designed such that every possible genetic state can be described by at least one hypothesis from the set. In some embodiments of the present disclosure, one aspect of the method is to determine which hypothesis corresponds to the actual genetic state of the individual in question.

A "copy number hypothesis," also called a "ploidy hypothesis," or a "ploidy state hypothesis," may refer to a hypothesis concerning a possible ploidy state for a given chromosome, or chromosome segment, in the target individual. It may also refer to the ploidy state at more than one of the chromosomes in the individual. A set of copy number hypotheses may refer to a set of hypotheses where each hypothesis corresponds to a different possible ploidy state in an individual. A set of hypotheses in certain examples is a set of possible ploidy states, a set of possible parental haplotype contributions, a set of possible fetal DNA percentages in the mixed sample, or combinations thereof.

A normal individual contains one of each chromosome from each parent. However, due to errors in meiosis and mitosis, it is possible for an individual to have 0, 1, 2, or more of a given chromosome from each parent. In practice, it is rare to see more that two of a given chromosomes from a parent. Certain embodiments of the invention, especially those involving NIPT, consider the possible hypotheses where 0, 1, or 2 copies of a given chromosome come from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2). These may also be written as $H_{00}$, $H_{01}$, $H_{02}$, $H_{10}$, $H_{12}$, $H_{20}$, $H_{21}$, and $H_{22}$. The different hypotheses correspond to different ploidy states. For example, (1,1) refers to a normal disomic chromosome; (2,1) refers to a maternal trisomy, and (0,1) refers to a paternal monosomy. Especially in the context of NIPT, two of these hypothesis are not feasible 0,0 and 2,2. In some embodiments, the case where two chromosomes are inherited from one parent and one chromosome is inherited from the other parent may be further differentiated into two cases: one where the two chromosomes are identical (matched copy error), and one where the two chromosomes are homologous but not identical (unmatched copy error). In these embodiments, there are sixteen possible hypotheses. It should be understood that it is possible to use other sets of hypotheses, and a different number of hypotheses.

Ploidy hypothesis are created during exemplary methods of the invention that use methods, algorithms, techniques, or subroutines that provide likelihoods. For example, in certain illustrative examples of embodiments for determining the presence or absence of aneuploidy, a set of ploidy hypotheses is created for each sample in the set of samples, wherein each hypothesis is associated with a specific copy number for the chromosome or chromosome segment of interest in a genome of a sample. For example, in embodiments that use quantitative non-allelic data, such as the QMM disclosed herein, the hypothesis can provide estimates of sample parameters, such as the variability in the starting quantity of DNA in a sample due to pipetting variability or errors or other measurement errors, which can be used to normalize the measurements (i.e. measured genetic data) at some or all of the positions on some or all of the chromosomes or chromosome segments of interest in that sample, and then a test statistic can be computed as the variance-weighted mean of these normalized measurements. Thus, in certain embodiments, the hypothesis provides a variance-weighted mean test statistic for a given ploidy condition. The expectation and variance of the test statistic is calculated under each of the chromosome copy number hypothesis to form Gaussian models for the maximum likelihood estimate. For example, a set of hypothesis in an NIPT analysis for a non-allelic quantitative analysis, can provide a variance-weighted mean test statistic for a disomy or a trisomy at one or more of chromosomes 13, 18, and 21. In exemplary embodiments of the present invention where the chromosome or chromosome segment of interest can be used to set sample parameters, the hypothesis can be a joint hypothesis on the copy numbers of some or all of the chromosomes, for example chromosome 13, 18, and 21. This is further discussed below with regards to a quantitative method that does not use non-target reference chromosomes.

In some embodiments of the present disclosure, the ploidy hypothesis may refer to a hypothesis concerning which chromosome from other related individuals correspond to a chromosome found in the target individual's genome. Some embodiments utilize the fact that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

An allelic hypothesis, or an "allelic state hypothesis" may refer to a hypothesis concerning a possible allelic state of a set of alleles. In some embodiments, the technique, algorithm, or method used utilizes the fact that, as described above, related individuals may share haplotype blocks, which may help the reconstruction of genetic data that was not perfectly measured. An allelic hypothesis can also refer to a hypothesis concerning which chromosomes, or chromosome segments, if any, from a related individual correspond genetically to a given chromosome from an individual. The theory of meiosis tells us that each chromosome in an individual is inherited from one of the two parents, and this is a nearly identical copy of a parental chromosome.

Therefore, if the haplotypes of the parents are known, that is, the phased genotype of the parents, then the genotype of the child may be inferred as well. (The term child, here, is meant to include any individual formed from two gametes, one from the mother and one from the father.) In one embodiment of the present disclosure, the allelic hypothesis describes a possible allelic state, at a set of alleles, including the haplotypes, at a chromosome or chromosome segment of interest, as well as which chromosomes from related individuals may match the chromosome(s) which contain the set of alleles.

Once the set of hypotheses have been defined the algorithms operate on the input genetic data and output a determined statistical probability for each of the hypotheses under consideration. For example, in an embodiment of the invention the method determines a probability value by comparing the genetic data to an expected result for each hypothesis, wherein the probability value indicates the likelihood that a sample has a certain number of copies of the chromosome or chromosome segment that is associated with the hypothesis.

The probabilities of the various hypotheses can be determined by mathematically calculating, for each of the various hypotheses, the value that the probability equals, as stated by one or more of the expert techniques, algorithms, and/or methods described elsewhere in this disclosure, using the relevant genetic data as input.

Once the probabilities of the different hypotheses are estimated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

The process of "combining probabilities," also called "combining hypotheses," or combining the results of expert techniques, is a concept that should be familiar to one skilled in the art of linear algebra. In exemplary methods of the present invention, two methods are utilized for determining the presence or absence of aneuploidy or for determining the number of copies of a chromosome that each provide a probability. In certain illustrative embodiments, the confidence of the determination is increased by combining the confidences that are selected for each method. For example, a confidence for a first method that performs a quantitative allelic analysis, can be combined with a confidence from a second method that performs a quantitative non-allelic analysis.

In cases where the likelihoods are determined by a first method in a way that is orthogonal, or unrelated, to the way in which a likelihood is determined for a second method, combining the likelihoods is straightforward and can be done by multiplication and normalization, or by using a formula such as:

$$R_{comb}=R_1R_2/[R_1R_2+(1-R_1)(1-R_2)]$$

Where $R_{comb}$ is the combined likelihood, and $R_1$ and $R_2$ are the individual likelihoods. In cases where the first and the second methods are not orthogonal, that is, where there is a correlation between the two methods, the likelihoods may still be combined, though the mathematics may be more complex.

In some embodiments, the $1^{st}$ probability and the $2^{nd}$ probability are weighted differently prior to the step of combining the probabilities. In some embodiments the $1^{st}$ probability and the $2^{nd}$ probability are considered independent events for the purposes of the step of combining the two probability values. In some embodiments the $1^{st}$ probability and the $2^{nd}$ probability are considered dependent events for the purposes of the step of combining the two probability values. In some embodiments, the method further comprises obtaining a third probability value where in the third probability value indicates the likelihood that the genome of the target has the number of copies of the chromosome or chromosome segment associated with a specific hypothesis wherein the third probability value is derived from information that is a non-non-genetic clinical assay. Many non-genetic clinical assays have a known probabilistic correlation with a specific chromosome copy number or chromosome segment copy number. For each hypothesis, the combined first and second probability values may be combined with the third probability value to give a combined probability value indicating the likelihood that the genome of the target cell has the number of copies of the chromosome or chromosome segment of interest, wherein that number is associated with the specific hypothesis. An examples of such non-genetic clinical assays include a nuchal translucency measurement. In some embodiments the non-genetic clinical assay is selected from the group consisting of measurements of: beta-human chorionic gonadotropin, pregnancy associated plasma protein A, estriol, inhibin-A, and alpha-fetoprotein.

Not to be limited by theory, the following disclosure further teaches how to combine probabilities. One possible way to combine probabilities is as follows: When an expert technique is used to evaluate a set of hypotheses given a set of genetic data, the output of the method is a set of probabilities that are associated, in a one-to-one fashion, with each hypothesis in the set of hypotheses. When a set of probabilities that were determined by a first expert technique, each of which are associated with one of the hypotheses in the set, are combined with a set of probabilities that were determined by a second expert technique, each of which are associated with the same set of hypotheses, then the two sets of probabilities are multiplied. This means that, for each hypothesis in the set, the two probabilities that are associated with that hypothesis, as determined by the two expert methods, are multiplied together, and the corresponding product is the output probability. This process may be expanded to any number of expert techniques. If only one expert technique is used, then the output probabilities are the same as the input probabilities. If more than two expert techniques are used, then the relevant probabilities may be multiplied at the same time. The products may be normalized so that the probabilities of the hypotheses in the set of hypotheses sum to 100%.

In some embodiments, if the combined probabilities for a given hypothesis are greater than the combined probabilities for any of the other hypotheses, then it may be considered that that hypothesis is determined to be the most likely. In some embodiments, a hypothesis may be determined to be the most likely, and the ploidy state, or other genetic state, may be called if the normalized probability is greater than a threshold. In one embodiment, this means that the number and identity of the chromosomes that are associated with that hypothesis may be called as the ploidy state. In one embodiment, this means that the identity of the alleles that are associated with that hypothesis are called as the allelic state. In some embodiments, the threshold is between about 50% and about 80%. In some embodiments the threshold is between about 80% and about 90%. In some embodiments the threshold is between about 90% and about 95%. In some embodiments the threshold is between about 95% and about 99%. In some embodiments the threshold is between about 99% and about 99.9%. In some embodiments the threshold is above 99.9%. In other embodiments, a set of rules are used for a final risk call for a sample wherein a combined probability threshold is set, but different scenarios can be considered and could override the results of the probability threshold, or used to enhance the calling ability of the combined probability. For example, if there is a wide disparity in probabilities for a given ploidy hypothesis, further analysis can be performed for example, to determine whether there was an error in one of the methods.

Some embodiments of the invention employ the step of producing a subset of patients from a larger set of patients. The original set of patients is used as the source of target cells and non-target cells for analysis. In some embodiments of the invention, the DNA samples obtained from the patients are modified using standard molecular biology techniques in order to be sequenced on the DNA sequencer. In some embodiments the technique will involve forming a genetic library containing priming sites for the DNA sequencing procedure. In some embodiments, a plurality of loci may be targeted for site specific amplification. In some embodiments the targeted loci are polymorphic loci, e.g., a single nucleotide polymorphisms. In embodiments implying the formation of genetic libraries, libraries may be encoded using a DNA sequence that is specific for the patient, e.g. barcoding, thereby permitting multiple patients to be analyzed in a single flow cell (or flow cell equivalent) of a high throughput DNA sequencer. Although the samples are mixed together in the DNA sequencer flow cell, the determination of the sequence of the barcode permits identification of the patient source that contributed the DNA that had been sequenced.

It will be appreciated by those of ordinary skill in the art that in those embodiments of the invention in which the target DNA is not enriched for specific loci, the entire genome may be sequenced, although assembly of the sequence into a complete genome is not required for use of the subject methods. Information about specific loci may be readily determined from all genome sequencing.

In one embodiment of the present disclosure, a confidence may be calculated on the accuracy of the determination of the ploidy state of the fetus. In one embodiment, the confidence of the hypothesis of greatest likelihood ($H_{major}$) may be calculated as $(1-H_{major}/\Sigma(\text{all } H)$. It is possible to determine the confidence of a hypothesis if the distributions of all of the hypotheses are known. It is possible to determine the distribution of all of the hypotheses if the parental genotype information is known. It is possible to calculate a confidence of the ploidy determination if the knowledge of the expected distribution of data for the euploid fetus and the expected distribution of data for the aneuploid fetus are known. It is possible to calculate these expected distributions if the parental genotype data are known. In one embodiment one may use the knowledge of the distribution of a test statistic around a normal hypothesis and around an abnormal hypothesis to determine both the reliability of the call as well as refine the threshold to make a more reliable call. This is particularly useful when the amount and/or percent of fetal DNA in the mixture is low. It will help to avoid the situation where a fetus that is actually aneuploid is found to be euploid because a test statistic, such as the Z statistic, does not exceed a threshold that is made based on a threshold that is optimized for the case where there is a higher percent fetal DNA.

An Example of a Quantitative Non-Allelic Maximum Likelihood Method ("QMM")

An example of a quantitative method that may be used to determine the number of copies of a chromosome of interest in a target individual is provided here. Note that this example involves normalization of the target chromosome data using a reference chromosome that is the same as the target chromosome (i.e. chromosome of interest), but found in other samples processed in a similar or identical manner. The instant method is described in the context of non-invasive prenatal aneuploidy testing, where the target individual is a fetus, and the DNA that is sequenced comprises fetal DNA, and in some cases, maternal DNA, for example as found in the maternal plasma. Non-invasive prenatal aneuploidy testing attempts to determine the chromosome copy number of a fetus based on the free-floating fetal DNA in maternal plasma. In the quantitative method, chromosome copy number classification is based on the number of sequence reads which map to each chromosome. Neither parental genotype nor allelic information is used, except possibly to estimate the fetal fraction in the plasma. In this targeted sequencing approach, the number of sequence reads at each targeted SNP (single nucleotide polymorphism) is informative, in contrast to untargeted sequencing approaches that tend to use a sliding window average depth of read, or similar averaged approach. Based on the estimated fetal fraction, a maximum likelihood estimate is calculated based on the set of copy number hypotheses including monosomy, disomy, and trisomy. In this example, chromosome segmental errors are not considered, meaning that all positions on the same chromosome are assumed to have the same copy number. It should be clear to one of ordinary skill in the art how to apply this method to chromosome segment copy number variants. One may also incorporate non-uniform fragmentation of the fetal or maternal genome; this is not done here.

Modeling an individual SNP: A fundamental assumption in this method is that the number of sequence reads generated at a genome position depends primarily on the number of genome copies of that position going into the sequencing process. The targeted sequencing approach is based on multiplexed PCR, which means that the number of genome copies going into sequencing is determined both by the chromosome copy number in the original sample, and the details of the PCR amplification process. Thus, this method requires a simplified models of both multiplex PCR and high throughput sequencing.

One may assume that in the original sample, the amount of genome copies is the same at all positions, except due to variations in chromosome copy number. However, in the PCR process, each targeted position is amplified with a different efficiency. For each of k PCR cycles, a position i is amplified by a factor $a_i$. The number of observed reads at the position is $x_i$. This model can be written as in equation 1, where the sample factor $c_s$ is constant per sample, and represents a sample parameter, for example the initial quantity of DNA and the total number of sequence reads. It can be thought of as the sample-specific amplification factor. The chromosome copy number $n_i$ is the ploidy state or copy number of the chromosome where position i is located.

$$x_i = c_s n_i a_i^k \tag{1}$$

However, slight variations in experimental conditions mean that the amplification efficiencies of the various PCR targets are not perfectly constant. This is represented by a multiplicative noise term $\epsilon_i$, for the amplification efficiency of each target. The model is thus extended to equation 2.

$$x_i = c_s n_i (a_i \epsilon_i)^k \tag{2}$$

Due to the multiplicative nature of the model, it is advantageous to work in log space, and then consider the expectation and the variance of log $x_i$. One may assume that the expectation of the log noise is zero. This is not quite the same as assuming zero-mean noise, but it makes the math feasible, shown in equation 3.

$$E \log x_i = \log n_i + k \log a_i$$

$$V \log x_i = k^2 V \log \epsilon_i \quad (3)$$

Sample normalization can be achieved by considering reads measured from positions located on chromosomes which are known, assumed, or hypothesized to have copy number equal to two. There are other methods of sample normalization such as using other reference chromosomes, for example chromosomes 1 and 2, which are known to be disomic. Let D be the set of positions i which are located on chromosomes assumed to be disomic. The sample normalizer $T_s$ is defined as the average log count over positions i in D, detailed in equation 4. This can be measured directly from each sample, and so will be considered a known quantity for further calculations.

$$T_s = E_i \in_D \log x_i \quad (4)$$
$$= \log c_s + \log 2 + k E_i \in_D \log a_i$$

Constructing a model from training data: A model for the efficiency of individual SNPs can be constructed from a set of training data with known chromosome copy number and fetal fraction. In the ideal case, plasma is collected from (euploid) women who are not pregnant, and so the fetal fraction is zero and there are no aneuploidies. In this case, all samples contribute data for the model of all targets. In the more difficult case, pregnancy plasma with known chromsome copy number is used, and aneuploid samples are excluded from the data set. Thus, the model is still constructed from data where all chromosomes have the same copy number relative to disomy.

Let $y_i$, be the logspace normalized depth of read at position i. One may define $\beta_i$ as the average over the set of samples, of $y_i$ (5). The term $\beta_i$ is the logspace amplification model for position i which measures how its amplification efficiency compares to the average amplification efficiency for positions on disomy chromosomes.

$$y_i = \log x_i - T_s \quad (5)$$
$$= k \log a_i + k \log \epsilon_i - k E_i \in_D \log a_i$$

$$\beta_i = E_s y_i$$
$$= k \log a_i - k E_i \in_D \log a_i$$

Similarly, $\sigma_i$ is defined as the standard deviation across samples of $y_i$. Combined, the set of $\beta_i$ and the set of $\sigma_i$ form the amplification model and the variance model for the set of SNPs i.

There are a number of subtleties associated with the model calculation. Most importantly, it is important to note that the model does not remain constant for a fixed set of targets subjected to a fixed protocol.

Although the models will be quite similar, attempts to use a fixed model across multiple sequencing runs have suffered from biases which are large enough to effect results at low fetal fraction, and may be eliminated by training separately for separate experiments. As a result, in some embodiments, it is important to ensure that each sequencing run contains a sufficient number of samples for modeling.

Even within an experiment, there are typically a number of samples which do not fit the model. These are often but not always explained by locus dropout, which is discussed in more detail in a later section. Outlier samples are not well predicted by quality control metrics such as contamination level, spike ratio (a measure of DNA starting quantity), fetal fraction, or overall depth of read. A sample is tested for goodness of fit by calculating the residual z, on each SNP with respect to the amplification and noise models.

$$z_i = (\log x_i - T_s - \beta_i)/\theta_i \quad (6)$$

Under the further assumption that $\log \epsilon_i$, is not just zero-mean, but Gaussian, then $z_i$ should be distributed according to the standard normal. The set of disomy-chromosome residuals $Z = \{z_i : i \in D\}$ is analyzed as an approximate metric for model fit. Regardless of fetal fraction or chromosome copy number, Z should be distributed according to the standard normal. A Kolmogorov-Smirnov (KS) test is used to measure goodness of fit of the residuals. The modeling process is implemented in an iterative fashion, where each iteration includes a recalculation of the model, followed by a KS test for the model fit of each sample. Outlier samples are removed from the training set at each iteration until the membership converges to a constant set.

Forming a test statistic and modeling SNP correlation: A test statistic for chromosome copy number classification can be formed by averaging the normalized measurements at all positions on a chromosome. A variance-weighted mean is selected in order to minimize the variance of the test statistic. Consider the normalized measurement $y_i$ defined above. For a position on a chromosome with unknown copy number $n_i$, $y_i$ has the properties described in equation 7.

$$E y_i = \log \frac{n_i}{2} + \beta_i \quad (7)$$
$$V y_i = \sigma_i^2$$

Let S be the set of positions on the current chromosome. The chromosome test statistic t is defined as the variance-weighted mean of $y_i$, averaged across SNPs i in S.

$$t = \frac{\sum_{i \in S} \frac{y_i}{\sigma_i^2}}{\sum_{i \in S} \frac{1}{\sigma_i^2}} \quad (8)$$

The expectation of t will be calculated under each of the chromosome copy number hypotheses to form Gaussian models for the maximum likelihood estimate. The variance of the model for each hypothesis does not follow uniquely from the assumptions made previously, which have not considered correlation between measurements. The simplest assumption of uncorrelated measurements was discarded because the observed variances on t were much higher than that model would suggest. Without suggesting any physical explanation for correlation, a single-parameter correlation model is proposed in which the covariance of $y_i$ with $y_j$ is $\rho \sigma_i \sigma_j$, corresponding to a constant correlation factor between all positions i and j on the same chromosome. This model uses a single parameter to represent the additional variance beyond what would be implied by the uncorrelated model. The variance of t using the constant correlation model is shown in equation 9 which follows directly from the formula for the variance of a sum of normal distributions with known correlation. (The assumption of Gaussian noise is continued throughout.)

$$V_t = \left(\sum_i \frac{1}{\sigma_i^2}\right)^{-2} \left(\rho \sum_i \sum_j \frac{1}{\sigma_i \sigma_j} + (1-\rho) \sum_i \frac{1}{\sigma_i^2}\right) \quad (9)$$

A maximum likelihood estimate of $\rho$ for each chromosome is calculated from the same modeling data following the estimation of $\{\beta_i\}$ and $\{\sigma_i\}$.

Chromosome copy number classification consists of the following steps which make use of the modeling developed in the sections above.

1. Confirm model fit. Using the disomy chromosomes (one and two) a set of residuals is calculated with respect to the provided model, and a KS test is used to compare them to the standard normal distribution. If the resulting p-value is too low, the sample is considered not to fit the model, and cannot be classified.

2. Copy number hypothesis generation. Using the supplied fetal fraction, the plasma copy number is calculated corresponding to each fetal copy number hypothesis. For fetal copy number hypotheses $\{h_1, h_2, h_3\} = \{1, 2, 3\}$, the plasma copy number hypotheses are calculated using the fetal fraction according to equation 10. The plasma copy number is a mixture of the fetal copy number, which depends on the hypothesis, and the maternal copy number, which is two.

$$n_i = fh_i + 2(1-f) \quad (10)$$

3. Hypothesis modeling. An expected value for the test statistic is calculated for the value of $n_i$ corresponding to the ploidy hypotheses. This is done according to equation 7 and the definition of the test statistic. The variance model for the test statistic does not depend on the hypothesis.

4. Calculate likelihoods. The value of the test statistic is observed for the current chromosome. The data likelihood of each hypothesis is the likelihood of the test statistic under each of the corresponding normal distributions. The maximum likelihood estimate can then be reported, or normalized using priors.

Copy Number Classification without Non-Target Reference Chromosomes (Also Referred to as a "QMM" Method)

As mentioned above, it is possible to identify copy number without using reference chromosomes or chromosome segments that are different than the target chromosome or chromosome segment, such that none of the chromosomes or chromosome segments can be assumed to have known copy numbers. This requires an alternate way of estimating the sample normalizer $T_s$ and the linear shift parameter $\alpha_s$, which are conditioned on the chromosome number hypotheses. Unlike the approach that uses copy number hypotheses for each individual chromosome, this hypothesis space contains joint hypotheses of all the training chromosomes.

In an embodiment, in order to connect the joint hypothesis to the individual hypothesis, the following technique may be used. For a training chromosome $k \in \{13, 18, 21\}$, let $p(D|h_k)$, $h_k \in \{1, 2, 3\}$ be the pdf of the data conditioned on the individual copy number hypothesis of that chromosome. So, for example, for chromosome 13 it would be:

$$P(D|h13) = \sum_{h18} \sum_{h21} p(D_{13}|h_{18}, h_{21}, h_{13})$$

$$p(D_{18}|h_{18}, h_{21}, h_{13}) p(D_{21}|h_{18}, h_{21}, h_{13}) P(h_{18}) P(h_{21})$$

Assuming equal priors for the hypothesis probabilities, i.e., $P(h_k=1) = P(h_k=2) = P(h_k=3) = 1/3$, the above pdf is computed. To compute $p(D_{13}|h_{18}, h_{21}, h_{13})$, the $T_s$ and $\alpha_s$ estimates corresponding to the hypothesis $(h_{18}, h_{21}, h_{13})$ are used, and a variance weighted mean test statistic is computed. Similarly, the respective pdfs of the other training chromosomes, $p(D|h_{18})$, $p(D|h_{21})$ are computed. Since equal priors are assumed, the posterior probabilities are also computed:

$$P(h\_k|D) = \left(\frac{p(D|h_k)}{\sum_{h_j \in \{1,2,3\}} p(D|h_j)}\right), \forall k \in \{13, 18, 21\}.$$

This represents a normalizing step which provides confidences for each of the training chromosomes.

Next, confidences of the rest of the chromosomes is computed. For this, an estimate of the joint hypothesis of the training chromosomes is obtained:

$$(\hat{h}_{13}, \hat{h}_{18}, \hat{h}_{21}) = \mathrm{argmax}_{h_{13}, h_{18}, h_{21}} p(D|h_{13}, h_{18}, h_{21})$$

The $T_s$ and $\alpha_s$ estimates corresponding to this hypothesis $(\hat{h}_{13}, \hat{h}_{18}, \hat{h}_{21})$ can then be used to compute the variance weighted mean test statistic for each of the test chromosomes.

In this method, a constant correlation coefficient model can be used to model the inter-SNP correlations of a particular chromosome. For example, for a particular chromosome $k$, the covariance of $y_i$ and $y_j$ is $\rho_i \sigma_i \sigma_j$, as discussed above. If chromosome K has $N_k$ loci, a covariance matrix is given by:

$$C(\rho_k) = (1-\rho_k) \times \mathrm{diag}(\sigma_k^2) + \rho_k \times \sigma_k \sigma_k^T$$

This represents a matrix with the $\sigma_i^2$s on the main diagonal and the off-diagonal elements are $\rho_k \sigma_i \sigma_j$. This can also be used to determine the maximum likelihood estimates for each of $T_s$ and $\alpha_s$ An example of a quantitative allelic maximum likelihood method ("het rate")

Provided herein are methods for determining the ploidy state using an allelic maximum likelihood method. The method will be illustrated in the context of NIPT, but a skilled artisan will appreciate that it can be utilized in detection of circulating free tumor cells. In addition to the discussion below, detailed examples of how to implement a het rate method can be found, among other places, in published US patent application US 2012/0270212 A1 and published US patent application US 2011/0288780 A1, all of which are herein incorporated in their entirety by reference. However, the het rate method disclosed in these sources, utilize data from separate reference chromosomes In the NIPT example, the ploidy state of a fetus given sequence data that was measured on free floating DNA isolated from maternal blood, wherein the free floating DNA contains some DNA of maternal origin, and some DNA of fetal/placental origin. In this example the ploidy state of the fetus is determined using the an allelic maximum likelihood method and a calculated fraction of fetal DNA in the mixture that has been analyzed. It will also describe an embodiment in which the fraction of fetal DNA or the percentage of fetal DNA in the mixture can be measured. In some embodiments the fraction can be calculated using only the genotyping measurements made on the maternal blood sample itself, which is a mixture of fetal and maternal DNA. In some embodiments the fraction may be calculated also using the measured or otherwise known genotype of the mother and/or the measured or otherwise known genotype of the father.

For a particular chromosome, suppose there are N SNPs, for which: Parent genotypes from ILLUMINA data, assumed to be correct: mother $m=(m_1, \ldots, m_N)$, father$=(f_1, \ldots, f_N)$, where $m_i, f_i \in (AA, AB, BB)$.
Set of NR sequence measurements $S=(s_1, \ldots, s_{nr})$.
Deriving Most Likely Copy Number from Data For each copy number hypothesis H considered, derive data log likelihood LIK(H) on a whole chromosome and choose the best hypothesis maximizing LIK, i.e.

$$H^* = \underset{H}{\operatorname{argmax}} LIK(H \mid D) = \underset{H}{\operatorname{argmax}} LIK(D \mid H) P(H),$$

where P(H) is a prior probability of the hypothesis, from prior knowledge or estimate.

Copy number hypotheses considered are:
Monosomy:
maternal H10(one copy from mother)
paternal H01(one copy from father)
Disomy: H11(one copy each mother and father)
Simple trisomy, no crossovers considered:
Maternal: H21_matched (two identical copies from mother, one copy from father), H21_unmatched (BOTH copies from mother, one copy from father)
Paternal: H12_matched (one copy from mother, two identical copies from father), H12_unmatched (one copy from mother, both copies from father)
Composite trisomy, allowing for crossovers (using a joint distribution model):
maternal H21 (two copies from mother, one from father),
paternal H12 (one copy from mother, two copies from father)

If there were no crossovers, each trisomy, whether the origin was mitosis, meiosis I, or meiosis II, would be one of the matched or unmatched trisomies. Due to crossovers, true trisomy is a combination of the two. First, a method to derive hypothesis likelihoods for simple hypotheses is described. Then a method to derive hypothesis likelihoods for composite hypotheses is described, combining individual SNP likelihood with crossovers. Initially, it is assumed that the true child fraction and other parameters such as beta noise parameter (N) and possible error rates are known. A method for deriving child fraction cf from data is also discussed below.

LIK(D|H) for Simple Hypotheses

For simple hypotheses H, LIK(D|H), the log likelihood of data given hypothesis H on a whole chromosome, is calculated as the sum of log likelihoods of individual SNPs, i.e.

$$LIK(D \mid H) = \sum_i LIK(D \mid H, cf, i)$$

This hypothesis does not assume any linkage between SNPs, and therefore does not utilize a joint distribution model.

Log Likelihood per SNP

On a particular SNP i, define $m_i$=true mother genotype, $f_i$=true father genotype, and cf=known or derived child fraction. Let $x_i=P(A|i,S)$ be the probability of having an A on SNP i, given the sequence measurements S. Assuming child hypothesis H, the log likelihood of observed data D on SNP i is defined as $P(D|m,f,c,H,cf,i)=P(SM|m,i)P(M|m,i)P(SF|f,i)P(F|f,i)$
$\quad P(S|m,c,H,cf,i),$ which results in:

$LIK(i,H)=\text{loglik}(x_i|m_i,f_i,H,cf)=\Sigma_c p(c|m_i,f_i,H)^*\text{loglik}$
$\quad (x_i|m_i,c,cf),$ where p(c|m, f, H) is the probability of getting true child genotype=c, given parents m, f, and assuming hypothesis H, which can be easily calculated. For example, for H11, H21 matched and H21 unmatched, p(c|m,f,H) is given below.

| | | \multicolumn{11}{c}{p(c\|m, f, H)} | | | | | | | | | | |
| | | H11 | | | H21 matched | | | | H21 unmatched | | | |
| m | f | AA | AB | BB | AAA | AAB | ABB | BBB | AAA | AAB | ABB | BBB |
|---|---|----|----|----|-----|-----|-----|-----|-----|-----|-----|-----|
| AA | AA | 1 | 0 | 0 | 1 | 0 | 0 | 0 | 1 | 0 | 0 | 0 |
| AB | AA | 0.5 | 0.5 | 0 | 0.5 | 0 | 0.5 | 0 | 0 | 1 | 0 | 0 |
| BB | AA | 0 | 1 | 0 | 0 | 0 | 1 | 0 | 0 | 0 | 1 | 0 |
| AA | AB | 0.5 | 0.5 | 0 | 0.5 | 0.5 | 0 | 0 | 0.5 | 0.5 | 0 | 0 |
| AB | AB | 0.25 | 0.5 | 0.25 | 0.25 | 0.25 | 0.25 | 0.25 | 0 | 0.5 | 0.5 | 0 |
| BB | AB | 0 | 0.5 | 0.5 | 0 | 0 | 0.5 | 0.5 | 0 | 0 | 0.5 | 0.5 |
| AA | BB | 0 | 1 | 0 | 0 | 1 | 0 | 0 | 0 | 1 | 0 | 0 |
| AB | BB | 0 | 0.5 | 0.5 | 0 | 0.5 | 0 | 0.5 | 0 | 0 | 1 | 0 |
| BB | BB | 0 | 0 | 1 | 0 | 0 | 0 | 1 | 0 | 0 | 0 | 1 |

P(D|m,f,c,H,i,cf) is the probability of given data D on SNP i, given true mother genotype m, true father genotype f, true child genotype c, hypothesis H, and child fraction cf. It can be broken down into probability of mother, father, and child data as follows: P(D|m, f, c, H, cf, i)=P(SM|m, i)P(M|m, i)P(SF|f, i)P(F|f, i)P(S|m, c, H, cf, i). lik($x_i$|m,c,cf) is the likelihood of getting derived probability $x_i$ on SNP i, assuming true mother m, true child c, defined as pdfx($x_i$) of the distribution that $x_i$ should be following if hypothesis H were true. In particular lik($x_i$|m, c, cf)=pdfx($x_i$)

In a simple case where Di of NR sequences in S line up to SNP i, $X \sim (1/D_i) \text{Bin}(p, D_i)$, where p=p(A|m,c,cf)=probability of getting an A, for this mother/child mixture, calculated as:

$$Hetrate_A = p(A \mid m, c, cf) = \frac{\#A(m)*(1-cf_{correct}) + \#A(c)*cf_{correct}}{n_m*(1-cf_{correct}) + n_c*cf_{correct}}$$

where $\#A(g)$=number of A's in genotype g, $n_m$=2 is somy of mother and $n_c$ is somy of the child, (1 for monosomy, 2 for disomy, 3 for trisomy). The initial cf may be determined using, for example, an allele ratio plot.

$cf_{correct}$ is corrected fraction of the child in the mixture:

$$cf_{correct} = cf * \frac{n_c}{n_m*(1-cf) + n_c*cf}$$

If child is a disomy $cf_{correct}$=cf, but for a trisomy fraction of the child in the mix for this chromosome is actually a bit higher:

$$cf_{correct} = cf * \frac{3}{2+cf}.$$

In a more complex case where there is not exact alignment, X is a combination of binomials integrated over possible $D_i$ reads per SNP.

Using a Joint Distribution Model: LIK(H) for a Composite Hypothesis

In real life, trisomy is usually not purely matched or unmatched, due to crossovers, so in this section results for composite hypotheses H21 (maternal trisomy) and H12 (paternal trisomy) are derived, which combine matched and unmatched trisomy, accounting for possible crossovers.

In the case of trisomy, if there were no crossovers, trisomy would be simply matched or unmatched trisomy. Matched trisomy is where child inherits two copies of the identical chromosome segment from one parent. Unmatched trisomy is where child inherits one copy of each homologous chromosome segment from the parent. Due to crossovers, some segments of a chromosome may have matched trisomy, and other parts may have unmatched trisomy. Described in this section is how to build a joint distribution model for the heterozygosity rates for a set of alleles.

Suppose that on SNP i, LIK(i, Hm) is the fit for matched hypothesis H, and LIK(i, Hu) is the fit for UNmatched hypothesis H, and pc(i)=probability of crossover between SNPs i−1,i. One may then calculate the full likelihood as:

$$LIK(H) = \Sigma_{S,E} LIK(S,E,1:N)$$

where LIK(S, E, 1:N) is the likelihood starting with hypothesis S, ending in hypothesis E, for SNPs 1:N. S=hypothesis of the first SNP, E=hypothesis of the last SNP, S,E ∈ (Hm, Hu). Recursivelly one may calculate:

$$LIK(S,E,1:i) = LIK(i,E) + \log(\exp(LIK(S,E,1:i-1))*(1-pc(i)) + \exp(LIK(S,\sim E,1:i-1))*pc(i))$$

where ~E is the other hypothesis (not E). In particular, one may calculate the likelihood of 1:i SNPs, based on likelihood of 1:(i−1) SNPs with either the same hypothesis and no crossover or the opposite hypothesis and a crossover times the likelihood of the SNP i For SNP i=1:

$$LIK(S, E, 1:1) = \begin{cases} LIK(1, S) & \text{if } S = E \\ 0 & \text{if } S \neq E \end{cases}$$

Then calculate: LIK(S, E, 1:2)=LIK(2, E)+log(exp(LIK(S, E, 1))*(1−pc(2))+exp(LIK(S, ~E, 1))*pc(2)) and so on until i=N.

Deriving Child Fraction

The above formulas assume a known child fraction, which is not always the case. In one embodiment, it is possible to find the most likely child fraction by maximizing the likelihood for disomy on selected chromosomes.

In particular, suppes that LIK(chr, H11, cf)=log likelihood as described above, for the disomy hypothesis, and for child fraction cf on chromosome chr. For selected chromosomes in Cset (usually 1:16). Then the full likelihood is:

$$LIK(cf) = \sum_{chr \in Cset} Lik(chr, H11, cf), \text{ and } cf^* = \underset{cf}{\mathrm{argmax}} LIK(cf).$$

It is possible to use any set of chromosomes. It is also possible to derive child fraction without paternal data, as follows.

Deriving Copy Number Without Paternal Data

Recall the formula of the simple hypothesis log likelihood on SNP i:

$$LIK(i, H) =$$
$$\log lik(x_i \mid m_i, f_i, H, cf) = \sum_c p(c \mid m_i, f_i, H) * \log lik(x_i \mid m_i, c, H, cf)$$

Determining the probability of the true child given parents $p(c \mid m_1, f_1, H)$ requires the knowledge of father genotype. If the father genotype is unknown, but pAi, the population frequency of A allele on this SNP, is known, it is possible to approximate the above likelihood with $$LIK(i,H) = \log lik(x_i \mid m_i, f_i, H, cf) = \Sigma_c p(c \mid m_i, H) * \log lik(x_i \mid m_i, c, H, cf)$$

where $$p(c \mid m_i, H) \sum_f p(c \mid m_i, f_i, H) * p(f \mid pA_i)$$

where $p(f \mid pA_i)$ is the probability of particular father genotype, given the frequency of A on SNP i.

In particular:

$$p(AA \mid pA_i) = (pA_i)^2, p(AB \mid pA_i) = 2(pA_i)*(1-pA_i), p(BB \mid pA_i) = (1-pA_i)^2$$

Training Method without Using a Control Chromosome or Chromosome Segment

Suppose, we have 3 data segments $D_1$, $D_2$ and $D_3$. Suppose that P(H) is the current prior on segment $D_1$. Suppose that p is a parameter with distribution P(p) (e.g., child fraction cf or noise parameter np). Then probability for a certain hypothesis H (with prior P(H)) to be true equals:

$$P(H \mid D_1, D_2, D_3) = \frac{1}{P(D_1, D_2, D_3)} \sum_p P(D_1, D_2, D_3, H, p)$$

which results in $$P(H\mid D_1, D_2, D_3) = \frac{P(D_2, D_3)}{P(D_1, D_2, D_3)}\sum_p P(D_1\mid H, p)P(H)P(p\mid D_2, D_3)$$

or, to approximate, $$P(H\mid D_1, D_2, D_3) \sim \sum_p P(D_1\mid H, p)P(H)P(p\mid D_2, D_3)$$

where the term $P(D_1|H, p)$ can be re-written as $$P(D_1\mid H, p) = P(D_1)\frac{P(H\mid D_1, p)}{P(H)}\frac{P(p\mid D_1)}{P(p)}$$

Thus, $$P(H\mid D_1, D_2, D_3) \sim \sum_p P(H\mid D_1, p)\frac{P(p\mid D_1)}{P(p)}P(p\mid D_2, D_3),$$

where the term $P(p|D_2,D_3)$ is a parameter distribution obtained from "training" on segments $D_2$ and $D_3$. $P(p|D_1)/P(p)$ depends on what the actual hypothesis for segment 1 is, and may be dropped if unknown. The approximation loses some information, but it can be more stable and intuitive, since each piece is on a probability scale, and fits call per grid point, scaled by grid point probability.

Significant processing advantages can be obtained if a control chromosome or chromosome segment is not required, as the tests can be run on only the chromosome(s) or chromosome segment(s) of interest. In an embodiment, the chromosomes or chromosome segments of interest themselves provide a baseline that can then be used to evaluate the accuracy of the given hypotheses. For example, by using the formula $$P(p\mid D_1, D_2, D_3) = \frac{P(p\mid D_1)}{P(p)}\cdot\frac{P(p\mid D_2)}{P(p)}\cdot\frac{P(p\mid D_3)}{P(p)}\cdot P(p),$$

the above probability equation can also be written as:

$$P(H\mid D_1, D_2, D_3) \sim \sum_p P(H\mid D_1, p)\frac{P(p\mid D_1)}{P(p)}P(p\mid D_2, D_3) = \sum_p P(H\mid D_1, p)P(p\mid D_1, D_2, D_3)$$

In this equation, the probability $P(H|D_1, p)$ is obtained per grid point, and is then scaled by the best parameter distribution estimate given $P(p, D_1, D_2, D_3)$. Once the grid points are fixed, $P(H|D_1, p)$ does not change. However, when no fixed hypothesis exists (i.e., no control chromosome or chromosome segment is used) for $P(p, D_1, D_2, D_3)$, the final answer for $P(H|D_1, D_2, D_3)$ can vary greatly depending on the prior put on each segment hypothesis.

In other words, since the parameter distribution given all the data is a composite of parameter distributions for each segment, $$P(p\mid D_i) \sim \sum_G P(D_i\mid p, G)P(G)P(p)$$

where $P(G)$ is the hypothesis prior used on this segment for purposes of parameter estimation.

To account for the lack of a control, a uniform hypothesis prior $f_{prior}(H)$ for hypothesis H is obtained. For example, this may be obtained by estimating child fraction using an allele ratio plot as discussed above. Then, for each grid point p, calculate a probability of the hypothesis ("per-grid call"):

$$P(H|D_1,p) \sim P(D_1|H,p)P(H)$$

where $P(H)$ is the hypothesis prior used for segment calling. In an embodiment, this is done only once to provide an idea of the calls for the entire grid space.

For the first pass, $f_{prior}(H)$ is set to be $P(H)$. The parameter distribution for each segment is then obtained using:

$$P(p\mid D_i) \sim \sum_H P(D_i\mid p, H)f_{prior}(H)P(p)$$

The composite parameter distribution is then obtained:

$$P(p\mid D_1, D_2, D_3) = \frac{P(p\mid D_1)}{P(p)}\frac{P(p\mid D_2)}{P(p)}\frac{P(p\mid D_3)}{P(p)}P(p)$$

The (posterior) probability of each hypothesis is then obtained by combining parameter scaling to the per grid call:

$$P(H\mid D_1, D_2, D_3) = \sum_p P(H\mid D_1, p)P(p\mid D_1, D_2, D_3).$$

This provides a new estimate of the distribution of the hypothesis per each segment. $F_{prior}(H)$ can be updated with the newly derived $P(H|D_1,D_2,D_3)$, and the process (starting with calculating the probability of the hypothesis for each grid point p) is repeated until convergence.

Convergence is reached the total likelihood does not change anymore to any appreciable extent. In an embodiment, this can be treated as an annealing problem, with the function to be optimized being the likelihood of the data $P(H|D_1,D_2,D_3)$ maximized by the best derived posterior $P(H)$ and $P(p)$ distributions. That is, the function to maximize is:

$$L(D)=P(D_1,D_2,D_3)\sim\Sigma_H\Sigma_p P(D|H,p)P(H)P(p).$$

The hypotheses with final probabilities (i.e., calls), child fraction, and noise parameters can then be output.

In certain embodiments of the present disclosure, a method of the invention for determining aneuploidy can include a quantitative allelic method, technique, or algorithm that can be used to determine the relative ratios of two or more different haplotypes that contain the same set of loci in a sample of DNA. The different haplotypes could represent two different homologous chromosomes from one individual, three different homologous chromosomes from a trisomic individual, three different homologous haplotypes from a mother and a fetus where one of the haplotypes is shared between the mother and the fetus, three or four haplotypes from a mother and fetus where one or two of the haplotypes are shared between the mother and the fetus, or other combinations. If one or more of the haplotypes are known, or the diploid genotypes of one or more of the individuals are known, then a set of alleles that are polymorphic between the haplotypes can be chosen, and average allele ratios can be determined based on the set of alleles that uniquely originate from each of the haplotypes.

Direct sequencing of such a sample, however, is extremely inefficient as it results in many sequences for regions that are not polymorphic between the different haplotypes in the sample and therefore reveal no information about the proportion of the two haplotypes. Described herein is a method that specifically targets and enriches segments of DNA in the sample that are more likely to be polymorphic in the genome to increase the yield of allelic information obtained by sequencing. Note that for the allele ratios measured in an enriched sample to be truly representative of the actual haplotype ratios it is critical that there is little or no preferential enrichment of one allele as compared to the other allele at a given loci in the targeted segments. Current methods known in the art to target polymorphic alleles are designed to ensure that at least some of any alleles present are detected. However, these methods were not designed for the purpose of measuring the allele ratio of polymorphic alleles present in the original mixture. It is non-obvious that any particular method of target enrichment would be able to produce an enriched sample wherein the proportion of various alleles in the enriched sample is about the same as to the ratios of the alleles in the original unamplified sample. While enrichment methods may be designed, in theory, to accomplish such an aim, an ordinary person skilled in the art is aware that there is a great deal of stochastic or deterministic bias in current methods. On embodiment of the method described herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. For the purposes of this disclosure, for the ratio to remain essentially the same, it is mean that the ratio of the alleles in the original mixture divided by the ratio of the alleles in the resulting mixture is between 0.5 and 1.5, between 0.8 and 1.2, between 0.9 and 1.1, between 0.95 and 1.05, between 0.98 and 1.02, between 0.99 and 1.01, between 0.995 and 1.005, between 0.998 and 1.002, between 0.999 and 1.001, or between 0.9999 and 1.0001.

Allele Distributions

In certain embodiments, the goal of the method is to detect fetal copy number based on a maternal blood sample which contains some free-floating fetal DNA. In some embodiments, the fraction of fetal DNA compared to the mother's DNA is unknown. The combination of a targeting method, such as LIPS, followed by sequencing results in a platform response that consists of the count of observed sequences associated with each allele at each SNP. The set of possible alleles, either A/T or C/G, is known at each SNP. Without loss of generality, the first allele will be labeled A and the second allele will be labeled B. Thus, the measurement at each SNP consists of the number of A sequences ($N_A$) and the number of B sequences ($N_B$). These will be transformed for the purpose of future calculations into the total sequence count (n) and the ratio of A alleles to total (r). The sequence count for a single SNP will be referred to as the depth of read. The fundamental principal which allows copy number identification from this data is that the ratio of A and B sequences will reflect the ratio of A and B alleles present in the DNA being measured.

$$n = N_A + N_B$$

$$r = N_A/(N_A + N_B)$$

Measurements will be initially aggregated over SNPs from the same parent context based on unordered parent genotypes. Each context is defined by the mother genotype and the father genotype, for a total of 9 contexts. For example, all SNPs where the mother's genotype is AA and the father's genotype is BB are members of the AA|BB context. The A allele is defined as present at ratio $r_m$ in the mother genotype and ratio $r_f$ in the father genotype. For example, the allele A is present at ratio $r_m=1$ where the mother is AA and ratio $r_f=0.5$ where the father is AB. Thus, each context defines values for $r_m$ and $r_f$. Although the child genotypes cannot always be predicted from the parent genotypes, the allele ratio averaged over a large number of SNPs can be predicted based on the assumption that a parent AB genotype will contribute A and B at equal rates.

Consider a copy number hypothesis for the child of the form $(n_m, n_f)$ where $n_m$ is the number of mother copies and $n_f$ is the number of father copies of the chromosome. The expected allele ratio $r_c$ in the child (averaged over SNPs in a particular parent context) depends on the allele ratios of the parent contexts and the parent copy numbers.

$$r_c = \frac{n_m r_m + n_f r_f}{n_m n_f} \quad (1)$$

In a mixture of maternal and fetal blood, allele copies will be contributed from both the mother directly and from the child. Assume that the fraction of child DNA present in the mixture is S. Then in the mixture, the ratio r of the A allele in a given context is a linear combination of the mother ratio $r_m$ and the child ratio $r_c$, which can be reduced to a linear combination of the mother ratio and father ratio using equation 1.

$$r = (1-\delta)r_m + \delta r_c \quad (2)$$

$$= \left(1 - \frac{\delta n_f}{n_m + n_f}\right) r_m + \frac{\delta n_f}{n_m + n_f} r_f$$

Equation 2 predicts the expected ratio of A alleles for SNPs in a given context as a function of the copy number hypothesis $(n_m, n_f)$. Note that the allele ratio on individual SNPs is not predicted by this equation because these depend on random assignment where at least one parent is heterozygous. Therefore, the set of sequences from all SNPs in a particular context will be combined. Assuming that the context contains m SNPs, and recalling that n sequences will be produced from each SNP, the data from that context consists of N=mn sequences. Each of the N sequences is considered an independent random trial where the theoretical rate of A sequences is the allele ratio r. The measured rate of A sequences $\hat{r}$ is therefore known to be Gaussian distributed with mean r and variance $\sigma^2 = r(1-r)/N$.

Recall that the theoretical allele ratio is a function of the parent copy numbers $(n_m, n_f)$. Thus, each hypothesis h results in a predicted allele ratio $r_i^h$ for the SNP in parent context i.

The data likelihood is defined as the probability of a given hypothesis producing the observed data. Thus, the likelihood of measurement $r_i^h$ from context i under hypothesis h is a binomial distribution, which can be approximated for large N as a Gaussian distribution with the following mean and variance. The mean is determined by the context and the hypothesis as described in equation 2.

$$p(\hat{r}_i | h) = N(\hat{r}_i; \mu, \sigma)$$

$$\mu = r_i^h$$

$$\sigma = \sqrt{\frac{r_i^h(1 - r_i^h)}{N_i}}$$

The measurements on each of the nine contexts are assumed independent given the parent copy numbers, due to the common assumption of independent noise on each SNP. Thus, the data from a particular chromosome consists of the sequence measurements from contexts i ranging from 1 to 9. The likelihood of the observed allele ratios $\{\hat{r}_1 \ldots, \hat{r}_9\}$ from the whole chromosome is therefore the product of the individual context likelihoods:

$$p(\hat{r}_1 \ldots, \hat{r}_9) = \prod_{i=1}^{9} p(\hat{r}_i | h)$$

$$= \prod_{i=1}^{9} N\left(\hat{r}_i; r_i^h, \sqrt{\frac{r_i^h(1 - r_i^h)}{N_i}}\right)$$

Parameter Estimation

Equation 2 predicts the allele ratio as a function of parent copy number hypothesis, but also includes the fraction of child DNA. Therefore, the data likelihood for each chromosome is a function of through its effect on $r_i^h$. This effect is highlighted through the notation $p(\hat{r}_1 \ldots, \hat{r}_9 | h; \delta)$. This parameter cannot be predicted with high accuracy, and therefore must be estimated from the data. A number of different approaches may be used for parameter estimation. One method involves the measurement of chromosomes for which copy number errors are not viable at the stage of development where testing will be performed. The other method measures only chromosomes on which errors are expected to occur.

Measure Some Chromosomes Known to be Disomy

In this method, certain chromosomes will be measured which cannot have copy number errors at the state of development when testing is performed. These chromosomes will be referred to as the training set T. The copy number hypothesis on these chromosomes is (1,1). Assuming that each chromosome is independent, the data likelihood of the measurements from all chromosomes t in T is the product of the individual chromosome likelihoods. The child fraction δ can be selected to maximize the data likelihood across the chromosomes in T conditioned on the disomy hypothesis. Let $R_t$ represent the set of measurements $\hat{r}_i$ from all contexts i on chromosome t. Then, the maximum likelihood estimate δ* solves the following:

$$\delta^* = \underset{\delta}{\mathrm{argmin}} \prod_{t \in T} p(R_t | h = (1, 1); \delta)$$

This optimization has only one degree of freedom constrained between zero and one, and therefore can easily be solved using a variety of numerical methods. The solution δ* can then be substituted into equation 2 in order to calculate the likelihoods of each hypothesis on each chromosome.

Measure Only Chromosomes which May have Copy Number Errors

If copy number errors are possible on all of the chromosomes being measured, the accuracy of the ploidy determination increases greatly if fetal fraction is estimated in parallel with the copy number hypotheses. Note that the same copy number error present on all measured chromosomes will be very difficult to detect. For example, maternal trisomy on all chromosomes at a given child concentration will result in the same theoretical allele ratios as disomy on all chromosomes at lower child concentration, because in both cases the contribution of mother alleles compared to father alleles increases uniformly across all chromosomes and contexts.

A straight forward approach for classification of a limited set of chromosomes t is to consider the joint chromosome hypothesis H, which consists of the joint set of hypotheses for all chromosomes being tested. If the chromosome hypotheses consist of disomy, maternal trisomy and paternal trisomy, the number of possible joint hypotheses is $3^T$ where T is the number of tested chromosomes. A maximum likelihood estimate δ*(H) can be calculated conditioned on each joint hypothesis. The likelihood of the joint hypothesis is thus calculated as follows:

$$\delta^*(H) = \underset{\delta}{\mathrm{argmin}} \prod_{t=1}^{T} p(R_t | H; \delta)$$

$$p(\text{all data} | H) = \prod_{t=1}^{T} p(R_t | H; \delta^*(H))$$

The joint hypothesis likelihoods p(all data|H) can be calculated for each joint hypothesis H, and the maximum likelihood hypothesis is selected, with its corresponding estimate δ*(H) of the child fraction.

Performance Specifications

The ability to distinguish between parent copy number hypotheses is determined by models discussed in the previous section. At the most general level, the difference in expected allele ratios under the different hypotheses must be large compared to the standard deviations of the measurements. Consider the example of distinguishing between disomy and maternal trisomy, or hypotheses $h_1=(1,1)$ and $h_2=(2,1)$. Hypothesis 1 predicts allele ratio $r^1$ and hypothesis 2 predictions allele ratio $r^2$, as a function of the mother allele ratio $r_m$ and father allele ratio $r_f$ for the context under consideration.

$$r^1 = \left(1 - \frac{\delta}{2}\right)r_m + \frac{\delta}{2}r_f$$

$$r^2 = \left(1 - \frac{\delta}{3}\right)r_m + \frac{\delta}{3}r_f$$

The measured allele ratio P is predicted to be Gaussian distributed, either with mean $r^1$ or mean $r^2$, depending on whether hypothesis 1 or 2 is true. The standard deviation of the measured allele ratio depends similarly on the hypothesis, according to equation 3. In a scenario where one can expect to identify either hypothesis 1 or 2 as truth based on the measurement $\hat{r}$, the means $r^1$, $r^2$ and standard deviations $\sigma^1$, $\sigma^2$ must satisfy a relationship such as the following, which guarantees that the means are far apart compared to the standard deviations. This criterion represents a 2 percent error rate, meaning a 2 percent chance of either false negative or false positive.

$$|r^1 - r^2| > 2\ \sigma^1 + \sigma^2$$

Substituting the copy numbers for disomy (1, 1) and maternal trisomy (2, 1) for hypotheses 1 and 2 results in the following condition:

$$\left|\frac{\delta}{6}(r_f - r_m)\right| > 2\sigma 1 + 2\sigma 2$$

$$\sigma^1 = \sqrt{\frac{r_1(1 - r^1)}{N}}$$

$$\sigma^2 = \sqrt{\frac{r_2(1 - r^2)}{N}}$$

$$\sigma^1 = \sqrt{\frac{r_2(1 - r^2)}{N}}$$

Overview of an Analysis Method Utilized in Methods Provided Herein

In certain examples of embodiments of the present disclosure, using the parent contexts, and chromosomes known to be euploid, it is possible to estimate, by a set of simultaneous equations, the proportion of DNA in the maternal blood from the mother and the proportion of DNA in the maternal blood from the fetus. These simultaneous equations are made possible by the knowledge of the alleles present on the father. In particular, alleles present on the father and not present on the mother provide a direct measurement of fetal DNA. One may then look at the particular chromosomes of interest, such as chromosome 21, and see whether the measurements on this chromosome under each parental context are consistent with a particular hypothesis, such as $H_{mp}$ where m represents the number of maternal chromosomes and p represents the number of paternal chromosomes e.g. $H_{11}$ representing euploid, $H_{21}$ and $H_{12}$ representing maternal and paternal trisomy respectively.

This method, unlike certain other methods for detecting chromosome ploid, does not use a reference chromosome as a basis by which to compare observed allelic ratios on the chromosome of interest to make a determination of aneuploidy.

This disclosure presents methods by which one may determine the ploidy state of a gestating fetus, at one or more chromosome, in a non-invasive manner, using genetic information determined from fetal DNA found in maternal blood. The fetal DNA may be purified, partially purified, or not purified; genetic measurements may be made on DNA that originated from more than one individual. Informatics type methods can infer genetic information of the target individual, such as the ploidy state, from the bulk genotypic measurements at a set of alleles. The set of alleles may contain various subsets of alleles, wherein one or more subsets may correspond to alleles that are found on the target individual but not found on the non-target individuals, and one or more other subsets may correspond to alleles that are found on the non-target individual and are not found on the target individual. The method may involve using comparing ratios of measured output intensities for various subsets of alleles to expected ratios given various potential ploidy states. The platform response may be determined, and a correction for the bias of the system may be incorporated into the method.

Key Assumptions of the Method:

The expected amount of genetic material in the maternal blood from the mother is constant across all loci.

The expected amount of genetic material present in the maternal blood from the fetus is constant across all loci assuming the chromosomes are euploid.

The chromosomes that are non-viable (all excluding 13,18,21,X,Y) are all euploid in the fetus. In one embodiment, only some of the non-viable chromosomes need be euploid on the fetus.

General Problem Formulation:

One may write $y_{ijk} = g_{ijk}(x_{ijk}) + v_{ijk}$ where $x_{ijk}$ is the quantity of DNA on the allele k=1 or 2 (1 represents allele A and 2 represents allele B), j=1 . . . 23 denotes chromosome number and i=1 . . . N denotes the locus number on the chromosome, gijk is platform response for particular locus and allele ijk, and $v_{ijk}$ is independent noise on the measurement for that locus and allele. The amount of genetic material is given by $x_{ijk} = am_{ijk} + \Delta c_{ijk}$ where a is the amplification factor (or net effect of leakage, diffusion, amplification etc.) of the genetic material present on each of the maternal chromosomes, $m_{ijk}$ (either 0,1,2) is the copy number of the particular allele on the maternal chromosomes, $\Delta$ is the amplification factor of the genetic material present on each of the child chromosomes, and $c_{ijk}$ is the copy number (either 0,1,2,3) of the particular allele on the child chromosomes. Note that for the first simplified explanation, a and $\Delta$ are assumed to be independent of locus and allele i.e. independent of j, and k. This gives:

$$y_{ijk} = g_{ijk}(am_{ijk} + \Delta c_{ijk}) + V_{ijk}$$

Approach Using an Affine Model that is Uniform Across all Loci:

One may model g with an affine model, and for simplicity assume that the model is the same for each locus and allele, although it will be understood after reading this disclosure how to modify the approach when the affine model is dependent on i,j,k. Assume the platform response model is $$g_{ijk}(x_{ijk}) = b + am_{ijk} + \Delta c_{ijk}$$

where amplification factors a and A have been used without loss of generality, and a y-axis intercept b has been added which defines the noise level when there is no genetic material. The goal is to estimate a and $\Delta$. It is also possible to estimate b independently, but assume for now that the noise level is roughly constant across loci, and only use the set of equations based on parent contexts to estimate a and A. The measurement at each locus is given by $$y_{ijk} = b + am_{ijk} + \Delta c_{ijk} + v_{ijk}$$

Assuming that the noise $v_{ijk}$ is i.i.d. for each of the measurements within a particular parent context, T, one can sum the signals within that parent context. The parent contexts are represented in terms of alleles A and B, where the first two alleles represent the mother and the second two alleles represent the father: T∈{AA|BB, BB|AA, AB|AB, AA|AA, BB|BB, AA|AB, AB|AA, AB|BB, BB|AB}. For each context T, there is a set of loci i,j where the parent DNA conforms to that context, represented i,j∈T. Hence:

$$y_{T,k} = \frac{1}{N_T} \sum_{i,j \in T} y_{i,j,k} = b + a\overline{m_{k,T}} + \Delta\overline{c_{k,T}} + v_{k,T}$$

Where $\overline{m_{k,T}}$, $\overline{c_{k,T}}$, and $\overline{v_{k,T}}$ represent the means of the respective values over all the loci conforming to the parent context T, or over all i, j∈T. The mean or expected values $\overline{c_{k,T}}$, will depend on the ploidy status of the child. The table below describes the mean or expected values $\overline{m_{k,T}}$, and $\overline{c_{k,T}}$, for k=1(allele A) or 2(allele B) and all the parent contexts T. One may calculate the expected values assuming different hypotheses on the child, namely euploidy and maternal trisomy. The hypotheses are denoted by the notation $H_{mp}$, where m refers to the number of chromosomes from the mother and f refers to the number of chromosomes from the father e.g. $H_{11}$ is euploid, $H_{21}$ is maternal trisomy. Note that there is symmetry between some of the states by switching A and B, but all states are included for clarity:

| Context | AA/BB | BB/AA | AB/AB | AA/AA | BB/BB | AA/AB | AB/AA | AB/BB | BB/AB |
|---|---|---|---|---|---|---|---|---|---|
| $\overline{M_{A,T}}$ | 2 | 0 | 1 | 2 | 0 | 2 | 1 | 1 | 0 |
| $\overline{M_{B,T}}$ | 0 | 2 | 1 | 0 | 2 | 0 | 1 | 1 | 2 |
| $\overline{c_{A,T}}\|H_{11}$ | 1 | 1 | 1 | 2 | 0 | 1.5 | 1.5 | 0.5 | 0.5 |
| $\overline{c_{B,T}}\|H_{11}$ | 1 | 1 | 1 | 0 | 2 | 0.5 | 0.5 | 1.5 | 1.5 |
| $\overline{c_{A,T}}\|H_{21}$ | 2 | 1 | 1.5 | 3 | 0 | 2.5 | 2 | 1 | 0.5 |
| $\overline{c_{B,T}}\|H_{21}$ | 1 | 2 | 1.5 | 0 | 3 | 0.5 | 1 | 2 | 2.5 |

It is now possible to write a set of equations describing all the expected values $y_T, k$, which can be cast in matrix form, as follows:

$$Y = B + A_H P + v$$

Where $$Y = \begin{bmatrix} y_{AA|BB,1} & y_{BB|AA,1} & y_{AB|AB,1} & y_{AA|AA,1} & y_{BB|BB,1} & y_{AA|AB,1} & y_{AB|AA,1} & y_{AB,BB,1} & y_{BB|AB,1} \\ y_{AA|BB,2} & y_{BB|AA,2} & y_{AB|AB,2} & y_{AA|AA,2} & y_{BB|BB,2} & y_{AA|AB,2} & y_{AB|AA,2} & y_{AB,BB,2} & y_{BB|AB,2} \end{bmatrix}^T$$

$$P = \begin{bmatrix} a \\ \Delta \end{bmatrix}$$

is the matrix of parameters to estimate $B = b\vec{1}$ where $\hat{1}$ is the 18×1 matrix of ones
$v = [\overline{v_{A,AA|BB}} \ldots \overline{v_{B,BB|BB}}]^T$ is the 18×1 matrix of noise terms and $A_H$ is the matrix encapsulating the data in the table, where the values are different for each hypothesis H on the ploidy state of the child. Below are examples of the Matrix $A_H$ for the ploidy hypotheses $H_{11}$ and $H_{21}$ $$A_{H_{11}} = \begin{bmatrix} 2.0 & 1.0 \\ 0 & 1.0 \\ 1.0 & 1.0 \\ 2.0 & 2.0 \\ 0 & 0 \\ 2.0 & 1.5 \\ 1.0 & 1.5 \\ 1.0 & 0.5 \\ 0 & 0.5 \\ 0 & 1.0 \\ 2.0 & 1.0 \\ 1.0 & 1.0 \\ 0 & 0 \\ 2.0 & 2.0 \\ 0 & 0.5 \\ 1.0 & 0.5 \\ 1.0 & 1.5 \\ 2.0 & 1.5 \end{bmatrix} \quad A_{H_{21}} = \begin{bmatrix} 2.0 & 2.0 \\ 0 & 1.0 \\ 1.0 & 1.5 \\ 2.0 & 3.0 \\ 0 & 0 \\ 2.0 & 2.5 \\ 1.0 & 2.0 \\ 1.0 & 1.0 \\ 0 & 0.5 \\ 0 & 1.0 \\ 2.0 & 2.0 \\ 1.0 & 1.5 \\ 0 & 0 \\ 2.0 & 3.0 \\ 0 & 0.5 \\ 1.0 & 1.0 \\ 1.0 & 2.0 \\ 2.0 & 2.5 \end{bmatrix}$$

In order to estimate a and Δ, or matrix P, aggregate the data across a set of chromosomes that one may assume are euploid on the child sample. This could include all chromosomes j=1 ... 23 except those that are under test, namely j=13, 18, 21, X and Y. (Note: one could also apply a concordance test for the results on the individual chromosomes in order to detect mosaic aneuploidy on the non-viable chromosomes.) In order to clarify notation, define Y' as Y measured over all the euploid chromosomes, and Y" as Y measured over a particular chromosome under test, such as chromosome 21, which may be aneuploid. Apply the matrix $A_{H_{11}}$ to the euploid data in order to estimate the parameters:

$$\hat{P} = \text{argmin}_P \|Y' - B - A_{H_{11}} P\|_2 = (A_{H_{11}}^T A_{H_{11}})^{-1} A_{H_{11}}^T \tilde{Y}$$

where $\tilde{Y} = Y' - B$, i.e., the measured data with the bias removed. The least-squares solution above is only the maximum-likelihood solution if each of the terms in the noise matrix v has a similar variance. This is not the case, most simply because the number of loci $N'_T$ used to compute the mean measurement for each context T is different for each context. As above, use the $N_T'$ to refer to the number of loci used on the chromosomes known to be euploid, and use the C' to denote the covariance matrix for mean measurements on the chromosomes known to be euploid. There are many approaches to estimating the covariance C' of the noise matrix v, which one may assume is distributed as v~N(0, C'). Given the covariance matrix, the maximum-likelihood estimate of P is $$\hat{P} = \text{argmin}_P \|C'^{-1/2}(Y' - B - A_{H_{11}} P)\|_2 = (A_{H_{11}}^T C'^{-1} A_{H_{11}})^{-1} A_{H_{11}}^T C'^{-1} \tilde{Y}$$

One simple approach to estimating the covariance matrix is to assume that all the terms of v are independent (i.e. no off-diagonal terms) and invoke the Central Limit Theorem so that the variance of each term of v scales as $1/N'_T$ so that one may find the 18×18 matrix $$C' = \begin{bmatrix} 1/N'_{AA|BB} & \cdots & 0 \\ \vdots & \ddots & \vdots \\ 0 & \cdots & 1/N'_{BB|AB} \end{bmatrix}$$

Once P' has been estimated, use these parameters to determine the most likely hypothesis on the chromosome under study, such as chromosome 21. In other words, choose the hypothesis:

$$H^* = \text{argmin}_H \|C''^{-1/2}(Y'' - B - A_H \hat{P})\|_2$$

Having found H* one may then estimate the degree of confidence that one may have in the determination of H*. Assume, for example, that there are two hypotheses under consideration: $H_{11}$ (euploid) and $H_{21}$ (maternal trisomy). Assume that $H^* = H_{11}$. Compute the distance measures corresponding to each of the hypotheses:

$$d_{11} = \|C''^{-1/2}(Y'' - B - A_{H_{11}} \hat{P})\|_2$$

$$d_{21} = \|C''^{-1/2}(Y'' - B - A_{H_{21}} \hat{P})\|_2$$

It can be shown that the square of these distance measures are roughly distributed as a Chi-Squared random variable with 18 degrees of freedom. Let $\chi 18$ represent the corresponding probability density function for such a variable. One may then find the ratio in the probabilities pH of each of the hypotheses according to:

$$\frac{P_{H_{11}}}{P_{H_{21}}} = \frac{\chi_{18}(d_{11}{}^2)}{\chi_{18}(d_{21}{}^2)}$$

One may then compute the probabilities of each hypothesis by adding the equation $P_{H_{11}}+P_{H_{21}}=1$. The confidence that the chromosome is in fact euploid is given by $P_{H_{11}}$.

Variations on the Method (1) One may modify the above approach for different biases b on each of the channels representing alleles A and B. The bias matrix B is redefined as follows:

$$B = \begin{bmatrix} b_A \vec{1} \\ b_B \vec{1} \end{bmatrix}$$

where $\vec{1}$ is a 9×1 matrix of ones. As discussed above, the parameters $b_e$ and $b_{ib}$ can either be assumed based on a-priori measurements, or can be included in the matrix P and actively estimated (i.e. there is sufficient rank in the equations over all the contexts to do so).

(2) In the general formulation, where $y_{ijk}=g_{ijk}(am_{ijk}+\Delta c_{ijk})+v_{ijk}$, one may directly measure or calibrate the function $g_{ijk}$ for every locus and allele, so that the function (which one may assume is monotonic for the vast majority of genotyping platforms) can be inverted. One may then use the function inverse to recast the measurements in terms of the quantity of genetic material so that the system of equations is linear i.e. $y'_{ijk}=g_{ijk}^{-1}(y_{ijk})=am_{ijk}+\Delta c_{ijk}+v'_{ijk}$. This approach is particularly good when $g_{ijk}$ is an affine function so that the inversion does not produce amplification or biasing of the noise in $v'_{ijk}$.

(3) The method above may not be optimal from a noise perspective since the modified noise term $v=g_{ijk}+(v_{ijk})$ may be amplified or biased by the function inversion. Another approach is to linearism the measurements around an operating point i.e. $y_{ijk}=g_{ijk}(am_{ijk}+\Delta c_{ijk})+v_{ijk}$ may be recast as: $y_{ijk}\approx g_{ijk}(am_{ijk})+g_{ijk}'(am_{ijk})\Delta c_{ijk}+v_{ijk}$. Since one may expect no more than 30% of the free-floating DNA in the maternal blood to be from the child, $\Delta<<a$, and the expansion is a reasonable approximation. Alternatively, for a platform response such as that of the ILLUMINA BEAD ARRAY, which is monotonically increasing and for which the second derivative is always negative, one could improve the linearization estimate according to $y_{ijk}\approx g_{ijk}(am_{ijk})+0.5$ $(g_{ijk}'(am_{ijk})+g_{ijk}'(am_{ijk}+\Delta c_{ijk}))$ $\Delta c_{ijk}+v_{ijk}$. The resulting set of equations may be solved iteratively for a and $\Delta$ using a method such as Newton-Raphson optimization.

(4) Another general approach is to measure at the total amount of DNA on the test chromosome (mother plus fetus) and compare with the amount of DNA on all other chromosomes, based on the assumption that amount of DNA should be constant across all chromosomes. Although this is simpler, one disadvantage is that it is now known how much is contributed by the child so it is not possible to estimate confidence bounds meaningfully. However, one could look at standard deviation across other chromosome signals that should be euploid to estimate the signal variance and generate a confidence bound. This method involves including measurements of maternal DNA which are not on the child DNA so these measurements contribute nothing to the signal but do contribute directly to noise. In addition, it is not possible to calibrate out the amplification biases amongst different chromosomes. To address this last point, it is possible to find a regression function linking each chromosome's mean signal level to every other chromosomes mean signal level, combine the signal from all chromosome by weighting based on variance of the regression fit, and look to see whether the test chromosome of interest is within the acceptable range as defined by the other chromosomes.

Incorporating Data Dropouts

Elsewhere in this disclosure it has been assumed that the probability of getting an A is a direct function of the true mother genotype, the true child genotype, the fraction of the child in the mix, and the child copy number. It is also possible that mother or child alleles can drop out, for example instead of having true child AB in the mix, there is only A, in which case the chance of getting a *nexus* sequence measurement of A are much higher. Assume that mother dropout rate is MDO, and child dropout rate is CDO. In some embodiments, the mother dropout rate can be assumed to be zero, and child dropout rates are relatively low, so the results in practice are not severely affected by dropouts. Nonetheless, they have been incorporated into the algorithm here. Elsewhere, $lik(x_i|m_i, c, cf)=pdf_x(x_i)$ has been defined as the likelihood of getting $x_i$ probability of A on SNP i, given sequence measurements S, assuming true mother $m_i$, true child c. If there is a dropout in the mother or child, the input data is NOT true mother($m_i$) or child(c), but mother after possible dropout ($m_d$) and child after a possible dropout ($c_d$). One can then rewrite the above formula as $$lik(x_i | m_i, c, cf) = \sum_{m_d, c_d} p(m_d | m_i) * p(c_d | c) * lik(x_i | m_d, c_d, cf)$$

where $p(m_d|m_i)$ is the probability of new mother genotype md, given true mother genotype m, assuming dropout rate mdo, and $p(c_d|c)$ is the probability of new child genotype $c_d$, given true child genotype c, assuming dropout rate CDO. If $nA_T$=number of A alleles in true genotype c, $nA_D$=number of A alleles in 'drop' genotype $c_d$, where $nA_T \geq nA_D$, and similarly $nB_T$=number of B alleles in true genotype c, $nB_D$=number of B alleles in 'drop' genotype $c_d$, where $nB_T > nB_D$ and d=dropout rate, then $$p(c_d | c) = \binom{nA_T}{nA_D} * d^{nA_T-nA_D} * (1-d)^{nA_D} * \binom{nB_T}{nB_D} * d^{nB_T-nB_D} * (1-d)^{nB_D}$$

For one set of experimental data, the parent genotypes have been measured, as well as the true child genotype, where the child has maternal trisomy on chromosomes 14 and 21. Sequencing measurements have been simulated for varying values of child fraction, N distinct SNPs, and total number of reads NR. From this data it is possible to derive the most likely child fraction, and derive copy number assuming known or derived child fraction.

In one embodiment, the method disclosed herein can be used to determine a fetal aneuploidy by determining the number of copies of maternal and fetal target chromosomes, having target sequences in a mixture of maternal and fetal genetic material. This method may entail obtaining maternal tissue containing both maternal and fetal genetic material; in some embodiments this maternal tissue may be maternal plasma or a tissue isolated from maternal blood. This method may also entail obtaining a mixture of maternal and fetal genetic material from said maternal tissue by processing the aforementioned maternal tissue. This method may entail distributing the genetic material obtained into a plurality of reaction samples, to randomly provide individual reaction samples that contain a target sequence from a target chromosome and individual reaction samples that do not contain a target sequence from a target chromosome, for example, performing high throughput sequencing on the sample. This method may entail analyzing the target sequences of genetic material present or absent in said individual reaction samples to provide a first number of binary results representing presence or absence of a presumably euploid fetal chromosome in the reaction samples and a second number of binary results representing presence or absence of a possibly aneuploid fetal chromosome in the reaction samples. Either of the number of binary results may be calculated, for example, by way of an informatics technique that counts sequence reads that map to a particular chromosome, to a particular region of a chromosome, to a particular locus or set of loci. This method may involve normalizing the number of binary events based on the chromosome length, the length of the region of the chromosome, or the number of loci in the set. This method may entail calculating an expected distribution of the number of binary results for a presumably euploid fetal chromosome in the reaction samples using the first number. This method may entail calculating an expected distribution of the number of binary results for a presumably aneuploid fetal chromosome in the reaction samples using the first number and an estimated fraction of fetal DNA found in the mixture, for example, by multiplying the expected read count distribution of the number of binary results for a presumably euploid fetal chromosome by $(1+n/2)$ where n is the estimated fetal fraction. The fetal fraction may be estimated by a plurality of methods, some of which are described elsewhere in this disclosure. This method may involve using a maximum likelihood approach to determine whether the second number corresponds to the possibly aneuploid fetal chromosome being euploid or being aneuploid. This method may involve calling the ploidy status of the fetus to be the ploidy state that corresponds to the hypothesis with the maximum likelihood of being correct given the measured data.

Simplified Explanation for Allele Ratio Method for Ploidy Calling in NPD

In one embodiment the ploidy state of a gestating fetus may be determined using a method that looks at allele ratios. Some methods determine fetal ploidy state by comparing numerical sequencing output DNA counts from a suspect chromosome to a reference euploid chromosome. In contrast to that concept, the allele ratio method determines fetal ploidy state by looking at allele ratios for different parental contexts on one chromosome. This method has no need to use a reference chromosome. For example, imagine the following possible ploidy states, and the allele ratios for various parental contexts:
(note: ratio 'r' is defined as follows: 1/r=fraction mother DNA/fraction fetal DNA)

| Parent context | A:B Euploidy | Child geno-type | A:B P-U tri* | Child genotype | A:B P-M tri* | Child geno-type |
|---|---|---|---|---|---|---|
| AA\|BB | 2 + r:r | AB | 2 + r:2r | ABB | 2 + r:2r | ABB |
| BB\|AA | r:2 + r | AB | 2 + 2r:r | AAB | 2 + 2r:r | AAB |
| AA\|AB | 1:0 | AA | 2 + 2r:r | AAB | 1:0 | AAA |
| AA\|AB | 2 + r:r | AB | — | — | 2 + 2r:r | AAB |
| AA\|AB | 4 + 2r:r | average | — | — | 4 + 4r:r | average |

*P-U tri = paternal matching trisomy; P-M tri = paternal matching trisomy;

Note that this table represents only a subset of the parental contexts and a subset of the possible ploidy states that this method is designed to differentiate. In this case, one can determine the A:B ratios for a plurality of alleles from a set of parental contexts in a set of sequencing data. One can then state a number of hypothesis for each ploidy state, and for each value of r; each hypothesis will have an expected pattern of A:B ratios for the different parental contexts. One can then determine which hypothesis best fits the experimental data.

For example, using the above set of parental contexts, and the value of r=0.2, one can rewrite the chart as follows: (For example, one can calculate [# reads of allele A/# reads of allele B]; thus 2+r:r becomes 2+0.2:0.2→2.2:0.2=11)

| Parent context | A:B Euploidy | Child geno-type | A:B P-U tri* | Child genotype | A:B P-M tri* | Child geno-type |
|---|---|---|---|---|---|---|
| AA\|BB | 11 | AB | 5.5 | ABB | 5.5 | ABB |
| BB\|AA | 0.91 | AB | 12 | AAB | 12 | AAB |
| AA\|AB | infinte | AA | 12 | AAB | infinite | AAA |
| AA\|AB | 11 | AB | — | — | 12 | AAB |
| AA\|AB | 21 | average | — | — | 44 | average |

Now, one can look at the ratios between the A:B ratios for different parental contexts. In this case, one may expect the $A:B_{AA|BB}/A:B_{AA|AB}$ to be $11/21=0.524$ on average for euploidy; to be $5.5/12=0.458$ on average for a paternal unmatched trisomy, and $5.5/44=0.125$ on average for a paternal matching trisomy. The profile of A:B ratios among different contexts will be different for different ploidy states, and the profiles should be distinctive enough that it will be possible to determine the ploidy state for a chromosome with high accuracy. Note that the calculated value of r may be determined using a different method, or it can be determined using a maximum likelihood approach to this method. In one embodiment, the method requires the maternal genotypic knowledge. In one embodiment the method requires paternal genotypic knowledge. In one embodiment the method does not require paternal genotypic knowledge. In an embodiment, the percent fetal fraction and the ratio of maternal to fetal DNA are essentially equivalent, and can be used interchangeably after applying the appropriate linear algebraic transformation. In some embodiments, r=[percent fetal fraction]/[1−percent fetal fraction].

SNP Classification Using Phred Scores

The phred score, q, is defined as follows: P(wrong base call)=$10^{(-q/10)}$
Let x=reference ratio of true genotype=number of reference alleles/number of total alleles. For disomy, x in $\{0, 0.5, 1\}$ corresponds to $\{MM, RM, RR\}$. Let z be the allele observed in a sequence, z in $\{R, M\}$. Here the likelihood of observing z=R is shown, conditioned on the true ratio of reference alleles in the genotype (ie, what is P(z=R|x)

$$P(z=R|x)=P(z=R|gc,x)P(gc)+P(z=R|bc,x)P(bc)$$

where gc is the event of a correct call and be is the event of a bad call.

P(gc) and P(bc) are calculated from the phred score. P(z=R|gc,x)=x and P(z=R|bc,x)=1−x, assuming that probes are unbiased.

Result, where b=P(wrong base call): P(z=R|x)=x(1−b)+(1−x)*b

Note that the probability of a reference allele measurement converges to the reference allele ratio as the phred score improves, as expected.

Assuming that each sequence is generated independently, conditioned on the true genotype, the likelihood of a set of measurements at the same SNP is simply the product of the individual likelihoods. This method accounts for varying phred scores. In another embodiment, it is possible to account for varying confidence in the sequence mapping. Given the set of n sequences for a single SNP, the combination of likelihoods results in a polynomial of order n that can be evaluated at the candidate allele ratios that represent the various hypotheses.

SNP Classification Using Phred Threshold

When a large number of sequences are available for a single SNP, the polynomial likelihood function on the allele ratio becomes intractable. An alternative is to consider only the base calls which have high phred score, and then assume that they are accurate. Each base read is now an IID Bernoulli according to the true allele ratio, and the likelihood function is Gaussian. If r is the ratio of reference reads in the data, the likelihood function on x (the true reference allele ratio) has mean=r and standard deviation=sqrt(r*(1−r)/n).

SNP Bias Correlation Across Samples

Using the two likelihood functions discussed above (polynomial, Gaussian) a SNP can be classified as RR, RM, or MM by considering the allele ratios {1, 0.5, 0}, or a maximum likelihood estimate of the allele ratio can be calculated. When the same SNP is classified as RM in two different samples, it is possible to compare the MLE estimates of the allele ratio to look for consistent "probe bias."

Using Sequence Length as a Prior to Determine the Origin of DNA

It has been reported that the distribution of length of sequences differ for maternal and fetal DNA, with fetal generally being shorter. In one embodiment of the present disclosure, it is possible to use previous knowledge in the form of empirical data, and construct prior distribution for expected length of both mother(P(X|maternal)) and fetal DNA (P(X|fetal)). Given new unidentified DNA sequence of length x, it is possible to assign a probability that a given sequence of DNA is either maternal or fetal DNA, based on prior likelihood of x given either maternal or fetal. In particular if P(x|maternal)>P(x|fetal), then the DNA sequence can be classified as maternal, with P(x|maternal)=P(x|maternal)/[(P(x|maternal)+P(x|fetal)], and if p(x|maternal)<p(x|fetal), then the DNA sequence can be classified as fetal, P(x|fetal)=P(x|fetal)/[(P(x|maternal)+P(x|fetal)]. In one embodiment of the present disclosure, a distributions of maternal and fetal sequence lengths can be determined that is specific for that sample by considering the sequences that can be assigned as maternal or fetal with high probability, and then that sample specific distribution can be used as the expected size distribution for that sample.

Methods for Determining the Average Copy Number in a Set of Target Cells

The methods described above assume that the DNA from the target cell is from one target cell, or else from target cells which are essentially genetically identical. There are circumstances where this assumption may not hold, for example, in the case of placental mosaicism, where the target is a fetus, and the DNA from the fetus originates from a plurality of cells where some of the placental cells are genetically distinct from other placental cells. For example, in many some case where the fetus is 47,XX+18 or 47,XY+18, the placenta is mosaic—a mixture of 46,XX and 47,XX+18 or 46,XY and 47,XY+18 respectively.

Another example involves detection of cancer through copy number variants, where the target cells are from a tumor, and where the non-target cells are non-cancerous cells from the host. The hallmark of cancer is the instability of the genome, and in many if not all cases, tumors are genetically heterogeneous. Even small biopsies of tumor tissue show heterogeneity. The ways in which the genome of the cancerous cells differ from the native host DNA are considered mutations; some but not necessarily all of these mutations may drive the oncogenic properties of the cancer. In the case of a liquid biopsy, i.e. detection of tumor DNA from cell free DNA (cfDNA) in the blood stream, the cell-free tumor DNA (ctDNA) is believed to originate from apoptotic or necrotic cancer cells, which are often heterogeneous, and are representative of some or all of the cells of the tumor. There are a number of types of mutations that are seen in cancers, including but not limited to point mutations, also called single nucleotide variants (SNVs), copy number variants (CNVs), hypomethylation, hypermethylation, deletions, and duplications.

If one considers the normal disomic genome of the host to be the baseline, then analysis of a mixture of normal and cancer cells will yield the average difference between the baseline and the DNA from the cells of origin of the ctDNA in the mixture. For example, imagine a case where 10% of the DNA in the sample originated from a cells with a deletion over a region of a chromosome that is targeted by the assay. A quantitative approach should show that the quantity of reads corresponding to that region would be expected to be 95% of what would be expected for a normal sample. This is because one of the two target chromosomal regions in each of the tumor cells with a deletion on of the targeted region is missing, and thus the total amount of DNA mapping to that region would be 90% (for the normal cells) plus ½×10% (for the tumor cells)=95%. Alternately, an allelic approach should show that the ratio of alleles at heterozygous loci averaged 19:20. Now imagine a case where 10% of the DNA in the sample originated from a cells with a five-fold focal amplification of a region of a chromosome that is targeted by the assay. A quantitative approach should show that the quantity of reads corresponding to that region would be expected to be 125% of what would be expected for a normal sample. This is because one of the two target chromosomal regions in each of the tumor cells with a five-fold focal amplification is copied an extra five times over the targeted region, and thus the total amount of DNA mapping to that region would be 90% (for the normal cells) plus (2+5)×10%/2 (for the tumor cells)=125%. Alternately, an allelic approach should show that the ratio of alleles at heterozygous loci averaged 25:20. Note that when using an allelic approach alone, a focal amplification of five-fold over a chromosomal region in a sample with 10% ctDNA may appear the same as a deletion over the same region in a sample with 40% ctDNA; in these two cases, the haplotype that is under-represented in the case of the deletion would appear to be the haplotype without a CNV in the case with the focal duplication, and the haplotype without a CNV in the case of the deletion would appear to be the over-represented haplotype in the case with the focal duplication. Combining the likelihoods produced by this allelic approach with likelihoods produced by a quantitative approach would differentiate between the two possibilities.

In certain embodiments, provided herein are kits for performing any of the methods for detecting aneuploidy provided herein, that include at least one tube of at least one reagent for performing such method and a computer readable medium or an access code to an online computer program, to perform one or more of the analytical techniques used in the method. For example, a kit in certain embodiments, includes a tube of oligonucleotides for amplifying a chromosome region of interest that includes a locus, and an access code for unlocking online software for making an initial copy number determination or for making a confirmatory copy number determination. The kit can further include a tube with one or more reagents for amplifying the locus. The components of the kit can be contained in the same physical container (e.g. box) or they can be arranged together on an Internet page.

Sample Preparation

Exemplary Sample Preparation Methods

In some embodiments, methods of the invention includes isolating or purifying the DNA and/or RNA. There are a number of standard procedures known in the art to accomplish such an end. In some embodiments, the sample may be centrifuged to separate various layers. In some embodiments, the DNA or RNA may be isolated using filtration. In some embodiments, the preparation of the DNA or RNA may involve amplification, separation, purification by chromatography, liquid liquid separation, isolation, preferential enrichment, preferential amplification, targeted amplification, or any of a number of other techniques either known in the art or described herein. In some embodiments for the isolation of DNA, RNase is used to degrade RNA. In some embodiments for the isolation of RNA, DNase (such as DNase I from Invitrogen, Carlsbad, CA, USA) is used to degrade DNA. In some embodiments, an RNeasy mini kit (Qiagen), is used to isolate RNA according to the manufacturer's protocol. In some embodiments, small RNA molecules are isolated using the mirVana PARIS kit (Ambion, Austin, TX, USA) according to the manufacturer's protocol (Gu et al., J. Neurochem. 122:641-649, 2012, which is hereby incorporated by reference in its entirety). The concentration and purity of RNA may optionally be determined using Nanovue (GE Healthcare, Piscataway, NJ, USA), and RNA integrity may optionally be measured by use of the 2100 Bioanalyzer (Agilent Technologies, Santa Clara, CA, USA) (Gu et al., J. Neurochem. 122:641-649, 2012, which is hereby incorporated by reference in its entirety). In some embodiments, TRIZOL or RNAlater (Ambion) is used to stabilize RNA during storage.

In some embodiments, universal tagged adaptors are added to make a library from isolated nucleic acids. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. In some embodiments, adaptor ligation is performed using the ligation kit found in the AGILENT SURESELECT kit. In some embodiments, the library is amplified using universal primers. In an embodiment, the amplified library is fractionated by size separation or by using products such as AGENCOURT AMPURE beads or other similar methods. In some embodiments, PCR amplification is used to amplify target loci. In some embodiments, the amplified DNA is sequenced (such as sequencing using an ILLUMINA IIGAX or HiSeq sequencer). In some embodiments, the amplified DNA is sequenced from each end of the amplified DNA to reduce sequencing errors. If there is a sequence error in a particular base when sequencing from one end of the amplified DNA, there is less likely to be a sequence error in the complementary base when sequencing from the other side of the amplified DNA (compared to sequencing multiple times from the same end of the amplified DNA).

In some embodiments, whole genome application (WGA) is used to amplify a nucleic acid sample. There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. In some embodiments, WGA is not performed.

In some embodiments, selective amplification or enrichment are used to amplify or enrich target loci. In some embodiments, the amplification and/or selective enrichment technique may involve PCR such as ligation mediated PCR, fragment capture by hybridization, Molecular Inversion Probes, or other circularizing probes. In some embodiments, real-time quantitative PCR (RT-qPCR), digital PCR, or emulsion PCR, single allele base extension reaction followed by mass spectrometry are used (Hung et al., J Clin Pathol 62:308-313, 2009, which is hereby incorporated by reference in its entirety). In some embodiments, capture by hybridization with hybrid capture probes is used to preferentially enrich the DNA. In some embodiments, methods for amplification or selective enrichment may involve using probes where, upon correct hybridization to the target sequence, the 3-prime end or 5-prime end of a nucleotide probe is separated from the polymorphic site of a polymorphic allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals In some embodiments, PCR (referred to as mini-PCR) is used to generate very short amplicons (U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, filed Nov. 18, 2011, and U.S. Ser. No. 61/994,791, filed May 16, 2014, which are each hereby incorporated by reference in its entirety). cfDNA (such as fetal cfDNA in maternal serum or necroptically- or apoptotically-released cancer cfDNA) is highly fragmented. For fetal cfDNA, the fragment sizes are distributed in approximately a Gaussian fashion with a mean of 160 bp, a standard deviation of 15 bp, a minimum size of about 100 bp, and a maximum size of about 220 bp. The polymorphic site of one particular target locus may occupy any position from the start to the end among the various fragments originating from that locus. Because cfDNA fragments are short, the likelihood of both primer sites being present the likelihood of a fragment of length L comprising both the forward and reverse primers sites is the ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. In certain embodiments that relate most preferably to cfDNA from samples of individuals suspected of having cancer, the cfDNA is amplified using primers that yield a maximum amplicon length of 85, 80, 75 or 70 bp, and in certain preferred embodiments 75 bp, and that have a melting temperature between 50 and 65° C., and in certain preferred embodiments, between 54-60.5° C. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons are less than 100 bp, less than 90 bp, less than 80 bp, less than 70 bp, less than 65 bp, less than 60 bp, less than 55 bp, less than 50 bp, or less than 45 bp.

In some embodiments, amplification is performed using direct multiplexed PCR, sequential PCR, nested PCR, doubly nested PCR, one-and-a-half sided nested PCR, fully nested PCR, one sided fully nested PCR, one-sided nested PCR, hemi-nested PCR, hemi-nested PCR, triply heminested PCR, semi-nested PCR, one sided semi-nested PCR, reverse semi-nested PCR method, or one-sided PCR, which are described in U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, and U.S. Ser. No. 61/994,791, filed May 16, 2014, which are hereby incorporated by reference in their entirety. If desired, any of these methods can be used for mini-PCR.

If desired, the extension step of the PCR amplification may be limited from a time standpoint to reduce amplification from fragments longer than 200 nucleotides, 300 nucleotides, 400 nucleotides, 500 nucleotides or 1,000 nucleotides. This may result in the enrichment of fragmented or shorter DNA (such as fetal DNA or DNA from cancer cells that have undergone apoptosis or necrosis) and improvement of test performance.

In some embodiments, multiplex PCR is used. In some embodiments, the method of amplifying target loci in a nucleic acid sample involves (i) contacting the nucleic acid sample with a library of primers that simultaneously hybridize to least 100; 200; 500; 750; 1,000; 2,000; 5,000; 7,500; 10,000; 20,000; 25,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, at least 50, 60, 70, 80, 90, 95, 96, 97, 98, 99, or 99.5% of the targeted loci are amplified. In various embodiments, less than 60, 50, 40, 30, 20, 10, 5, 4, 3, 2, 1, 0.5, 0.25, 0.1, or 0.05% of the amplified products are primer dimers. In some embodiments, the primers are in solution (such as being dissolved in the liquid phase rather than in a solid phase). In some embodiments, the primers are in solution and are not immobilized on a solid support. In some embodiments, the primers are not part of a microarray. In some embodiments, the primers do not include molecular inversion probes (MIPs).

In some embodiments, two or more (such as 3 or 4) target amplicons (such as amplicons from the miniPCR method disclosed herein) are ligated together and then the ligated products are sequenced. Combining multiple amplicons into a single ligation product increases the efficiency of the subsequent sequencing step. In some embodiments, the target amplicons are less than 150, 100, 90, 75, or 50 base pairs in length before they are ligated. The selective enrichment and/or amplification may involve tagging each individual molecule with different tags, molecular barcodes, tags for amplification, and/or tags for sequencing. In some embodiments, the amplified products are analyzed by sequencing (such as by high throughput sequencing) or by hybridization to an array, such as a SNP array, the ILLUMINA INFINIUM array, or the AFFYMETRIX gene chip. In some embodiments, nanopore sequencing is used, such as the nanopore sequencing technology developed by Genia (see, for example, the world wide web at geniachip.com/technology, which is hereby incorporated by reference in its entirety). In some embodiments, duplex sequencing is used (Schmitt et al., "Detection of ultra-rare mutations by next-generation sequencing," Proc Natl Acad Sci USA. 109(36): 14508-14513, 2012, which is hereby incorporated by reference in its entirety). This approach greatly reduces errors by independently tagging and sequencing each of the two strands of a DNA duplex. As the two strands are complementary, true mutations are found at the same position in both strands. In contrast, PCR or sequencing errors result in mutations in only one strand and can thus be discounted as technical error. In some embodiments, the method entails tagging both strands of duplex DNA with a random, yet complementary double-stranded nucleotide sequence, referred to as a Duplex Tag. Double-stranded tag sequences are incorporated into standard sequencing adapters by first introducing a single-stranded randomized nucleotide sequence into one adapter strand and then extending the opposite strand with a DNA polymerase to yield a complementary, double-stranded tag. Following ligation of tagged adapters to sheared DNA, the individually labeled strands are PCR amplified from asymmetric primer sites on the adapter tails and subjected to paired-end sequencing. In some embodiments, a sample (such as a DNA or RNA sample) is divided into multiple fractions, such as different wells (e.g., wells of a WaferGen SmartChip). Dividing the sample into different fractions (such as at least 5, 10, 20, 50, 75, 100, 150, 200, or 300 fractions) can increase the sensitivity of the analysis since the percent of molecules with a mutation are higher in some of the wells than in the overall sample. In some embodiments, each fraction has less than 500, 400, 200, 100, 50, 20, 10, 5, 2, or 1 DNA or RNA molecules. In some embodiments, the molecules in each fraction are sequenced separately. In some embodiments, the same barcode (such as a random or non-human sequence) is added to all the molecules in the same fraction (such as by amplification with a primer containing the barcode or by ligation of a barcode), and different barcodes are added to molecules in different fractions. The barcoded molecules can be pooled and sequenced together. In some embodiments, the molecules are amplified before they are pooled and sequenced, such as by using nested PCR. In some embodiments, one forward and two reverse primers, or two forward and one reverse primers are used.

The use of a method to target certain alleles followed by sequencing as part of a method for allele calling or ploidy calling may confer a number of unexpected advantages. Some methods by which DNA may be targeted, or selectively enriched, include using circularizing probes, linked inverted probes (LIPs), capture by hybridization methods such as SURE SELECT, and targeted PCR amplification strategies.

Some embodiments of the present disclosure involve the use of "Linked Inverted Probes" (LIPs), which have been previously described in the literature. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or the circularizing probes. The LIPs probe may be a linear DNA molecule between 50 and 500 nucleotides in length, and in a preferred embodiment between 70 and 100 nucleotides in length; in some embodiments, it may be longer or shorter than described herein. Others embodiments of the present disclosure involve different incarnations, of the LIPs technology, such as Padlock Probes and Molecular Inversion Probes (MIPs).

In There are many methods that may be used to measure the genetic data of the individual and/or the related individuals in the aforementioned contexts. The different methods comprise a number of steps, those steps often involving amplification of genetic material, addition of olgionucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases, the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

Note that in theory it is possible to target any number loci in the genome, anywhere from one loci to well over one million loci. If a sample of DNA is subjected to targeting, and then sequenced, the percentage of the alleles that are read by the sequencer will be enriched with respect to their natural abundance in the sample. The degree of enrichment can be anywhere from one percent (or even less) to tens fold, hundred fold, thousand fold or even many million fold. In the human genome there are roughly 3 billion base pairs, and nucleotides, containing approximately 75 million polymorphic loci. The more loci that are targeted, the smaller the degree of enrichment is possible. The fewer the number of loci that are targeted, the greater degree of enrichment is possible, and the greater depth of read may be achieved at those loci for a given number of sequence reads.

In one embodiment of the present disclosure, the targeting may focus entirely on SNPs. A number of commercial targeting products are available to enrich exons. Targeting exclusively loci that include SNPs is particularly advantageous when using a method for NPD that relies on allele distributions. In one embodiment of the present disclosure, it is possible to use a targeting method that focuses on SNPs to enrich a genetic sample in polymorphic regions of the genome. In one embodiment, it is possible to focus on a small number of SNPs, for example between 1 and 100 SNPs, or a larger number, for example, between 100 and 1,000, between 1,000 and 10,000, between 10,000 and 100,000 or more than 100,000 SNPs. In one embodiment, it is possible to focus on one or a small number of chromosomes that are correlated with live trisomic births, for example chromosomes 13, 18, 21, X and Y, or some combination thereof. In one embodiment, it is possible to enrich the targeted SNPs by a small factor, for example between 1.01 fold and 100 fold, or by a larger factor, for example between 100 fold and 1,000,000 fold. In one embodiment of the present disclosure, it is possible to use a targeting method to create a sample of DNA that is preferentially enriched in polymorphic regions of the genome. In one embodiment, it is possible to use the method to create a sample of DNA that is preferentially enriched in a small number of SNPs, for example between 1 and 100 SNPs, or a larger number of SNPs, for example, between 100 and 50,000 SNPs. In one embodiment, it is possible to use the method to create a DNA sample that is enriched in SNPs located on one or a small number of chromosomes that are correlated with live trisomic births, for example chromosomes 13, 18, 21, X and Y, or some combination thereof. In one embodiment, it is possible to use the method to create a sample of DNA that is preferentially enriched in a small number of SNPs, for example between 1 and 100 SNPs, or a larger number of SNPs, for example, between 100 and 50,000 SNPs. In one embodiment, it is possible to use the method to create a sample of DNA that is enriched targeted SNPs by a small factor, for example between 1.01 fold and 100 fold, or by a larger factor, for example between 100 fold and 1,000,000 fold. In one embodiment, it is possible to use this method to create a mixture of DNA with any of these characteristics where the mixture of DNA contains maternal DNA and also free floating fetal DNA. In one embodiment, it is possible to use this method to create a mixture of DNA that has any combination of these factors. For example, a mixture of DNA that contains maternal DNA and fetal DNA, and that is preferentially enriched in 200 SNPs, all of which are located on either chromosome 18 or 21, and which are enriched an average of 1000 fold. In another example, it is possible to use the method to create a mixture of DNA that is preferentially enriched in 50,000 SNPs that are all located on chromosomes 13, 18, 21, X and Y, and the average enrichment per loci is 200 fold. Any of the targeting methods described herein can be used to create mixtures of DNA that are preferentially enriched in certain loci.

In some embodiments, the method may further comprise measuring the DNA contained in the mixed fraction using a DNA sequencer, and the DNA contained in the mixed fraction contains a disproportionate number of sequences from one or more chromosomes, wherein the one or more chromosomes are selected from the group consisting of chromosome 13, chromosome 18, chromosome 21, chromosome X, chromosome Y and combinations thereof.

In one embodiment, once a mixture has been preferentially enriched at the set of target loci, it may be sequenced using any one of the previous, current, or next generation of sequencing instruments that sequences a clonal sample (a sample generated from a single molecule; examples include ILLUMINA GAIIx, ILLUMINA HISEQ or MiSEQ, LIFE TECHNOLOGIES SOLiD, 5500XL, or Ion Torrent PGM or Proton). The ratios can be evaluated by sequencing through the specific alleles within the targeted region. These sequencing reads can be analyzed and counted according the allele type and the rations of different alleles determined accordingly. For variations that are one to a few bases in length, detection of the alleles will be performed by sequencing and it is essential that the sequencing read span the allele in question in order to evaluate the allelic composition of that captured molecule. The total number of captured molecules assayed for the genotype can be increased by increasing the length of the sequencing read. Full sequencing of all molecules would guarantee collection of the maximum amount of data available in the enriched pool. However, sequencing is currently expensive, and a method that can measure a certain number of allele ratios using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. While allele variations come in all types, the examples provided herein focus on SNPs or variants comprised of just a few neighboring base pairs. Larger variants such as segmental copy number variants can be detected by aggregations of these smaller variations in many cases as whole collections of SNP internal to the segment are duplicated. Variants larger than a few bases, such as STRs require special consideration and some targeting approaches work while others will not. The evaluation of the allelic rations is herein determined There are multiple targeting approaches that can be used to specifically isolate and enrich a one or a plurality of variant positions in the genome. Typically, these rely on taking advantage of invariant sequence flanking the variant sequence. There is prior art related to targeting in the context of sequencing where the substrate is maternal plasma (see, e.g., Liao et al., Clin. Chem.; 57(1): pp. 92-101). However, these approaches all use targeting probes that target exons, and do not focus on targeting polymorphic regions of the genome. In one embodiment of the present disclosure, the method involves using targeting probes that focus exclusively or almost exclusively on polymorphic regions. In one embodiment of the present disclosure, the method involves using targeting probes that focus exclusively or almost exclusively on SNPs. When polymorphic targeted DNA mixtures are sequenced and analyzed using an algorithm that determined ploidy using allele ratios, this targeting method is able to provide far more accurate ploidy determinations for a given number of sequence reads. In some embodiments of the present disclosure, the targeted polymorphic regions consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98% SNPs, at least 99% SNPs, at least 99.9% SNPs, exclusively SNPs.

Targeted Sequencing Using PCR Approaches

In some embodiments, PCR can be used to target specific locations of the genome. In plasma samples, the original DNA is highly fragmented (~100-200 bp, 150 peak). In PCR, both forward and reverse primers must anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as SNPs, are typically designed such that the 3' end of the primer will hybridize to the base immediately adjacent to the polymorphic base or bases. In one embodiment of the present disclosure, the 3' ends of both the forward and reverse PCR primers are designed to hybridize to bases that are one or a few positions away from the variant positions (polymorphic regions) of the targeted allele. The number of bases between the polymorphic region (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic region.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 1000 assays per reaction. Samples with large quantities of DNA can be split among multiple sub-reactions and then recombined before sequencing. For samples where either the overall sample or some subpopulation of DNA molecules is limited, splitting the sample would introduce statistical noise. In one embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations, a pre-amplification step may be used to increase the overall sample quantity. However, this pre-amplification step should not appreciably alter the allelic ratios.

In one embodiment, the method can generate hundreds to thousands of PCR products (can be 10,000 and more), e.g. for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. In next generation sequencing the vast majority of the sequencing reads would sequence such artifacts and not the desired target sequences in a sample. In general, to perform targeted sequencing of multiple (n) targets of a sample (greater than 10, 50 or 1000's), one can split the sample into n parallel reactions that amplify one individual target, which is problematic for samples with a limited amount of DNA. This has been performed in PCR multiwell plates or can be done in commercial platforms such as the Fluidigm Access Array (48 reactions per sample in microfluidic chips) or droplet PCR by Rain Dance Technologies (100s to a few thousands of targets). Described here is a method to effectively amplify many PCR reactions, that is applicable to cases where only a limited amount of DNA is available. In one embodiment, the method may be applied for analysis of single cells, body fluids, biopsies, environmental and/or forensic samples.

Solution

A) Generate and amplify a library with adaptor sequences on both ends of DNA fragments. Divide into multiple reactions after library amplification.

B) Generate (and possibly amplify) a library with adaptor sequences on both ends of DNA fragments. Perform 1000-plex amplification of selected targets using one target specific "Forward" primer per target and one tag specific primer. One can perform a second amplification from this product using "Reverse" target specific primers and one (or more) primer specific to a universal tag that was introduced as part of the target specific forward primers in the first round.

C) Perform a 1000-plex preamplification of selected target for a limited number of cycles. Divide the product into multiple aliquots and amplify subpools of targets in individual reactions (for example, 50 to 500-plex, though this can be used all the way down to singleplex). Pool products of parallel subpools reactions.

D) During these amplifications primers may carry sequencing compatible tags (partial or full length) such that the products can easily be sequenced.

There is significant diagnostic value in accurately determining the relative proportion of alleles present in a sample. The interpretation of the result depends on the source of the material. In some embodiments of the present disclosure, the allelic ratio information can be used to determine the genetic state of an individual. In some embodiments of the present disclosure, this information can be used to determine the genetic state of a plurality of individuals from one DNA sample, wherein the DNA sample contains DNA from each of the plurality of individuals. In one embodiment, the allelic ratio information can be used to determine copy number of whole chromosomes from individual cells, or bulk samples. In one embodiment, the allelic ratio information can be used to determine copy number of parts, regions, or segments of chromosomes individual cells, or bulk samples. In one embodiment, the allelic ratio information can be used to determine the relative contribution of different cell types in mosaic samples. In one embodiment, the allelic ratio information can be used to determine the fraction of fetal DNA in maternal plasma samples as well as the chromosome copy number of the fetal chromosomes.

Generation of Targeted Sequencing Libraries by PCR of Greater than 100 Targets

Described herein is a method for amplifying a region of a chromosome of interest that includes a locus of interest by first globally amplify the plasma DNA of a sample and then dividing the sample up into multiple multiplexed target enrichment reactions with multiple target sequences per reaction. In one embodiment, the method can be used for preferentially enriching a DNA mixture at a plurality of loci, the method comprising generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In one embodiment, the method may further comprise performing a second amplification using "reverse" target specific primers and one or a plurality of primers specific to a universal tag that was introduced as part of the target specific forward primers in the first round. In one embodiment, the method may be used for preferentially enriching a DNA mixture at a plurality of loci, the method comprising performing a multiplex preamplification of selected targets for a limited number of cycles, dividing the product into multiple aliquots and amplifying subpools of targets in individual reactions, and pooling products of parallel subpools reactions. In one embodiment, the primers carry partial or full length sequencing compatible tags.

Workflow:
1. Extract plasma DNA
2. Prepare fragment library with universal adaptors on both ends of fragments.
3. Amplify library using universal primers specific to the adaptors.
4. Divide the amplified sample "library" into multiple aliquots. Perform multiplex (e.g. 100-plex, or 1000-plex with one target specific primer per target and a tag-specific primer) amplifications on aliquots.
5. Pool aliquots of one sample.
6. Barcode sample if not already done.
7. Mix samples, adjust concentration.
8. Perform sequencing.

The workflow may contain multiple sub-steps that comprise one of the listed steps (e.g. step 2. Library preparation may comprise 3 enzymatic steps (blunt ending, dA tailing and adaptor ligation) and 3 purification steps).

Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mononucleosomal DNA fragments as the cell free fetal DNA (of placental origin) found in the circulation of pregnant women.

PCR Assays:
Can have the tags for sequencing (usually a truncated form of 15-25 bases). After multiplexing, PCR multiplexes of a sample are pooled and then the tags are completed (including bar coding) by a tag-specific PCR (could also be done by ligation).

The full sequencing tags can be added in the same reaction as the multiplexing. In the first cycles targets are amplified with the target specific primers, subsequently the tag-specific primers take over to complete the SQ-adaptor sequence.

The PCR primers carry no tags. After m.p. PCR the sequencing tags are appended to the amplification products by ligation.

Sequencing Results:
The 12 samples were pooled at equal volumes
Pool cleaned into 100 ul Elution buffer
Pool diluted to 30 nM (was 75 nM)
Sent for sequencing
QC by qPCR Preparation of 15 cy Replicates
(Orange: 8 replicates with barcodes 5 to 12)
15 cycles STA
(RED STA protocol: 95 C×10 min; 95 C×15 s, 65 C×1 min, 60 C×4 min, 65 C×30 s, 72 C×30 s; 72 C×2 min)
Used the 50 nM primers reactions
Performed a first ExoSAP straight from product failed to remove all primers (Bioanalyzer): just leave this step out in the future.
Dilute 1/10 (adding 90 ul H$_2$O)
2 ul in 14 ul ExoSAP reaction→dilute to 50 ul=1/25 dilution in this step=total 1/250
Append SQ tags (longer, full F-SQ and R-m.p. adaptor without barcodes):
1 ul DNA in 10 ul PCR: F-SQ×R-SQ-m.p.; concentrations: 200 nM?
15 cycles: 95 C×10 min; 95 C×15 s, 60 C×30 s, 65 C×15 s, 72 C×30 s; 72 C×2 min
Add 90 ul H2O, use 1 ul for next step, primer carry over will be 1/100 of conc in this reaction
Barcoding PCR (p.9 quick book):
1 ul DNA in 10 ul PCR: F-SQ×R-SQ-BC1 to 12-lib.; concentrations: 1 uM
15 cycles: 95 C×10 min; 95 C×15 s, 60 C×15 s, 72 C×30 s; 72 C×2 min
Add 40 ul H$_2$O
→check 1 ul on Bioanalyzer DNA1000 chip→pool samples→clean up→Bioanalyzer, adjust conc→sequencing Prep of 30 cy Replicate
(Yellow: 1 replicates with barcode 4 into sequencing)
30 cycles STA
(Yellow STA protocol: 95 C×10 min; 95 C×15 s, 65 C×1 min, 60 C×4 min, 65 C×30 s, 72 C×30 s; 72 C×2 min)
Used the 50 nM primers reactions
Performed a first ExoSAP straight from product failed to remove all primers (Bioanalyzer): just leave this step out in the future.
Dilute 1/10 (adding 90 ul H$_2$O)
Dilute 1/100→1/25 dilution=total 1/25,000
Probably did not perform ExoSAP clean up, small uncertainty from notes
Append SQ tags (longer, full F-SQ and R-m.p. adaptor without barcodes):
1 ul DNA in 10 ul PCR: F-SQ×R-SQ-m.p.; concentrations: 200 nM?
15 cycles: 95 C×10 min; 95 C×15 s, 60 C×30 s, 65 C×15 s, 72 C×30 s; 72 C×2 min
Add 90 ul H2O, use 1 ul for next step, primer carry over will be 1/100 of conc in this reaction
Barcoding PCR (p.9 quick book):
1 ul DNA in 10 ul PCR: F-SQ×R-SQ-BC1 to 12-lib.; concentrations: 1 uM
15 cycles: 95 C×10 min; 95 C×15 s, 60 C×15 s, 72 C×30 s; 72 C×2 min
Add 40 ul H$_2$O
→check 1 ul on Bioanalyzer DNA1000 chip→pool samples→clean up→Bioanalyzer, adjust conc→sequencing Prep of 1000-plex reactions
(Blue: 1000-plex; from amplified SQ libraries (p.32 lab book BZ1))
BC2=ASQ8=pregnancy plasma 2666 or 2687; BC3=ASQ4=apo sup 16777
15 cycles STA
(RED STA protocol: 95 C×10 min; 95 C×15 s, 65 C×1 min, 60 C×4 min, 65 C×30 s, 72 C×30 s; 72 C×2 min)
50 nM target specific tagged R-primers and 200 nM F-SQ-primer
Performed a first ExoSAP straight from product failed to remove all primers (Bioanalyzer): just leave this step out in the future.
Dilute 1/5 (adding 40 ul H$_2$O)
2 ul in 14 ul ExoSAP reactiondilute to 100 ul=1/50 dilution in this step=total 1/250
Append SQ tags (longer, full F-SQ and R-m.p. adaptor without barcodes):
1 ul DNA in 10 ul PCR: F-SQ×R-SQ-m.p.; concentrations: 200 nM?
15 cycles: 95 C×10 min; 95 C×15 s, 60 C×30 s, 65 C×15 s, 72 C×30 s; 72 C×2 min
Add 90 ul H2O, use 1 ul for next step, primer carry over will be 1/100 of conc in this reaction
Barcoding PCR (p.9 quick book):
1 ul DNA in 10 ul PCR: F-SQ×R-SQ-BC1 to 12-lib.; concentrations: 1 uM
15 cycles: 95 C×10 min; 95 C×15 s, 60 C×15 s, 72 C×30 s; 72 C×2 min
Add 40 ul H$_2$O →check 1 ul on Bioanalyzer DNA1000 chip→pool samples→clean up→Bioanalyzer, adjust conc→sequencing By making use of targeting approaches in sequencing the mixed sample, it may be possible to achieve a certain level of accuracy with fewer sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

There are a number of published methods in the prior art that demonstrate how one may determine the ploidy state of a fetus from a mixed sample of maternal and fetal DNA, for example: G.J. W. Liao et al. Clinical Chemistry 2011; 57(1) pp. 92-101. These methods target thousands of locations along each chromosome. The number of locations along a chromosome that may be targeted while still resulting in a high accuracy ploidy determination on a fetus, for a given number of sequence reads, from a mixed sample of DNA is unexpectedly low. In one embodiment of the present disclosure, an accurate ploidy determination may be made by using targeted sequencing, using any method of targeting, for example qPCR, capture by hybridization, or circularizing probes, wherein the number of loci along a chromosome that need to be targeted may be between 1,000 and 500 loci; it may be between 500 and 300 loci; it may be between 300 and 200 loci; it may be between 200 and 150 loci; it may be between 150 and 100 loci; it may be between 100 and 50 loci; it may be between 50 and 20 loci; it may be between 20 and 10 loci. Optimally, it may be between 100 and 500 loci. The high level of accuracy may be achieved by targeting a small number of loci and executing an unexpectedly small number of sequence reads. The number of reads may be between 5 million and 2 million reads; the number of reads may be between 2 million and 1 million; the number of reads may be between 1 million and 500,000; the number of reads may be between 500,000 and 200,000; the number of reads may be between 200,000 and 100,000; the number of reads may be between 100,000 and 50,000; the number of reads may be between 50,000 and 20,000; the number of reads may be between 20,000 and 10,000; the number of reads may be below 10,000.

In some embodiments, there is a composition comprising a mixture of DNA of fetal origin, and DNA of maternal origin, wherein the percent of sequences that uniquely map to chromosome 13 is greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 18 is greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 21 is greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome X is greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome Y is greater than 1%, greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%.

In some embodiments, there is a composition comprising a mixture of DNA of fetal origin, and DNA of maternal origin, wherein the percent of sequences that uniquely map to a chromosome, that contains at least one single nucleotide polymorphism is greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, and where the chromosome is taken from the group 13, 18, 21, X, or Y. In some embodiments of the present disclosure, there is a composition comprising a mixture of DNA of fetal origin, and DNA of maternal origin, wherein the percent of sequences that uniquely map to a chromosome and that contain at least one single nucleotide polymorphism from a set of single nucleotide polymorphisms is greater than 0.15%, greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, where the chromosome is taken from the set of chromosome 13, 18, 21, X and Y, and where the number of single nucleotide polymorphisms in the set of single nucleotide polymorphisms is between 1 and 10, between 10 and 20, between 20 and 50, between 50 and 100, between 100 and 200, between 200 and 500, between 500 and 1,000, between 1,000 and 2,000, between 2,000 and 5,000, between 5,000 and 10,000, between 10,000 and 20,000, between 20,000 and 50,000, and between 50,000 and 100,000.

In theory, each cycle in the amplification doubles the amount of DNA present, however, in reality, the degree of amplification is slightly lower than two. In theory, amplification, including targeted amplification, will result in bias free amplification of a DNA mixture. When DNA is amplified, the degree of allelic bias typically increases with the number of amplification steps. In some embodiments, the methods described herein involve amplifying DNA with a low level of allelic bias. Since the allelic bias compounds, one can determine the per cycle allelic bias by calculating the nth root of the overall bias where n is the base 2 logarithm of degree of enrichment. In some embodiments, there is a composition comprising a second mixture of DNA, where the second mixture of DNA has been preferentially enriched at a plurality of polymorphic loci from a first mixture of DNA where the degree of enrichment is at least 10, at least 100, at least 1,000, at least 10,000, at least 100,000 or at least 1,000,000, and where the ratio of the alleles in the second mixture of DNA at each locus differs from the ratio of the alleles at that locus in the first mixture of DNA by a factor that is, on average, less than 1,000%, 500%, 200%, 100%, 50%, 20%, 10%, 5%, 2%, 1%, 0.5%, 0.2%, 0.1%, 0.05%, 0.02%, or 0.01%. In some embodiments, there is a composition comprising a second mixture of DNA, where the second mixture of DNA has been preferentially enriched at a plurality of polymorphic loci from a first mixture of DNA where the per cycle allelic bias for the plurality of polymorphic loci is, on average, less than 10%, 5%, 2%, 1%, 0.5%, 0.2%, 0.1%, 0.05%, or 0.02%. In some embodiments, the plurality of polymorphic loci comprises at least 10 loci, at least 20 loci, at least 50 loci, at least 100 loci, at least 200 loci, at least 500 loci, at least 1,000 loci, at least 2,000 loci, at least 5,000 loci, at least 10,000 loci, at least 20,000 loci, or at least 50,000 loci.

Experimental Section

The presently disclosed embodiments are described in the following Example, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to use the described embodiments, and is not intended to limit the scope of the disclosure nor is it intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by volume, and temperature is in degrees Centigrade. It should be understood that variations in the methods as disclosed may be made without changing the fundamental aspects that the experiments are meant to illustrate.

Example 1

This example provides a protocol that was used to validate the performance of a test method for determining the presence or absence of aneuploidy according to the present invention. The test method includes a first allelic analysis method that uses a joint distribution model to identify samples that are high confidence diploid samples that utilizes only data from chromosomes of interest without control chromosomes. The identity of these diploid samples are then passed to a second analysis method that is a non-allelic method that produces a likelihood of a ploidy state. Aneuploid probabilities for each test chromosome for each sample were analyzed for each method and a set of rules were used to determine whether to call a given sample as a high risk sample, that is a sample with a high probability of aneuploidy. The set of rules included at least one rule that combines the aneuploidy confidences from the first method and the second method for a given chromosome of interest for a given sample. The test method eliminates the additional expense and variability introduced by the use of a separate control chromosome. The validation protocol was used to validate test method accuracy with measurements of test sensitivity and specificity on clinical samples (Arm 1) and to validate test method precision with measurements of test reproducibility of clinical sample results and quality control (QC) pass rate (Arm 2).

BACKGROUND

The test method estimates the fetal copy number of chromosomes 13, 18, 21, X, and Y from a maternal blood sample. The test method utilizes cell free DNA (cfDNA), a mixture of maternal and fetal DNA isolated from the plasma of pregnant women. The cfDNA is first made into a library by ligation of adapters followed by amplification to increase the available total DNA. 13,392 distinct genetic loci are amplified by targeted multiplex PCR, each containing a single nucleotide polymorphism (SNP). The SNP amplicons are then sequenced using next generation sequencing technology to determine the frequency of the SNP alleles at each locus. In parallel, genomic DNA is extracted from the maternal blood cells and, optionally, paternal cheek cells. These genomic DNAs are amplified and sequenced in a similar manner to plasma DNA libraries. The resultant SNP allele ratios from the plasma sample and parental samples are analyzed to create a maximum-likelihood estimate of the fetal chromosome copy number for each targeted chromosome.

After sequencing, the sequence data first goes through a QC process which determines whether the samples have been successfully prepared and are eligible to be run through the Panorama copy number algorithms. If a sample fails in either the QC process, it is typically re-prepared or resequenced. In general, all samples are expected to eventually pass the various QC thresholds. In contrast, the algorithm data review thresholds are the criteria used to determine a chromosome copy number result. These algorithm data review thresholds were only applied to data that has already passed through the QC process.

In Arm 1 of the validation protocol, >750 clinical samples (>300 high risk and >450 low risk) were tested to validate that the test sensitivity and specificity meet the product requirements as described in PRD-00104 Requirements Document—NIPT Panorama Rev 04.

In Arm 2 of the validation protocol, 192 samples were split into three daughter replicates that were tested with three lots of selected reagents, three sets of selected instrumentation, three operators, and on three separate days to validate laboratory reproducibility.

Reagents.

Table 1 provides a list of reagents that were used for the execution of the validation protocol. DNA sequencing was carried out on a HiSeq Model 2500 (Illumina, San Diego, CA). Thermocycling was performed using a GeneAmp PCR System 9700 (Model N8050001) (Life Technologies, Carlsbad CA)

TABLE 1

List of Required Reagents

| Reagent | Manufacturer | Manufacturer Part Number |
|---|---|---|
| 4X Qiagen Multiplex PCR Master Mix Lots 1-3 | Qiagen | 1076436 |
| 5M TMAC lots 1-3 | Sigma | 639202 |
| cfDNA Multiplex PCR Reagents: Lots 1-3 | Natera | 111100 |
| cfDNA OneStar | Natera | 1121144 |
| cfDNA OneStar | Natera | 1121100 |
| gDNA Multiplex PCR Reagents | Natera | 121144 |
| gDNA STAR 1 | Natera | 1221144 |
| gDNA STAR 2 | Natera | 1222144 |
| Molecular biology grade, DI water | Life Technologies | 10977-023 |
| F-BC (Barcoding) Primer | IDT | n/a |
| R-SQ_NB4 Barcode Plates | IDT | n/a |
| QIAquick PCR Purification Kit | Qiagen | 28106 |
| 3M Sodium Acetate Solution | Life Technologies | AM9740 |
| Quant-iT dsDNA Broad-Range Assay Kit (1000) | Life Technologies | Q33130 |
| TruSeq Rapid SR Cluster Kit | Illumina | TG-402-4000 or GD-402-4001 |
| 10 nM Barcoded PhiX (NB2: 271 PhiX) | IDT | n/a |
| PhiX kit 10 nM stock for cbot (10 UL) | Illumina | FC-110-3001 |
| TruSeq Rapid SBS Kit (50 cycle) | Illumina | TG-402-4002 or FC-402-4002 |

TABLE 1-continued

List of Required Reagents

| Reagent | Manufacturer | Manufacturer Part Number |
|---|---|---|
| 2N Sodium Hydroxide | Fisher Scientific | SS264-1 |
| 1N Sodium Hydroxide | Fisher Scientific | SS266-1 |

Statistical Approach/Sample Size

Justifications for the sampling strategy and statistical techniques used for each arm of the validation protocol are provided below.

Arm 1 consisted of ≥300 samples known to be from women carrying a fetus with Trisomy 13, 18, or 21, Monosomy X, or triploidy. This positive sample cohort consists of all available samples for which copy number truth has been confirmed. The positive set was selected to produce the best possible measurement of test sensitivity.

≥450 samples known to be from women carrying a euploid fetus were selected for Arm 1. The desired specificity of 0.998 corresponds to one error in 500. The sample set was selected to achieve maximal resolution on the specificity measurement, while maintaining compatibility with the requirements related to automation and plate layout, and practical feasibility given the high cost of running samples. Although the specificity calculation will be performed using a child fraction estimate adjustment (described in the analysis section), the distribution of child fraction estimates in the samples is not known a priori and therefore cannot be used to set the sample size.

Arm 2 consisted of three replicates of a test unit of 192 samples. This number of samples is driven by the automation protocol which requires at least two plates of 96 samples each All plasma-derived samples used in the validation protocol entered the protocol workflow in the form of an amplified purified cfDNA library produced from the extracted DNA of maternal plasma.

Parental samples from two sources were used in the protocol: Maternal gDNA extracted from centrifuged maternal blood samples from which plasma has been removed; and paternal gDNA prepared from a buccal sample.

Arm 1: Sensitivity and Specificity

In the sensitivity and specificity arm, the accuracy of the test method was determined by comparing test results of the samples used in the validation protocol to their known fetal chromosome copy number.

QC failure in a plasma sample due to contamination or low NOR required that those plasma samples were rerun through the protocol. However, due to the limited volume of plasma library available for some samples, it was not be possible to rerun some samples. In those cases, samples were excluded from all Arm 1 analyses. Failed mother samples were rerun at most 2 times. Failed father samples were not rerun. Due to the high maximum capacity of the laboratory automation workflow, all plasma DNA library samples in Arm 1 will be processed in a single batch.

Arm 2: Laboratory Reproducibility

In the laboratory reproducibility arm, the reproducibility of the test method were assessed using multiple reagent lots, sets of equipment, test operators, and days. For non-critical reagents and instruments, single lots were used because they are outside the scope of this reproducibility testing. Specific reagents, instruments, operators, and execution dates were used for each run of 192 samples.

192 samples were tested for each of the three runs in the reproducibility test. Samples were isolated and extracted prior to the execution of the validation protocol. For each sample, four tubes of plasma (~3-5 mL each) were extracted in two pairs of tubes. Each of the two extractions per sample were prepared into purified plasma DNA library, and then pooled into a single well for each case. The pooling generated approximately 70-75 µL of library material for each case. Each pooled library sample was distributed into 3 replicate sample plates (22 µL each) for use in the validation protocol.

Replicate number 1 of the 192 samples tested in Arm 2 were included in Arm 1 and underwent high depth of read reflex and rerun as necessary to generate results for Arm 1 analysis. Arm 2 replicate numbers 2 and 3 did not undergo high depth of read reflex or rerun. For all three replicates in the Arm 2, only low depth of read analysis were performed.

Only samples from replicate 1, 2, and 3 with sufficient child fraction estimate (≥6% for low risk calls and ≥10% for high risk calls) to be called at low depth of read were analyzed in the Arm 2 reproducibility experiment.

While each plasma sample was tested three times for reproducibility, the corresponding parent samples for each plasma sample trio was not amplified and sequenced as replicates. Mother samples were rerun as necessary to generate a passing QC result. Father samples were not rerun. The resultant parent sample data was used in the analysis of all three plasma sample replicates.

Data Analysis

Structural changes were made to the test method algorithms to reflect the removal of all targeted loci on chromosomes 1 and 2. The resultant SNP allele ratios from the plasma sample and parental samples were analyzed to create a maximum-likelihood estimate of the fetal chromosome copy number for each targeted chromosome. The maximum-likelihood estimate was based on two different algorithms as disclosed elsewhere herein, the het rate method and the quantitative modeling method (QMM). The het rate algorithm is based on analysis of the observed allele ratios (fraction of reference allele) at each SNP using a joint distribution model. The QMM algorithm is based on non-allelic analysis of the number of sequencing reads at each SNP in a method that produces a maximum likelihood of various pleudy hypothesis.

Data from both Arms were processed through the test method.

Analysis of Arm 1

Analysis will be performed using the father sample when available.

Samples with unrecoverable QC failures were not included in syndrome analysis nor count toward syndrome denominator for rate calculations, including no-call rate.

The criteria for aneuploidy detection were verified by observation.

The criteria for detection of at least one male and one female sample were verified by observation. The number of incorrect gender calls were computed and compared to the acceptance criteria.

Each sample was evaluated for each syndrome for a result from {high risk, low risk, risk unchanged}.

Each syndrome in the set (Trisomy 13, Trisomy 18, Trisomy 21, Monosomy X) was analyzed independently for sensitivity and specificity and the results were compared to the acceptance criteria for UR0070. Sensitivity and specificity were computed for each syndrome according to the CFE projection method described in Appendix A below, along with an approximate variance. The CFE distribution from the article Pergament et al. (2014) (Obstet Gynecol August: 124; 210-8) was used. The acceptance criteria was met if the desired sensitivity and specificity fall within the confidence bounds of the estimates from the data. The confidence bounds were defined as 3 times the square root of the estimated approximate variance.

Results with unchanged risk were not included in the sensitivity or specificity computations but were reflected in the computed no-call rate.

The requirement on no-call rate was evaluated on the subset of euploid-truth samples passing QC, rather than the complete data set. The no-call rate was computed using the CFE projection method provided in Appendix A and the commercial CFE distribution. The aneuploidy rate in commercial data is less than 2 percent and so the contribution of aneuploid samples to the commercial no-call rate is negligible.

Analysis of Arm 2

Reproducibility of clinical calls was evaluated on eligible trios. An eligible trio was one that passed QC and produced calls on more than 1 sample replicate. The acceptance criterion is that there were not more than one changed call in the set of eligible trios. This is defined as a change from high risk to low risk or the opposite. The number of changed calls were identified and compared to the acceptance criteria.

Appendix A: Computational Details for Sensitivity, Specificity and No-Call Rate Projected to a Known CFE Distribution (Generated by a Commercial Test)

Commercial data from Panorama Version 1 (Natera, CA) that used control chromosomes was used to support the analysis by providing a representative commercial CFE distribution. The metrics calculated from the study data will be used to calculate projected performance metrics for the commercial product using this distribution.

Previous experiments with the test method led to the following relationship between Panorama Version 1 CFE (f1) and the test method CFE (f2) for the same blood draw. This relationship holds in the observed range of CFE, from approximately (f1=0.01) to (f1=0.35).

$$f_2 = 0.3533 f_1^2 + 0.9136 f_1$$

The commercial child fraction estimate distribution was determined using a set of approximately 50,000 commercial test results (Panorama Version 1, Natera, CA), which analyzes samples using a method that utilized control chromosomes.

The equation above was used to convert the Panorama Version 1 commercial test CFE distribution into the test method CFE equivalent. This was regarded as the commercial child fraction estimate distribution going forward, such that all computations were done on the test method CFE.

The same approach can be used to generate the CFE distribution from the Pergament et al. (2014) publication.

A metric such as sensitivity can be projected to the commercial child fraction estimate distribution as follows:

Define a set of CFE intervals, i=1 to N.

Observe the population rate of each interval from the commercial data distribution, $p_i$.

Compute the metric of interest, xi, such as sensitivity, for the subset of the syndrome data that falls within each child fraction estimate interval.

The projected value of the metric of interest is a weighted sum across the CFE intervals.

$$x = \sum_{i=1}^{N} p_i x_i$$

The variance of the projected value of the metric can be approximated by a similar method.

$$VAR[x] = \sum_{i=1}^{N} p_i VAR[x_i]$$

Results and Analysis

Arm 1 Analysis: Detection, Accuracy, Failure Rate

The analysis for detection, accuracy and failure rate includes both the set of "arm 1" samples and the first replicate of the set of "arm 2" samples. Thus the starting count of eligible samples is the combined count of 587.

Samples Excluded from all Arm 1 Analysis Due to Quality Control Failures

As defined in the test protocol, samples failing quality control metrics were not included in detection, accuracy or failure rate performance computations of Arm 1, which was analyzed with all samples from the Arm 1 cohort and replicate 1 of the Arm 2 cohort. Eight such cases were removed. Those failing samples are described below in Table 2. Collectively, these samples are comprised of 5 cases of trisomy 21 and 3 euploid cases.

TABLE 2

Summary of Quality Control Failures for Arm 1 Analysis

| sample count | failure reason | affected cases |
|---|---|---|
| 3 | Contamination | 339370, 339242, 339486 |
| 2 | sample handling error | 339415, 338867 |
| 1 | unrecoverable mother sample failure | 339617 |
| 2 | failed sequencing number of reads | 339397, 339229 |

Aneuploidy Detection and Gender Detection

The acceptance criteria were as follows:

The test was able to detect at least one sample each of Trisomy 13, 18, 21, Monosomy X, and triploidy The test was able to detect gender for at least one male and one female sample Not more than two incorrect gender calls will occur for eligible samples. An incorrect gender call is defined as incorrect reporting of the presence or absence of the Y chromosome.

Table 3 shows the number and type of calls for each syndrome. Note that female samples include monosomy X and a large number (248) of samples do not include gender truth.

TABLE 3

| | Arm 1 Analysis Results Summary | | | | | | | | |
|---|---|---|---|---|---|---|---|---|---|
| | Negative | T13 | T18 | T21 | MX | Triploidy | Total | Male | Female |
| Eligible | 335 | 15 | 37 | 179 | 9 | 4 | 579 | 170 | 162 |
| Algorithm Limitation (No Call) | 11 | 1 | 9 | 13 | 2 | 0 | 36 | 7 | 18 |
| Correct Calls | 324 | 14 | 28 | 163 | 7 | 4 | 540 | 163 | 144 |

TABLE 3-continued

Arm 1 Analysis Results Summary

|  | Negative | T13 | T18 | T21 | MX | Triploidy | Total | Male | Female |
|---|---|---|---|---|---|---|---|---|---|
| Incorrect Calls | 0 | 0 | 0 | 2 | 0 | 0 | 2 | 0 | 0 |
| Other Abnormality | 0 | 0 | 0 | 1 | 0 | 0 | 1 | | |

All calls were correct with the exception of 2 trisomy 21 cases called false negative and 1 trisomy 21 case called "other abnormality". The latter is discussed in more detail below.

Case 338833 was identified as having trisomy 21 through karyotype analysis of the CVS biopsy. The case was reported as "no-call due to suspected abnormality" because in addition to the trisomy 21, which was detected, there were also abnormal indications on the X chromosome. This case was not counted as a negative call in the sensitivity computation because the result was suspected abnormality including trisomy 21.

Thus, the test method was able to detect at least one sample each of Trisomy 13, 18, 21, Monosomy X, and triploidy, was able to detect gender for at least one male and one female sample, and no incorrect gender calls occurred. Therefore, the aneuploidy detection and gender detection acceptance criteria were met by the test method.

Sensitivity and Specificity

The acceptance criteria were that the sensitivity and specificity thresholds listed below fell within or below the 3-sigma bounds estimated from the data. Only samples with algorithm results were included in the analysis and the raw sensitivity and specificity values were normalized to meet the fetal fraction distribution observed in the publication by Pergament et al (2014).

T21: Sensitivity ≥99.01% and specificity ≥99.89%
T18: Sensitivity ≥96.00% and specificity ≥99.98%
T13: Sensitivity ≥90.00% and specificity ≥99.91%
MX: Sensitivity ≥90.00% and specificity ≥99.91%

Raw and fetal fraction distribution-adjusted measurements of sensitivity and specificity with confidence bounds are presented in Table 4 below.

TABLE 4

| | Sensitivity | | | |
|---|---|---|---|---|
| | Trisomy 13 | Trisomy 18 | Trisomy 21 | Monosomy X |
| Correct Calls | 14 | 28 | 163 | 7 |
| Incorrect Calls | 0 | 0 | 2 | 0 |
| Observed Sensitivity | 100% | 100% | 98.8% | 100% |
| Observed 95% CI | 76.8-100 | 87.7-100 | 95.7-99.9 | 59.0-100 |
| Projected Sensitivity | 100% | 100% | 97.1% | 100% |
| Projected 3-Sigma Bounds | 78.8-100 | 87.3-100 | 87.7-100 | N/A |

The observed sensitivity for trisomy 21 was 98.8%. After fetal fraction adjustment, the estimated sensitivity was 97.1% with a standard deviation of 3.1% and 3-sigma confidence bounds of 87.7%-100%.

The observed specificity for trisomy 13, trisomy 18, trisomy 21 and monosomy X was 100%. No adjustment to the fetal fraction distribution was applied. Monosomy X had too few calls to evaluate the fetal fraction adjustment in the confidence interval, so projected bounds were not given.

Therefore, all syndromes meet the sensitivity and specificity acceptance criteria that the required minimum values fall within or below 3 standard deviations of the observed value.

Although test sensitivity for sex chromosome trisomies such as XXX, XXY, and XYY was not specifically addressed by this study, there were no false positives for these syndromes among any of the called cases, suggesting that sex chromosome trisomy specificity was near 100%.

Algorithm Failure Rate

The acceptance criterion was that the maximum tolerable algorithm failure rate of 4.20% fell within or above the 3 sigma bounds estimated from the data. This estimate was based on projection to the currently observed commercial fetal fraction distribution and was computed from the set of negative samples with gestational age ≥10 weeks.

Raw and adjusted measurements of algorithm failure rate with confidence bounds are presented in Table 5 below.

TABLE 5

| Summary of Algorithm Failure Rate Analysis | |
|---|---|
| | Count |
| Eligible Negatives any GA | 335 |
| Eligible Negatives GA ≥ 10 Weeks | 279 |
| Called Low Risk | 273 |
| Not Called (Algorithm Limitation) | 6 |

The observed algorithm failure rate was 2.1% before fetal fraction distribution adjustment. After adjustment the algorithm failure rate in a commercial cohort was projected to be 3.67% with a standard deviation of 2.06% and 3-sigma bounds of 0%-9.86%. Therefore, the acceptance criteria for algorithm failure rate were met.

Note that fetal fraction adjustment computations for sensitivity and algorithm failure rate followed a method based on dividing the range of fetal fractions into bins, and combining those bins according to their population in commercial data.

Arm 2: Reproducibility

Samples Excluded from all Arm 2 Analyses Due to Quality Control Failures

Samples that failed in all 3 replicates were excluded from the reproducibility analysis. Case 339617 had a failed mother gDNA sample that did not produce a passing result and, as such, was excluded leaving 89 eligible samples.

Rate of Samples Passing QC

The acceptance criterion requires that fewer than 10% of the samples in each test unit fail QC. This criterion was evaluated on each test unit independently.

Out of 89 cases, there were 87 cases where all three replicates pass QC. Two different cases (339683, 339700) each had a replicate in test unit one which failed the number of reads QC threshold. Thus the highest observed QC failure rate was two samples out of 89, or 2.2%, per test unit. This met the acceptance criterion.

Reproducibility of Clinical Results

The acceptance criterion was that of the sample triplicates that produce 2 or 3 result calls, not more than one triplicate produced an inconsistent call. At least 50 of the 192 sample triplicates had to be eligible for clinical calls in all three test units for the reproducibility analysis to be performed.

Of the 89 cases where at least 2 replicates pass QC, 22 were ineligible for review at low depth of read due to their fetal fraction. Six cases went through review and were selected (in all replicates) for resequencing at high depth of read due to suspected aneuploidy call. Two cases had all replicates identified as "uninformative DNA pattern" and were not called. Combined, 30 cases were uncallable in all three replicates, leaving 59 eligible samples that had at least two calls.

Two cases were called in one replicate and selected for resequencing at high depth of read in two replicates. Repeatability analysis was only performed for samples producing results at low depth of read and did not include analysis based on reflex to high depth of read.

Three cases each had one replicate with a QC failure or reflex request and the calls were consistent in the remaining two replicates. 54 cases had calls on all three replicates. There were no cases with inconsistent calls. Therefore, the acceptance criteria were satisfied.

CONCLUSIONS

All acceptance criteria were met by the test method. In other words, the test method was able to effectively determine the presence or absence of aneuploidy of chromosomes of interest in test samples even when scrutinized against commercial test performance.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims.

What is claimed is:

1. A method for preparing a non-naturally occurring composition of amplified DNA from a test sample useful for determining the likelihood of aneuploidy of a chromosome or chromosome segment of interest in the test sample, comprising:
   a. extracting a mixture of fetal cell-free genomic DNA and maternal cell-free genomic DNA from the test sample which is a blood sample of a pregnant woman;
   b. preparing a non-naturally occurring composition of amplified DNA extracted in a. by performing amplification of at least 100 polymorphic loci on the chromosome or chromosome segment of interest in a single reaction from the mixture of fetal cell-free genomic DNA and maternal cell-free genomic DNA; and
   c. analyzing the non-naturally occurring composition of amplified DNA produced in b. by performing sequencing to generate genetic data for the chromosome or chromosome segment of interest from each sample in a set of samples comprising the test sample and at least one diploid sample, wherein the genetic data is obtained from a parallel analysis of the samples, and wherein the analyzing comprises:
      (i) setting a first bias model using the genetic data for the chromosome or chromosome segment of interest from the at least one diploid sample determined to be disomic for the chromosome or chromosome segment of interest,
      (ii) normalizing the genetic data for the chromosome or chromosome segment of interest for the test sample using the first bias model, and
      (iii) determining the likelihood of aneuploidy for the chromosome or chromosome segment of interest in the test sample using the normalized data, wherein the normalized data comprise quantitative allelic data from a plurality of polymorphic loci in the chromosome or chromosome segment of interest and quantitative non-allelic data from a plurality of polymorphic and/or non-polymorphic loci in the chromosome or chromosome segment of interest, and wherein the determining the likelihood of aneuploidy comprises obtaining a first probability value indicating the likely copy number of the chromosome or chromosome segment of interest by quantitative allelic analysis of the allelic data, obtaining a second probability value indicating the likely copy number of the chromosome or chromosome segment of interest by quantitative non-allelic analysis of the non-allelic data, and combining the first probability value and the second probability value to produce a combined probability value to determine the likely copy number of the chromosome or chromosome segment of interest,
   wherein the quantitative allelic analysis is performed by quantitative allelic maximum likelihood method or het rate method, and wherein the quantitative non-allelic analysis is performed by quantitative non-allelic maximum likelihood method or QMM method and the het rate method is based on analysis of observed allele ratios at each SNP using a joint distribution model, and wherein the QMM method is based on analysis of the number of sequencing reads at each SNP,
   wherein the at least one diploid sample is determined to be disomic for the chromosome or chromosome segment of interest by analyzing the genetic data from the parallel analysis, and
   wherein the likelihood of aneuploidy is determined by:
      creating a plurality of ploidy hypotheses wherein each ploidy hypothesis is associated with a specific copy number for the chromosome or chromosome segment of interest,
      determining a ploidy probability value for each ploidy hypothesis, wherein the ploidy probability value indicates the likelihood that the target sample has the number of copies of the chromosome or chromosome segment of interest that is associated with the ploidy hypothesis, wherein the ploidy probability values are derived from the normalized genetic data,
      selecting the ploidy hypothesis with the maximum likelihood as the ploidy hypothesis most likely to be correct; and
      outputting the likely ploidy state of the test sample as an indication of the likelihood of aneuploidy.

2. A method for preparing a non-naturally occurring composition of amplified DNA from a test sample useful for determining the likelihood of aneuploidy of a chromosome or chromosome segment of interest in the test sample, comprising:
   a. extracting a mixture of fetal cell-free genomic DNA and maternal cell-free genomic DNA from the test sample which is a blood sample of a pregnant woman;
   b. preparing a non-naturally occurring composition of amplified DNA extracted in a. by performing amplification of at least 100 polymorphic loci on the chromosome or chromosome segment of interest in a single reaction from the mixture of fetal cell-free genomic DNA and maternal cell-free genomic DNA; and
   c. analyzing the non-naturally occurring composition of amplified DNA produced in b. by performing sequencing to generate genetic data for the chromosome or chromosome segment of interest from each sample in a set of samples comprising the test sample and at least one diploid sample, wherein the genetic data is obtained from a parallel analysis of the samples, and wherein the analyzing comprises:
(i) setting a first bias model using the genetic data for the chromosome or chromosome segment of interest from the at least one diploid sample determined to be disomic for the chromosome or chromosome segment of interest,
(ii) normalizing the genetic data for the chromosome or chromosome segment of interest for the test sample using the first bias model, and
(iii) determining the likelihood of aneuploidy for the chromosome or chromosome segment of interest in the test sample using the normalized data, wherein the normalized data comprise quantitative allelic data from a plurality of polymorphic loci in the chromosome or chromosome segment of interest and quantitative non-allelic data from a plurality of polymorphic and/or non-polymorphic loci in the chromosome or chromosome segment of interest, and wherein the determining the likelihood of aneuploidy comprises obtaining a first probability value indicating the likely copy number of the chromosome or chromosome segment of interest by quantitative allelic analysis of the allelic data, obtaining a second probability value indicating the likely copy number of the chromosome or chromosome segment of interest by quantitative non-allelic analysis of the non-allelic data, and combining the first probability value and the second probability value to produce a combined probability value to determine the likely copy number of the chromosome or chromosome segment of interest,
wherein the at least one diploid sample is determined to be disomic for the chromosome or chromosome segment of interest by analyzing the genetic data from the parallel analysis,
wherein the genetic data comprises an amount of DNA corresponding to each locus in a set of loci wherein the loci are present on the chromosome or chromosome segment of interest, and
wherein the chromosome or chromosome segment of interest in the at least one diploid sample is determined to be disomic by:
creating, for each sample in the set of samples, a plurality of first hypotheses wherein each first hypothesis is associated with a specific copy number for the chromosome or chromosome segment of interest,
determining a first probability value for each first hypothesis, wherein the first probability value indicates the likelihood that the sample has the number of copies of the chromosome or chromosome segment that is associated with the first hypothesis, wherein the first probability values are derived from the genetic data associated with the sample, and
selecting the at least one diploid sample by selecting the at least one sample that matches a disomic copy number hypothesis for the chromosome or chromosome segment of interest,
wherein the at least one diploid sample that is determined to be disomic for the chromosome or chromosome segment of interest is determined by, for each sample in the set of samples,
calculating a proportion of reads that map to the chromosome or chromosome segment of interest;
calculating a z-score for the proportion of reads that map to the chromosome or chromosome segment of interest; and selecting one or more samples where the absolute value of the z-score is below a threshold value or where the z-score indicates disomy at a level of confidence of at least 90%.

3. The method according to claim 2, wherein the determining is performed using a quantitative non-allelic method.

4. The method according to claim 2, wherein the determining is performed using a quantitative allelic method.

5. The method according to claim 1, wherein the first bias model comprises sample bias.

6. The method according to claim 2, wherein the method further comprises estimating a fetal fraction and setting a second bias model, wherein the fetal fraction and the second bias model are used to determine the at least one diploid sample and/or to determine the ploidy probability.

7. The method according to claim 6, wherein determining a first probability value for each first hypothesis comprises:
(a) determining an initial probability of each first hypothesis for each grid point using a uniform hypothesis prior on a 2d grid of fetal fraction and the second bias model;
(b) determining a parameter distribution for each chromosome or chromosome segment of interest based on the initial probability;
(c) determining a composite parameter distribution from the parameter distribution for each chromosome or chromosome segment of interest;
(d) determining a posterior probability of each first hypothesis based on the composite parameter distribution; and
(e) repeating steps (a)-(e) using the posterior probability as a new initial probability for each iteration until convergence is reached.

8. The method according to claim 6, wherein determining a ploidy probability value for each ploidy hypothesis comprises:
(a) determining an initial probability of each ploidy hypothesis for each grid point using a uniform hypothesis prior on a 2d grid of fetal fraction and the first bias model;
(b) determining a parameter distribution for each chromosome or chromosome segment of interest based on the initial probability;
(c) determining a composite parameter distribution from the parameter distribution for each chromosome or chromosome segment of interest;
(d) determining a posterior probability of each ploidy hypothesis based on the composite parameter distribution; and
(e) repeating steps (a)-(e) using the posterior probability as a new initial probability for each iteration until convergence is reached.

9. The method according claim 2, further comprising outputting the selected one or more samples as an indication of the likely presence of aneuploidy.

10. The method according to claim 2, wherein the at least one diploid sample is determined to be disomic for the chromosome or chromosome segment of interest without using a control chromosome or control chromosome segment that is different than the chromosome or chromosome segment of interest.

11. A method for preparing a non-naturally occurring composition of amplified DNA from a test sample useful for determining the likelihood of aneuploidy for a first chromosome or chromosome segment of interest in a test sample from the test subject, comprising:
a. extracting a mixture of fetal cell-free genomic DNA and maternal cell-free genomic DNA from the test sample which is a blood sample of a pregnant woman;
b. producing a non-naturally occurring composition of amplified DNA extracted in a. by performing amplification of at least 100 polymorphic loci on the chromosome or chromosome segment of interest in a single reaction from the mixture of fetal cell-free genomic DNA and maternal cell-free genomic DNA and sequence the amplification products;

c. analyzing the non-naturally occurring composition of amplified DNA produced in b. by performing sequencing to generate genetic sequencing data from a parallel analysis of the first chromosome or chromosome segment of interest from cell free DNA from each sample in a set of liquid samples comprising the test sample, wherein the set of liquid samples comprises at least 3 samples, wherein the genetic sequencing data determines an amount of DNA corresponding to each locus in a first set of loci present on the first chromosome or chromosome segment of interest respectively, and wherein the analyzing comprises:
  (i) estimating a fetal fraction for each sample in the set of samples,
  (ii) selecting a diploid subset of samples from the set of liquid samples, wherein the diploid subset of samples are samples that are initially determined to be disomic for the first chromosome or chromosome segment of interest using an initial bias model, wherein the subset of samples comprises at least 2 samples,
  (iii) setting a confirmatory bias model from the genetic data from the first chromosome or chromosome segment of interest from the diploid subset of patients,
  (iv) normalizing the genetic data for the test subject using the confirmatory bias model, to give normalized genetic data for the test subject, and
  (v) determining, using the normalized data, whether genetic data from the test subject is indicative of an aneuploidy in the first chromosome or chromosome segment of interest, wherein the normalized data comprise quantitative allelic data from a plurality of polymorphic loci in the chromosome or chromosome segment of interest and quantitative non-allelic data from a plurality of polymorphic and/or non-polymorphic loci in the chromosome or chromosome segment of interest, and wherein the determining the likelihood of aneuploidy comprises obtaining a first probability value indicating the likely copy number of the chromosome or chromosome segment of interest by quantitative allelic analysis of the allelic data, obtaining a second probability value indicating the likely copy number of the chromosome or chromosome segment of interest by quantitative non-allelic analysis of the non-allelic data, and combining the first probability value and the second probability value to produce a combined probability value to determine the likely copy number of the chromosome or chromosome segment of interest,
  wherein the fetal fraction is used to select the diploid subset of samples and/or to determine whether the genetic data from the test subject is indicative of an aneuploidy, and
  wherein the at least one diploid sample that is determined to be disomic for the chromosome or chromosome segment of interest is determined by, for each sample in the set of samples:
    calculating a proportion of reads that map to the chromosome or chromosome segment of interest;
    calculating a z-score for the proportion of reads that map to the chromosome or chromosome segment of interest; and
    selecting one or more samples where the absolute value of the z-score is below a threshold value.

12. The method according to claim 11, wherein the set of samples comprises at least 40 samples and the diploid subset of samples comprises at least 10 diploid samples.

13. The method according to claim 11, wherein the selecting is performed by a method comprising, for each sample in the set of samples,
  creating a plurality of first hypotheses considering the fetal fraction estimate and the initial bias model, wherein each first hypothesis is associated with a specific copy number for the chromosome or chromosome segment of interest in a genome of a target sample,
  determining a first probability value for each first hypothesis, wherein the first probability value indicates the likelihood that the genome of the target cell has the number of copies of the chromosome or chromosome segment that is associated with the first hypothesis, wherein the first probability values are derived from the genetic data associated with that sample, and
  selecting the subset of samples from those samples that match a disomic copy number hypothesis for the chromosome or chromosome segment of interest.

14. The method according to claim 11, wherein determining whether the normalized data is indicative of aneuploidy is performed by, for each sample in the set of samples,
  creating a plurality of second hypotheses wherein each second hypothesis is associated with a specific copy number for the chromosome or chromosome segment in the genome of the test sample,
  determining a second probability value for each second hypothesis, wherein the second probability value indicates the likelihood that the genome of the target sample has the number of copies of the chromosome or chromosome segment that is associated with the second hypothesis, wherein the second probability values are derived from the normalized genetic data,
  selecting the second hypothesis with the maximum likelihood as the second hypothesis most likely to be correct; and
  outputting the ploidy state of the test sample as an indication of the likelihood of aneuploidy.

15. The method according to claim 14, wherein the first hypothesis, the second hypothesis, or both the first and second hypothesis provide an expected distribution of quantitative data for each of the first, second, and third sets of loci.

16. The method according to claim 14, wherein the plurality of first hypotheses, the plurality of second hypotheses, or both the first and second hypothesis comprise estimates of sample parameters for each sample of the set of samples at a given ploidy state.

17. The method according to claim 14, wherein the genetic data comprises quantitative allelic data from a plurality of polymorphic loci in the set of loci, and wherein each of the first hypotheses specifies an expected distribution of quantitative allelic data at the plurality of polymorphic loci, and wherein the first probability values are determined by calculating, for each of the first hypotheses, the fit between the expected genetic data and the obtained genetic data.

18. The method according to claim 17, wherein the genetic data comprises quantitative non-allelic data from the plurality of polymorphic loci in the set of loci, and wherein each of the second hypotheses specifies an expected mean value of quantitative non-allelic data at the plurality of polymorphic loci, and wherein the second probability values are determined by calculating, for each of the second hypotheses, the fit between the expected genetic data and the obtained genetic data.

19. The method according to claim 18, wherein the first probability values and the second probability values for hypotheses that are indicative of aneuploidy are separately combined for each of the first chromosome or chromosome segments of interest for the test sample, to determine whether aneuploidy is likely present in the first chromosome or chromosome segment of interest for the test sample.

20. The method according to claim 17, wherein the method is performed by analyzing a second chromosome or chromosome segment of interest and a third chromosome or chromosome of interest in the parallel analysis, wherein the diploid samples are identified by a method comprising comparing genetic data from the first, second, and third chromosome or chromosome segments of interest for each sample of the set of samples.

21. The method according to claim 11, wherein the sample is blood, or a fraction thereof, from the mother of the fetus and the method is performed by analyzing in the parallel analysis chromosomes 13, 18, and 21, or chromosome segments thereof.

22. The method according to claim 11, wherein the first chromosome or chromosome segment of interest is selected from the group consisting of one or more of chromosome 22q11.2, chromosome 1p36, chromosome 15q11-q13, chromosome 4p16.3, chromosome Sp15.2, chromosome 17p13.3, chromosome 22q13.3, chromosome 2q37, chromosome 3q29, chromosome 9q34, chromosome 17q21.31, and the terminus of a chromosome.

23. The method according to claim 11, wherein the test sample is blood, or a fraction thereof and wherein at least a portion of the genetic data is generated from circulating tumor DNA.

24. The method according claim 11, further comprising outputting the selected one or more samples as an indication of the likely presence of aneuploidy.

* * * * *